United States Patent
La et al.

(10) Patent No.: US 11,472,817 B2
(45) Date of Patent: Oct. 18, 2022

(54) HETEROCYCLIC COMPOUND AND ORGANIC LIGHT-EMITTING DEVICE COMPRISING SAME

(71) Applicant: LT MATERIALS CO., LTD., Yongin (KR)

(72) Inventors: Hyun-Ju La, Osan-si (KR); Yu-Jin Heo, Osan-si (KR); Won-Jang Jeong, Hwaseong-si (KR)

(73) Assignee: LT MATERIALS CO., LTD., Yongin (KR)

( * ) Notice: Subject to any disclaimer, the term of this patent is extended or adjusted under 35 U.S.C. 154(b) by 328 days.

(21) Appl. No.: 16/756,639

(22) PCT Filed: Sep. 19, 2019

(86) PCT No.: PCT/KR2019/012142
§ 371 (c)(1),
(2) Date: Apr. 16, 2020

(87) PCT Pub. No.: WO2020/060225
PCT Pub. Date: Mar. 26, 2020

(65) Prior Publication Data
US 2020/0255452 A1    Aug. 13, 2020

(30) Foreign Application Priority Data
Sep. 19, 2018 (KR) .......................... 10-2018-0112497

(51) Int. Cl.
*C07D 519/00* (2006.01)
*C07D 471/14* (2006.01)
(Continued)

(52) U.S. Cl.
CPC ......... *C07D 519/00* (2013.01); *C07D 471/14* (2013.01); *H01L 51/0054* (2013.01);
(Continued)

(58) Field of Classification Search
CPC ............... C07D 519/00; C07D 471/14; H01L 51/0054; H01L 51/0067; H01L 51/0069;
(Continued)

(56) References Cited

U.S. PATENT DOCUMENTS 4,356,429 A    10/1982  Tang
9,331,290 B2   5/2016   Stoessel et al.
(Continued)

FOREIGN PATENT DOCUMENTS

KR    10-2013-0095259 A    8/2013
KR    10-2014-0007759 A    1/2014
(Continued)

OTHER PUBLICATIONS

STIC full search attached (Year: 2013).*
(Continued)

*Primary Examiner* — Mamadou L Diallo
(74) *Attorney, Agent, or Firm* — Birch, Stewart, Kolasch & Birch, LLP

(57) ABSTRACT

The present specification relates to a heterocyclic compound represented by Chemical Formula 1, and an organic light emitting device comprising the same.

13 Claims, 3 Drawing Sheets

(51) Int. Cl.
*H01L 51/00* (2006.01)
*H01L 51/50* (2006.01)

(52) U.S. Cl.
CPC ...... *H01L 51/0067* (2013.01); *H01L 51/0069* (2013.01); *H01L 51/0072* (2013.01); *H01L 51/5092* (2013.01); *H01L 51/5096* (2013.01); *H01L 51/504* (2013.01); *H01L 51/5056* (2013.01); *H01L 51/5072* (2013.01)

(58) Field of Classification Search
CPC ............. H01L 51/0072; H01L 51/5092; H01L 51/5096; H01L 51/504; H01L 51/5056; H01L 51/5072; H01L 51/5278; H01L 51/50; C07F 9/6561
See application file for complete search history.

(56) References Cited

U.S. PATENT DOCUMENTS

| | | | |
|---|---|---|---|
| 10,577,342 B2 | 3/2020 | Parham et al. | |
| 2014/0309231 A1* | 10/2014 | Kanai | A61K 9/0019 514/249 |
| 2017/0179407 A1 | 6/2017 | Park et al. | |
| 2019/0288218 A1 | 9/2019 | La et al. | |
| 2019/0393422 A1* | 12/2019 | Sakamoto | H01L 51/0067 |

FOREIGN PATENT DOCUMENTS

| | | |
|---|---|---|
| KR | 10-2014-0029183 A | 3/2014 |
| KR | 10-2017-0074731 A | 6/2017 |
| KR | 10-2017-0084190 A | 7/2017 |
| KR | 10-2018-0062343 A | 6/2018 |
| WO | WO-2018124588 A1 * | 7/2018 ............. C09K 11/06 |

OTHER PUBLICATIONS

International Search Report (PCT/ISA/210) issued in PCT/KR2019/012142, dated Dec. 30, 2019.
Kuwabara et al., "Thermally Stable Multilayered Organic Electroluminescent Devices Using Novel Starburst Molecules, 4,4',4"-Tri(N-carbazoly)triphenylamine (TCTA) and 4,4',4"-Tris(3-methylphenylphenyl-amino)triphenylamine (m-MTDATA), as Hole-Transport Materials", Advanced Materials, 1994, vol. 6, No. 9, pp. 677-679.

* cited by examiner

[FIG. 1]
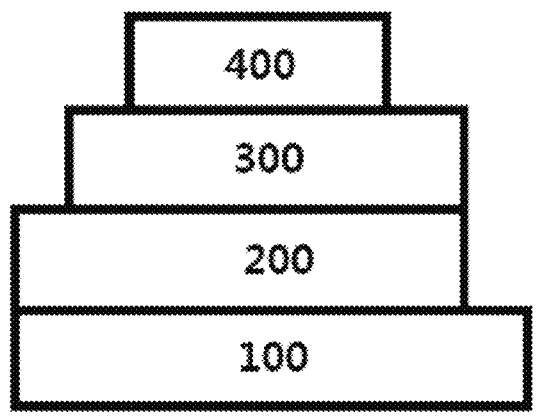
[FIG. 2]
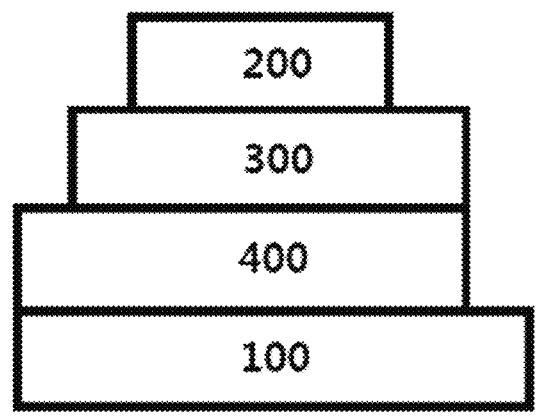

【FIG. 3】
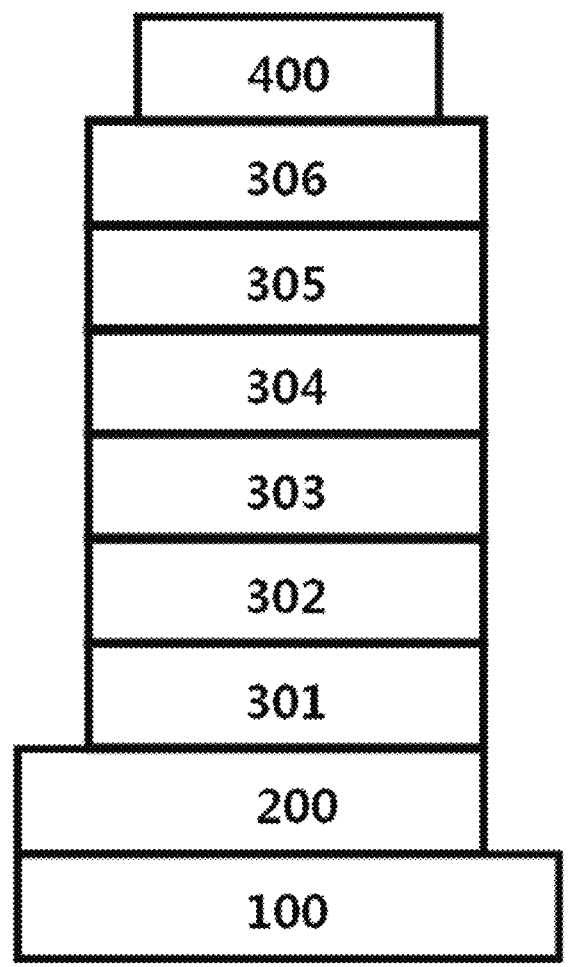

[FIG. 4]

| CATHODE |
|---|
| ELECTRON INJECTION LAYER |
| SECOND ELECTRON TRANSFER LAYER |
| SECOND HOLE BLOCKING LAYER |
| SECOND STACK LIGHT EMITTING LAYER |
| SECOND ELECTRON BLOCKING LAYER |
| SECOND HOLE TRANSFER LAYER |
| P-TYPE CHARGE GENERATION LAYER |
| N-TYPE CHARGE GENERATION LAYER |
| FIRST ELECTRON TRANSFER LAYER |
| FIRST HOLE BLOCKING LAYER |
| FIRST STACK LIGHT EMITTING LAYER |
| FIRST ELECTRON BLOCKING LAYER |
| FIRST HOLE TRANSFER LAYER |
| FIRST HOLE INJECTION LAYER |
| ANODE |
| SUBSTRATE |

HETEROCYCLIC COMPOUND AND ORGANIC LIGHT-EMITTING DEVICE COMPRISING SAME

TECHNICAL FIELD

This application claims priority to and the benefits of Korean Patent Application No. 10-2018-0112497, filed with the Korean Intellectual Property Office on Sep. 19, 2018, the entire contents of which are incorporated herein by reference.

The present specification relates to a heterocyclic compound, and an organic light emitting device comprising the same.

BACKGROUND ART

An electroluminescent device is one type of self-emissive display devices, and has an advantage of having a wide viewing angle, and a high response speed as well as having an excellent contrast.

An organic light emitting device has a structure disposing an organic thin film between two electrodes. When a voltage is applied to an organic light emitting device having such a structure, electrons and holes injected from the two electrodes bind and pair in the organic thin film, and light emits as these annihilate. The organic thin film may be formed in a single layer or a multilayer as necessary.

A material of the organic thin film may have a light emitting function as necessary. For example, as a material of the organic thin film, compounds capable of forming a light emitting layer themselves alone may be used, or compounds capable of performing a role of a host or a dopant of a host-dopant-based light emitting layer may also be used. In addition thereto, compounds capable of performing roles of hole injection, hole transfer, electron blocking, hole blocking, electron transfer, electron injection and the like may also be used as a material of the organic thin film.

Development of an organic thin film material has been continuously required for enhancing performance, lifetime or efficiency of an organic light emitting device.

PRIOR ART DOCUMENTS

Patent Documents

U.S. Pat. No. 4,356,429

DISCLOSURE

Technical Problem

The present disclosure is directed to providing a heterocyclic compound, and an organic light emitting device comprising the same.

Technical Solution

One embodiment of the present application provides a heterocyclic compound represented by the following Chemical Formula 1.

[Chemical Formula 1]

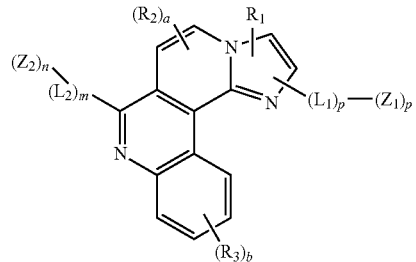

In Chemical Formula 1, $L_1$ and $L_2$ are the same as or different from each other, and each independently a direct bond; a substituted or unsubstituted arylene group; or a substituted or unsubstituted heteroarylene group, $Z_1$ and $Z_2$ are the same as or different from each other, and each independently a substituted or unsubstituted alkyl group; a substituted or unsubstituted aryl group; a substituted or unsubstituted heteroaryl group; —SiRR'R"; —P(=O)RR'; or NRR', $R_1$ to $R_3$ are the same as or different from each other, and each independently selected from the group consisting of hydrogen; deuterium; a substituted or unsubstituted alkyl group; a substituted or unsubstituted aryl group; a substituted or unsubstituted heteroaryl group; —SiRR'R"; —P(=O)RR'; and an amine group unsubstituted or substituted with a substituted or unsubstituted alkyl group, a substituted or unsubstituted aryl group or a substituted or unsubstituted heteroaryl group, or two or more groups adjacent to each other bond to each other to form a substituted or unsubstituted aromatic hydrocarbon ring or a substituted or unsubstituted heteroring, R, R' and R" are the same as or different from each other, and each independently hydrogen; a substituted or unsubstituted alkyl group; a substituted or unsubstituted aryl group; or a substituted or unsubstituted heteroaryl group, m, p, n and q are each an integer of 1 to 5, a is an integer of 0 to 2, b is an integer of 0 to 4, when m, p, n, q and b are an integer of 2 or greater, substituents in the parentheses are the same as or different from each other, and when a is an integer of 2, substituents in the parentheses are the same as or different from each other.

Another embodiment of the present application provides an organic light emitting device comprising a first electrode; a second electrode provided opposite to the first electrode; and one or more organic material layers provided between the first electrode and the second electrode, wherein one or more layers of the organic material layers comprise the heterocyclic compound represented by Chemical Formula 1.

Advantageous Effects

A compound described in the present specification can be used as a material of an organic material layer of an organic light emitting device. The compound is capable of performing a role of a hole injection material, a hole transfer material, a light emitting material, an electron transfer material, an electron injection material, a charge generation material and the like. Particularly, the compound can be used as a charge generation layer material or an electron transfer layer material of an organic light emitting device.

When using the compound represented by Chemical Formula 1 in an organic material layer, a device driving voltage can be lowered, light efficiency can be enhanced, and device lifetime properties can be enhanced by thermal stability of the compound.

DESCRIPTION OF DRAWINGS

FIG. 1 to FIG. 4 are diagrams each schematically illustrating a lamination structure of an organic light emitting device according to one embodiment of the present application.

REFERENCE NUMERAL

100: Substrate
200: Anode
300: Organic Material Layer
301: Hole Injection Layer
302: Hole Transfer Layer
303: Light Emitting Layer
304: Hole Blocking Layer
305: Electron Transfer Layer
306: Electron Injection Layer
400: Cathode Mode for Disclosure Hereinafter, the present application will be described in detail.

In the present specification, the halogen may be fluorine, chlorine, bromine or iodine.

In the present specification, the alkyl group comprises linear or branched having 1 to 60 carbon atoms, and may be further substituted with other substituents. The number of carbon atoms of the alkyl group may be from 1 to 60, specifically from 1 to 40 and more specifically from 1 to 20. Specific examples thereof may comprise a methyl group, an ethyl group, a propyl group, an n-propyl group, an isopropyl group, a butyl group, an n-butyl group, an isobutyl group, a tert-butyl group, a sec-butyl group, a 1-methyl-butyl group, a 1-ethylbutyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 2-methylpentyl group, a 4-methylhexyl group, a 5-methylhexyl group and the like, but are not limited thereto.

In the present specification, the alkenyl group comprises linear or branched having 2 to 60 carbon atoms, and may be further substituted with other substituents. The number of carbon atoms of the alkenyl group may be from 2 to 60, specifically from 2 to 40 and more specifically from 2 to 20. Specific examples thereof may comprise a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenyl-vinyl-1-yl group, a 2-phenylvinyl-1-yl group, a 2,2-diphenylvinyl-1-yl group, a 2-phenyl-2-(naphthyl-1-yl)vinyl-1-yl group, a 2,2-bis(diphenyl-1-yl)vinyl-1-yl group, a stilbenyl group, a styrenyl group and the like, but are not limited thereto.

In the present specification, the alkynyl group comprises linear or branched having 2 to 60 carbon atoms, and may be further substituted with other substituents. The number of carbon atoms of the alkynyl group may be from 2 to 60, specifically from 2 to 40 and more specifically from 2 to 20.

In the present specification, the alkoxy group may be linear, branched or cyclic. The number of carbon atoms of the alkoxy group is not particularly limited, but is preferably from 1 to 20. Specific examples thereof may comprise methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy and the like, but are not limited thereto.

In the present specification, the cycloalkyl group comprises monocyclic or polycyclic having 3 to 60 carbon atoms, and may be further substituted with other substituents. Herein, the polycyclic means a group in which the cycloalkyl group is directly linked to or fused with other cyclic groups. Herein, the other cyclic groups may be a cycloalkyl group, but may also be different types of cyclic groups such as a heterocycloalkyl group, an aryl group and a heteroaryl group. The number of carbon groups of the cycloalkyl group may be from 3 to 60, specifically from 3 to 40 and more specifically from 5 to 20. Specific examples thereof may comprise a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group and the like, but are not limited thereto.

In the present specification, the heterocycloalkyl group comprises O, S, Se, N or Si as a heteroatom, comprises monocyclic or polycyclic having 2 to 60 carbon atoms, and may be further substituted with other substituents. Herein, the polycyclic means a group in which the heterocycloalkyl group is directly linked to or fused with other cyclic groups. Herein, the other cyclic groups may be a heterocycloalkyl group, but may also be different types of cyclic groups such as a cycloalkyl group, an aryl group and a heteroaryl group. The number of carbon atoms of the heterocycloalkyl group may be from 2 to 60, specifically from 2 to 40 and more specifically from 3 to 20.

In the present specification, the aryl group comprises monocyclic or polycyclic having 6 to 60 carbon atoms, and may be further substituted with other substituents. Herein, the polycyclic means a group in which the aryl group is directly linked to or fused with other cyclic groups. Herein, the other cyclic groups may be an aryl group, but may also be different types of cyclic groups such as a cycloalkyl group, a heterocycloalkyl group and a heteroaryl group. The aryl group comprises a spiro group. The number of carbon atoms of the aryl group may be from 6 to 60, specifically from 6 to 40 and more specifically from 6 to 25. Specific examples of the aryl group may comprise a phenyl group, a biphenyl group, a triphenyl group, a naphthyl group, an anthryl group, a chrysenyl group, a phenanthrenyl group, a perylenyl group, a fluoranthenyl group, a triphenylenyl group, a phenalenyl group, a pyrenyl group, a tetracenyl group, a pentacenyl group, a fluorenyl group, an indenyl group, an acenaphthylenyl group, a benzofluorenyl group, a spirobifluorenyl group, a 2,3-dihydro-1H-indenyl group, a fused ring thereof, and the like, but are not limited thereto.

In the present specification, the silyl group is a substituent comprising Si, having the Si atom directly linked as a radical, and is represented by —SiR$_{104}$R$_{105}$R$_{106}$. R$_{104}$ to R$_{106}$ are the same as or different from each other, and may be each independently a substituent formed with at least one of hydrogen; deuterium; a halogen group; an alkyl group; an alkenyl group; an alkoxy group; a cycloalkyl group; an aryl group; and a heterocyclic group. Specific examples of the silyl group may comprise a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the fluorenyl group may be substituted, and adjacent substituents may bond to each other to form a ring.

When the fluorenyl group is substituted,

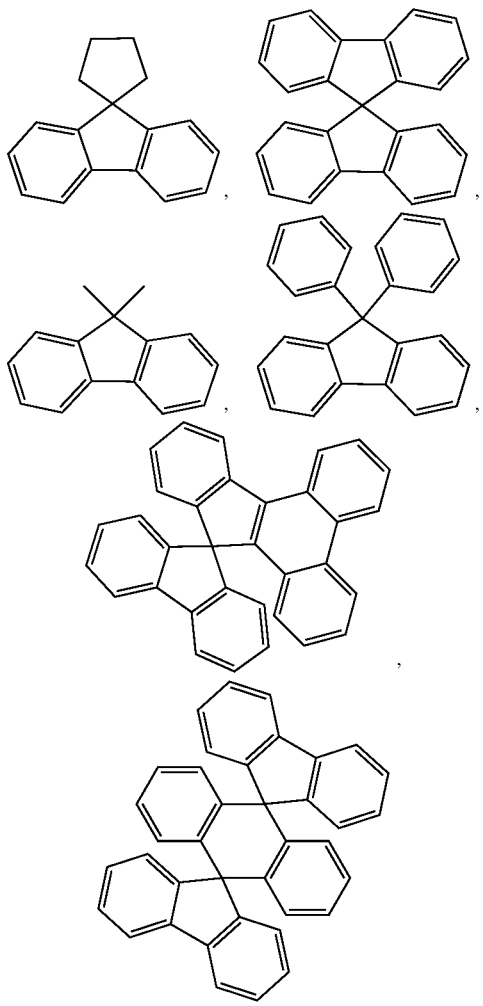

and the like may be included, however, the structure is not limited thereto.

In the present specification, the heteroaryl group comprises O, S, Se, N or Si as a heteroatom, comprises monocyclic or polycyclic having 2 to 60 carbon atoms, and may be further substituted with other substituents. Herein, the polycyclic means a group in which the heteroaryl group is directly linked to or fused with other cyclic groups. Herein, the other cyclic groups may be a heteroaryl group, but may also be different types of cyclic groups such as a cycloalkyl group, a heterocycloalkyl group and an aryl group. The number of carbon atoms of the heteroaryl group may be from 2 to 60, specifically from 2 to 40 and more specifically from 3 to 25. Specific examples of the heteroaryl group may comprise a pyridyl group, a pyrrolyl group, a pyrimidyl group, a pyridazinyl group, a furanyl group, a thiophene group, an imidazolyl group, a pyrazolyl group, an oxazolyl group, an isoxazolyl group, a thiazolyl group, an isothiazolyl group, a triazolyl group, a furazanyl group, an oxadiazolyl group, a thiadiazolyl group, a dithiazolyl group, a tetrazolyl group, a pyranyl group, a thiopyranyl group, a diazinyl group, an oxazinyl group, a thiazinyl group, a dioxynyl group, a triazinyl group, a tetrazinyl group, a quinolyl group, an isoquinolyl group, a quinazolinyl group, an isoquinazolinyl group, a qninozolinyl group, a naphthyridyl group, an acridinyl group, a phenanthridinyl group, an imidazopyridinyl group, a diazanaphthalenyl group, a triazaindene group, an indolyl group, an indolizinyl group, a benzothiazolyl group, a benzoxazolyl group, a benzimidazolyl group, a benzothiophene group, a benzofuran group, a dibenzothiophene group, a dibenzofuran group, a carbazolyl group, a benzocarbazolyl group, a dibenzocarbazolyl group, a phenazinyl group, a dibenzosilole group, spirobi(dibenzosilole), a dihydrophenazinyl group, a phenoxazinyl group, a phenanthridyl group, an imidazopyridinyl group, a thienyl group, an indolo[2,3-a]carbazolyl group, an indolo[2,3-b]carbazolyl group, an indolinyl group, a 10,11-dihydrodibenzo[b,f]azepine group, a 9,10-dihydroacridinyl group, a phenanthrazinyl group, a phenothiazinyl group, a phthalazinyl group, a naphthylidinyl group, a phenanthrolinyl group, a benzo[c][1,2,5]thiadiazolyl group, a 5,10-dihydrobenzo[b,e][1,4]azasilinyl, a pyrazolo[1,5-c]quinazolinyl group, a pyrido[1,2-b]indazolyl group, a pyrido[1,2-a]imidazo[1,2-e]indolinyl group, a 5,11-dihydroindeno[1,2-b]carbazolyl group and the like, but are not limited thereto.

In the present specification, the amine group may be selected from the group consisting of a monoalkylamine group; a monoarylamine group; a monoheteroarylamine group; —NH$_2$; a dialkylamine group; a diarylamine group; a diheteroarylamine group; an alkylarylamine group; an alkylheteroarylamine group; and an arylheteroarylamine group, and although not particularly limited thereto, the number of carbon atoms is preferably from 1 to 30. Specific examples of the amine group may comprise a methylamine group, a dimethylamine group, an ethylamine group, a diethylamine group, a phenylamine group, a naphthylamine group, a biphenylamine group, a dibiphenylamine group, an anthracenylamine group, a 9-methyl-anthracenylamine group, a diphenylamine group, a phenylnaphthylamine group, a ditolylamine group, a phenyltolylamine group, a triphenylamine group, a biphenylnaphthylamine group, a phenylbiphenylamine group, a biphenylfluorenylamine group, a phenyltriphenylenylamine group, a biphenyltriphenylenylamine group and the like, but are not limited thereto.

In the present specification, the arylene group means the aryl group having two bonding sites, that is, a divalent group. Descriptions on the aryl group provided above may be applied thereto except for those that are each a divalent. In addition, the heteroarylene group means the heteroaryl group having two bonding sites, that is, a divalent group. Descriptions on the heteroaryl group provided above may be applied thereto except for those that are each a divalent.

In the present specification, specific examples of the phosphine oxide group may comprise a diphenylphosphine oxide group, a dinaphthylphosphine oxide group and the like, but are not limited thereto.

In the present specification, an "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

In the present specification, the term "substitution" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

In the present specification, "substituted or unsubstituted" means being substituted with one or more substituents selected from the group consisting of C1 to C60 linear or branched alkyl; C2 to C60 linear or branched alkenyl; C2 to C60 linear or branched alkynyl; C3 to C60 monocyclic or polycyclic cycloalkyl; C2 to C60 monocyclic or polycyclic heterocycloalkyl; C6 to C60 monocyclic or polycyclic aryl; C2 to C60 monocyclic or polycyclic heteroaryl; —SiRR'R"; —P(=O)RR'; C1 to C20 alkylamine; C6 to C60 monocyclic or polycyclic arylamine; and C2 to C60 monocyclic or polycyclic heteroarylamine, or being unsubstituted, or being substituted with a substituent linking two or more substituents selected from among the substituents illustrated above, or being unsubstituted.

One embodiment of the present application provides a compound represented by Chemical Formula 1.

In one embodiment of the present application, Chemical Formula 1 may be represented by the following Chemical Formula 2 or Chemical Formula 3.

[Chemical Formula 2]

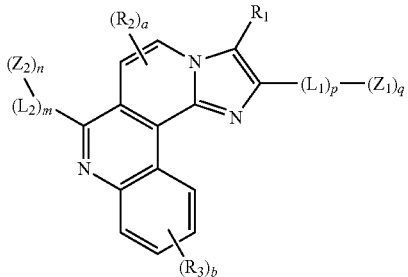

[Chemical Formula 3]

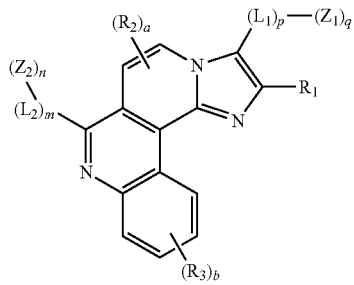

In Chemical Formulae 2 and 3, $L_1$, $L_2$, $Z_1$, $Z_2$, $R_1$ to $R_3$, a, b, m, n, p and q have the same definitions as in Chemical Formula 1.

In one embodiment of the present application, $L_1$ and $L_2$ are the same as or different from each other, and may be each independently a direct bond; a substituted or unsubstituted arylene group; or a substituted or unsubstituted heteroarylene group.

In another embodiment, $L_1$ and $L_2$ are the same as or different from each other, and may be each independently a direct bond; a substituted or unsubstituted C6 to C60 arylene group; or a substituted or unsubstituted C2 to C60 heteroarylene group.

In another embodiment, $L_1$ and $L_2$ are the same as or different from each other, and may be each independently a direct bond; a substituted or unsubstituted C6 to C40 arylene group; or a substituted or unsubstituted C2 to C40 heteroarylene group.

In another embodiment, $L_1$ and $L_2$ are the same as or different from each other, and may be each independently a direct bond; a C6 to C40 monocyclic or polycyclic arylene group; or a C2 to C40 heteroarylene group unsubstituted or substituted with a C6 to C40 aryl group.

In another embodiment, $L_1$ may be a direct bond; a phenylene group; a biphenylene group; a naphthylene group; a phenanthrene group; an anthracene group; a triphenylene group; a pyrene group; a divalent pyrimidine group unsubstituted or substituted with a phenyl group; a divalent triazine group unsubstituted or substituted with a phenyl group; a divalent pyridine group; a divalent quinoline group; a divalent quinazoline group; a divalent benzothiazole group; or a divalent imidazo[1,2-a]pyridine group.

In another embodiment, $L_2$ may be a direct bond; a phenylene group; a biphenylene group; an anthracene group; a divalent quinazoline group; or a divalent imidazo[1,2-a] pyridine group.

In one embodiment of the present application, $Z_1$ and $Z_2$ are the same as or different from each other, and may be each independently a substituted or unsubstituted alkyl group; a substituted or unsubstituted aryl group; a substituted or unsubstituted heteroaryl group; —SiRR'R"; —P(=O)RR'; or NRR'.

In another embodiment, $Z_1$ and $Z_2$ are the same as or different from each other, and may be each independently a substituted or unsubstituted C1 to C60 alkyl group; a substituted or unsubstituted C6 to C60 aryl group; a substituted or unsubstituted C2 to C60 heteroaryl group; or —P(=O)RR'.

In another embodiment, $Z_1$ and $Z_2$ are the same as or different from each other, and may be each independently a substituted or unsubstituted C1 to C40 alkyl group; a substituted or unsubstituted C6 to C40 aryl group; a substituted or unsubstituted C2 to C40 heteroaryl group; or —P(=O)RR'.

In another embodiment, $Z_1$ and $Z_2$ are the same as or different from each other, and may be each independently a C1 to C40 alkyl group; a C6 to C40 aryl group unsubstituted or substituted with one or more substituents selected from the group consisting of a C6 to C40 aryl group and a C2 to C40 heteroaryl group; a C2 to C40 heteroaryl group unsubstituted or substituted with one or more substituents selected from the group consisting of a C1 to C20 alkyl group, a C6 to C40 aryl group and a C2 to C40 heteroaryl group; or —P(=O)RR'.

In another embodiment, $Z_1$ may be an ethyl group; —P(=O)RR'; a phenyl group unsubstituted or substituted with one or more substituents selected from the group consisting of a pyridine group and a carbazole group; a naphthyl group; an anthracene group unsubstituted or substituted with a naphthyl group; a phenanthrene group; a biphenyl group unsubstituted or substituted with a phenyl group; a pyridine group unsubstituted or substituted with a pyridine group; a phenanthroline group unsubstituted or substituted with a phenyl group; a triazine group unsubstituted or substituted with one or more substituents selected from the group consisting of a phenyl group, a pyridine group and a naphthyl group; a carbazole group; a pyrimidine group unsubstituted or substituted with one or more substituents selected from the group consisting of a phenyl group, a pyridine group, a biphenyl group and a naphthyl group; a quinazoline group unsubstituted or substituted with one or more substituents selected from the group consisting of a phenyl group, a biphenyl group and a naphthyl group; an imidazole group unsubstituted or substituted with a phenyl group or an ethyl group; a benzothiazole group unsubstituted or substituted with a phenyl group; an imidazo[1,2-a]pyridine group unsubstituted or substituted with a phenyl group or an ethyl group; or a benzo[h]imidazo[2,1-a][2.6]naphthyridine group unsubstituted or substituted with a phenyl group.

In another embodiment, $Z_2$ may be an ethyl group; a phenyl group; a biphenyl group; a naphthyl group; a pyrimidine group unsubstituted or substituted with one or more substituents selected from the group consisting of a phenyl group, a biphenyl group and a naphthyl group; a triazine group unsubstituted or substituted with one or more substituents selected from the group consisting of a phenyl group and a naphthyl group; a quinazoline group unsubstituted or substituted with a biphenyl group; an imidazole group unsubstituted or substituted with an ethyl group; an imidazo[1,2-a]pyridine group unsubstituted or substituted with a phenyl group; or —P(=O)RR'.

In one embodiment of the present application, R, R' and R" are the same as or different from each other, and may be each independently hydrogen; a substituted or unsubstituted alkyl group; a substituted or unsubstituted aryl group; or a substituted or unsubstituted heteroaryl group.

In another embodiment, R, R' and R" are the same as or different from each other, and may be each independently a substituted or unsubstituted C1 to C60 alkyl group; or a substituted or unsubstituted C6 to C60 aryl group.

In another embodiment, R, R' and R" are the same as or different from each other, and may be each independently a substituted or unsubstituted C1 to C40 alkyl group; or a substituted or unsubstituted C6 to C40 aryl group.

In another embodiment, R, R' and R" are the same as or different from each other, and may be each independently a C1 to C40 alkyl group; or a C6 to C40 aryl group.

In another embodiment, R, R' and R" are the same as or different from each other, and may be each independently a methyl group; or a phenyl group.

In one embodiment of the present application, $R_1$ to $R_3$ are the same as or different from each other, and each independently selected from the group consisting of hydrogen; deuterium; a substituted or unsubstituted alkyl group; a substituted or unsubstituted aryl group; a substituted or unsubstituted heteroaryl group; —SiRR'R"; —P(=O)RR'; and an amine group unsubstituted or substituted with a substituted or unsubstituted alkyl group, a substituted or unsubstituted aryl group or a substituted or unsubstituted heteroaryl group, or two or more groups adjacent to each other may bond to each other to form a substituted or unsubstituted aromatic hydrocarbon ring or a substituted or unsubstituted heteroring.

In one embodiment of the present application, $R_1$ may be hydrogen; a substituted or unsubstituted alkyl group; a substituted or unsubstituted aryl group; or a substituted or unsubstituted heteroaryl group.

In another embodiment, $R_1$ may be hydrogen; or a substituted or unsubstituted aryl group.

In another embodiment, $R_1$ may be hydrogen; or a substituted or unsubstituted C6 to C60 aryl group.

In another embodiment, $R_1$ may be hydrogen; or a substituted or unsubstituted C6 to C40 aryl group.

In another embodiment, $R_1$ may be hydrogen; a phenyl group; or a naphthyl group.

In one embodiment of the present application, $R_2$ may be hydrogen.

In one embodiment of the present application, $R_3$ may be hydrogen; a substituted or unsubstituted alkyl group; a substituted or unsubstituted aryl group; a substituted or unsubstituted heteroaryl group; or —P(=O)RR'.

In another embodiment, $R_3$ may be hydrogen; a substituted or unsubstituted C1 to C60 alkyl group; a substituted or unsubstituted C6 to C60 aryl group; a substituted or unsubstituted C2 to C60 heteroaryl group; or —P(=O)RR'.

In another embodiment, $R_3$ may be hydrogen; a substituted or unsubstituted C1 to C40 alkyl group; a substituted or unsubstituted C6 to C40 aryl group; a substituted or unsubstituted C2 to C40 heteroaryl group; or —P(=O)RR'.

In one embodiment of the present application, $R_3$ is represented by $-(L_3)_c-(Z_3)_d$, $L_3$ is a direct bond; a substituted or unsubstituted arylene group; or a substituted or unsubstituted heteroarylene group, $Z_3$ is hydrogen; a substituted or unsubstituted alkyl group; a substituted or unsubstituted aryl group; a substituted or unsubstituted heteroaryl group; or —P(=O)RR', c is an integer of 0 to 3, d is an integer of 1 to 5, and R and R' have the same definitions as in Chemical Formula 1.

In one embodiment of the present application, $L_3$ may be a direct bond; a substituted or unsubstituted arylene group; or a substituted or unsubstituted heteroarylene group.

In another embodiment, $L_3$ may be a direct bond; a substituted or unsubstituted C6 to C60 arylene group; or a substituted or unsubstituted C2 to C60 heteroarylene group.

In another embodiment, $L_3$ may be a direct bond; a substituted or unsubstituted C6 to C40 arylene group; or a substituted or unsubstituted C2 to C40 heteroarylene group.

In another embodiment, $L_3$ may be a direct bond; a C6 to C40 arylene group; or a C2 to C40 heteroarylene group unsubstituted or substituted with a C6 to C40 aryl group.

In another embodiment, $L_3$ may be a direct bond; a phenylene group; a biphenylene group; an anthracene group; a divalent triazine group unsubstituted or substituted with a phenyl group; or a pyrimidine group unsubstituted or substituted with a phenyl group.

In one embodiment of the present application, $Z_3$ may be hydrogen; a substituted or unsubstituted alkyl group; a substituted or unsubstituted aryl group; a substituted or unsubstituted heteroaryl group; or —P(=O)RR'.

In another embodiment, $Z_3$ may be hydrogen; a substituted or unsubstituted C1 to C60 alkyl group; a substituted or unsubstituted C6 to C60 aryl group; a substituted or unsubstituted C2 to C60 heteroaryl group; or —P(=O)RR'.

In another embodiment, $Z_3$ may be hydrogen; a substituted or unsubstituted C1 to C40 alkyl group; a substituted or unsubstituted C6 to C40 aryl group; a substituted or unsubstituted C2 to C40 heteroaryl group; or —P(=O)RR'.

In another embodiment, $Z_3$ may be hydrogen; a C6 to C40 aryl group unsubstituted or substituted with a C2 to C40 heteroaryl group; a C2 to C40 heteroaryl group unsubstituted or substituted with a C6 to C40 aryl group; or —P(=O)RR'.

In another embodiment, $Z_3$ may be hydrogen; a phenyl group unsubstituted or substituted with a carbazole group; a biphenyl group; a carbazole group; a pyrimidine group unsubstituted or substituted with a phenyl group; a triazine group unsubstituted or substituted with a phenyl group; a phenanthroline group unsubstituted or substituted with a phenyl group; or P(=O)RR'.

In one embodiment of the present application, Chemical Formula 1 may be represented by any one of the following Chemical Formulae 4 to 9.

[Chemical Formula 4]

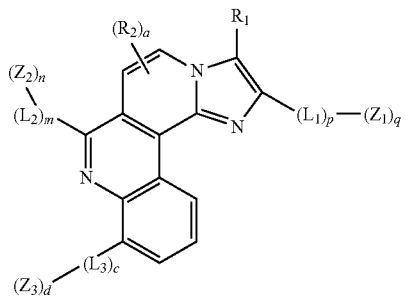

[Chemical Formula 5]

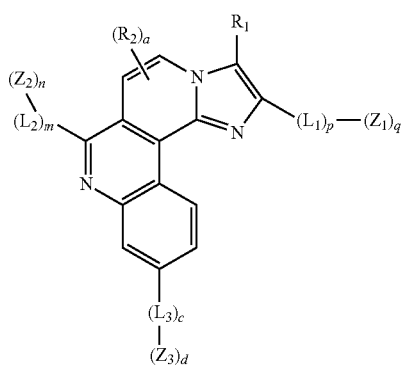

[Chemical Formula 6]

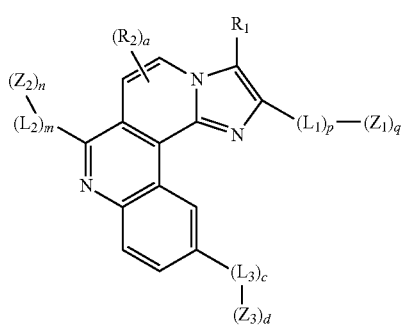

[Chemical Formula 7]

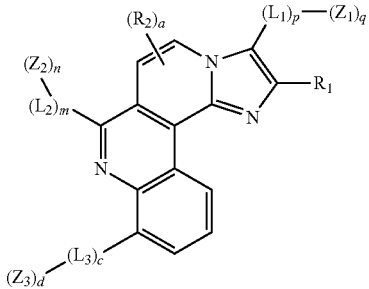

[Chemical Formula 8]

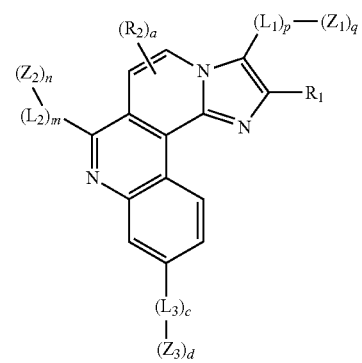

[Chemical Formula 9]

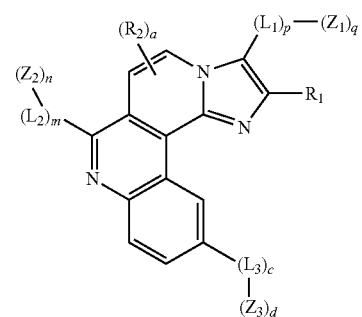

In Chemical Formulae 4 to 9, $L_1$, $L_2$, $Z_1$, $Z_2$, $R_1$, $R_2$, a, m, n, p and q have the same definitions as in Chemical Formula 1, $L_3$ is a direct bond; a substituted or unsubstituted arylene group; or a substituted or unsubstituted heteroarylene group, $Z_3$ is hydrogen; a substituted or unsubstituted alkyl group; a substituted or unsubstituted aryl group; a substituted or unsubstituted heteroaryl group; or —P(=O)RR', c is an integer of 0 to 3, d is an integer of 1 to 5, and R and R' have the same definitions as in Chemical Formula 1.

In the heterocyclic compound provided in one embodiment of the present application, Chemical Formula 1 is represented by any one of the following compounds.

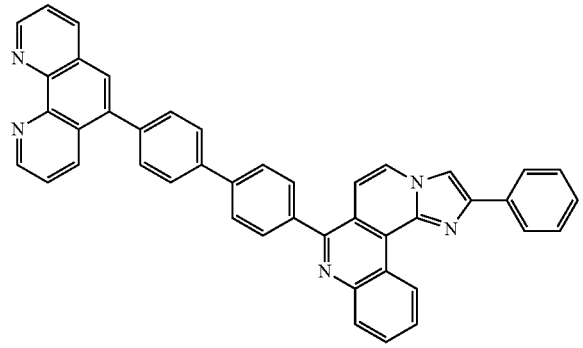
16
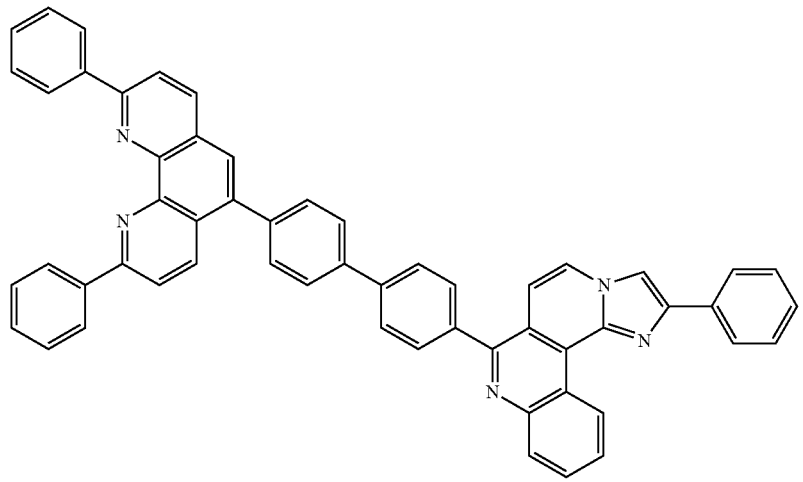
17
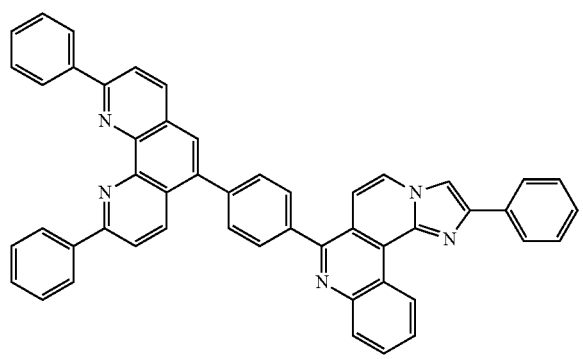
18
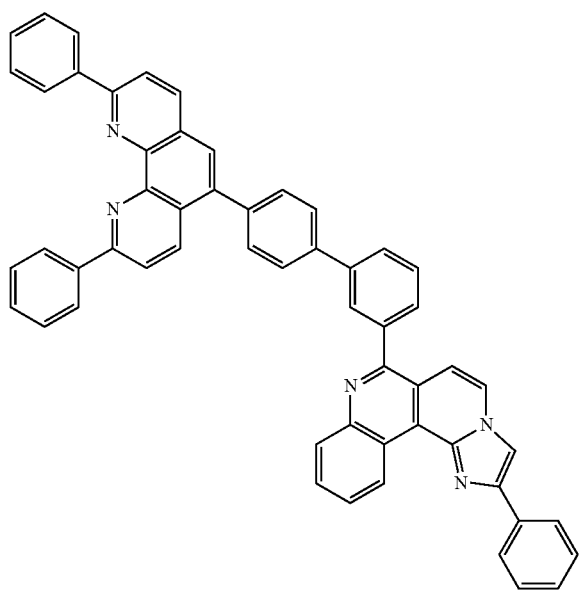
19

-continued
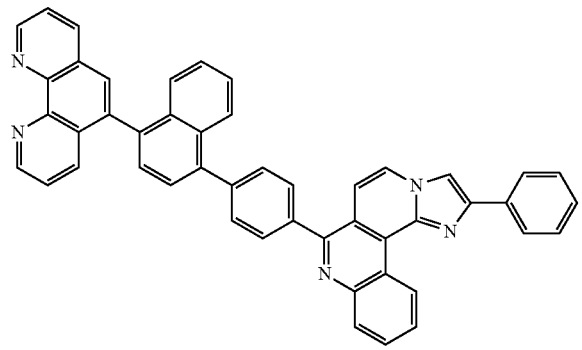
20
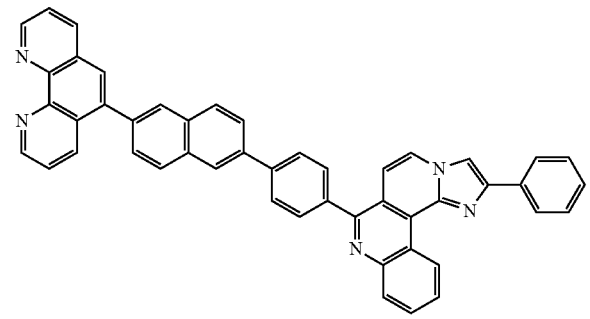
21
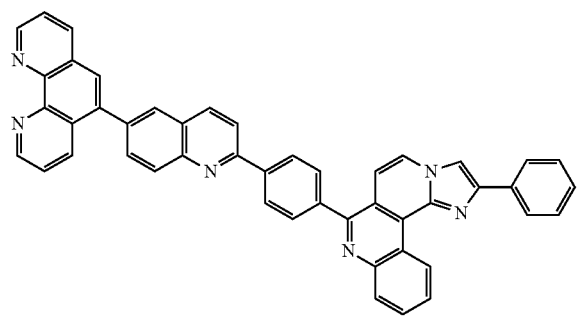
22
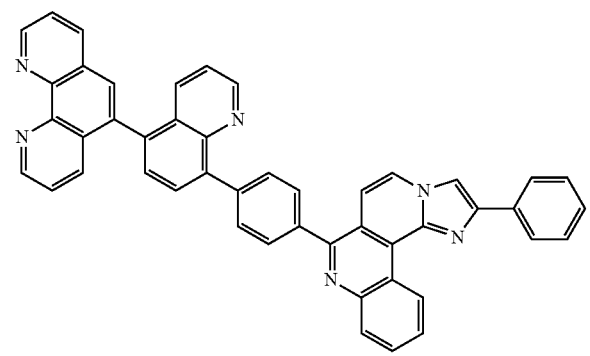
23
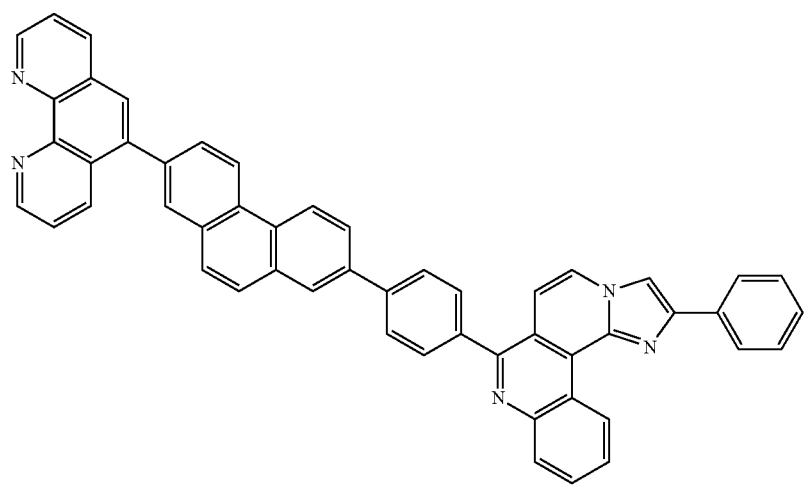
24

-continued
25
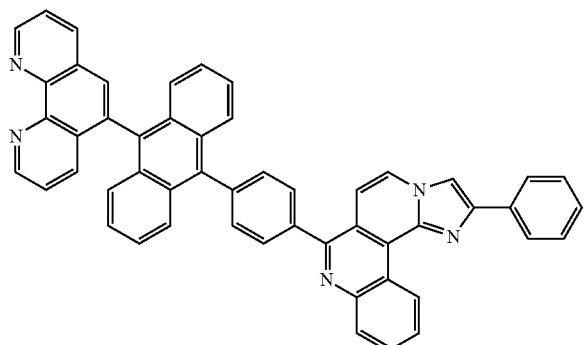
26
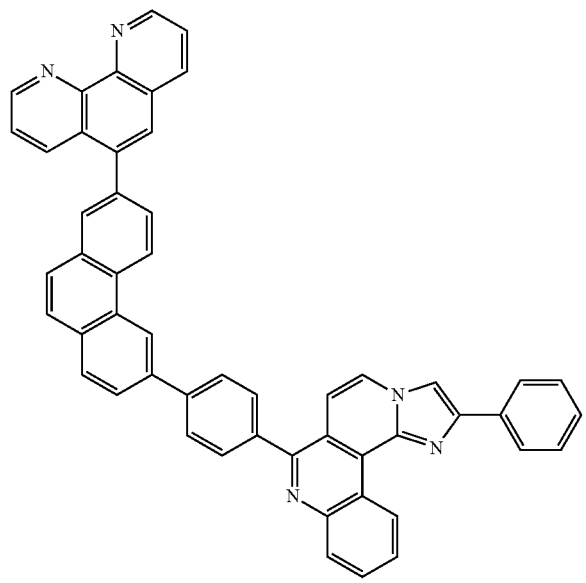
27
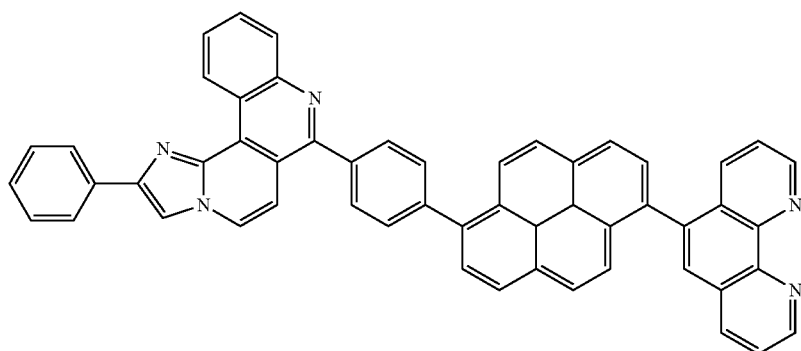
28
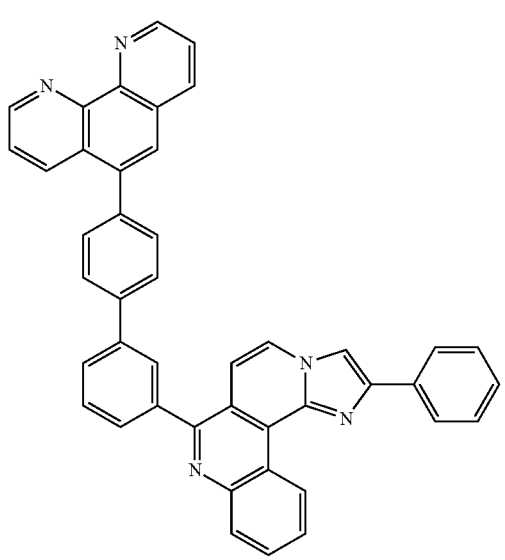
29
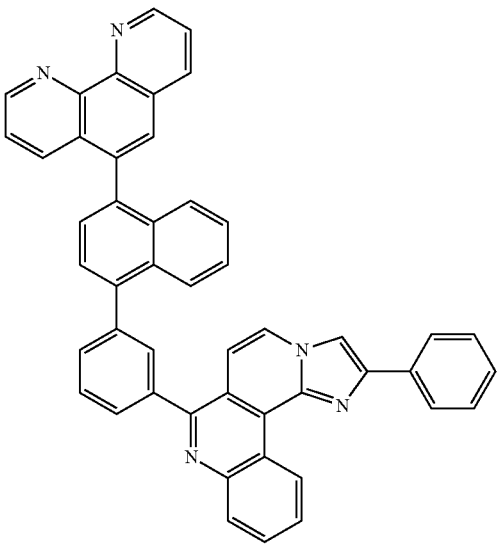

30
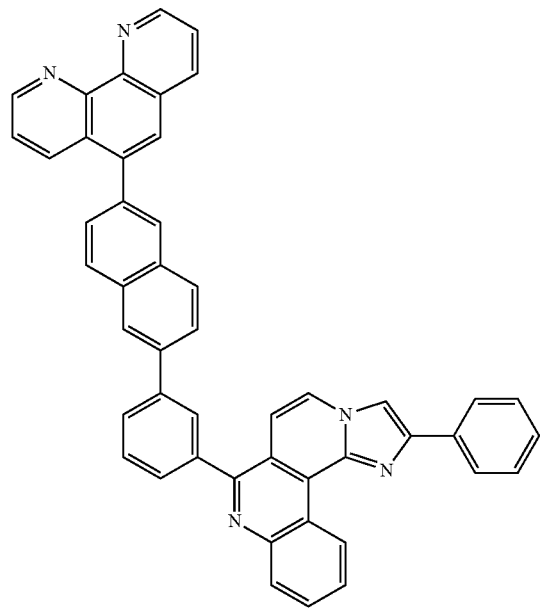
31
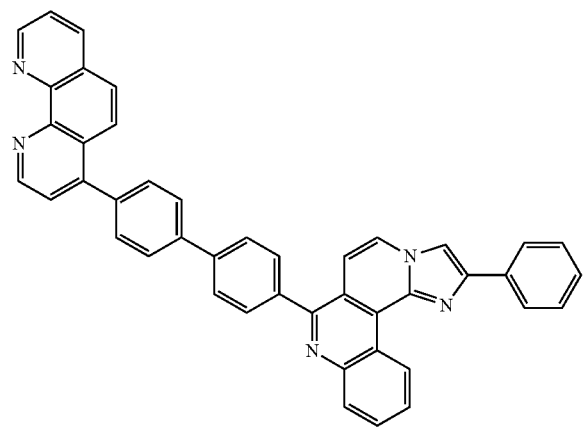
32
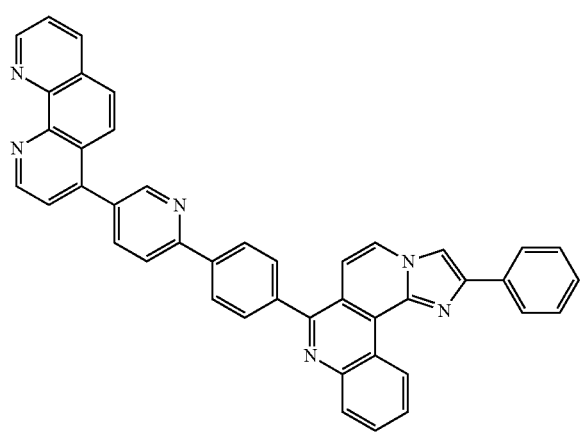
33
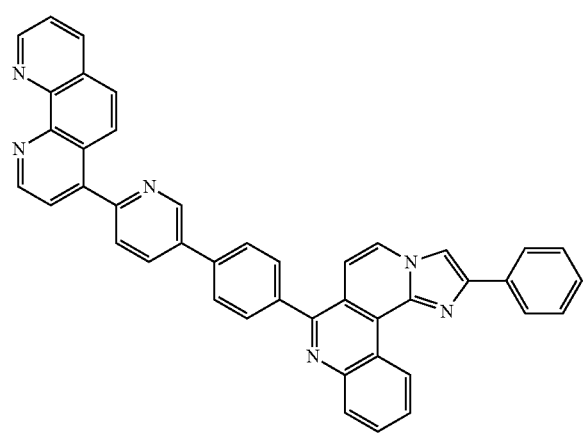
34

35
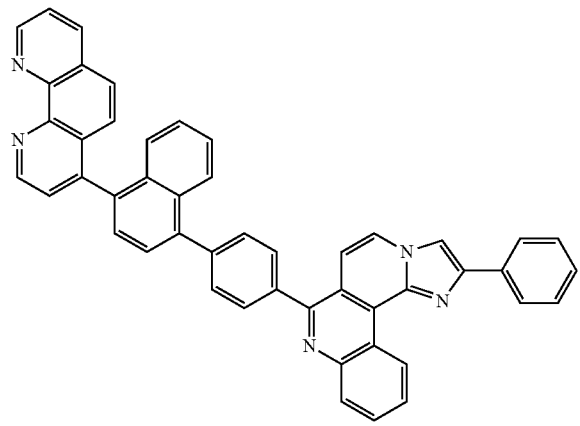
36
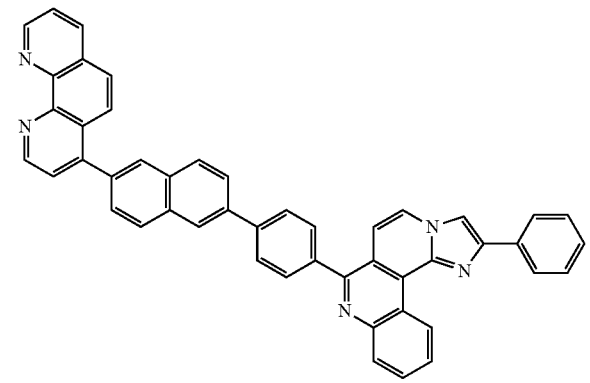
37
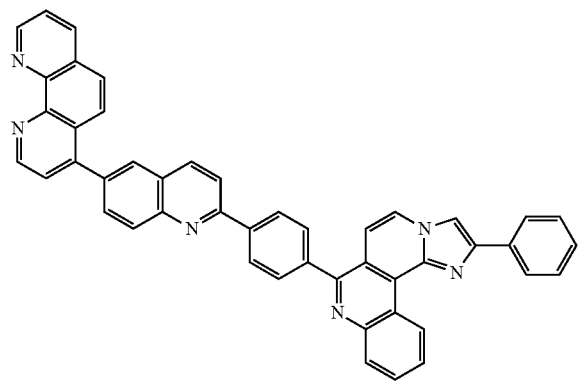
38
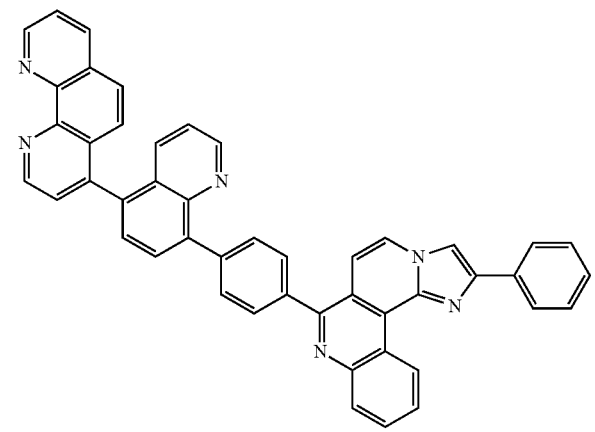
39
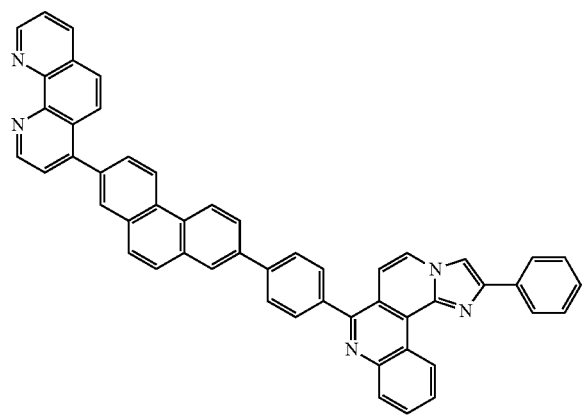
40
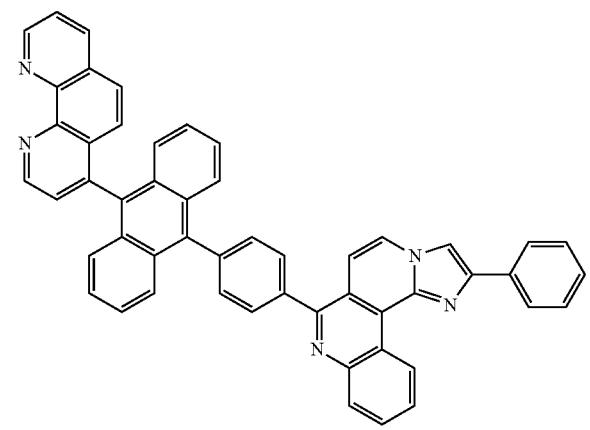

41
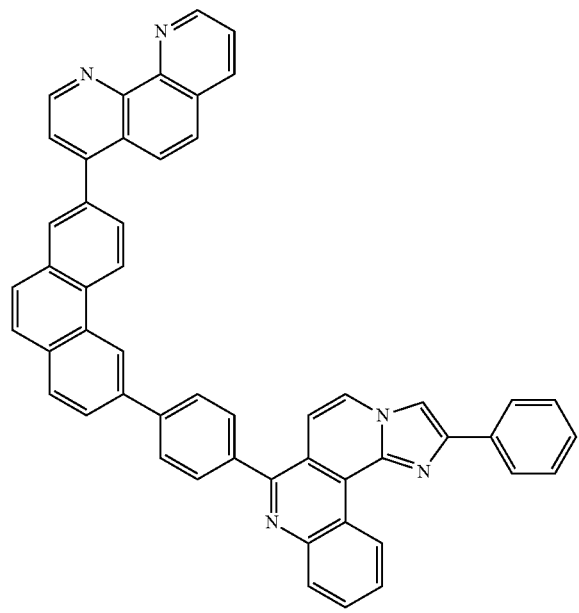
42
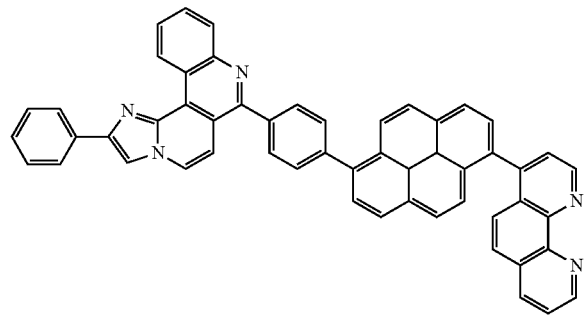
43
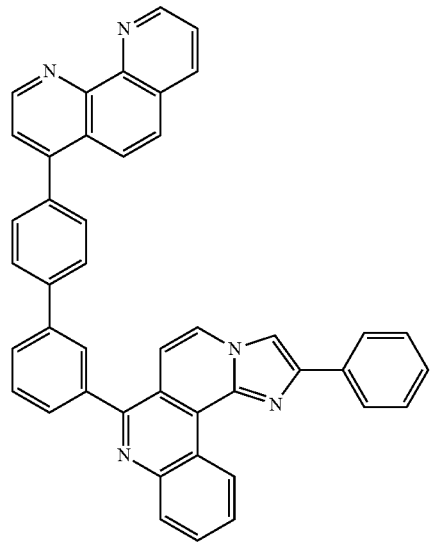
44
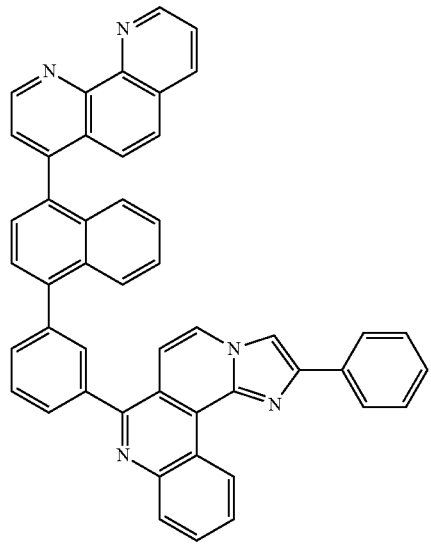

45
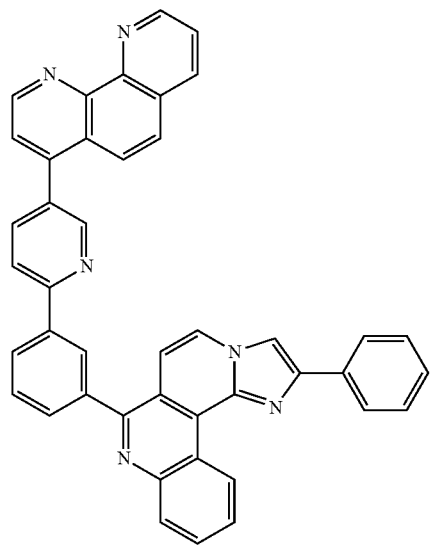
46 47
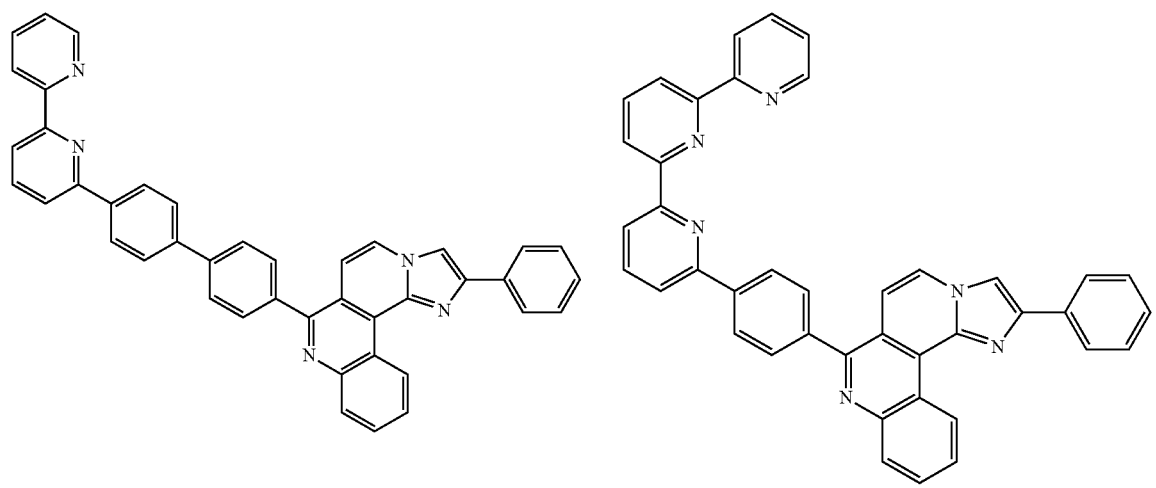
48
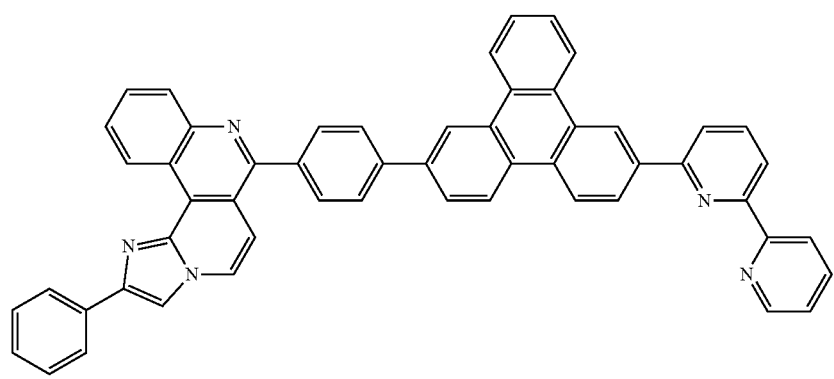

49
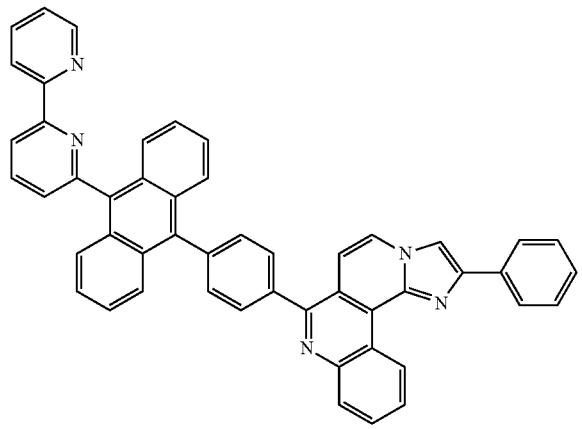
50
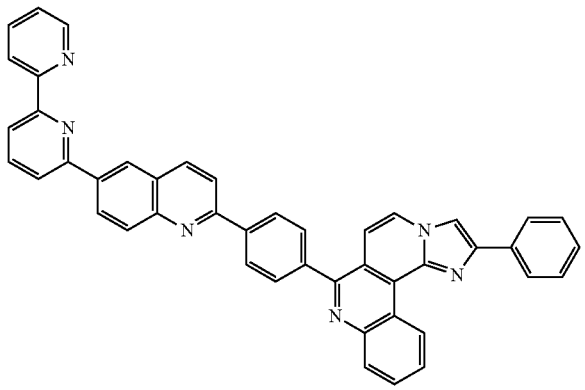
51
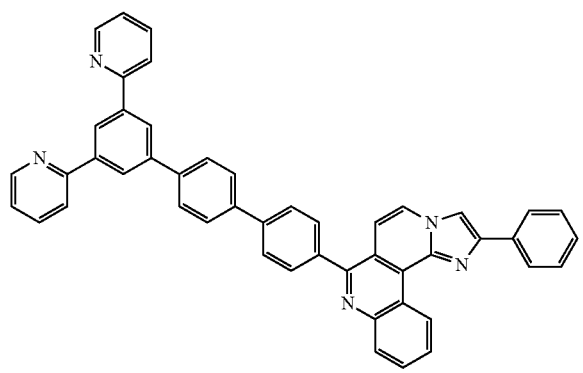
52
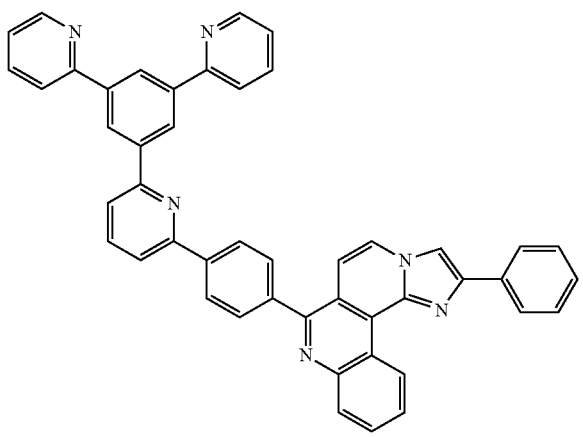
53
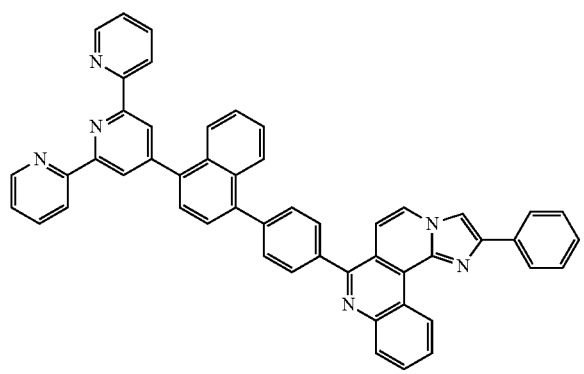
54
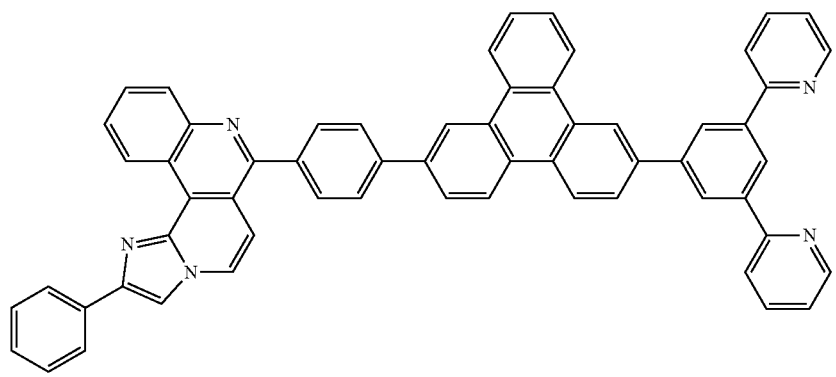

-continued
55
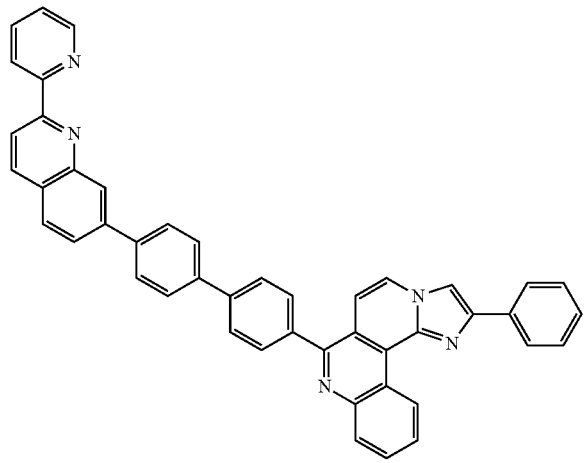
56
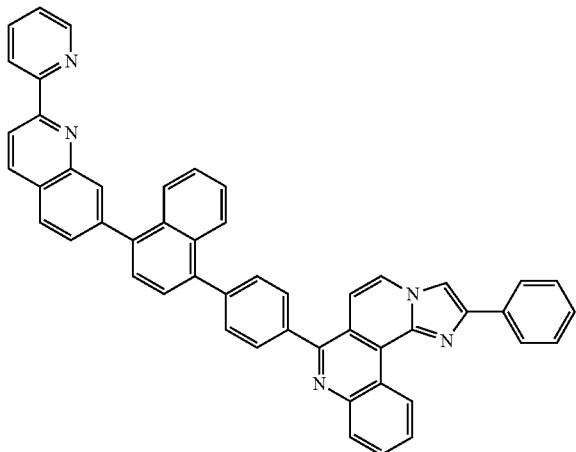
57
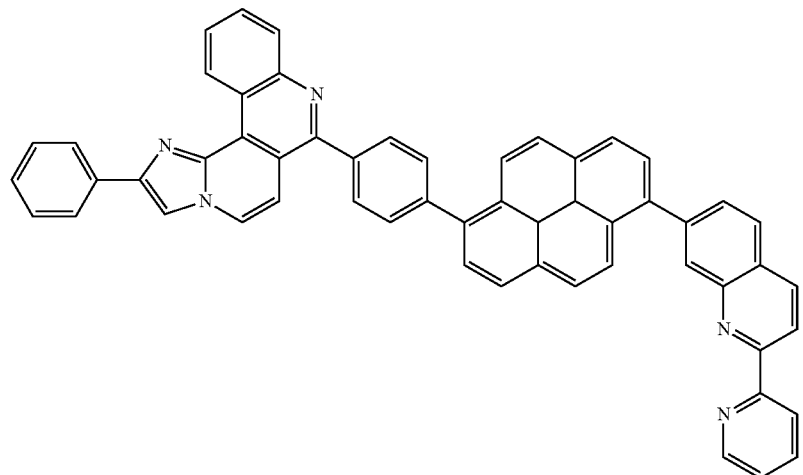
58
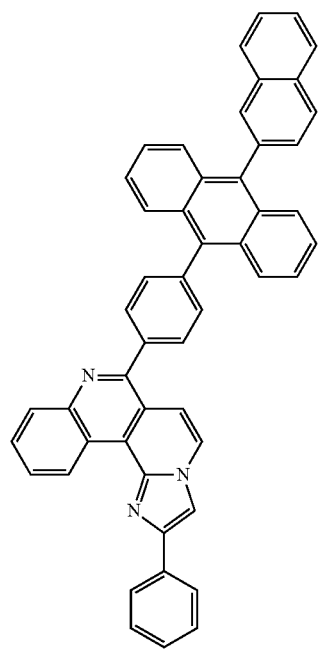
59
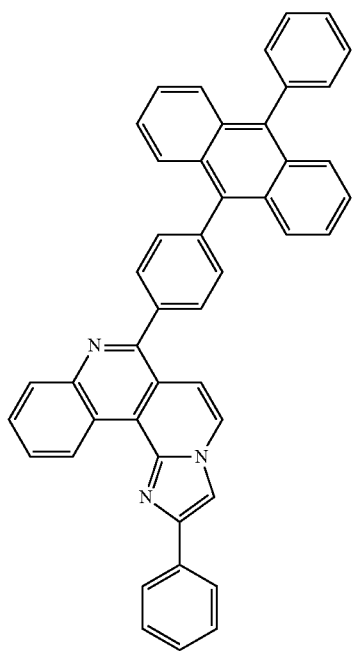

-continued
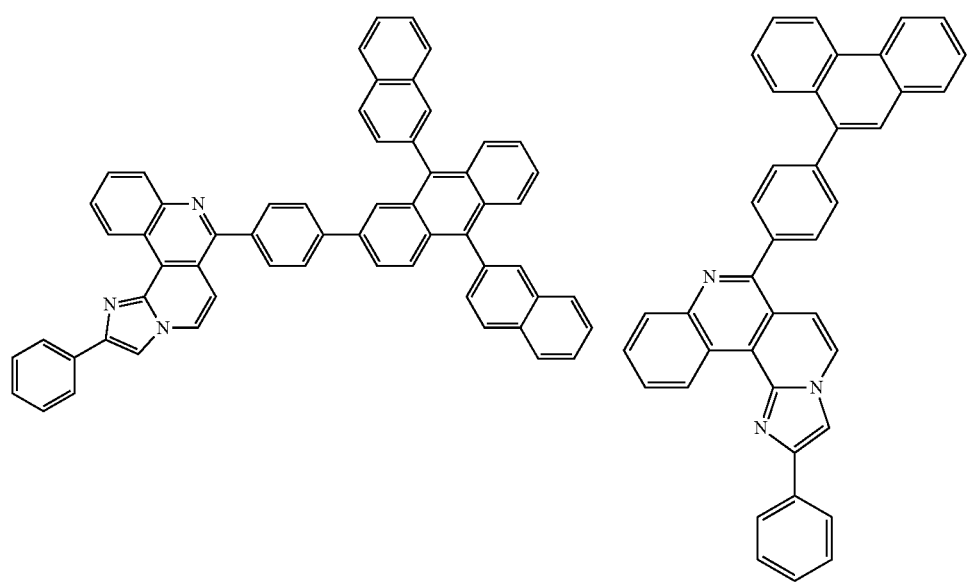
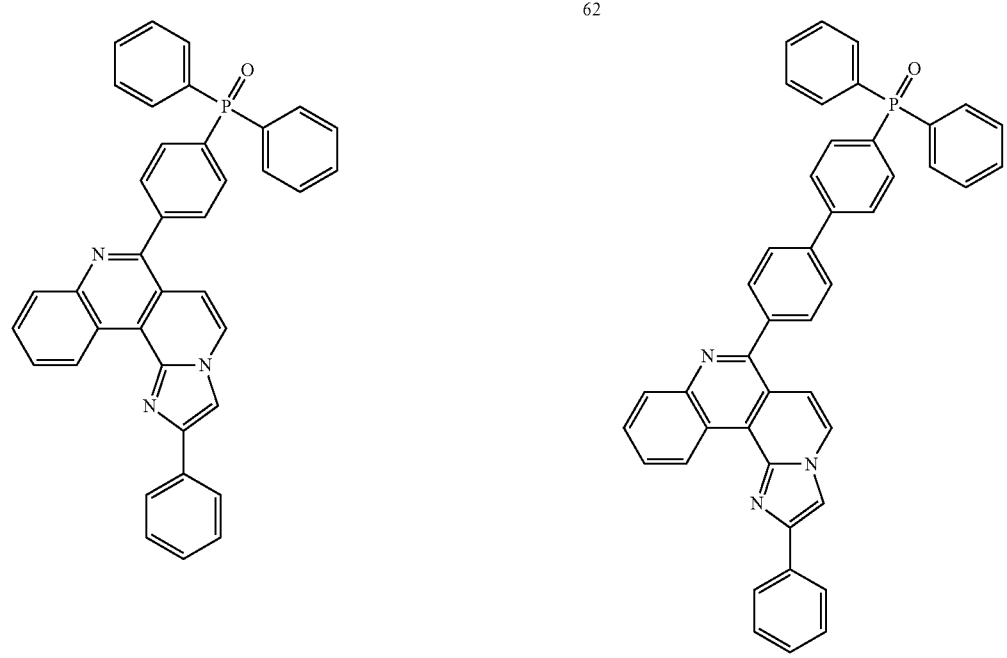

-continued
64
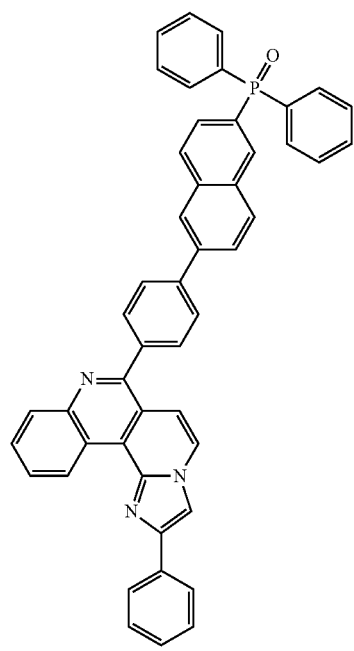
65
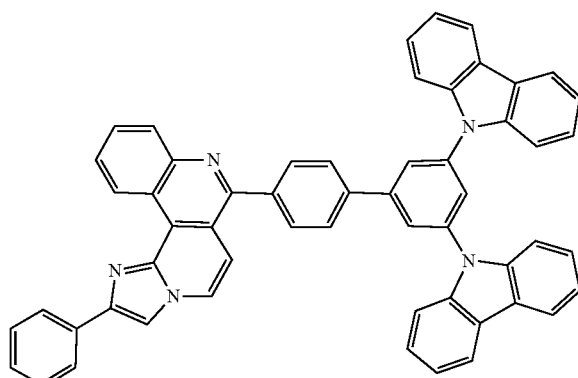
66
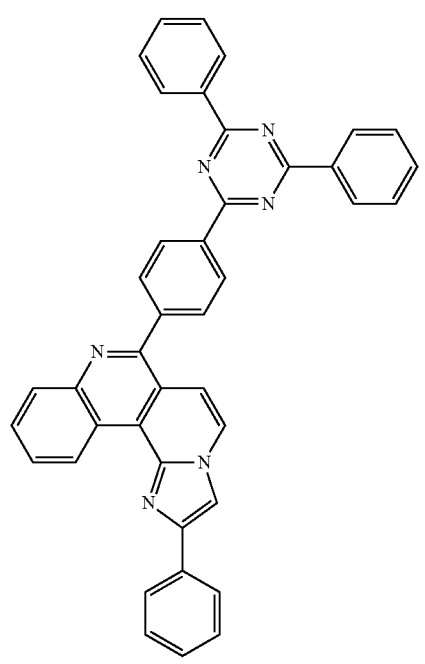
67
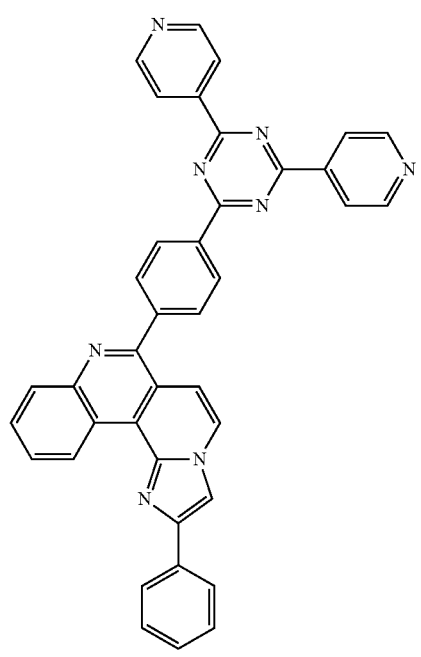

-continued
68 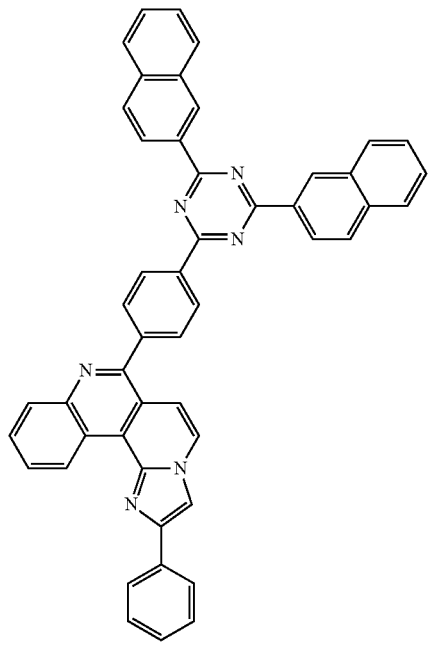
69 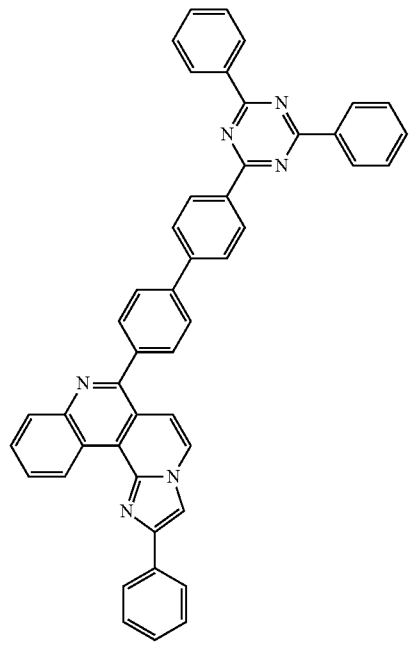
70 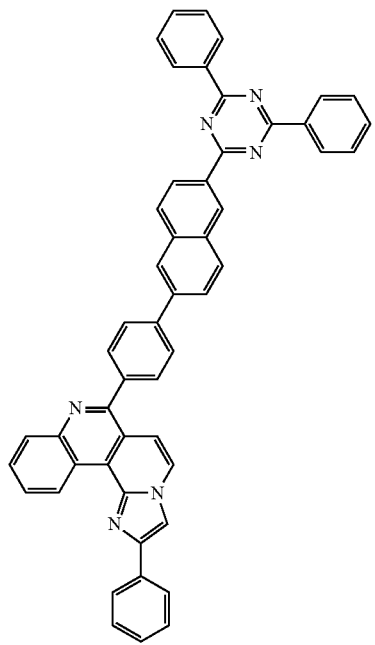
71 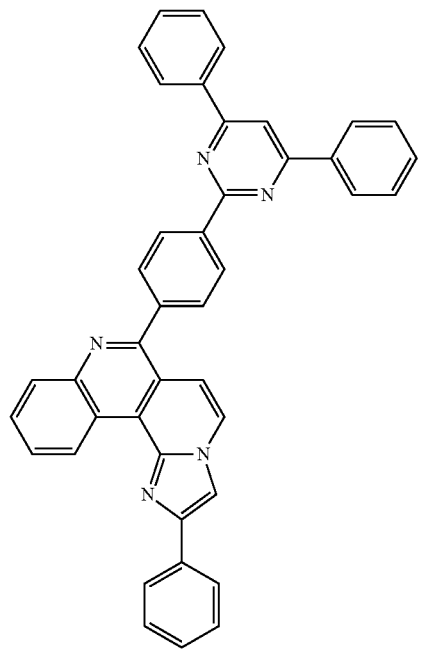

-continued
72 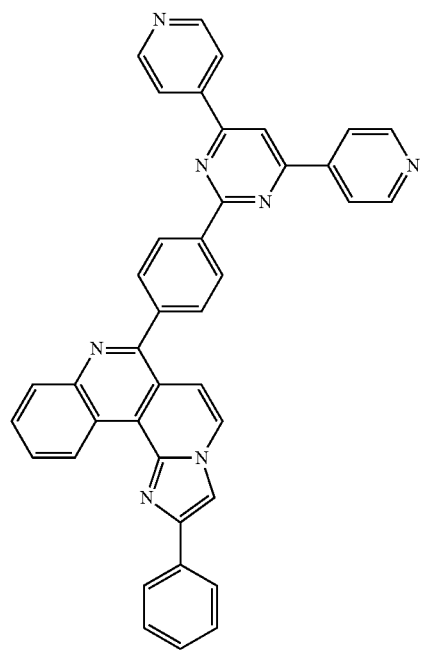
73 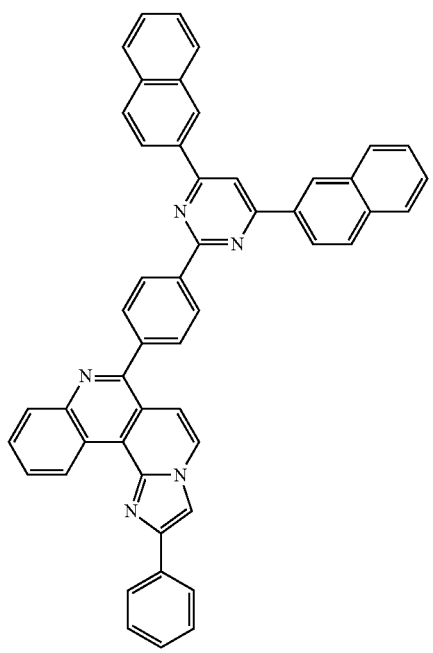
74 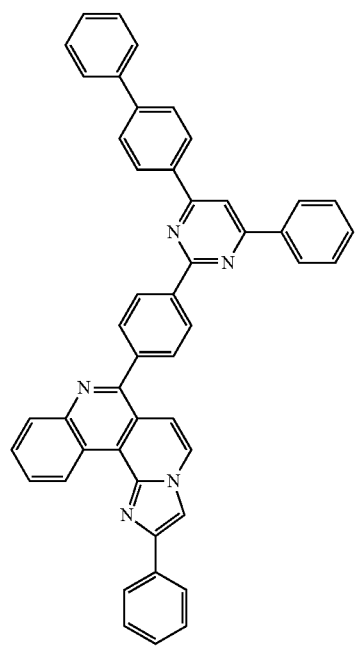
75 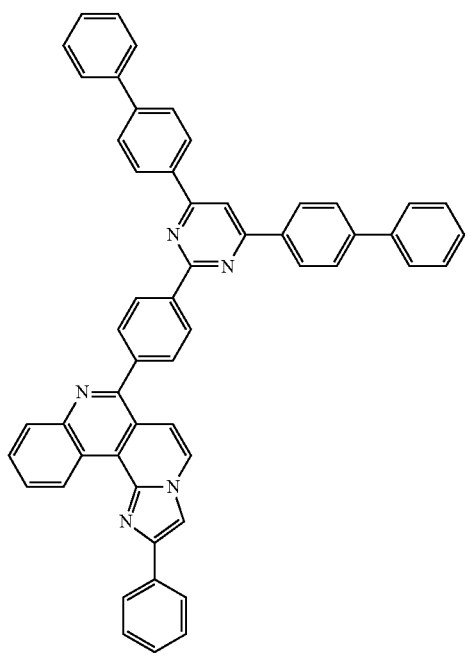

-continued
76
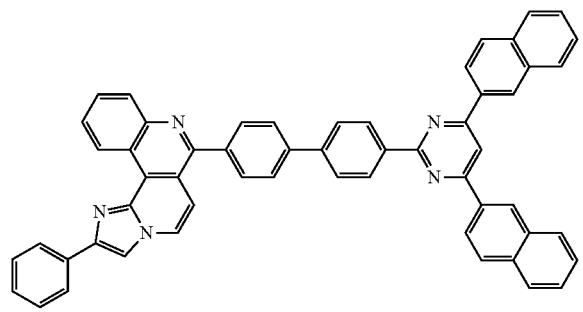
77
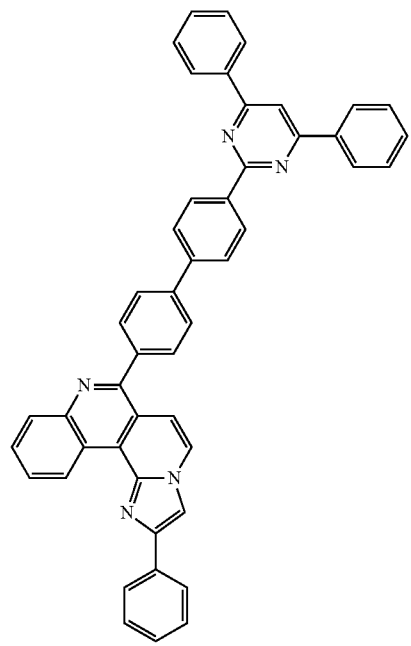
78
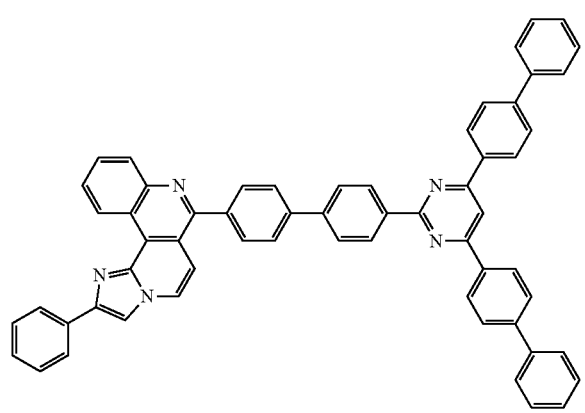
79
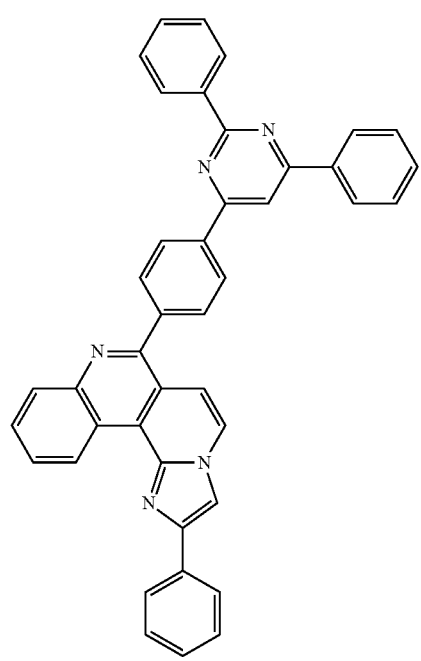

-continued
80
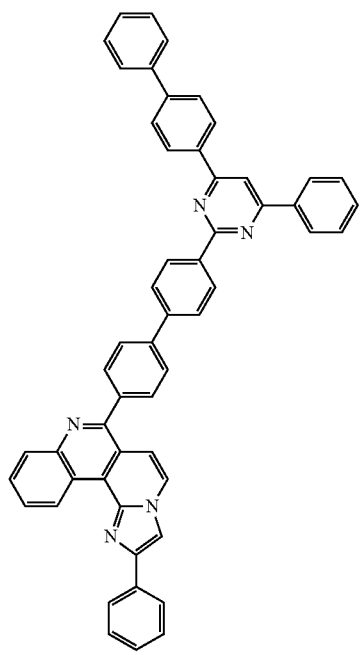
81
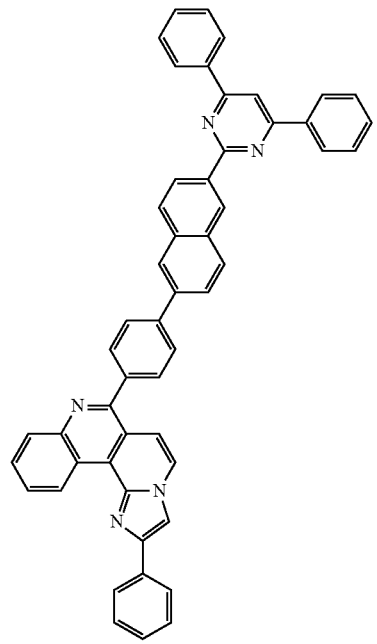
82
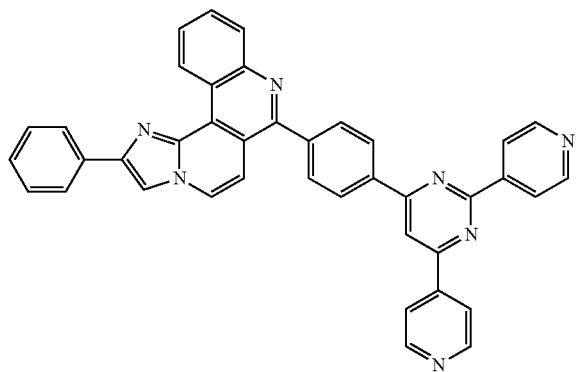
83
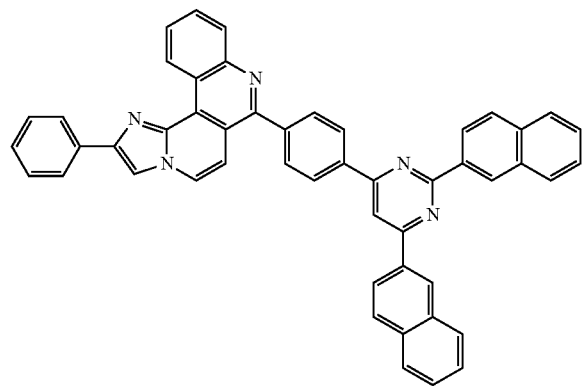
84
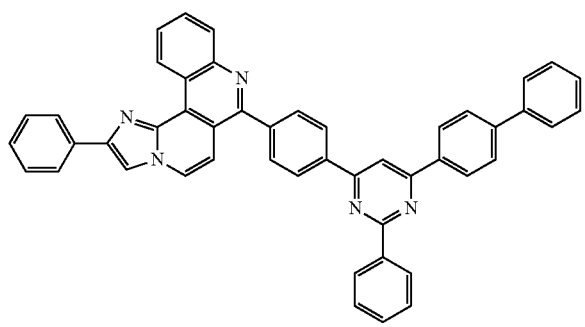
85
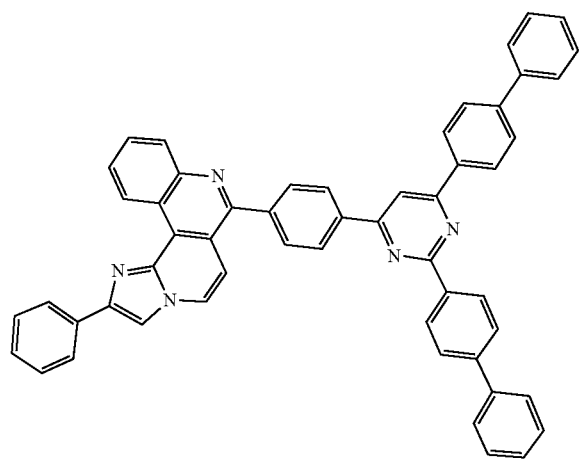

-continued
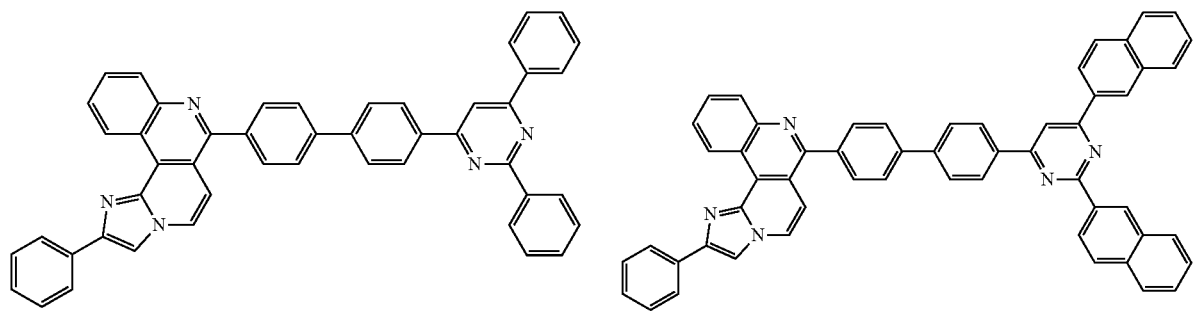
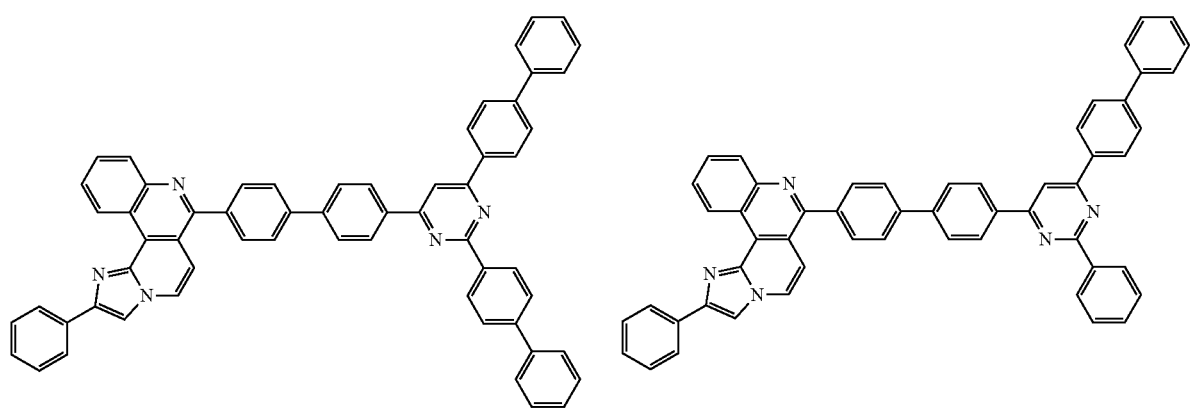
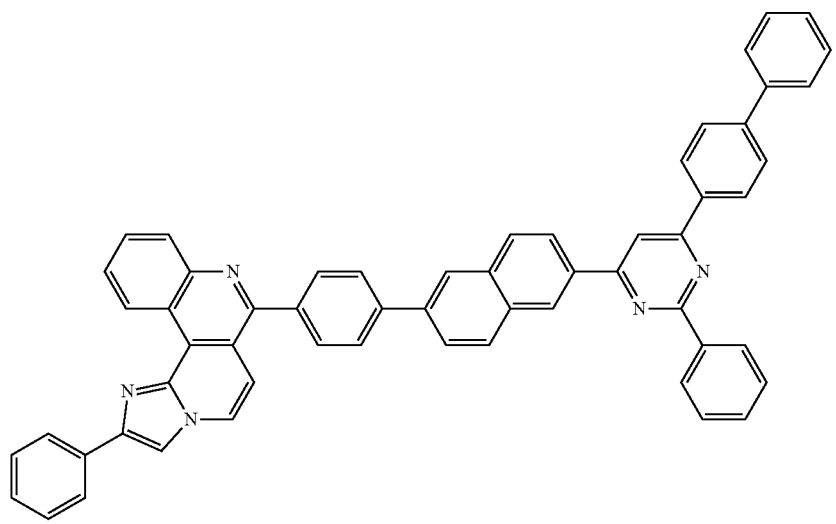
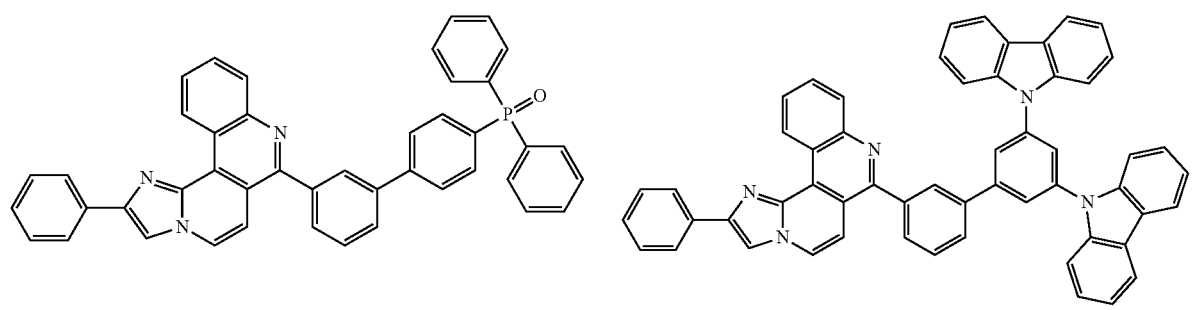

-continued
93
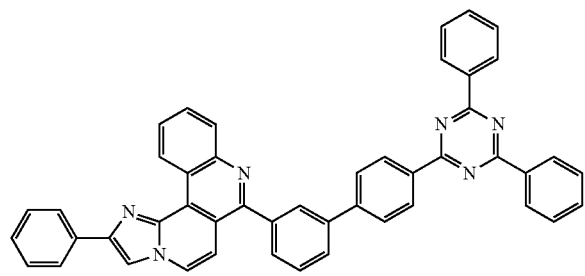
94
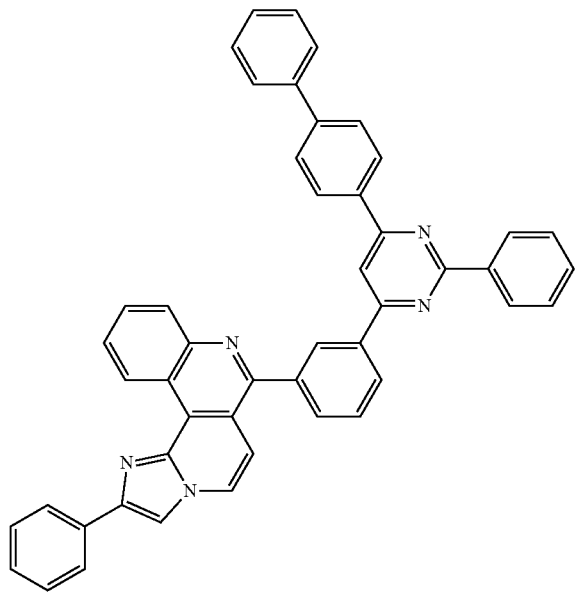
95
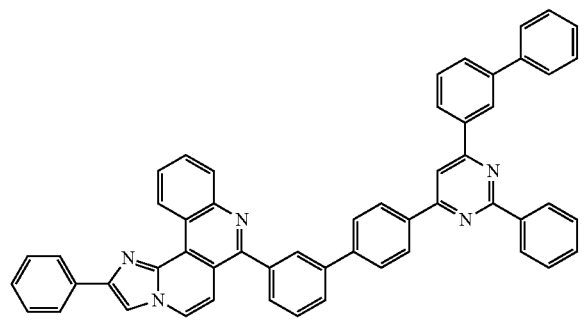
96
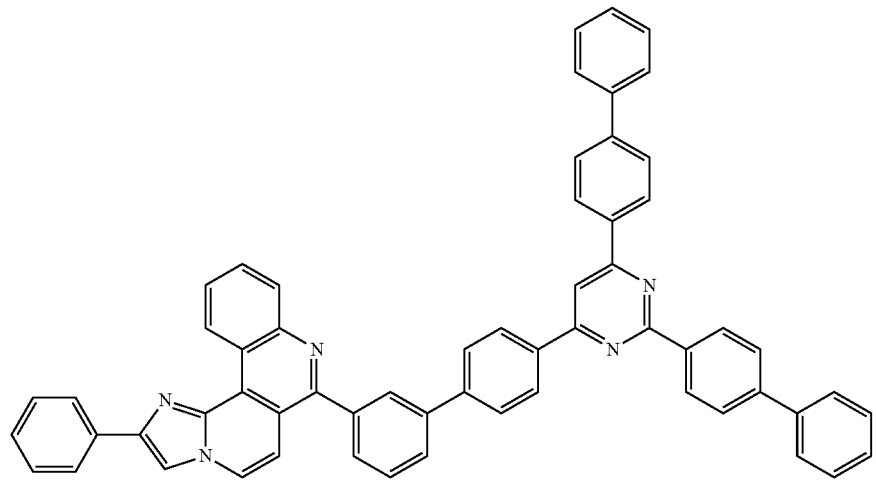

97
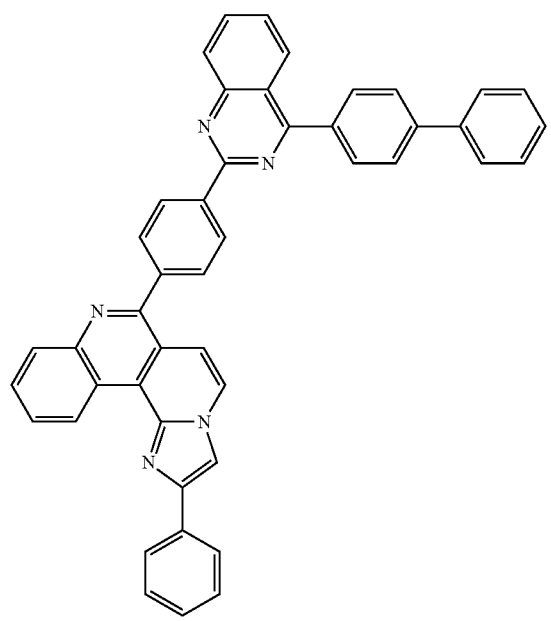
98
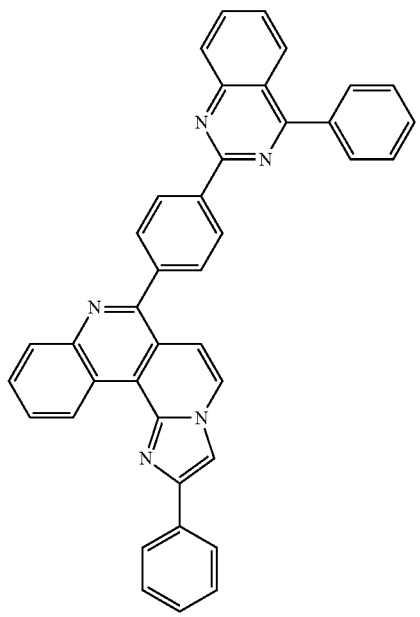
99
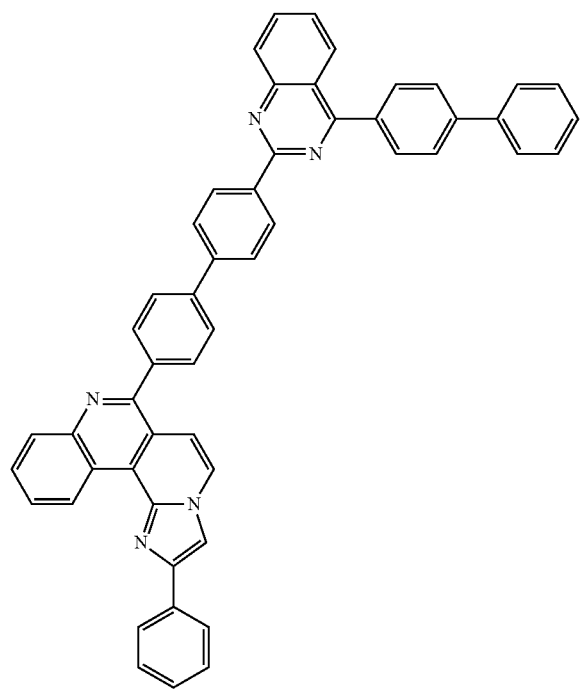
100
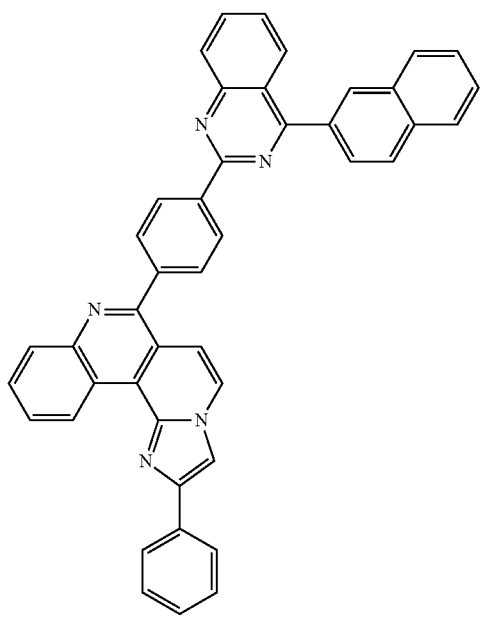

-continued
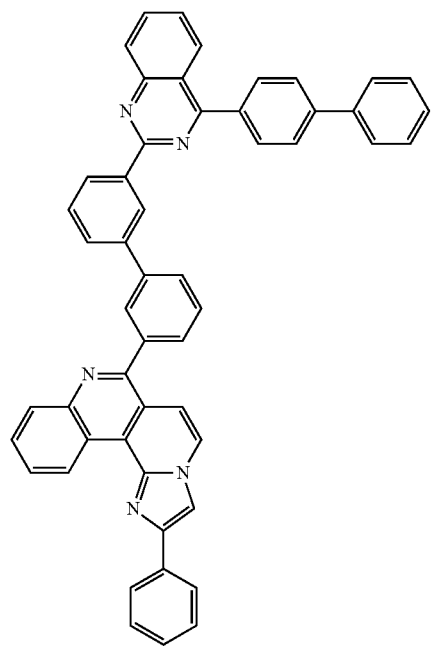
101
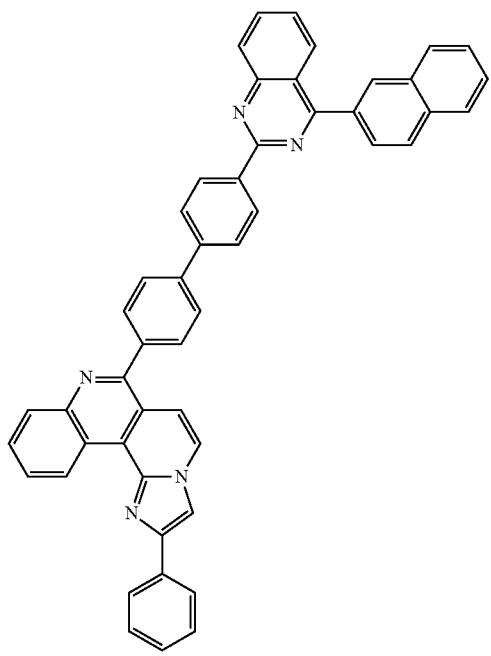
102
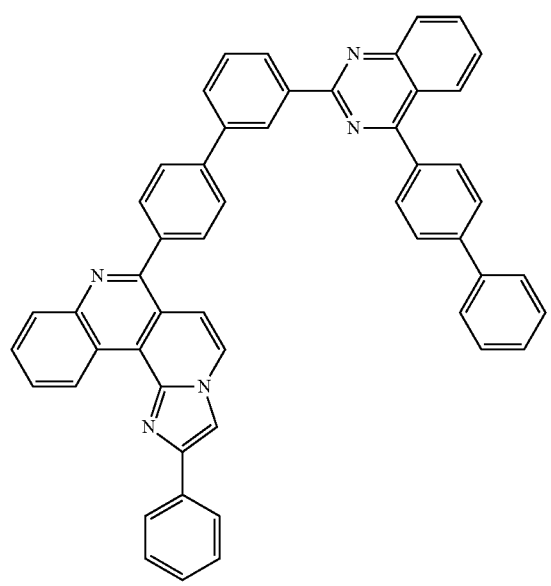
103
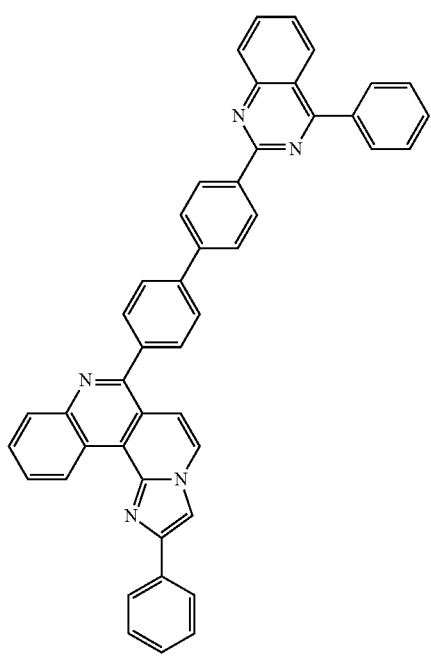
104

105
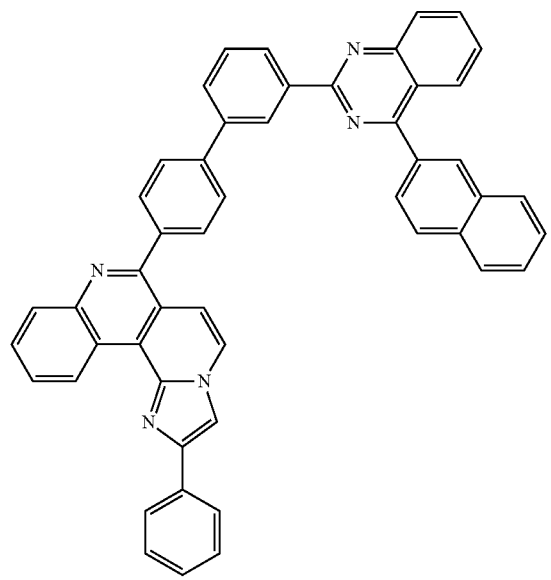
106
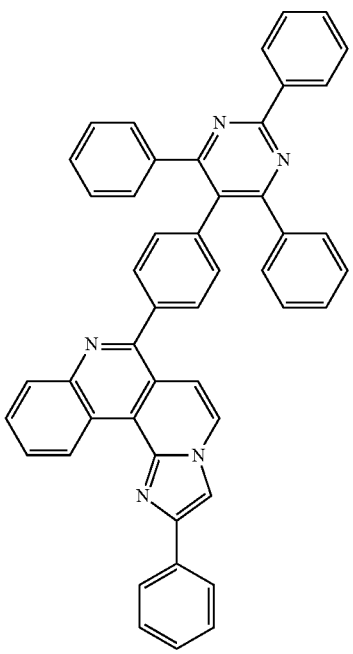
107
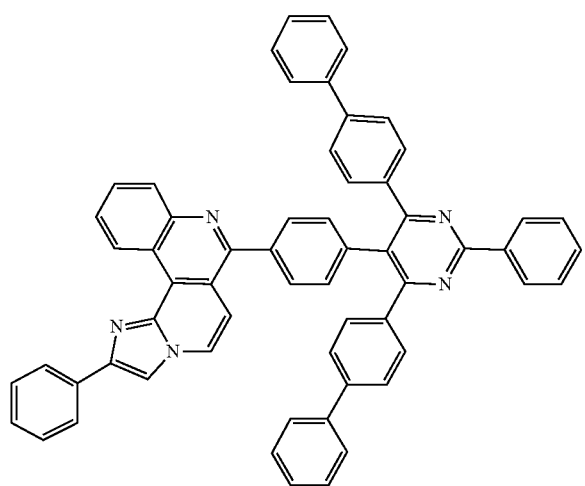
108
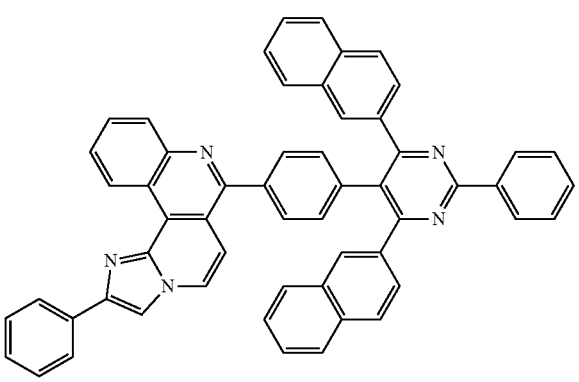

-continued
109
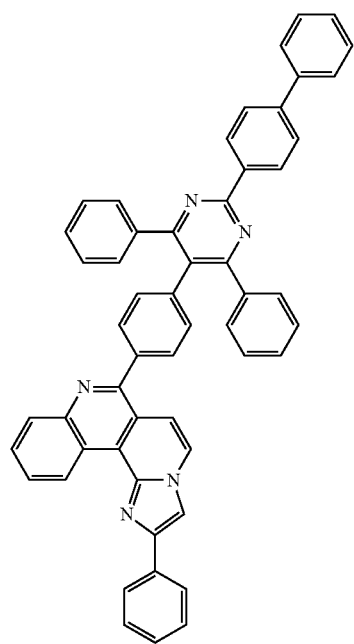
110
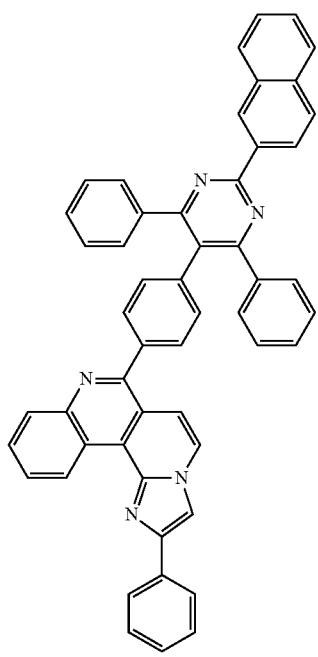
111
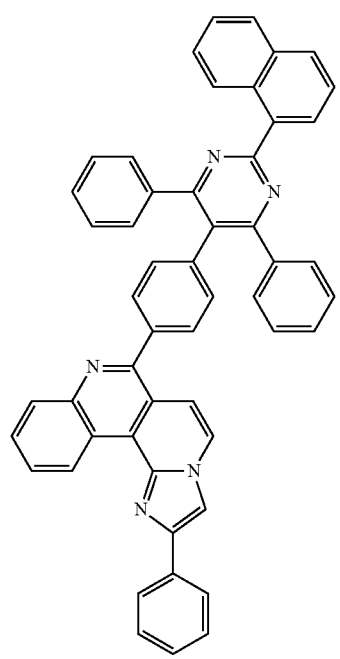
112
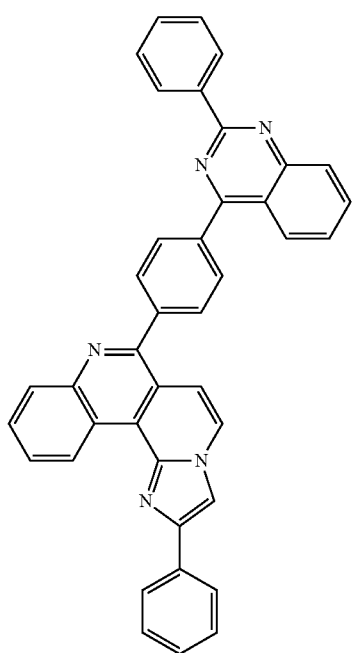

-continued
113
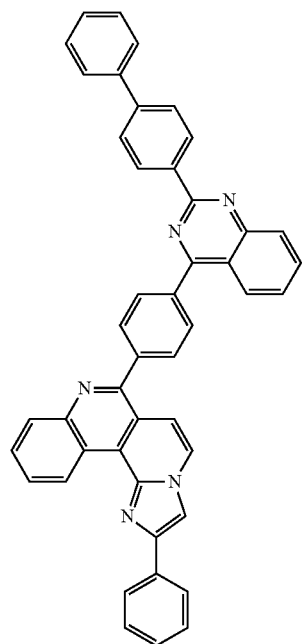
114
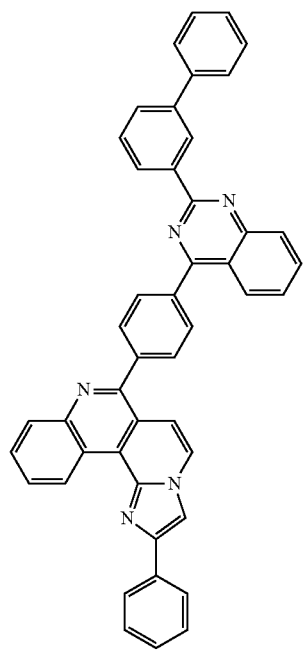
115
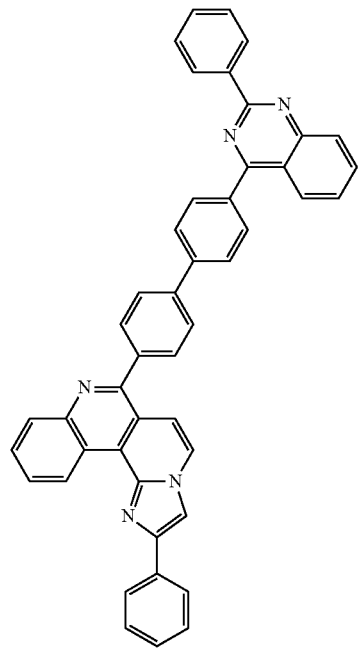
116
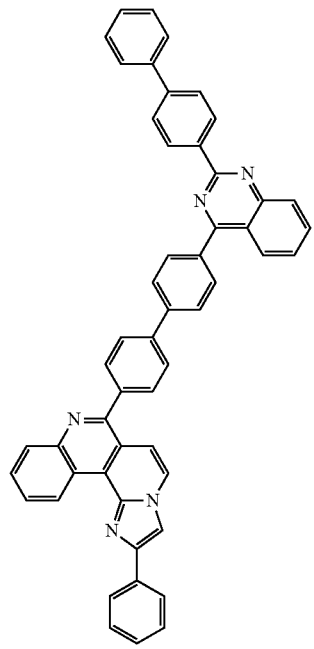

-continued
117
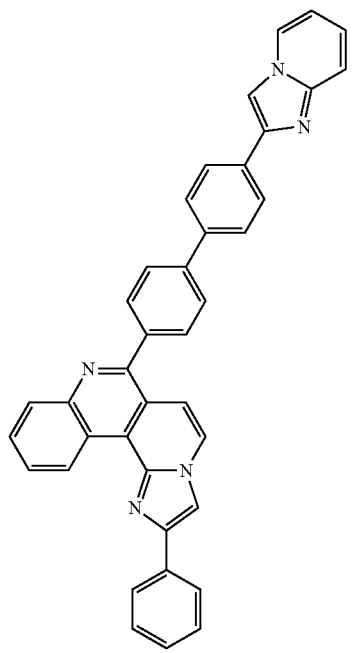
118
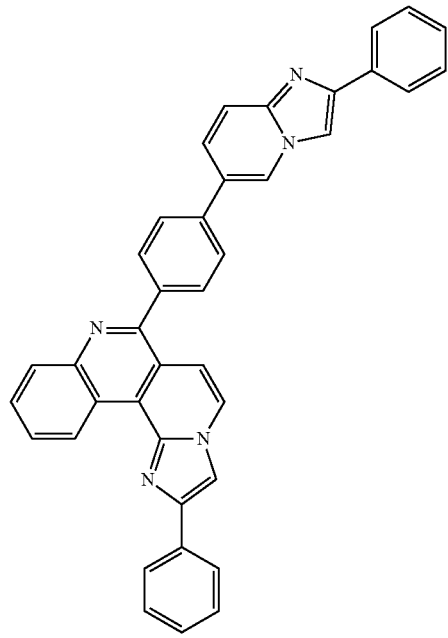
119
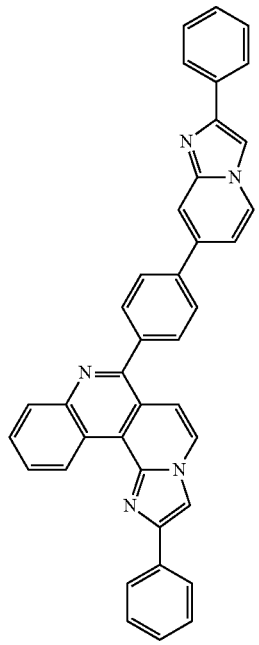
120
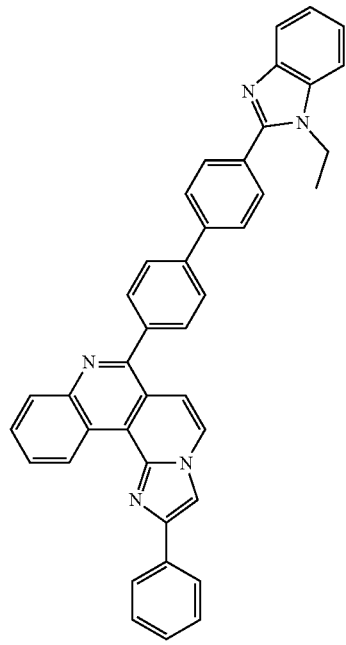

-continued
121 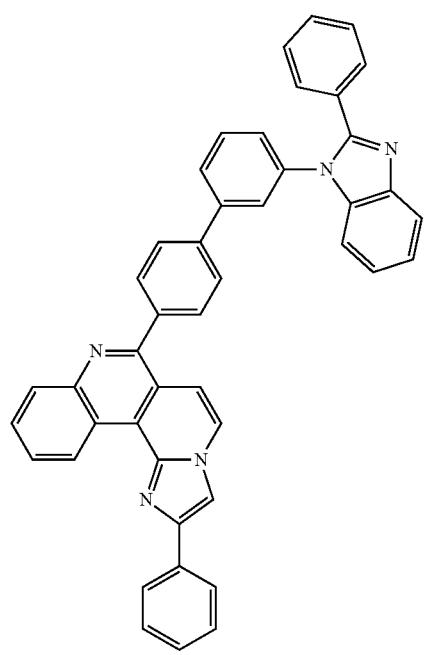
122 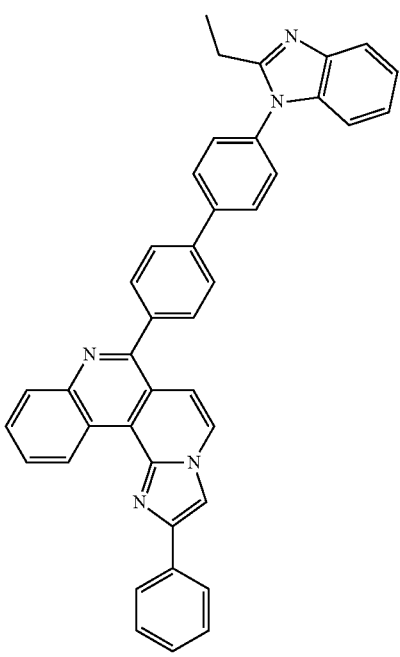
123 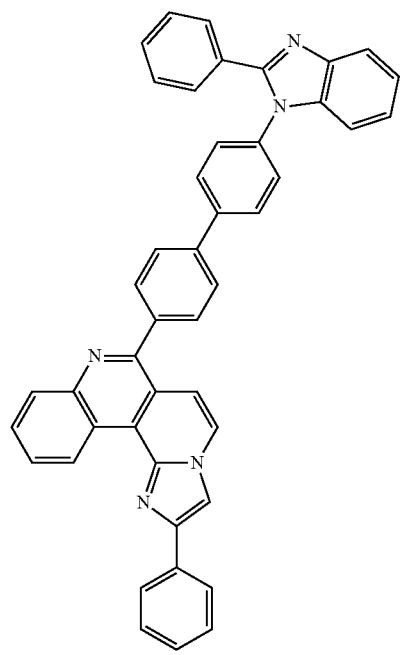
124 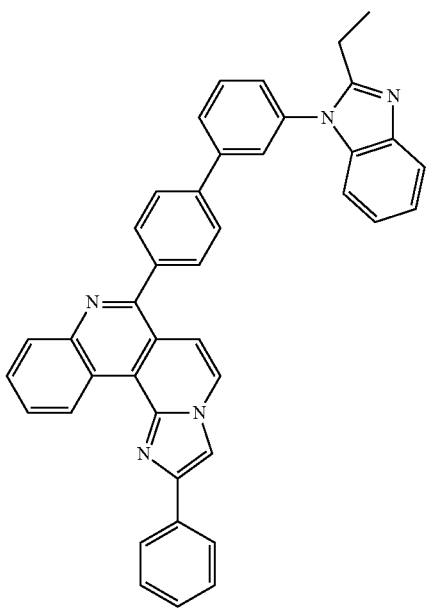

-continued
61 125 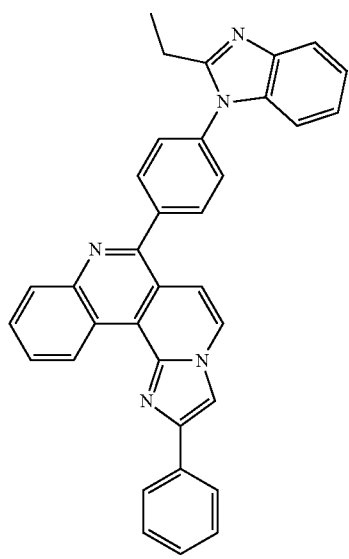
62 126 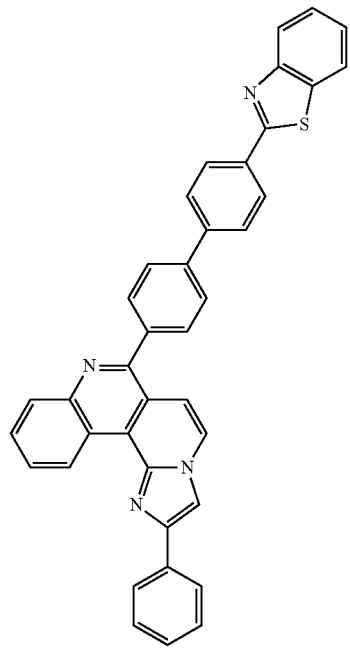
127 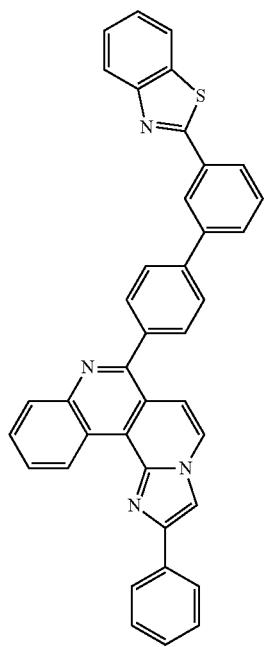
128

-continued
129
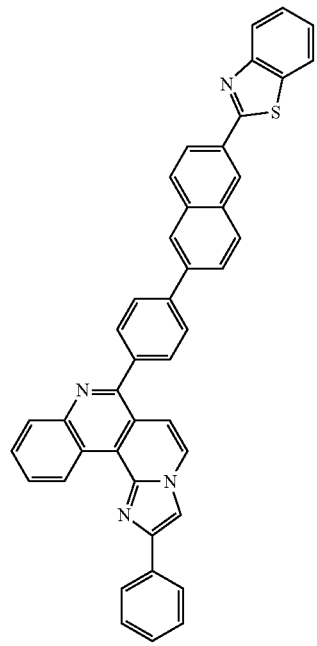
130
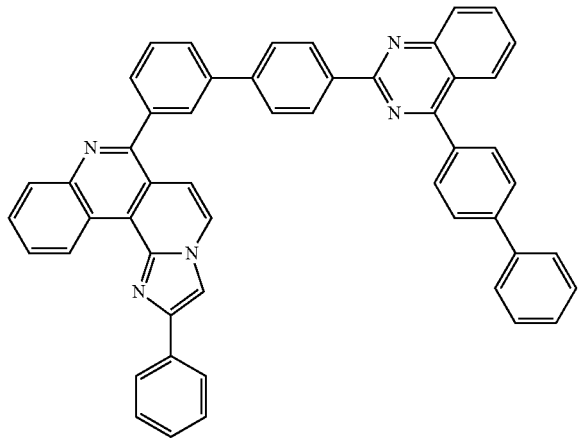
131
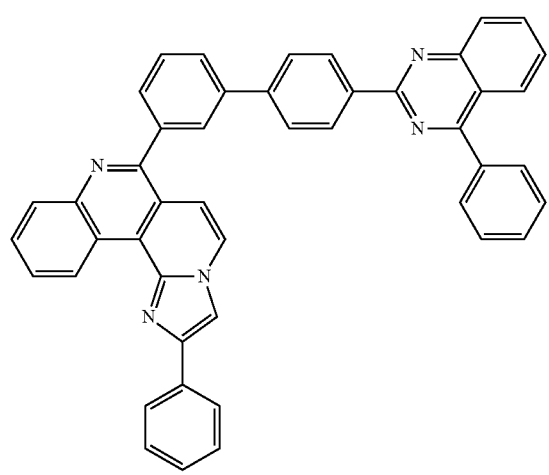
132
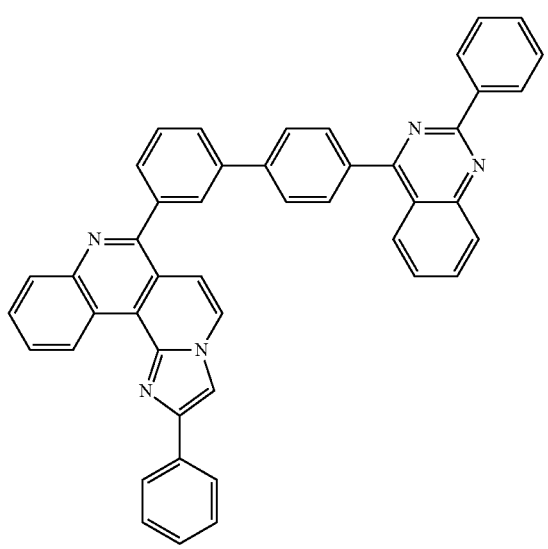
133
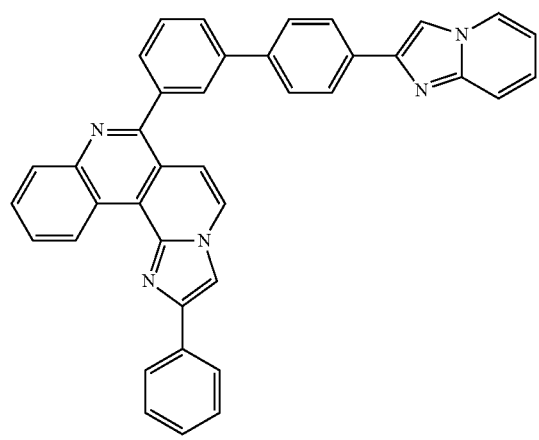
134
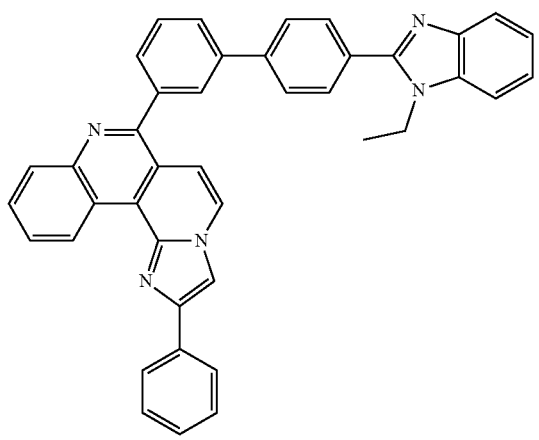

-continued
135
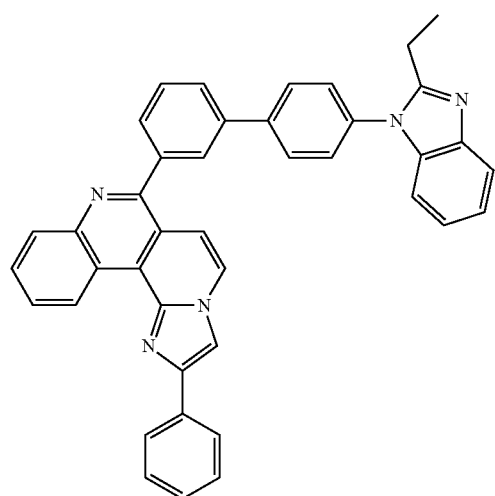
136
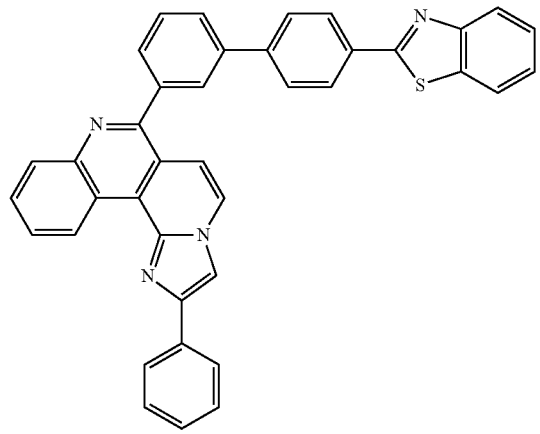
137
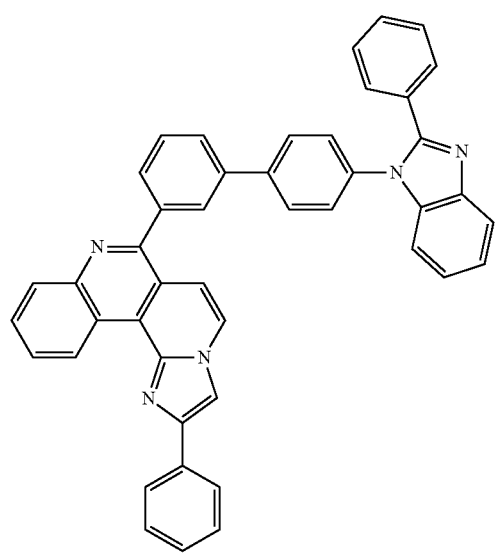
138
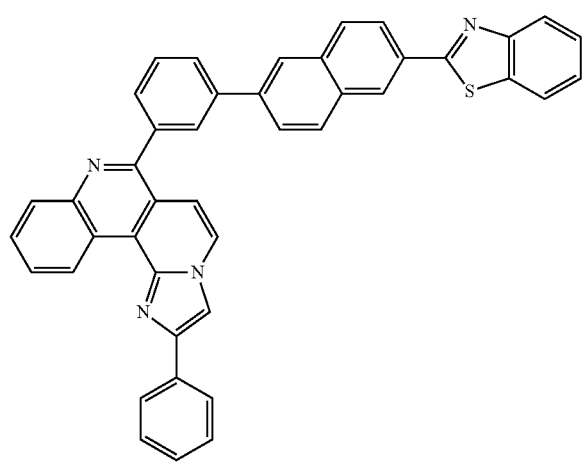

-continued
139
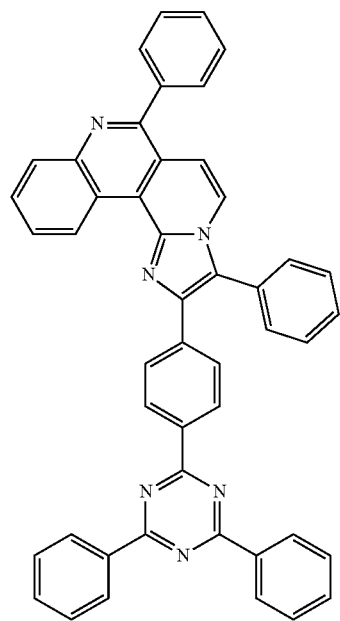
140
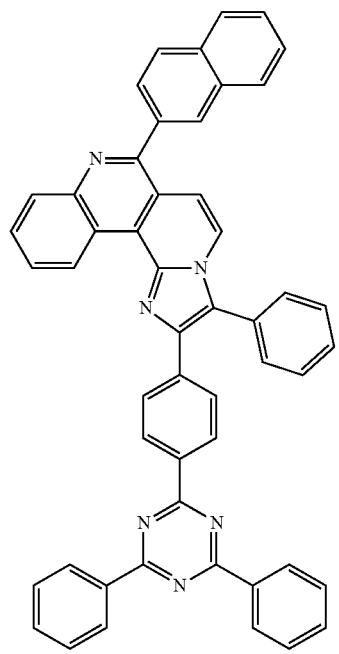
141
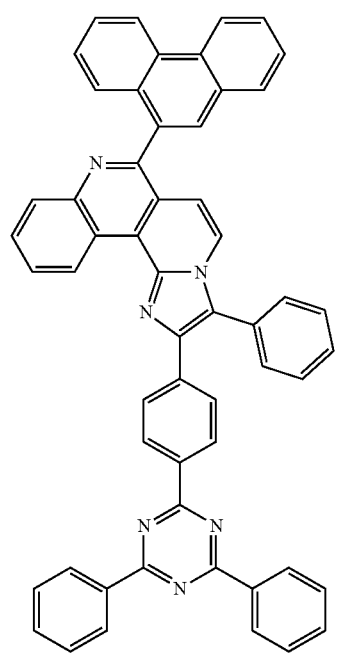
142
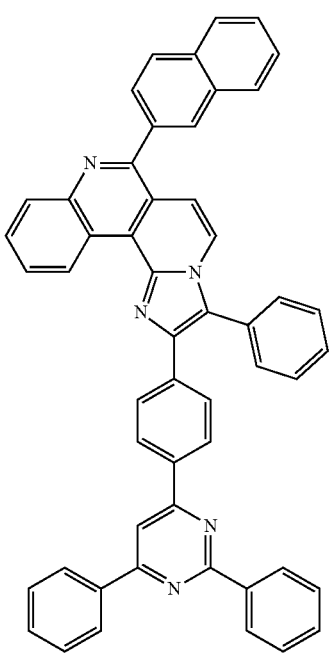

143
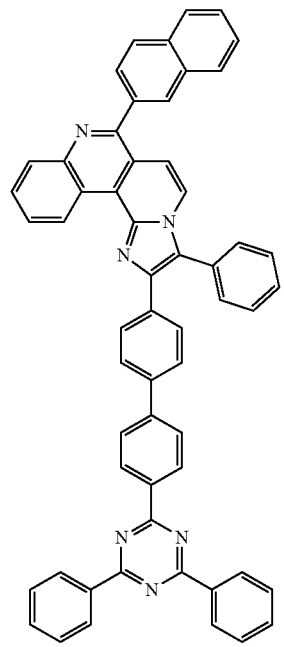
144
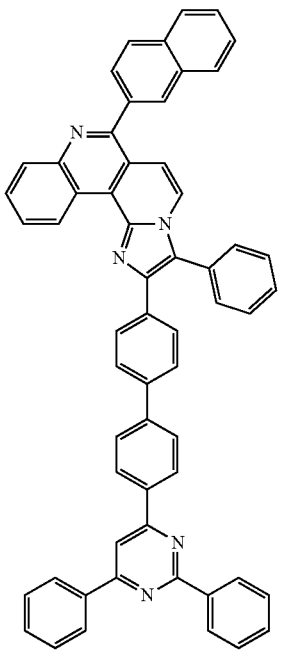
145
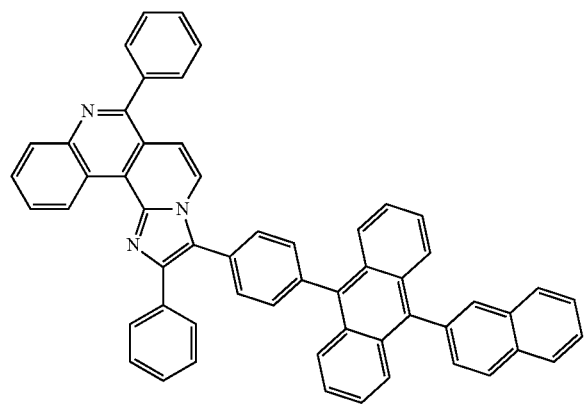
146
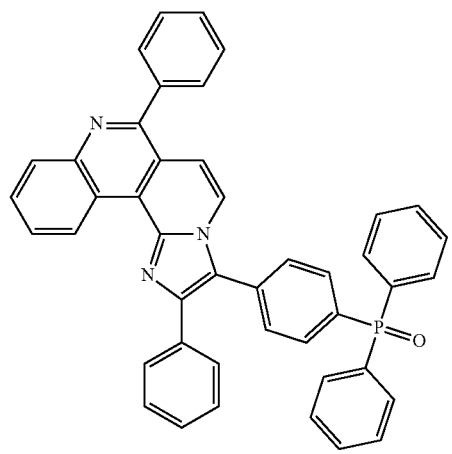
147
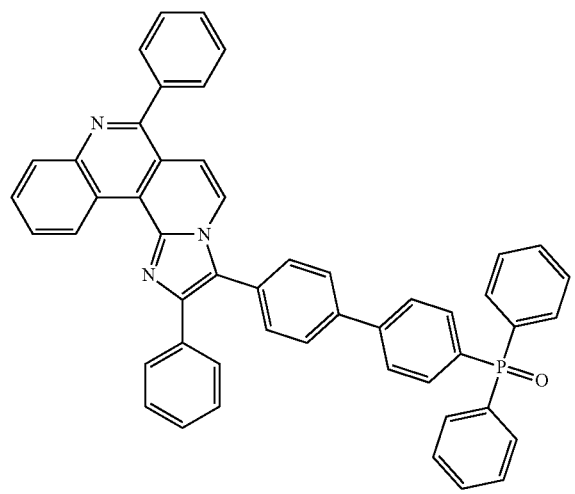
148
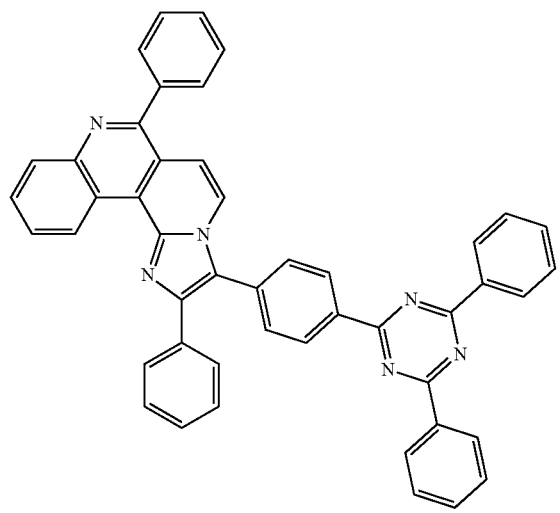

-continued
149
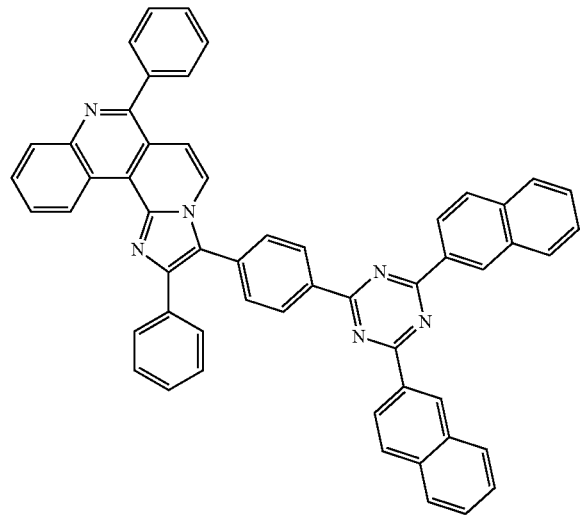
150
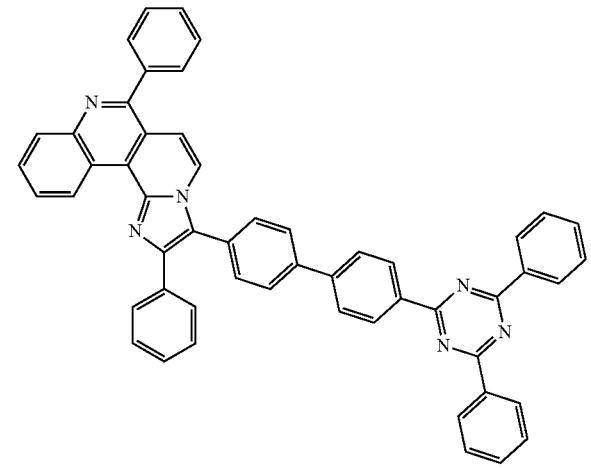
151
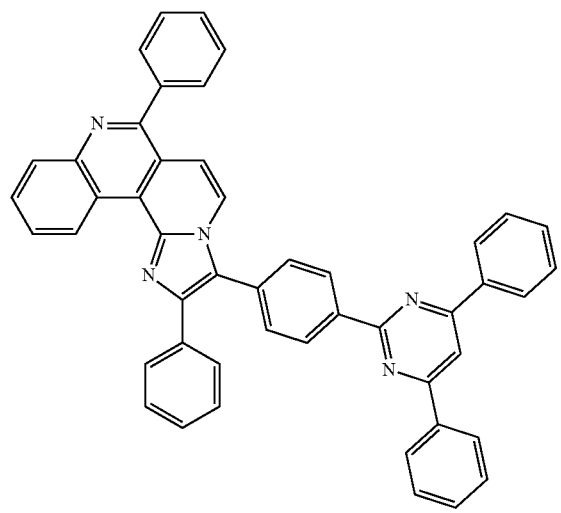
152
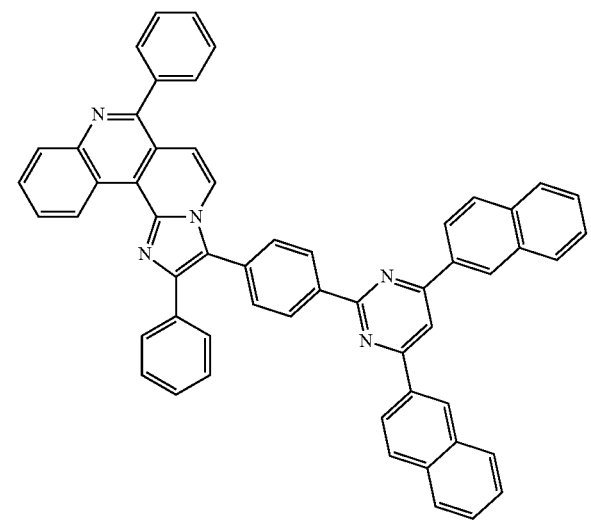
153
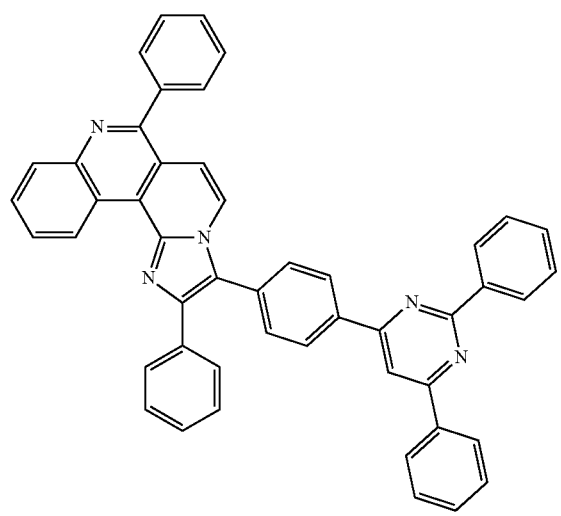
154
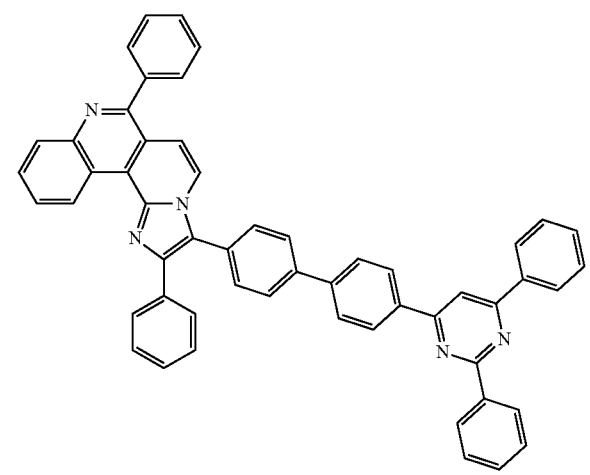

155
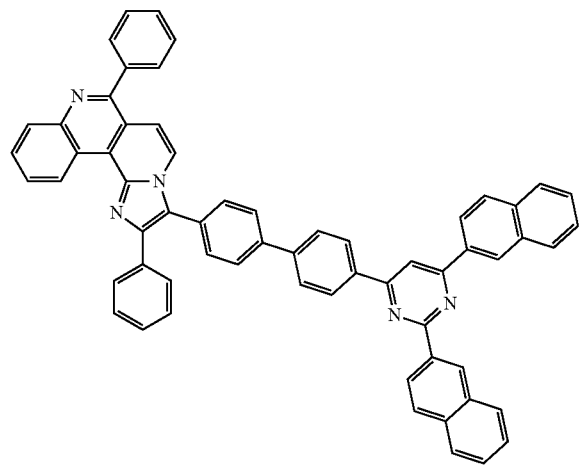
156
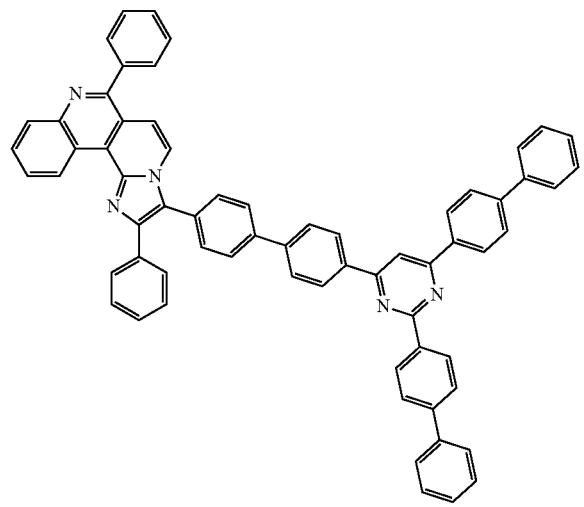
157
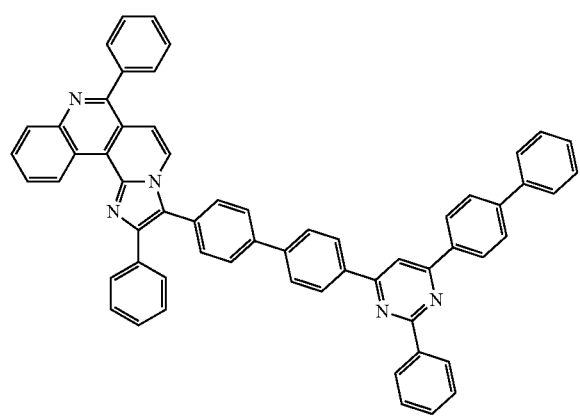
158
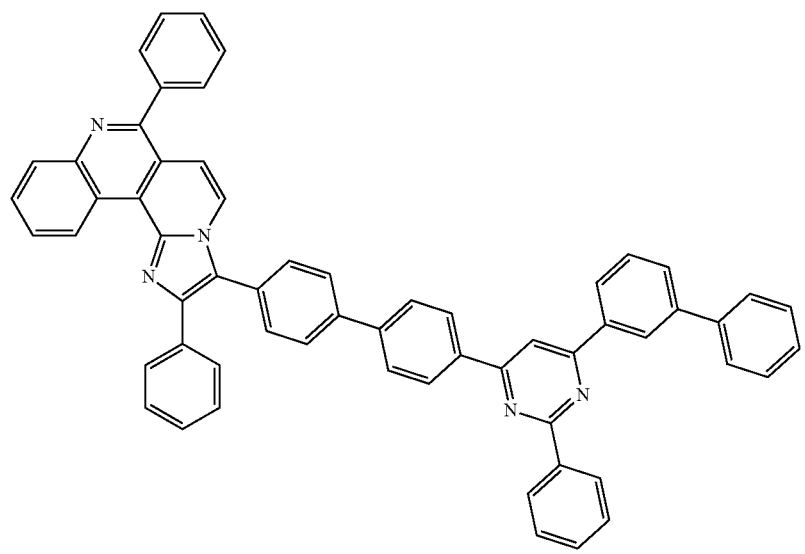

-continued
159
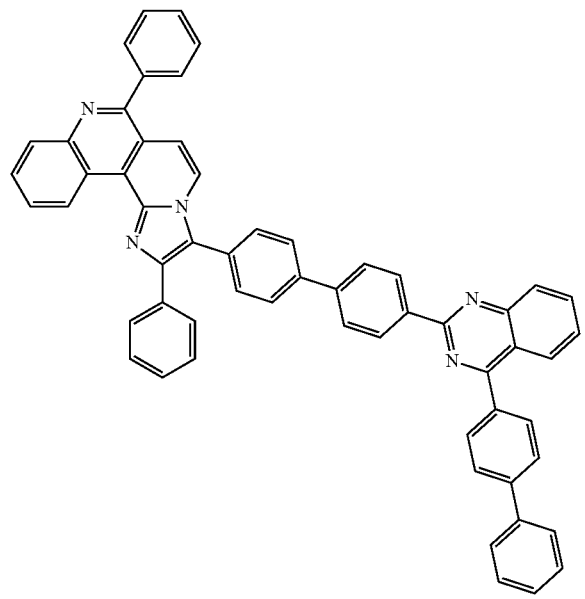
160
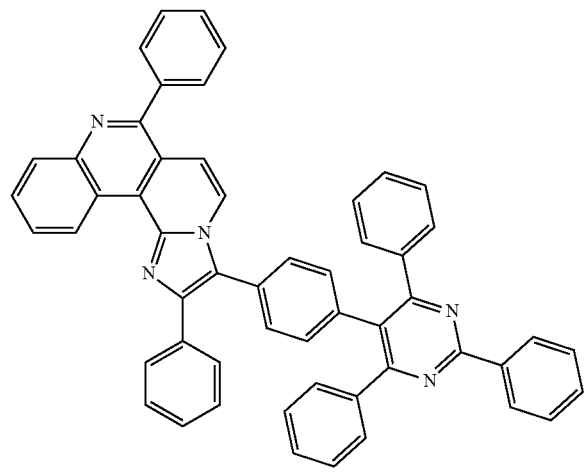
161
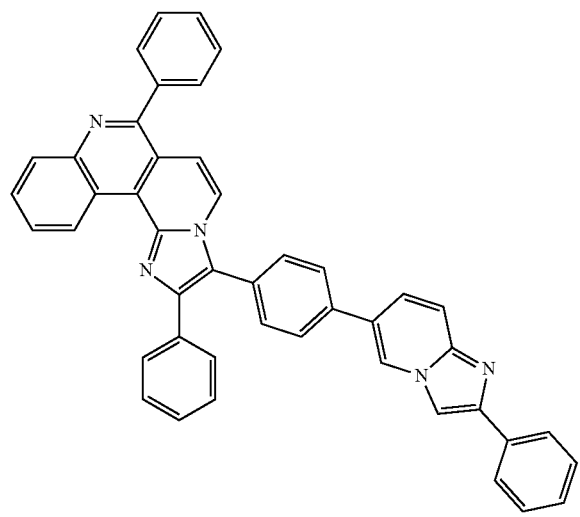
162
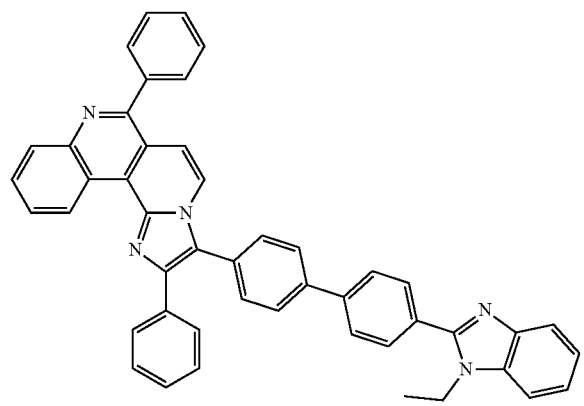
163
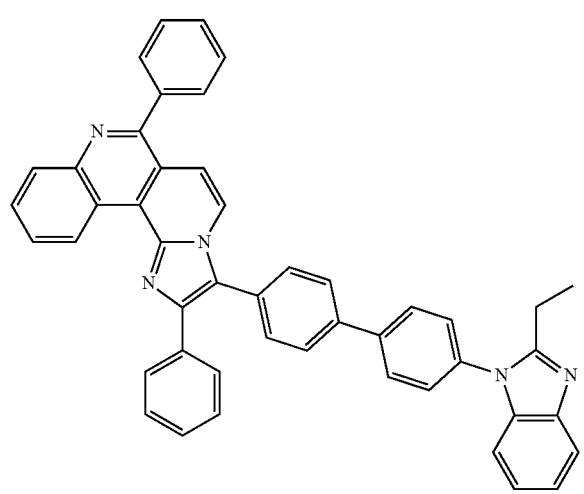
164
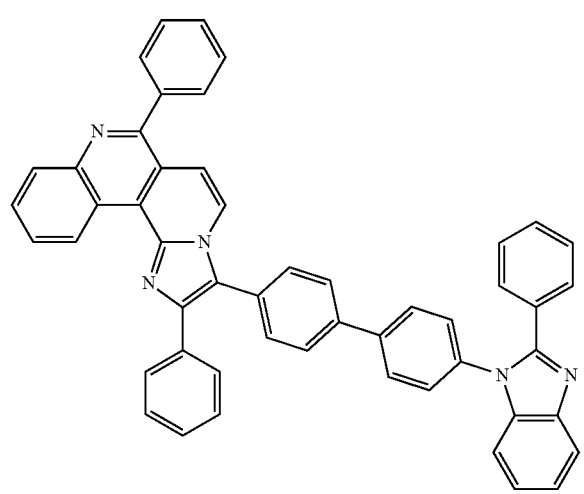

-continued
165
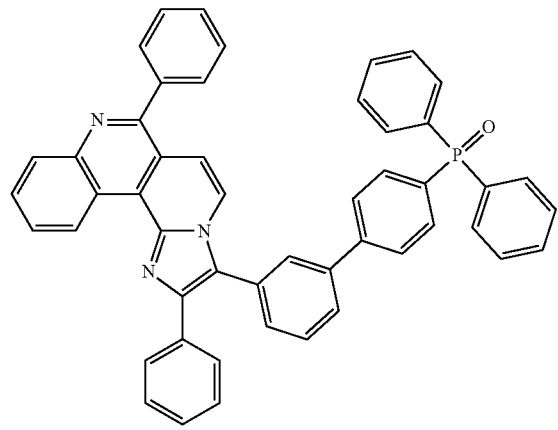
166
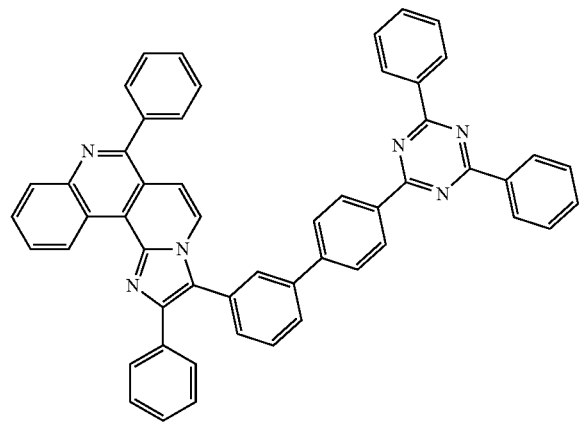
167
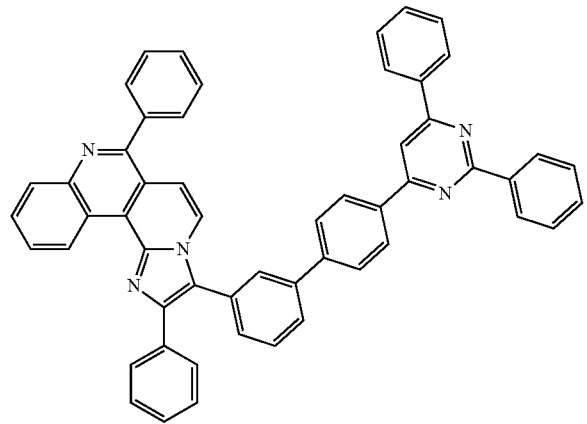
168
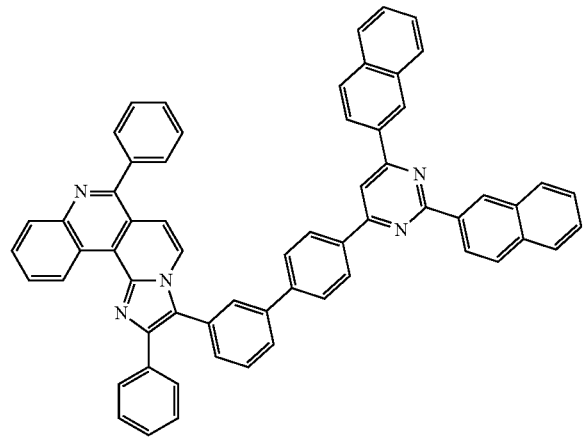
169
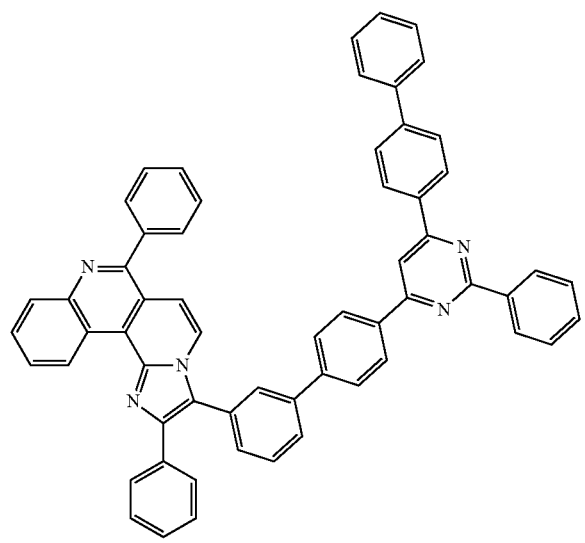
170
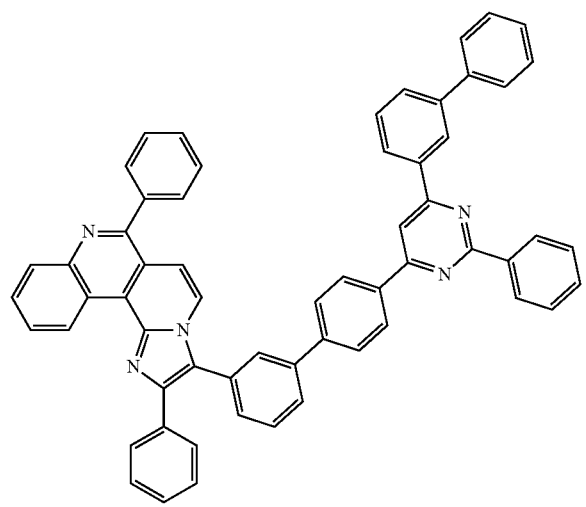

-continued
171
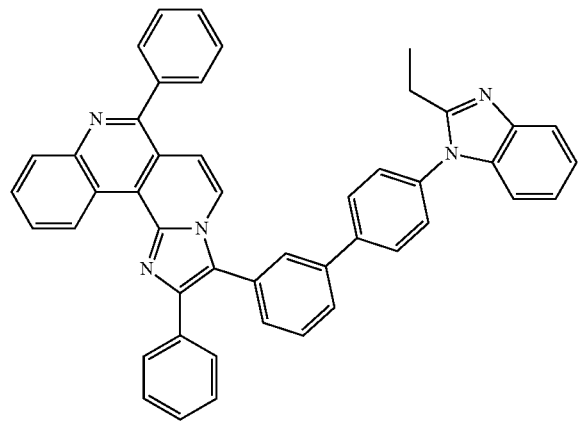
172
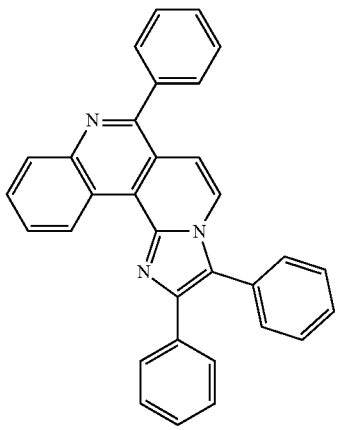
173
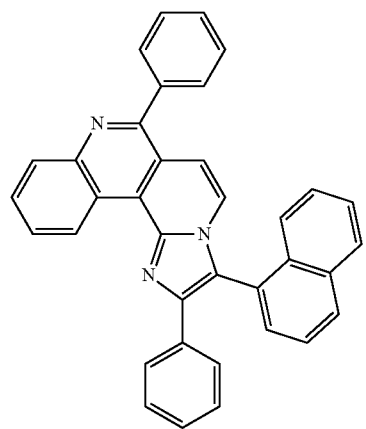
174
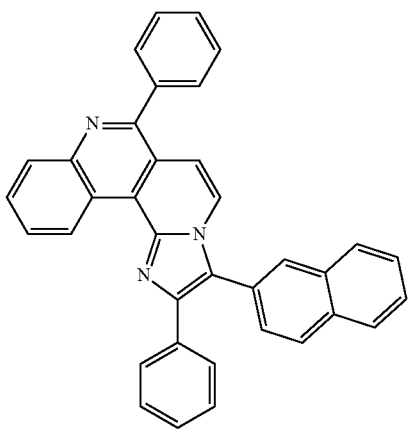
175
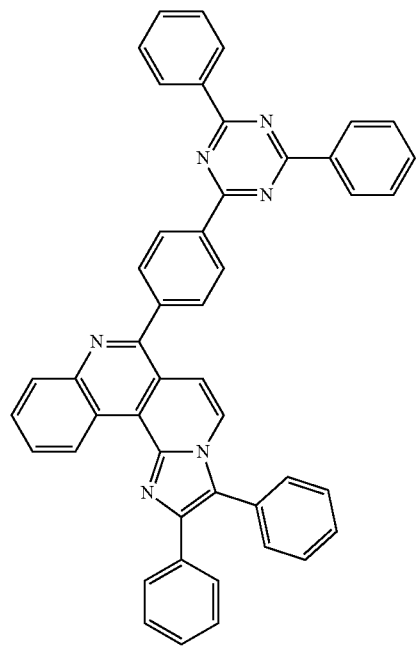
176
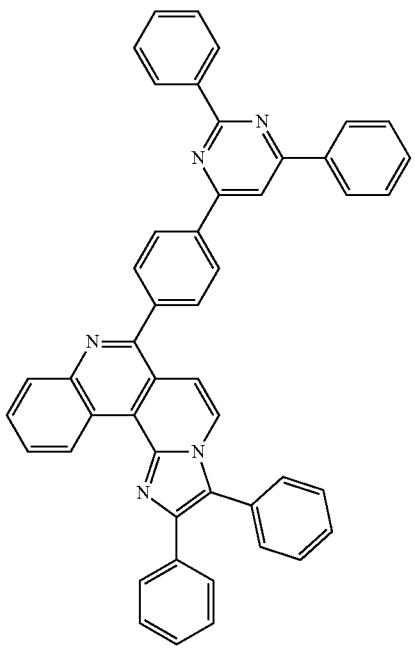

177
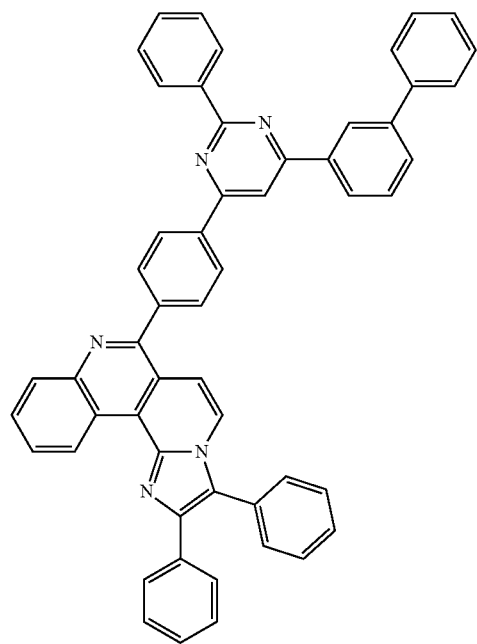
178
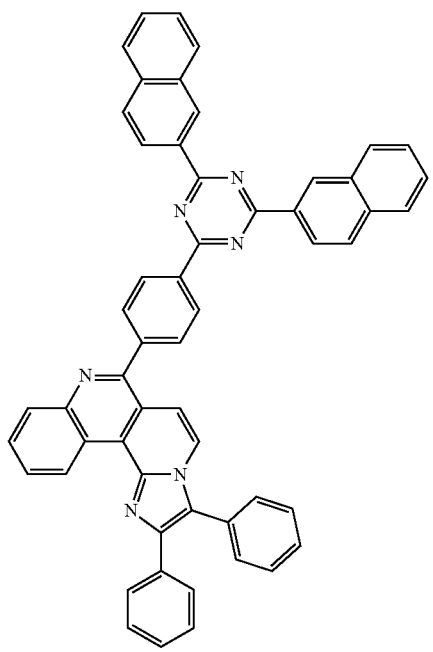
179
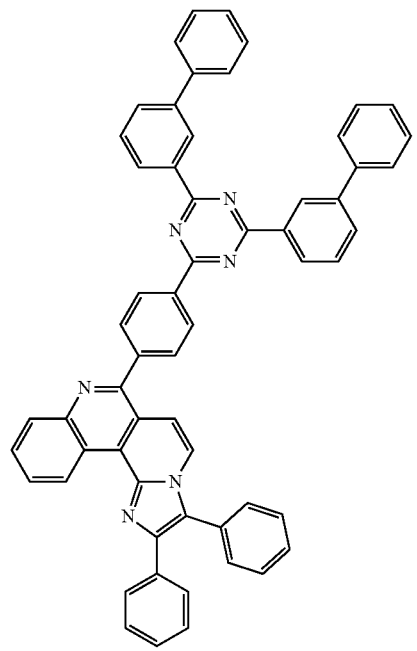
180
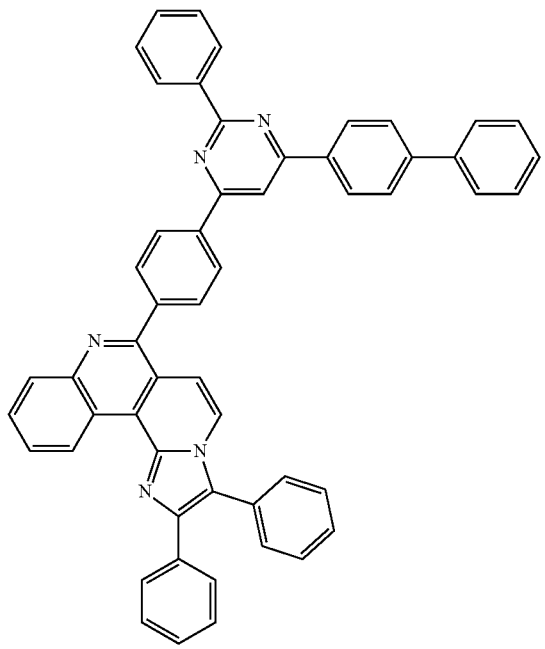

-continued
181
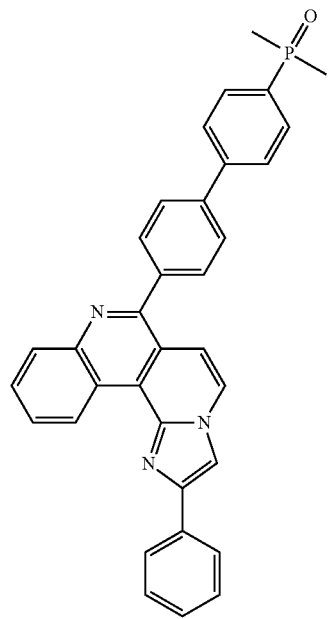
182
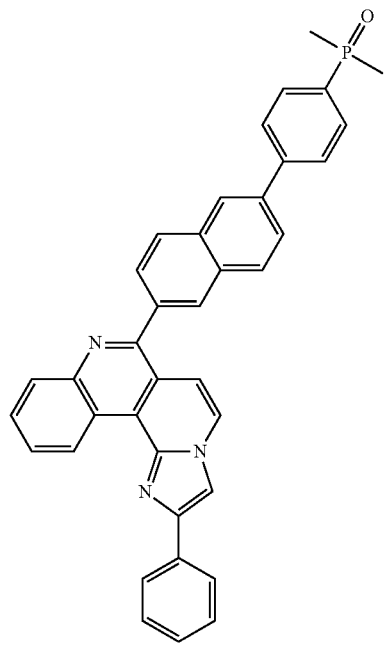
183
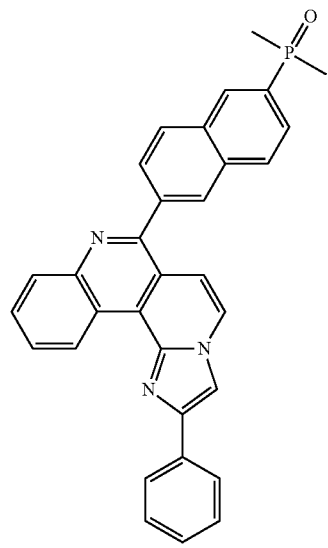
184
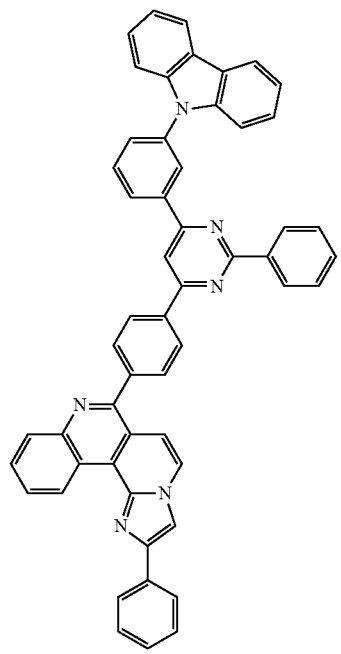

-continued
185 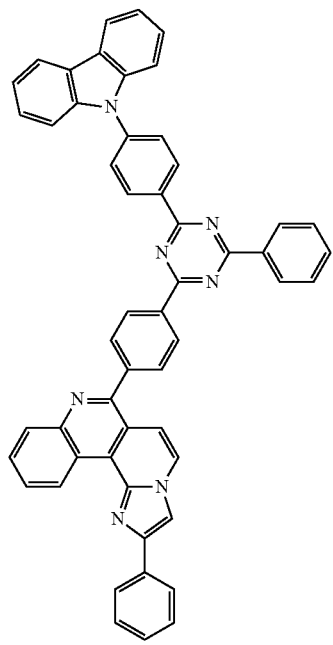
186 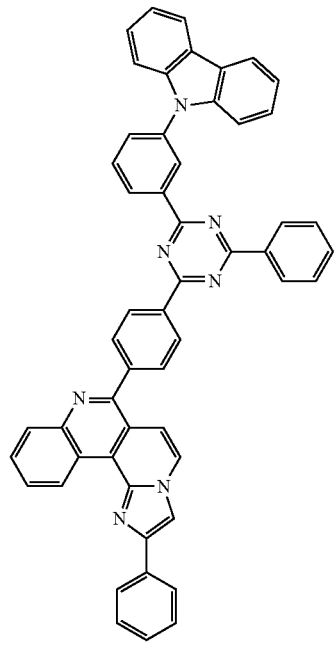
187 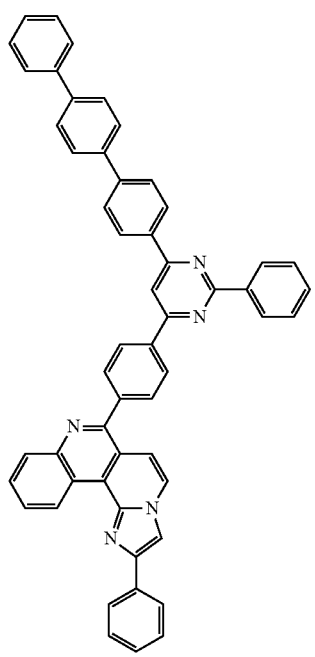
188 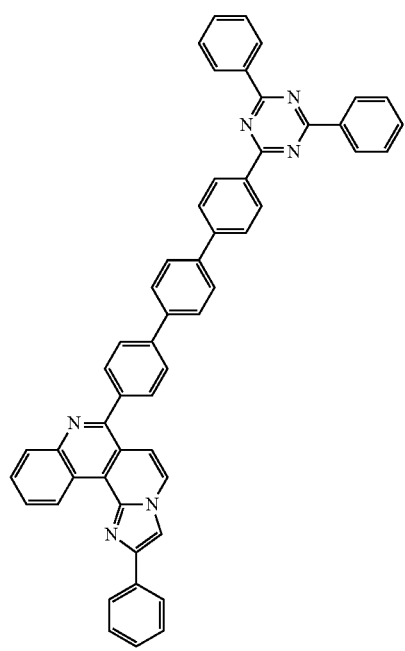

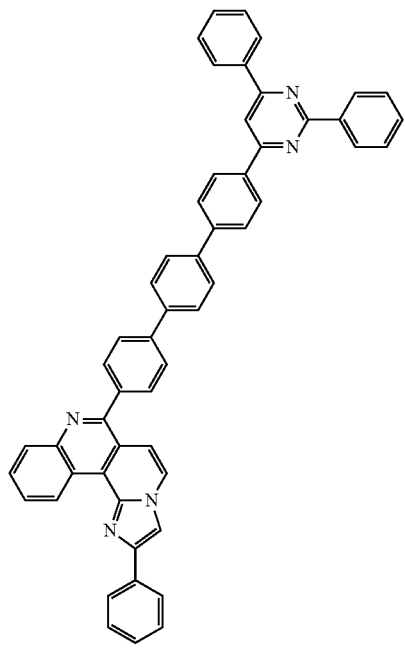
189
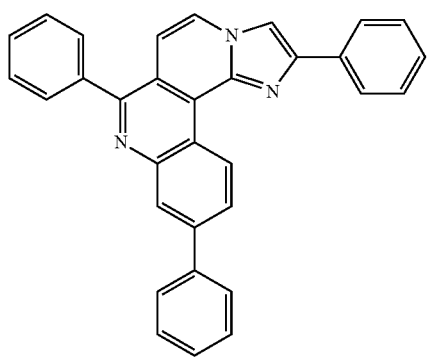
190
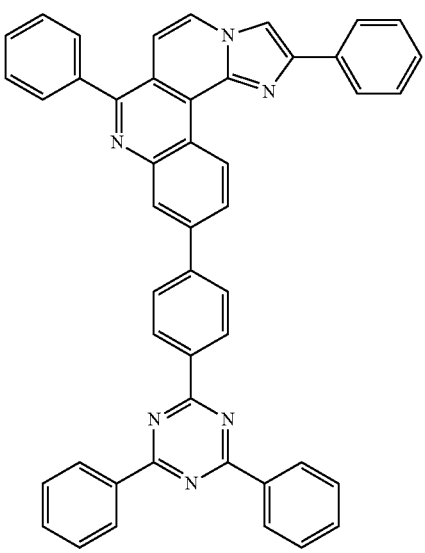
191

-continued
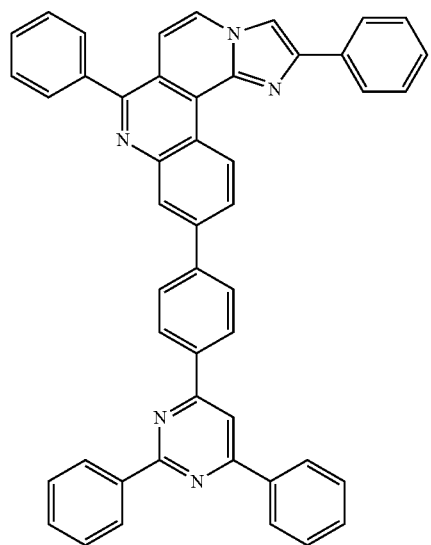
192
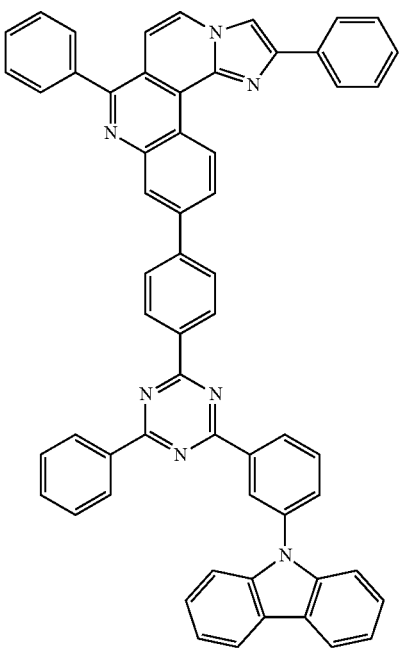
193
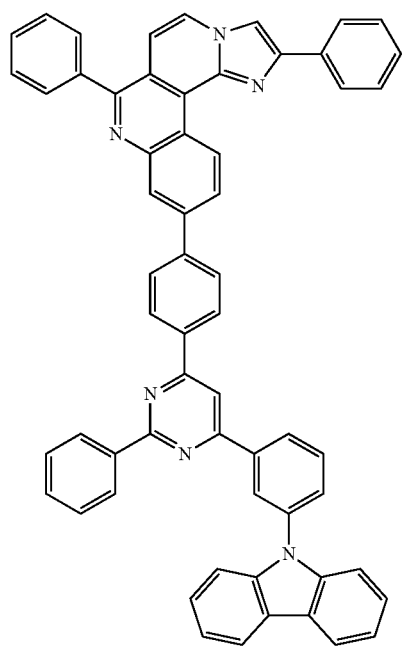
194
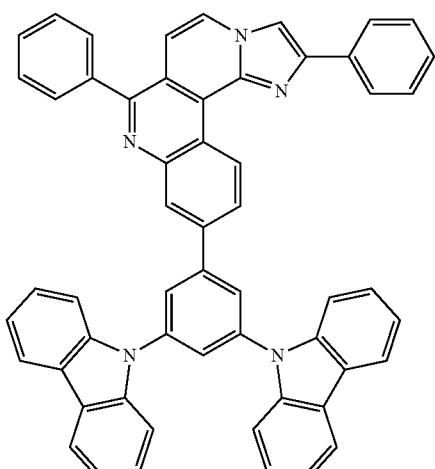
195

91
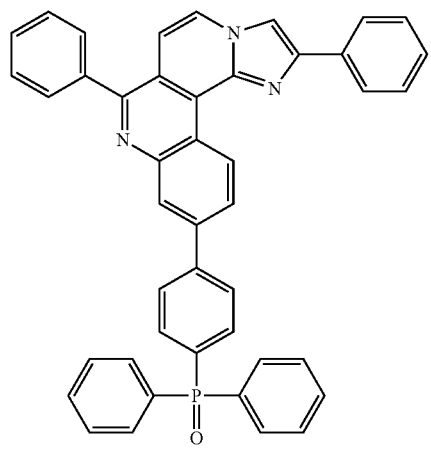
-continued
92
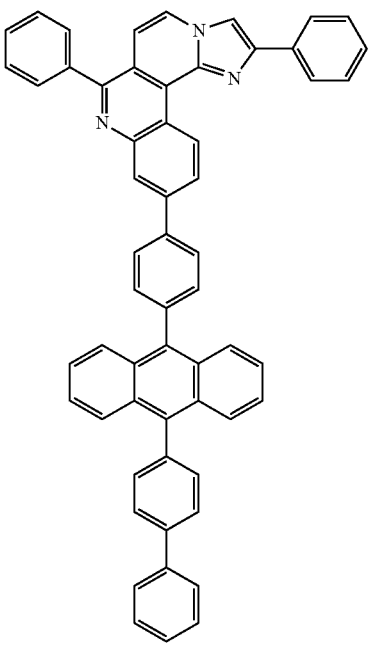
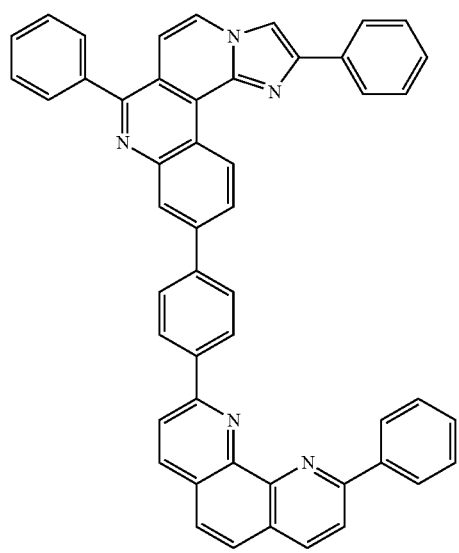
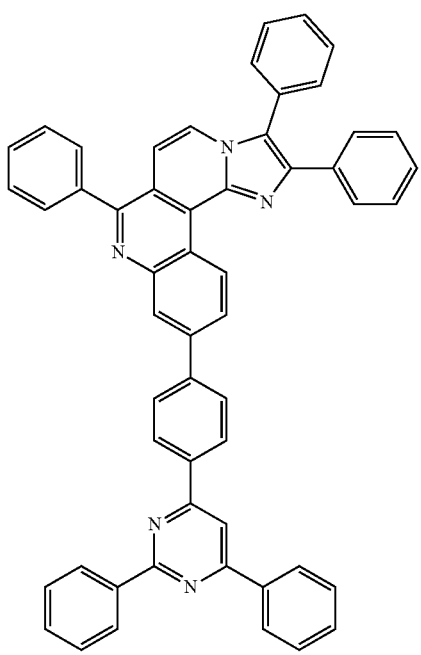

-continued
200
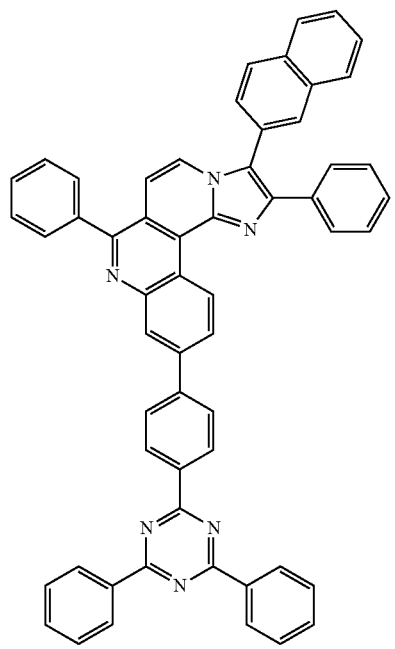
201
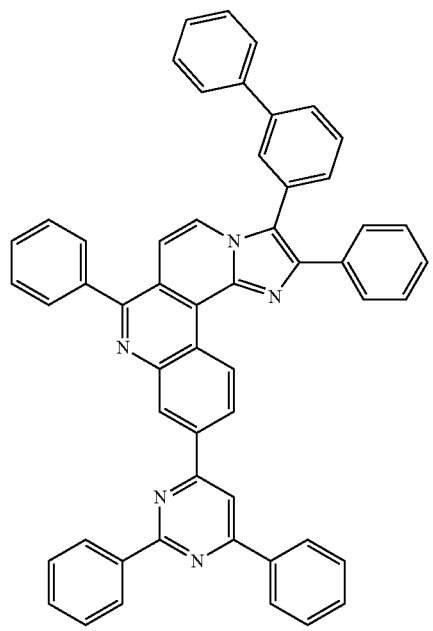
202
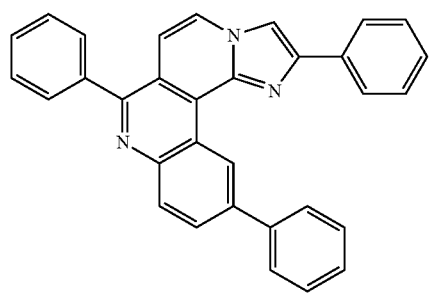
203
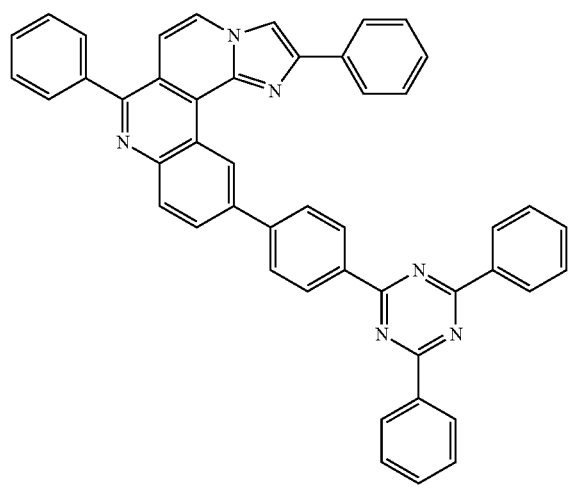
204
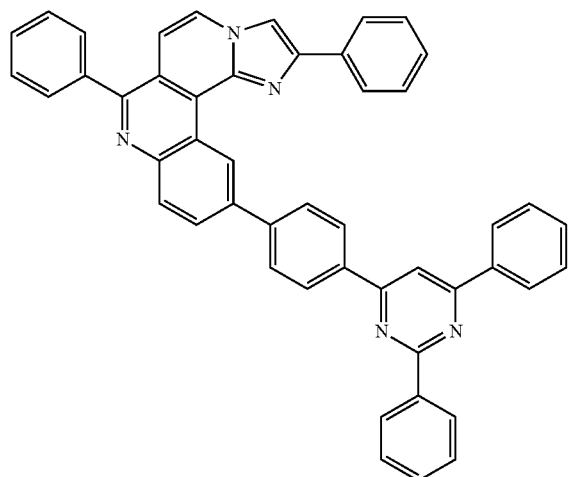
205
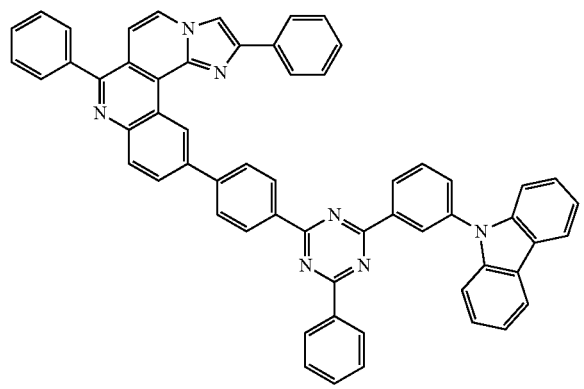

-continued
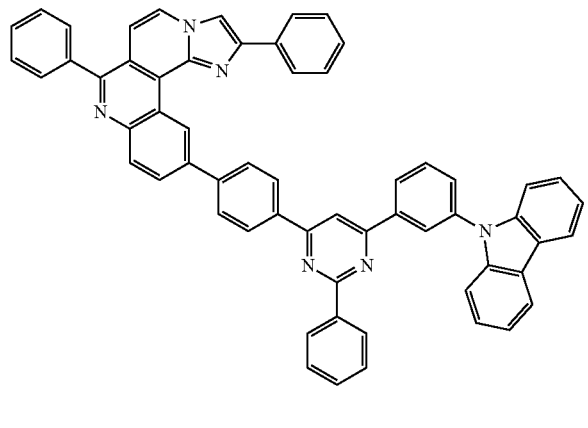
206
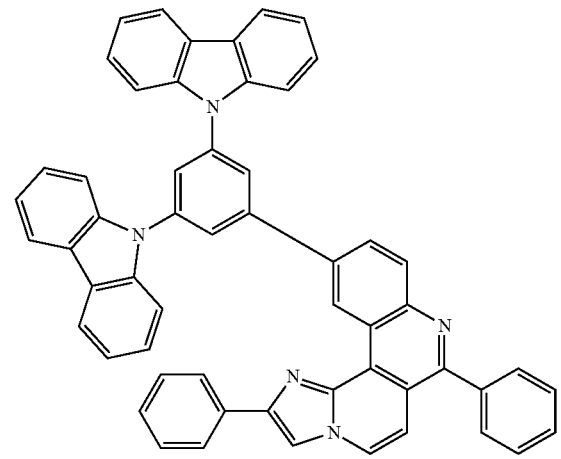
207
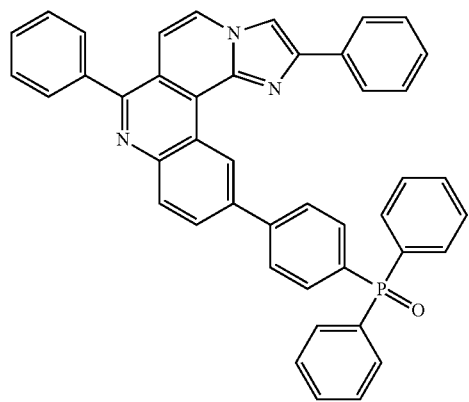
208
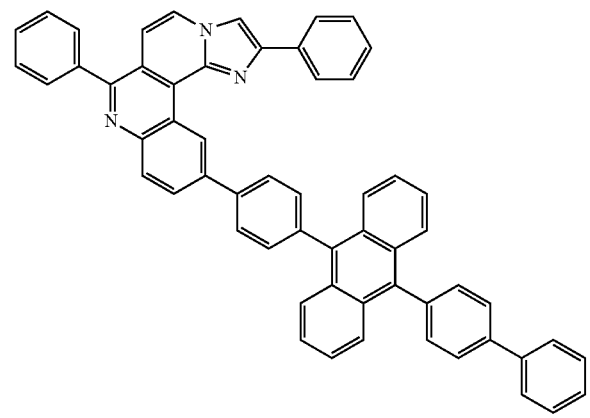
209
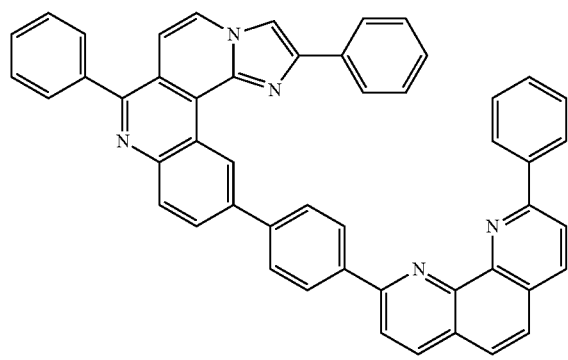
210
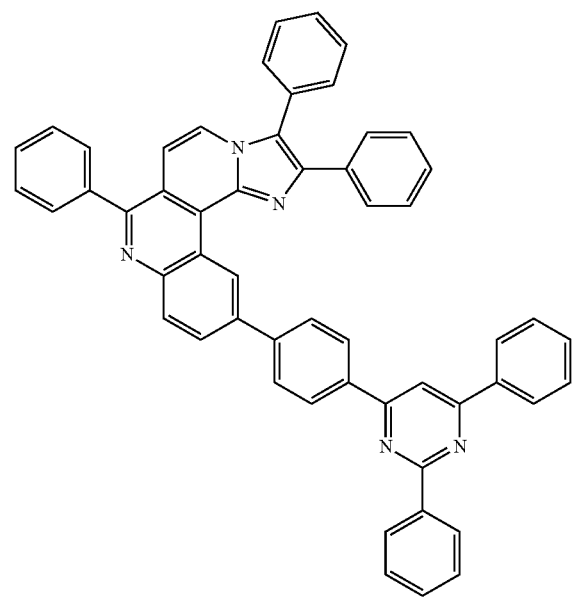
211

212
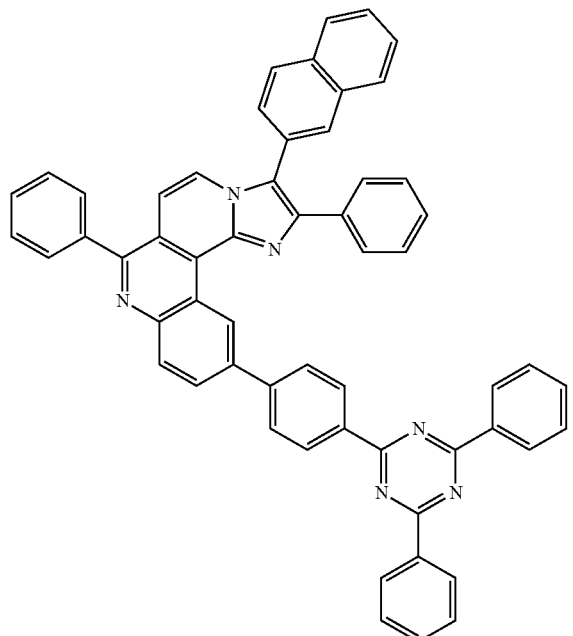
213
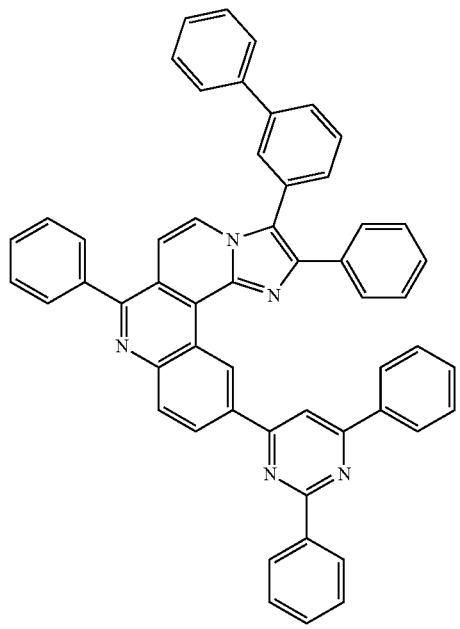
214
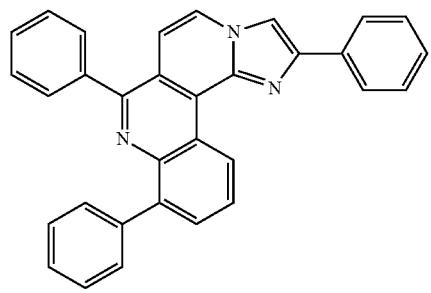
215
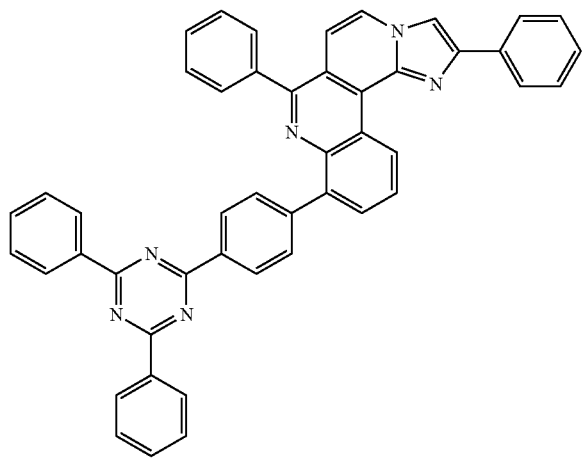
216
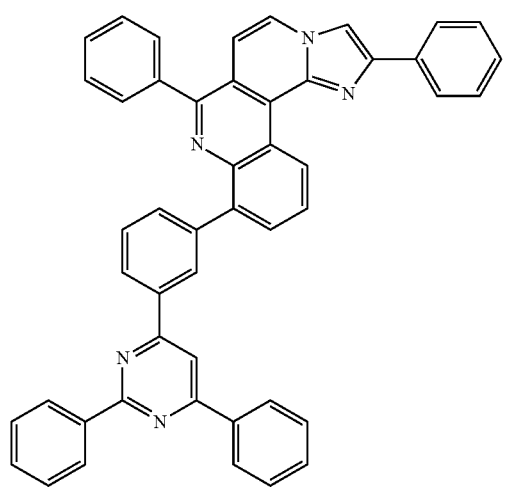

217
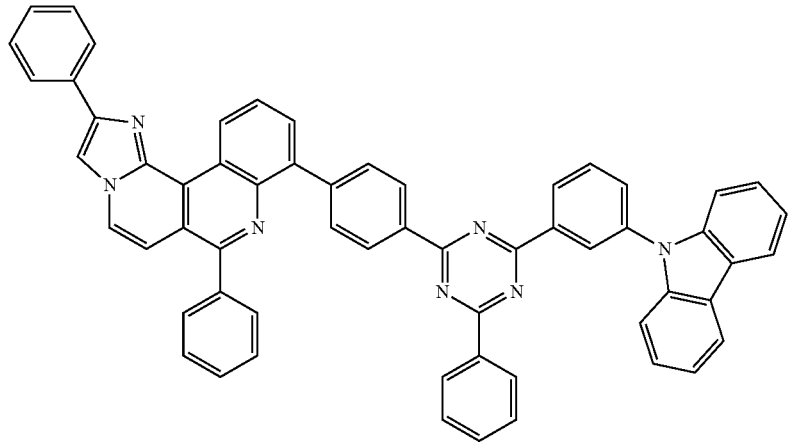
218
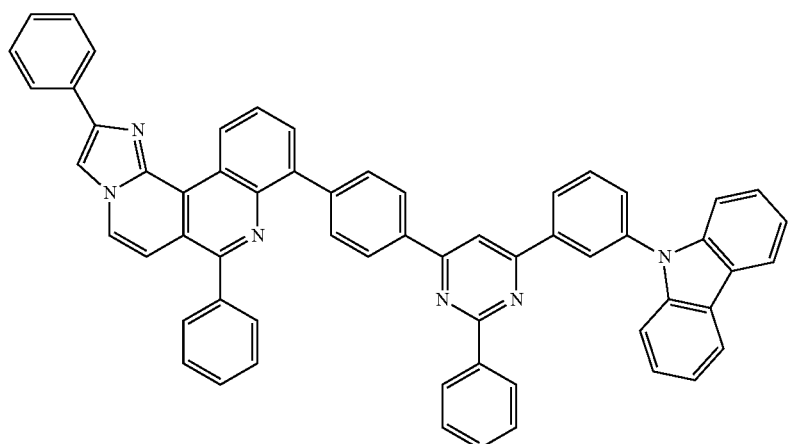
219 220
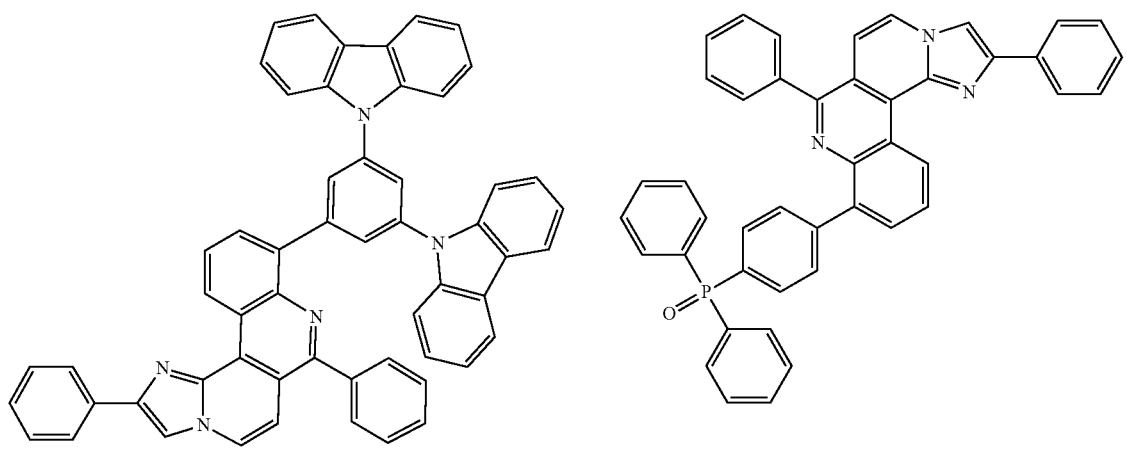

-continued
101
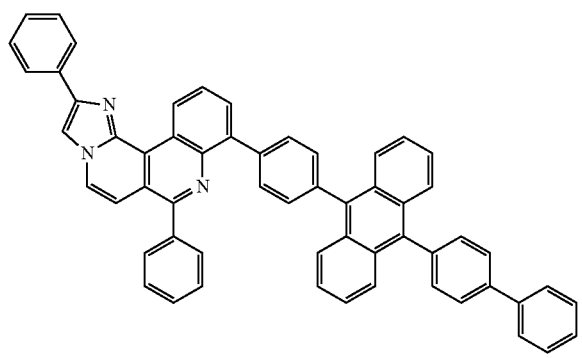
221
102
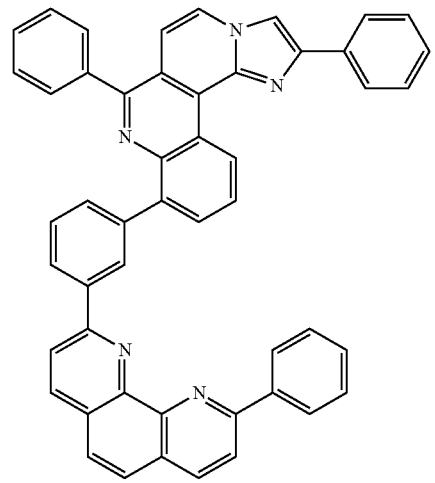
222
223
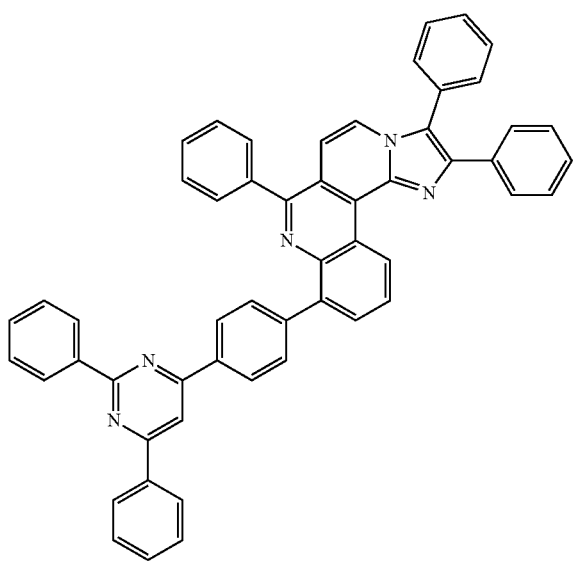
224
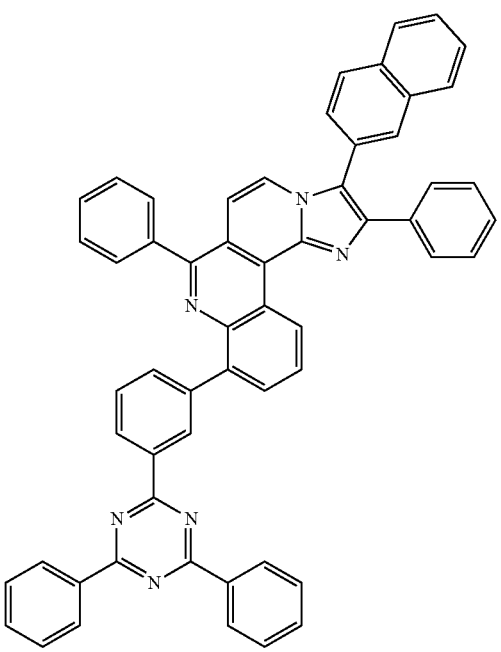

-continued

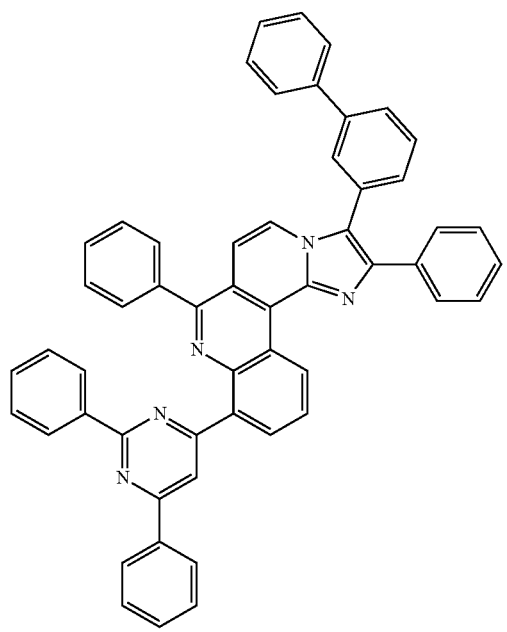

In addition, by introducing various substituents to the structure of Chemical Formula 1, compounds having unique properties of the introduced substituents may be synthesized. For example, by introducing substituents normally used as hole injection layer materials, hole transfer layer materials, light emitting layer materials, electron transfer layer materials and charge generation layer materials used for manufacturing an organic light emitting device to the core structure, materials satisfying conditions required for each organic material layer may be synthesized.

In addition, by introducing various substituents to the structure of Chemical Formula 1, the energy band gap may be finely controlled, and meanwhile, properties at interfaces between organic materials are enhanced, and material applications may become diverse.

Meanwhile, the compound has a high glass transition temperature (Tg), and has excellent thermal stability. Such an increase in the thermal stability becomes an important factor providing driving stability to a device.

Another embodiment of the present application provides an organic light emitting device comprising a first electrode; a second electrode provided opposite to the first electrode; and one or more organic material layers provided between the first electrode and the second electrode, wherein one or more layers of the organic material layers comprise the heterocyclic compound represented by Chemical Formula 1.

In one embodiment of the present application, the first electrode may be an anode, and the second electrode may be a cathode.

In another embodiment, the first electrode may be a cathode, and the second electrode may be an anode.

Specific details on the heterocyclic compound represented by Chemical Formula 1 are the same as the descriptions provided above.

In one embodiment of the present application, the organic light emitting device may be a blue organic light emitting device, and the heterocyclic compound according to Chemical Formula 1 may be used as a material of the blue organic light emitting device.

In one embodiment of the present application, the organic light emitting device may be a green organic light emitting device, and the heterocyclic compound according to Chemical Formula 1 may be used as a material of the green organic light emitting device.

In one embodiment of the present application, the organic light emitting device may be a red organic light emitting device, and the heterocyclic compound according to Chemical Formula 1 may be used as a material of the red organic light emitting device.

The organic light emitting device of the present disclosure may be manufactured using common organic light emitting device manufacturing methods and materials except that one or more organic material layers are formed using the heterocyclic compound described above.

The heterocyclic compound may be formed into an organic material layer through a solution coating method as well as a vacuum deposition method when manufacturing the organic light emitting device. Herein, the solution coating method means spin coating, dip coating, inkjet printing, screen printing, a spray method, roll coating and the like, but is not limited thereto.

The organic material layer of the organic light emitting device of the present disclosure may be formed in a single layer structure, or may also be formed in a multilayer structure in which two or more organic material layers are laminated. For example, the organic light emitting device according to one embodiment of the present disclosure may have a structure comprising a hole injection layer, a hole transfer layer, a light emitting layer, an electron transfer layer, an electron injection layer and the like as the organic material layer. However, the structure of the organic light emitting device is not limited thereto, and may comprise a smaller number of organic material layers.

In the organic light emitting device of the present disclosure, the organic material layer comprises an electron injection layer or an electron transfer layer, and the electron injection layer or the electron transfer layer may comprise the heterocyclic compound.

In the organic light emitting device of the present disclosure, the organic material layer comprises an electron transfer layer, and the electron transfer layer may comprise the heterocyclic compound.

In another organic light emitting device, the organic material layer comprises an electron blocking layer or a hole blocking layer, and the electron blocking layer or the hole blocking layer may comprise the heterocyclic compound.

In another organic light emitting device, the organic material layer comprises a hole blocking layer, and the hole blocking layer may comprise the heterocyclic compound.

In another organic light emitting device, the organic material layer comprises an electron transfer layer, a light emitting layer or a hole blocking layer, and the electron transfer layer, the light emitting layer or the hole blocking layer may comprise the heterocyclic compound.

The organic light emitting device of the present disclosure may further comprise one, two or more layers selected from the group consisting of a light emitting layer, a hole injection layer, a hole transfer layer, an electron injection layer, an electron transfer layer, an electron blocking layer and a hole blocking layer.

FIGS. 1 to 4 illustrate a lamination order of electrodes and organic material layers of an organic light emitting device according to one embodiment of the present application. However, the scope of the present application is not limited to these diagrams, and structures of organic light emitting devices known in the art may also be used in the present application.

FIG. 1 illustrates an organic light emitting device in which an anode (200), an organic material layer (300) and a cathode (400) are consecutively laminated on a substrate (100). However, the structure is not limited to such a structure, and as illustrated in FIG. 2, an organic light emitting device in which a cathode, an organic material layer and an anode are consecutively laminated on a substrate may also be obtained.

FIG. 3 illustrates a case of the organic material layer being a multilayer. The organic light emitting device according to FIG. 3 comprises a hole injection layer (301), a hole transfer layer (302), a light emitting layer (303), a hole blocking layer (304), an electron transfer layer (305) and an electron injection layer (306). However, the scope of the present application is not limited to such a lamination structure, and as necessary, other layers except the light emitting layer may not be included, and other necessary functional layers may be further included.

The organic material layer comprising the compound of Chemical Formula 1 may further comprise other materials as necessary.

In addition, the organic light emitting device according to one embodiment of the present application comprises an anode, a cathode, and two or more stacks provided between the anode and the cathode, and the two or more stacks each independently comprise a light emitting layer, a charge generation layer is included between the two or more stacks, and the charge generation layer comprises the heterocyclic compound represented by Chemical Formula 1.

In addition, the organic light emitting device according to one embodiment of the present application comprises an anode, a first stack provided on the anode and comprising a first light emitting layer, a charge generation layer provided on the first stack, a second stack provided on the charge generation layer and comprising a second light emitting layer, and a cathode provided on the second stack. Herein, the charge generation layer may comprise the heterocyclic compound represented by Chemical Formula 1. In addition, the first stack and the second stack may each independently further comprise one or more types of the hole injection layer, the hole transfer layer, the hole blocking layer, the electron transfer layer, the electron injection layer and the like described above.

The charge generation layer may be an N-type charge generation layer, and the charge generation layer may further comprise a dopant known in the art in addition to the heterocyclic compound represented by Chemical Formula 1.

As the organic light emitting device according to one embodiment of the present application, an organic light emitting device having a 2-stack tandem structure is schematically illustrated in the following FIG. 4.

Herein, the first electron blocking layer, the first hole blocking layer, the second hole blocking layer and the like described in FIG. 4 may not be included in some cases.

In the organic light emitting device according to one embodiment of the present application, materials other than the compound of Chemical Formula 1 are illustrated below, however, these are for illustrative purposes only and not for limiting the scope of the present application, and may be replaced by materials known in the art.

As the anode material, materials having relatively large work function may be used, and transparent conductive oxides, metals, conductive polymers or the like may be used. Specific examples of the anode material comprise metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene] (PEDOT), polypyrrole and polyaniline, and the like, but are not limited thereto.

As the cathode material, materials having relatively small work function may be used, and metals, metal oxides, conductive polymers or the like may be used. Specific examples of the cathode material comprise metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

As the hole injection material, known hole injection materials may be used, and for example, phthalocyanine compounds such as copper phthalocyanine disclosed in U.S. Pat. No. 4,356,429, or starburst-type amine derivatives such as tris(4-carbazoyl-9-ylphenyl)amine (TCTA), 4,4',4"-tri[phenyl(m-tolyl)amino]triphenylamine (m-MTDATA) or 1,3,5-tris[4-(3-methylphenylphenylamino)phenyl]benzene (m-MTDAPB) described in the literature [Advanced Material, 6, p. 677 (1994)], polyaniline/dodecylbenzene sulfonic acid, poly(3,4-ethylenedioxythiophene)/poly(4-styrenesulfonate), polyaniline/camphor sulfonic acid or polyaniline/poly(4-styrene-sulfonate) that are conductive polymers having solubility, and the like, may be used.

As the hole transfer material, pyrazoline derivatives, arylamine-based derivatives, stilbene derivatives, triphenyldiamine derivatives and the like may be used, and low molecular or high molecular materials may also be used.

As the electron transfer material, metal complexes of oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, 8-hydroxyquinoline and derivatives thereof, and the like, may be used, and high molecular materials may also be used as well as low molecular materials.

As examples of the electron injection material, LiF is typically used in the art, however, the present application is not limited thereto.

As the light emitting material, red, green or blue light emitting materials may be used, and as necessary, two or more light emitting materials may be mixed and used. Herein, two or more light emitting materials may be used by being deposited as individual sources of supply or by being premixed and deposited as one source of supply. In addition, fluorescent materials may also be used as the light emitting material, however, phosphorescent materials may also be used. As the light emitting material, materials emitting light by bonding electrons and holes injected from an anode and a cathode, respectively, may be used alone, however, materials having a host material and a dopant material involving in light emission together may also be used.

When mixing light emitting material hosts, same series hosts may be mixed, or different series hosts may be mixed. For example, any two or more types of materials among n-type host materials or p-type host materials may be selected, and used as a host material of a light emitting layer.

The organic light emitting device according to one embodiment of the present application may be a top-emission type, a bottom-emission type or a dual-emission type depending on the materials used.

The heterocyclic compound according to one embodiment of the present application may also be used in an organic electronic device comprising an organic solar cell, an organic photo conductor, an organic transistor and the like under a similar principle used in the organic light emitting device.

Hereinafter, the present specification will be described in more detail with reference to examples, however, these are for illustrative purposes only, and the scope of the present application is not limited thereto.

PREPARATION EXAMPLE

[Preparation Example 1] Preparation of Compound 1

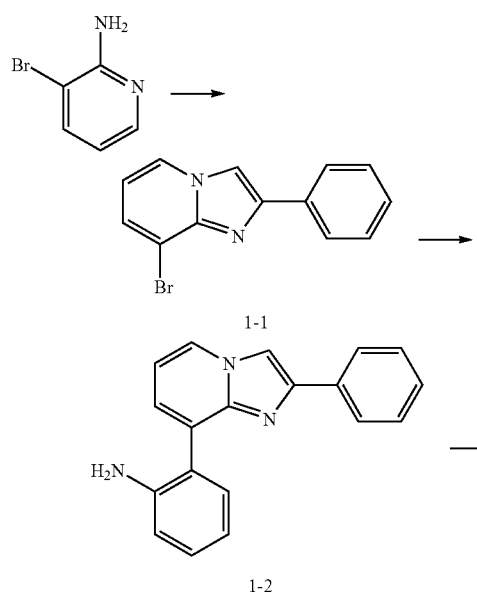

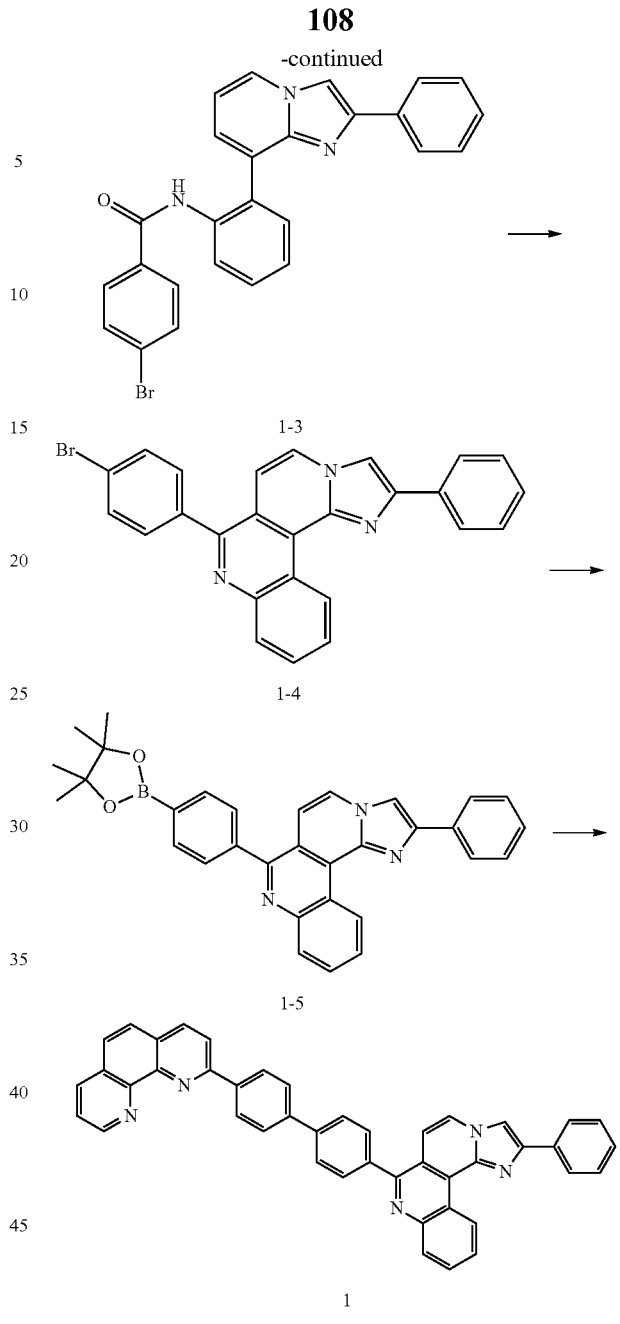

Preparation of Compound 1-1

After dissolving 2-amino-3-bromopyridine (100 g, 578.0 mmol, 1 eq.) in EtOH, phenacyl bromide (138 g, 693.60 mmol, 1.2 eq.) was added thereto, and the result was stirred under reflux. After the reaction was finished, the result was cooled to room temperature (25° C.), and produced solids were filtered to obtain target Compound 1-1 (127 g, 81%).

Preparation of Compound 1-2

After dissolving Compound 1-1-bromopyridine (00 g, 366.13 mmol, 1 eq.) in 1,4-dioxane/H$_2$O, 2-(4,4,5,5-tetramethyl-1,3,2-dioxaborolan-2-yl)aniline (96.2 g, 439.35 mmol, 1.2 eq.), Pd(PPh$_3$)$_4$ (21 g, 18.31 mmol, 0.05 eq.) and K$_2$CO$_3$ (151.8 g, 1098.4 mmol, 3 eq.) were added thereto, and the result was stirred for 4 hours at 100° C. After the reaction was finished, the result was cooled to room temperature, and extracted with distilled water and ethyl acetate (EA). The organic layer was dried with MgSO₄, and then filtered and concentrated. The concentrated residue was purified by column chromatography using ethyl acetate and hexane as a developing solvent to obtain target Compound 1-2 (92 g, 88%).

Preparation of Compound 1-3

After dissolving Compound 1-2 (92 g, 322.41 mmol, 1 eq.) in tetrahydrofuran (THF), triethanolamine (TEA) (135 ml, 967.23 mmol, 3 eq.) and 4-bromobenzoyl chloride (20.78 g, 81.85 mmol, 1.5 eq.) were added thereto at 0° C., and the result was stirred for 1 hour at room temperature. After the reaction was finished, the result was extracted with distilled water and EA. The organic layer was dried with MgSO₄, and then filtered and concentrated. The concentrated residue was purified by column chromatography using ethyl acetate and hexane as a developing solvent to obtain target Compound 1-3 (122 g, 81%).

Preparation of Compound 1-4

After dissolving Compound 1-3 (122.3 g, 261.13 mmol, 1 eq.) in nitrobenzene, POCl₃ (36.5 mL, 391.7 mmol, 1.5 eq.) was added thereto, and the result was stirred for 6 hours at 150° C. After the reaction was finished, the result was neutralized at room temperature, and then extracted with distilled water and dichloromethane. The organic layer was dried with MgSO₄, and then filtered and concentrated. The concentrated residue was stirred with ethyl acetate, and then filtered to obtain target Compound 1-4 (75.2 g, 64%).

Preparation of Compound 1-5

After dissolving Compound 1-4 (10 g, 22.2 mmol) in 1,4-dioxane, bis(pinacolato)diboron, Pd(dppf)Cl₂ and potassium acetate were added thereto, and the result was stirred for 2 hours at 110° C. After the reaction was completed, the result was extracted with distilled water and EA. The organic layer was dried with anhydrous MgSO₄, and, after removing the solvent using a rotary evaporator, passed through silica gel to obtain target Compound 1-5 (10.3 g, 93%).

Preparation of Compound 1

After adding 2-(4-bromophenyl)-1,10-phenanthroline (9.4 g, 24.7 mmol), Pd (PPh₃)₄ (1.23 mmol), K₂CO₃ (74.1 mmol) and toluene/EtOH/H₂O to Compound 1-5 (10.3 g, 20.6 mmol), the result was stirred for 6 hours at 110° C. After the reaction was completed, the result was cooled to room temperature, and extracted with distilled water and EA. The organic layer was dried with anhydrous MgSO₄, and, after removing the solvent using a rotary evaporator, purified by column chromatography using dichloromethane and hexane as a developing solvent to obtain target Compound 1 (10.7 g, 83%).

[Preparation Example 2] Preparation of Compound 2

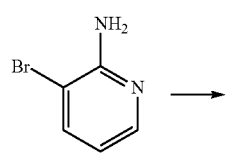

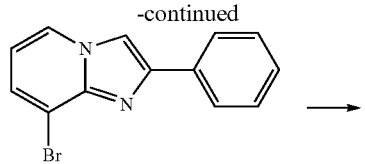

1-1

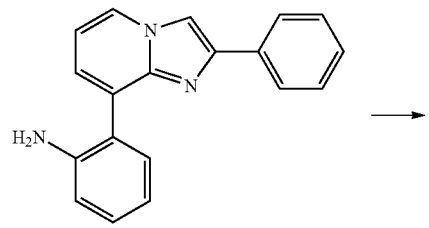

1-2

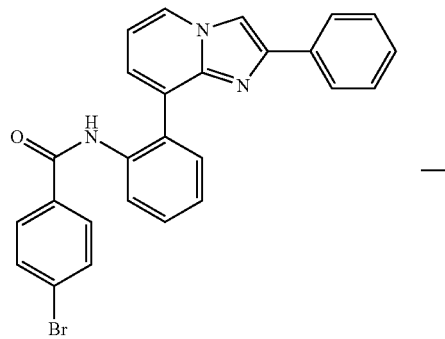

1-3

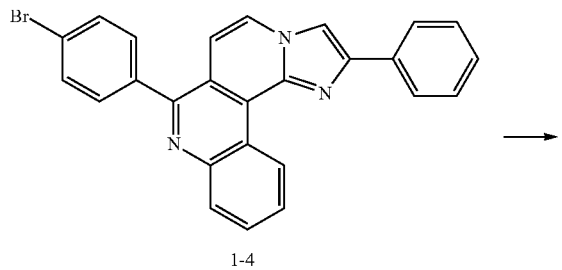

1-4

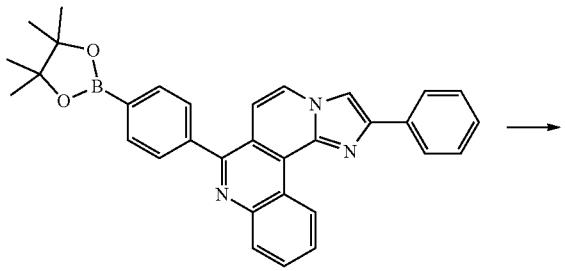

1-5

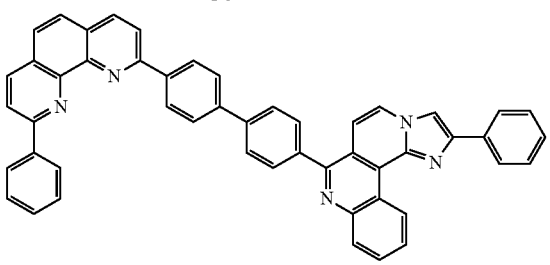

2

Preparation of Compound 2

After adding 2-(4-bromophenyl)-9-phenyl-1,10-phenanthroline (1.2 eq.), Pd(PPh$_3$)$_4$ (0.05 eq.), K$_2$CO$_3$ (3.0 eq.) and toluene/EtOH/H$_2$O to Compound 1-5 (10.0 g, 20.1 mmol), the result was stirred for 6 hours at 110° C. After the reaction was completed, the result was cooled to room temperature, and extracted with distilled water and EA. The organic layer was dried with anhydrous MgSO$_4$, and, after removing the solvent using a rotary evaporator, purified by column chromatography using dichloromethane and hexane as a developing solvent to obtain target Compound 2 (12.2 g, 87%).

[Preparation Example 3] Preparation of Compound 4

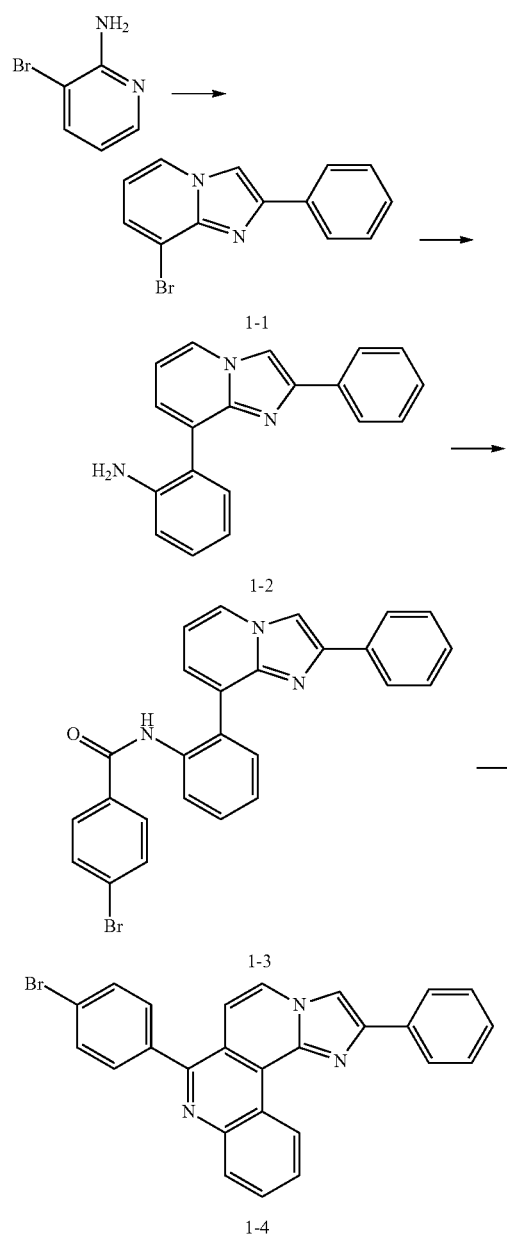

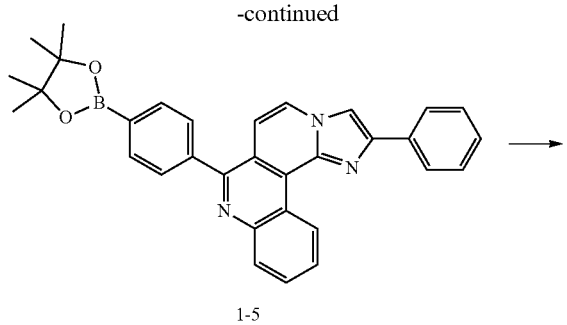

1-5

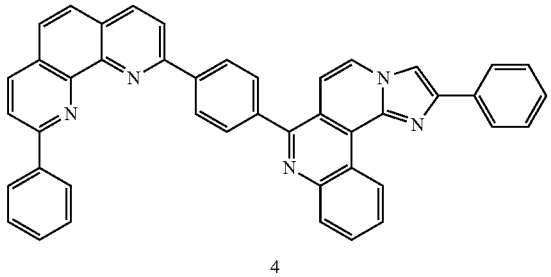 [SMILES: c1ccc(-c2ccc3ccc4ccc(-c5ccc(-c6nc7ccccc7c7c6ccn6cc(-c8ccccc8)nc76)cc5)nc4c3n2)cc1]

4

Preparation of Compound 4

After adding 2-bromo-9-phenyl-1,10-phenanthroline (1.2 eq.), Pd(PPh$_3$)$_4$ (0.05 eq.), K$_2$CO$_3$ (3.0 eq.) and toluene/EtOH/H$_2$O to Compound 1-5 (10.0 g, 20.1 mmol), the result was stirred for 6 hours at 110° C. After the reaction was completed, the result was cooled to room temperature, and extracted with distilled water and EA. The organic layer was dried with anhydrous MgSO$_4$, and, after removing the solvent using a rotary evaporator, purified by column chromatography using dichloromethane and hexane as a developing solvent to obtain target Compound 4 (10.7 g, 85%).

[Preparation Example 4] Preparation of Compound 13

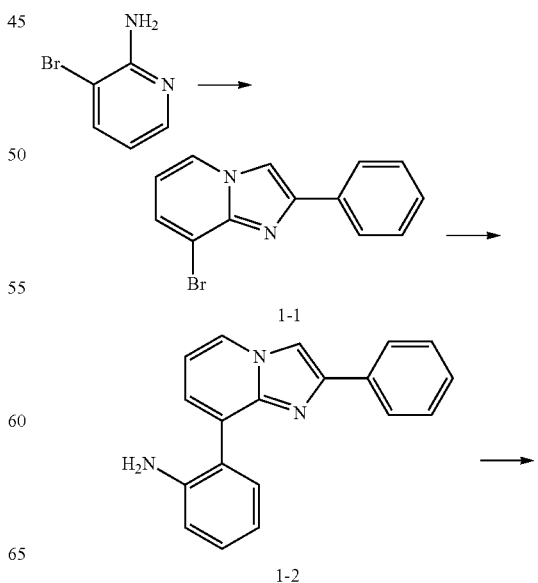

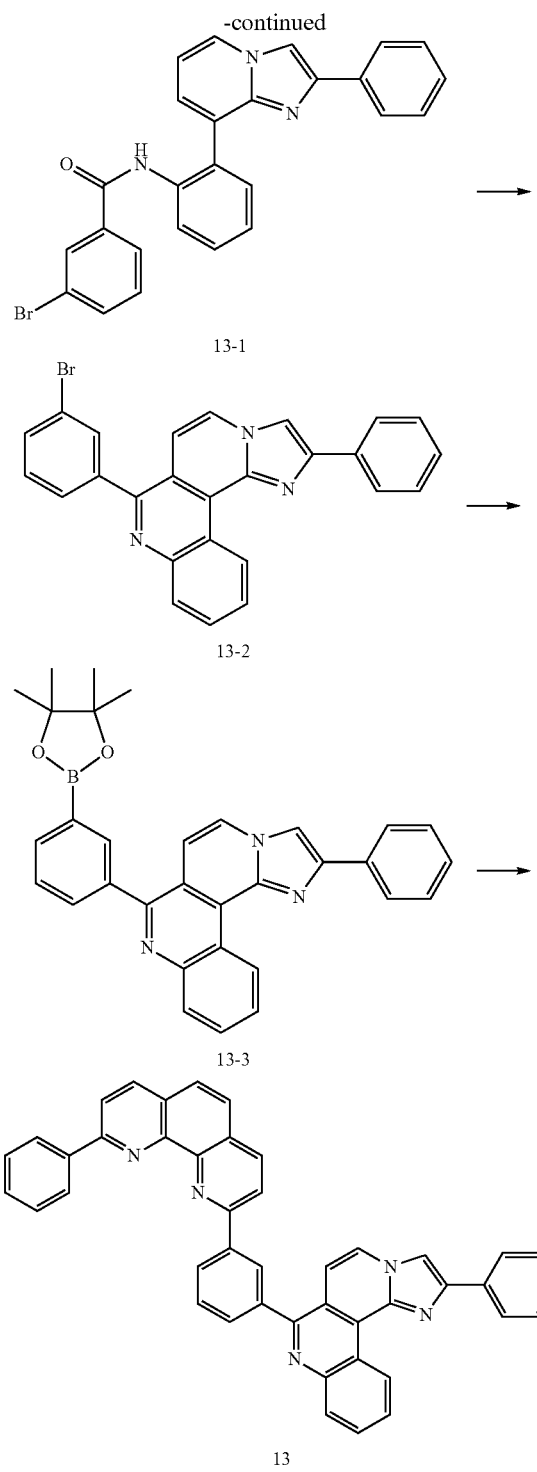

13-1

13-2

13-3

13

Preparation of Compound 13-1

After dissolving Compound 1-2 (20 g, 70.1 mmol, 1 eq.) in tetrahydrofuran (THF), TEA (3 eq.) and 3-bromobenzoyl chloride (1.5 eq.) were added thereto at 0° C., and the result was stirred for 1 hour at room temperature. After the reaction was finished, the result was extracted with distilled water and EA. The organic layer was dried with MgSO$_4$, and then filtered and concentrated. The concentrated residue was purified by column chromatography using ethyl acetate and hexane as a developing solvent to obtain target Compound 13-1 (27.6 g, 84%).

Preparation of Compound 13-2

After dissolving Compound 13-1 (27.6 g, 58.8 mmol, 1 eq.) in nitrobenzene, POCl$_3$ (1.5 eq.) was added thereto, and the result was stirred for 6 hours at 150° C. After the reaction was finished, the result was neutralized at room temperature, and then extracted with distilled water and dichloromethane. The organic layer was dried with MgSO$_4$, and then filtered and concentrated. The concentrated residue was stirred with ethyl acetate, and then filtered to obtain target Compound 13-2 (17.7 g, 67%).

Preparation of Compound 13-3

After dissolving Compound 13-2 (17.7 g, 39.4 mmol) in 1,4-dioxane, bis(pinacolato)diboron, Pd(dppf)Cl$_2$ and potassium acetate were added thereto, and the result was stirred for 2 hours at 110° C. After the reaction was completed, the result was extracted with distilled water and EA. The organic layer was dried with anhydrous MgSO$_4$, and, after removing the solvent using a rotary evaporator, passed through silica gel to obtain target Compound 13-3 (18.8 g, 96%).

Preparation of Compound 13

After adding 2-bromo-9-phenyl-1,10-phenanthroline (1.2 eq.), Pd(PPh$_3$)$_4$ (0.05 eq.), K$_2$CO$_3$ (3.0 eq.) and toluene/EtOH/H$_2$O to Compound 13-3 (10 g, 20.1 mmol), the result was stirred for 6 hours at 110° C. After the reaction was completed, the result was cooled to room temperature, and extracted with distilled water and EA. The organic layer was dried with anhydrous MgSO$_4$, and, after removing the solvent using a rotary evaporator, purified by column chromatography using dichloromethane and hexane as a developing solvent to obtain target Compound 13 (9.8 g, 78%).

[Preparation Example 5] Preparation of Compound 28

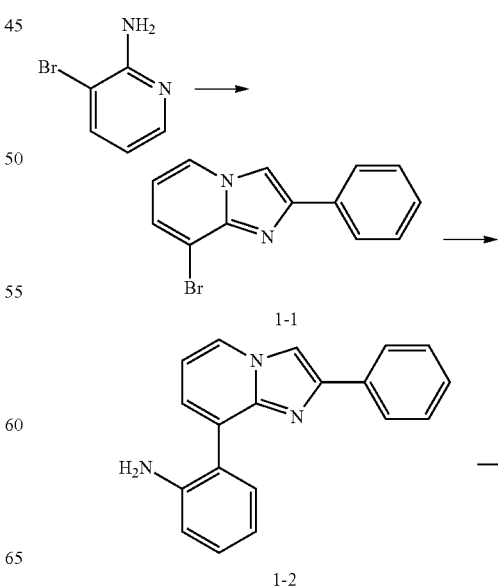

1-1

1-2

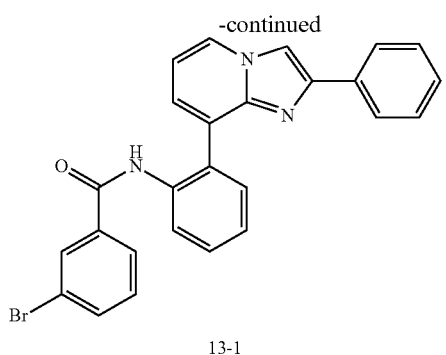

13-1

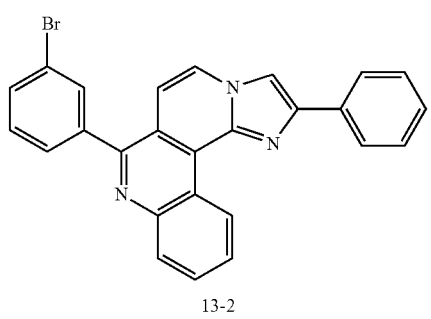

13-2

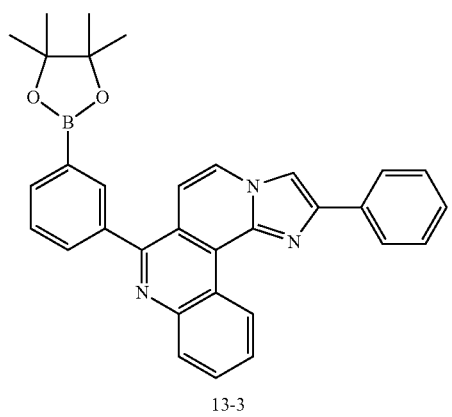

13-3

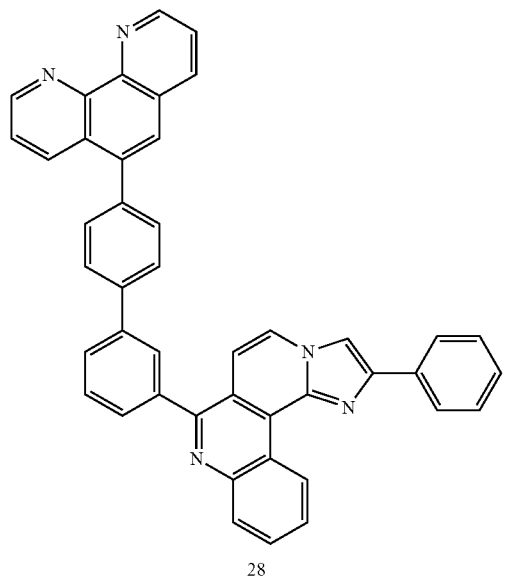 [SMILES: c1ccc(-c2cn3ccc4c(-c5cccc(-c6ccc(-c7cc8cccnc8c8ncccc78)cc6)c5)nc5ccccc5c4c3n2)cc1]

28

Preparation of Compound 28

After adding 5-(4-bromophenyl)-1,10-phenanthroline (1.2 eq.), Pd (PPh$_3$)$_4$ (0.05 eq.), K$_2$CO$_3$ (3.0 eq.) and toluene/EtOH/H$_2$O to Compound 13-3 (10 g, 20.1 mmol), the result was stirred for 6 hours at 110° C. After the reaction was completed, the result was cooled to room temperature, and extracted with distilled water and EA. The organic layer was dried with anhydrous MgSO$_4$, and, after removing the solvent using a rotary evaporator, purified by column chromatography using dichloromethane and hexane as a developing solvent to obtain target Compound 28 (9.1 g, 72%).

[Preparation Example 6] Preparation of Compound 51

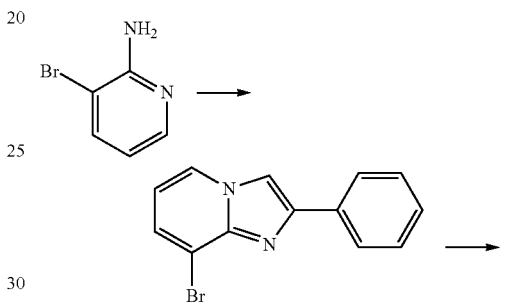

1-1

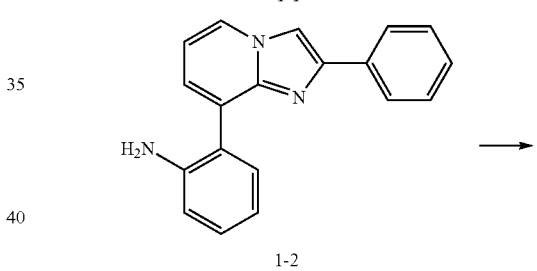

1-2

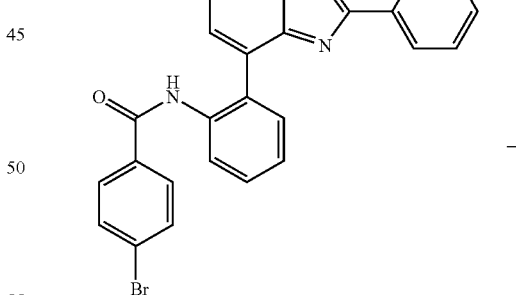

1-3

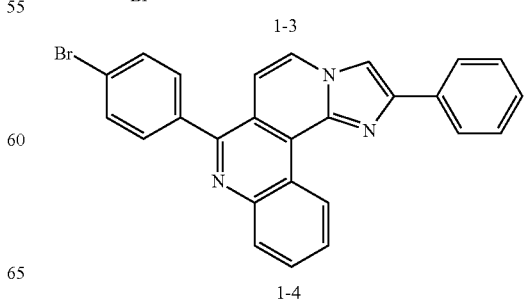

1-4

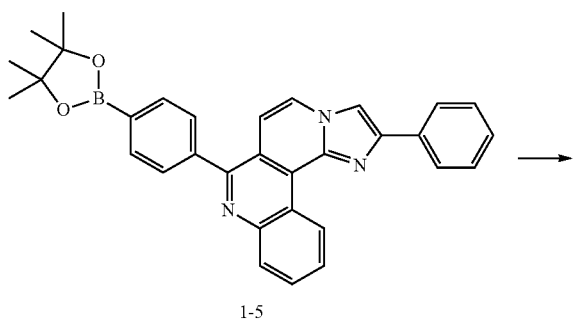

1-5

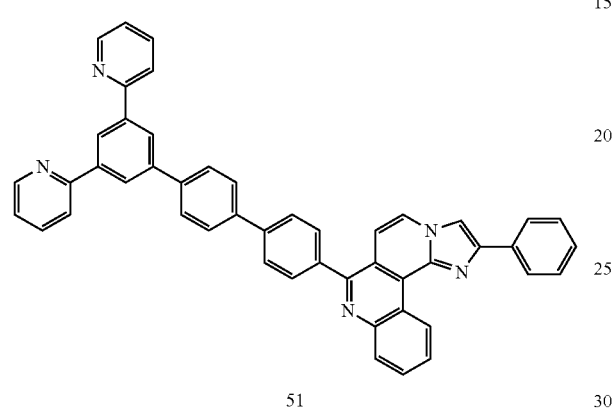

51

Preparation of Compound 51

After adding 2,2'-(4'-bromo-[1,1'-biphenyl]-3,5-diyl)dipyridine (1.2 eq.), Pd(PPh$_3$)$_4$ (0.05 eq.), K$_2$CO$_3$ (3.0 eq.) and toluene/EtOH/H$_2$O to Compound 1-5 (10.0 g, 20.1 mmol), the result was stirred for 6 hours at 110° C. After the reaction was completed, the result was cooled to room temperature, and extracted with distilled water and EA. The organic layer was dried with anhydrous MgSO$_4$, and, after removing the solvent using a rotary evaporator, purified by column chromatography using dichloromethane and hexane as a developing solvent to obtain target Compound 51 (10.7 g, 79%).

[Preparation Example 7] Preparation of Compound 60

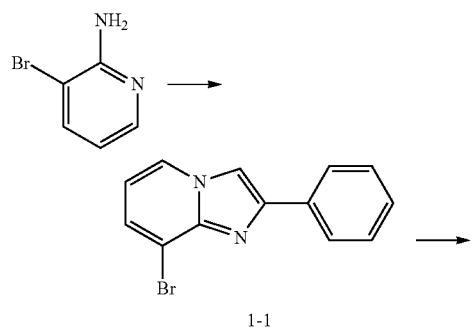

1-1

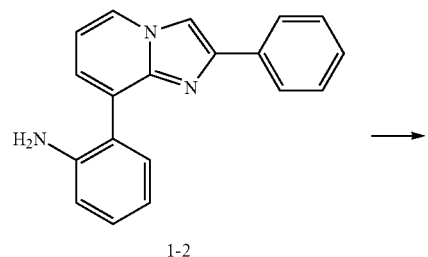

1-2

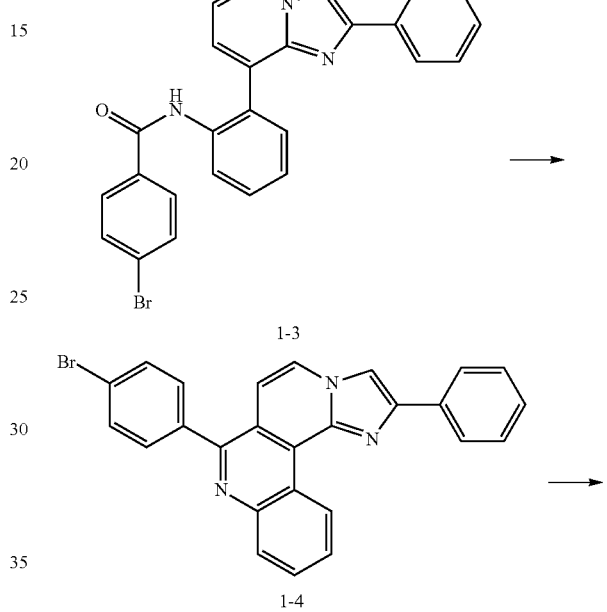

1-3

1-4

1-5

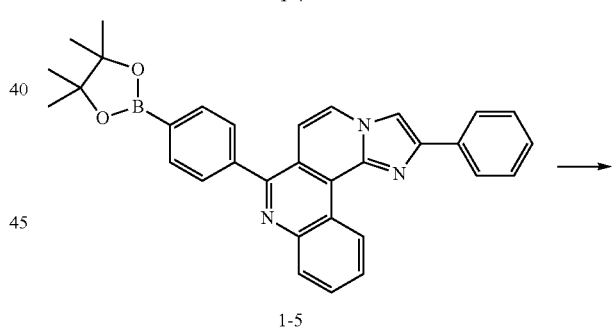

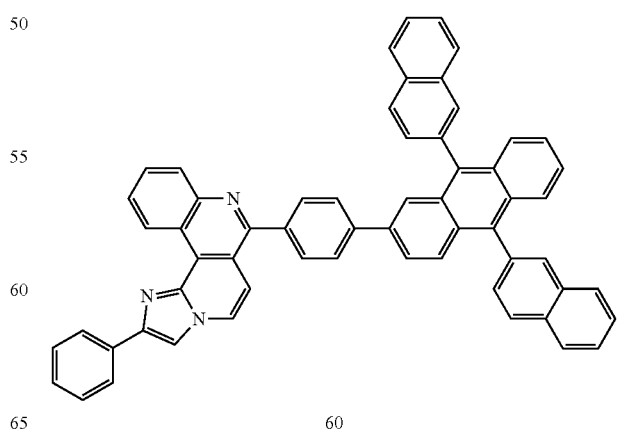

60

Preparation of Compound 60

Target Compound 60 was obtained in the same manner as in Preparation of Compound 51 of Preparation Example 6 except that 2-bromo-9,10-di(naphthalen-2-yl)anthracene was used instead of 2,2'-(4'-bromo-[1,1'-biphenyl]-3,5-diyl) dipyridine.

[Preparation Example 8] Preparation of Compound 62

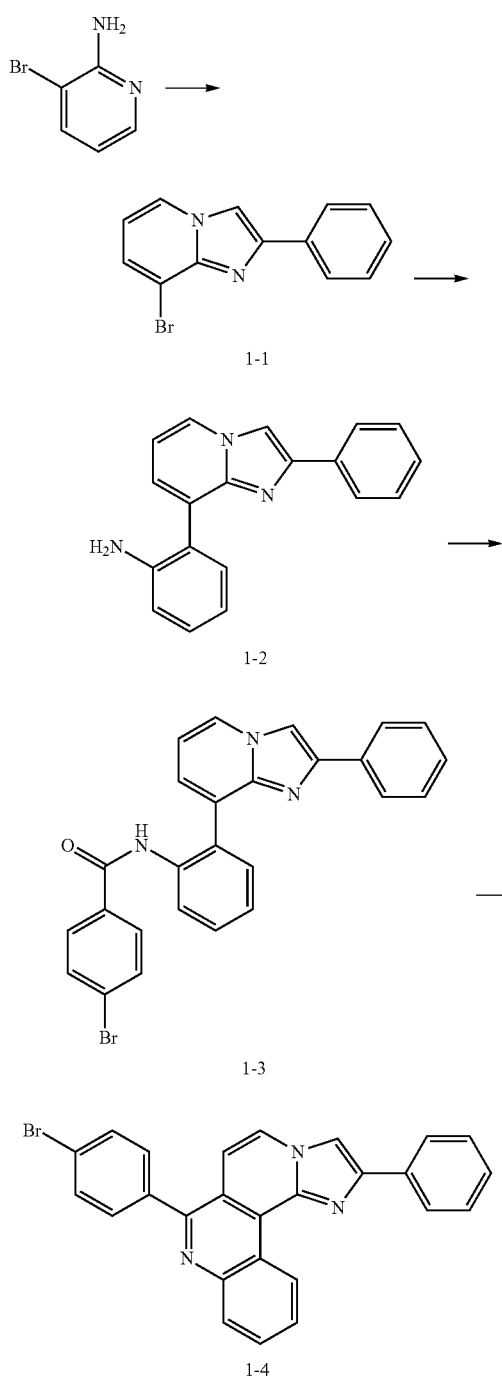

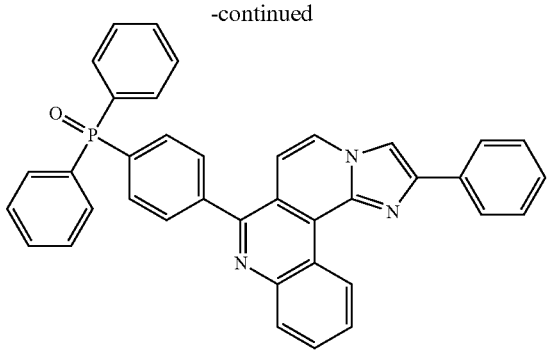

Preparation of Compound 62

After dissolving Compound 1-4 (8 g, 17.764 mmol, 1 eq.) in benzonitrile, NiCl$_2$ (1.38 g, 10.66 mmol, 0.6 eq.) was added thereto, the result was stirred for 1 hour at 180° C., and after introducing ethoxyphenylphosphine (23 mL, 106.59 mmol, 6 eq.) thereto, the result was stirred for 1 hour at 180° C. After the reaction was finished, the layer was separated using distilled water and EA, and the organic layer was dried with MgSO$_4$, and then filtered and concentrated. The result was purified by column chromatography using dichloromethane and hexane as a developing solvent to obtain target Compound 62 (2.6 g, 26%).

[Preparation Example 9] Preparation of Compound 63

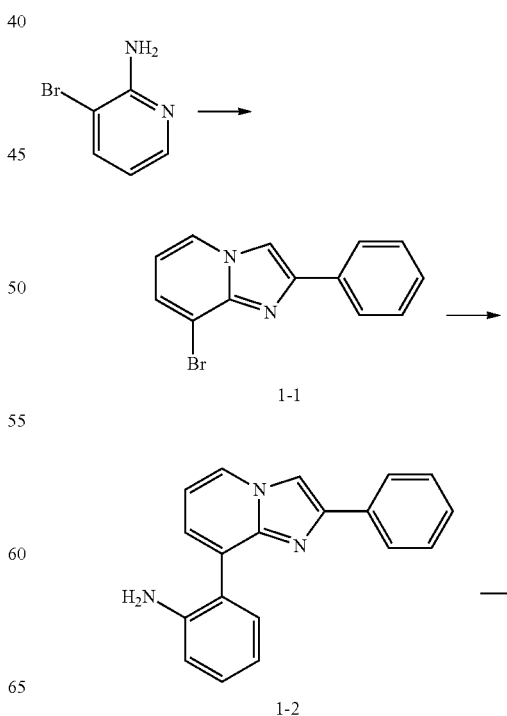

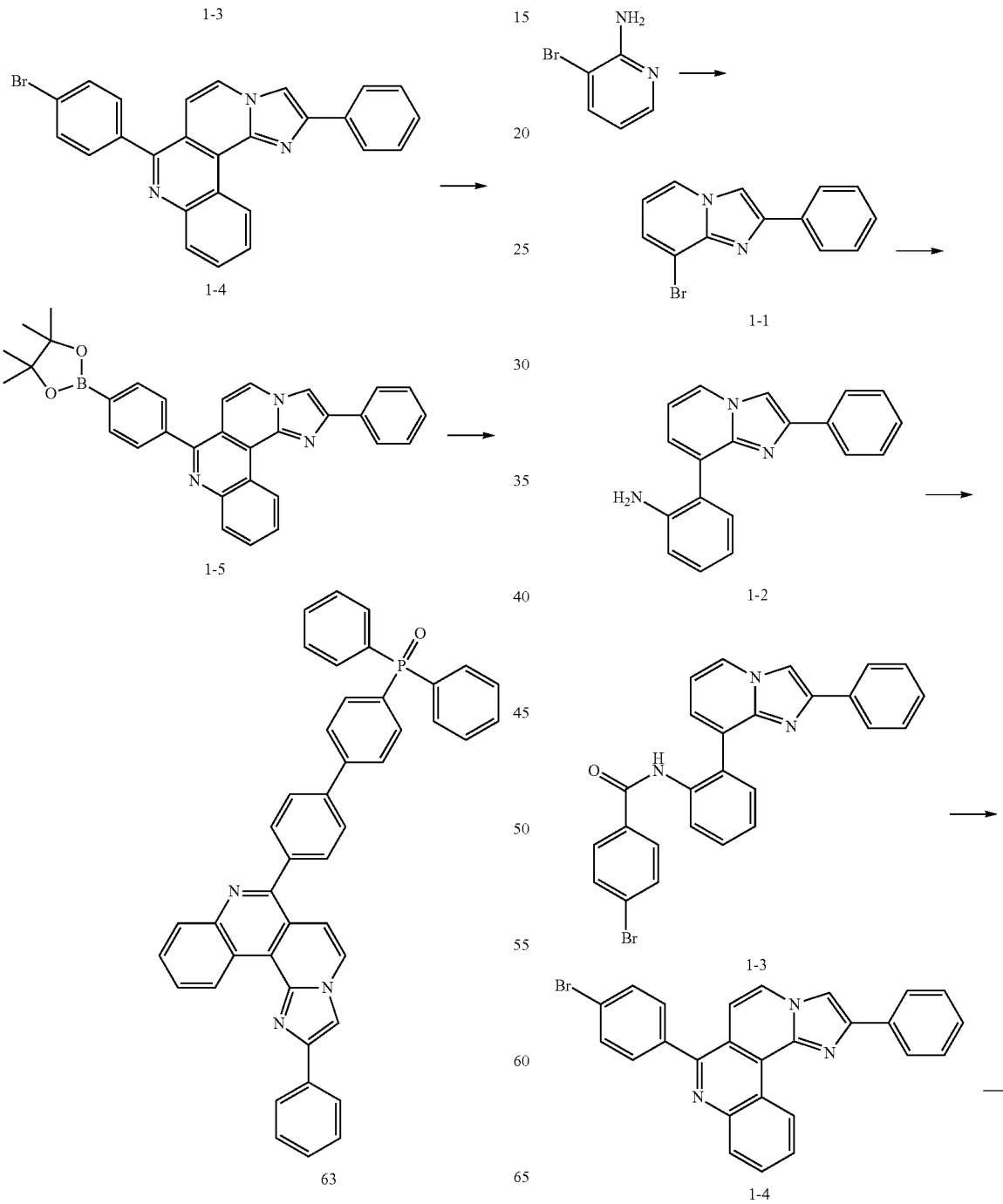
Preparation of Compound 63
Target Compound 63 was obtained in the same manner as in Preparation of Compound 51 of Preparation Example 6 except that (4-bromophenyl)diphenylphosphine oxide was used instead of 2,2'-(4'-bromo-[1,1'-biphenyl]-3,5-diyl)dipyridine).
[Preparation Example 10] Preparation of Compound 65

123
-continued
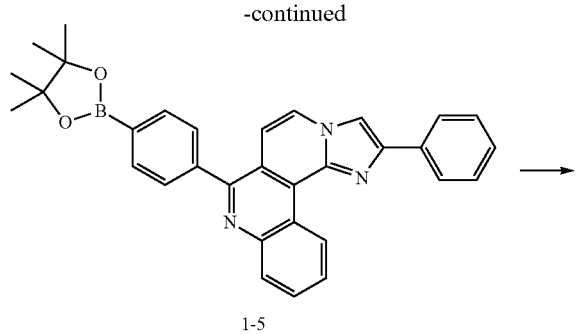
1-5
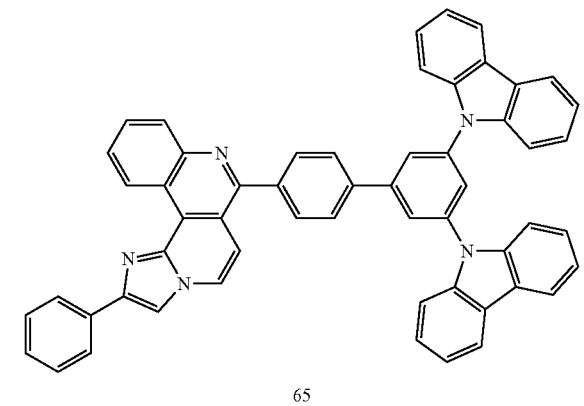 [SMILES: c1ccc(-c2cn3ccc4c(-c5ccc(-c6cc(-n7c8ccccc8c8ccccc87)cc(-n7c8ccccc8c8ccccc87)c6)cc5)nc5ccccc5c4c3n2)cc1]
65
Preparation of Compound 65
Target Compound 65 was obtained in the same manner as in Preparation of Compound 51 of Preparation Example 6 except that 9,9'-(5-bromo-1,3-phenylene)bis(9H-carbazole) was used instead of 2,2'-(4'-bromo-[1,1'-biphenyl]-3,5-diyl)dipyridine.
[Preparation Example 11] Preparation of Compound 66
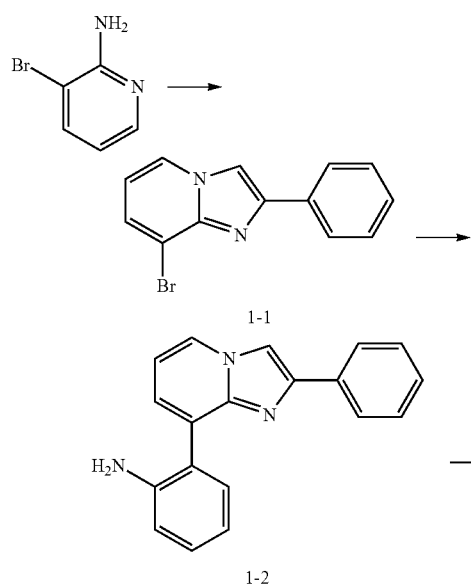
124
-continued
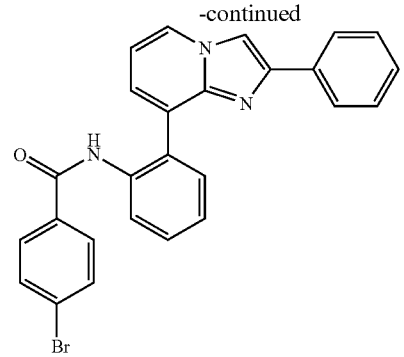
1-3
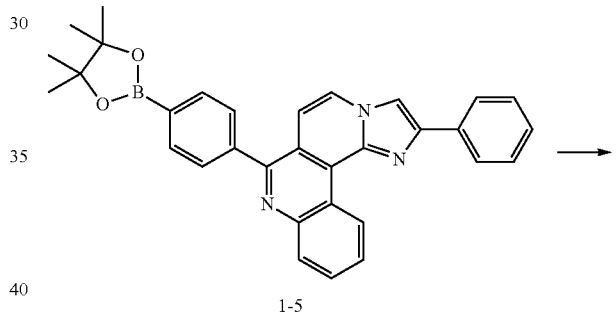
1-4
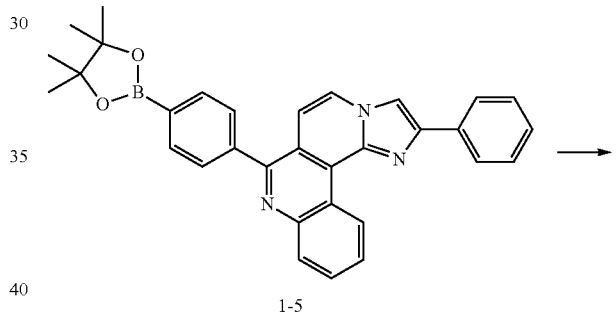
1-5
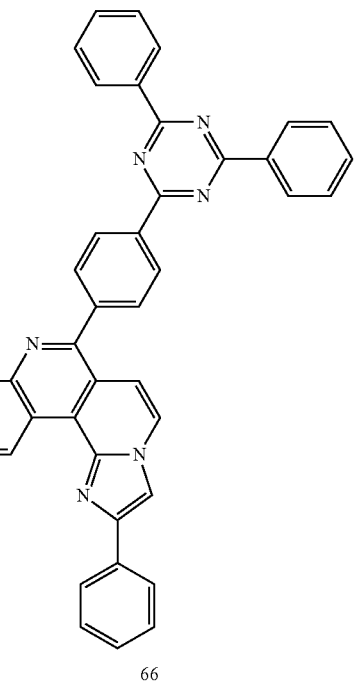
66

125

Preparation of Compound 66

Target Compound 66 was obtained in the same manner as in Preparation of Compound 51 of Preparation Example 6 except that 2-bromo-4,6-diphenyl-1,3,5-triazine was used instead of 2,2'-(4'-bromo-[1,1'-biphenyl]-3,5-diyl)dipyridine.

[Preparation Example 12] Preparation of Compound 79

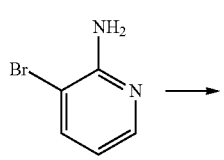

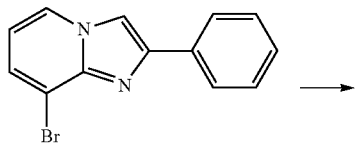

1-1

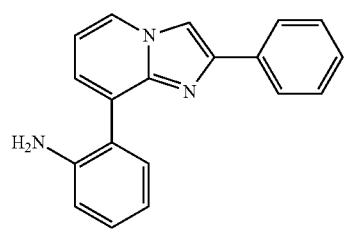

1-2

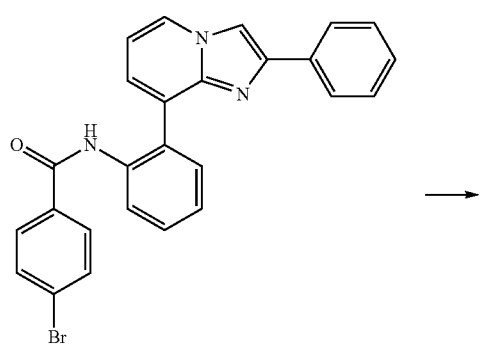

1-3

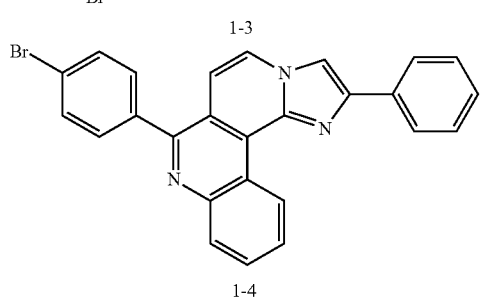

1-4

126

-continued

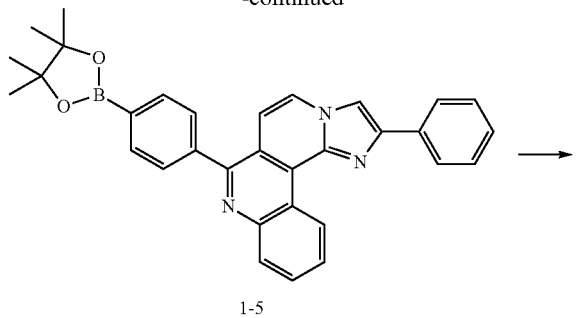

1-5

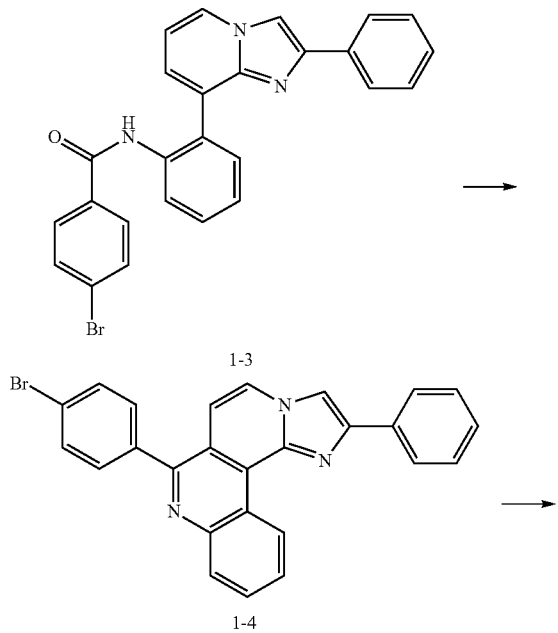

79

Preparation of Compound 79

Target Compound 79 was obtained in the same manner as in Preparation of Compound 51 of Preparation Example 6 except that 4-bromo-2,6-diphenylpyrimidine was used instead of 2,2'-(4'-bromo-[1,1'-biphenyl]-3,5-diyl)dipyridine.

[Preparation Example 13] Preparation of Compound 95

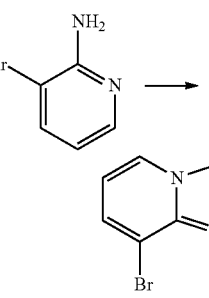

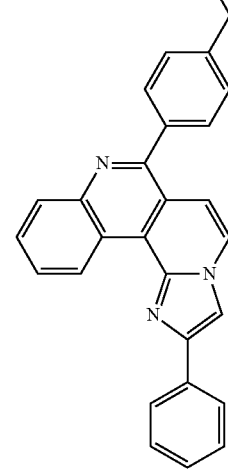

1-1

127
-continued
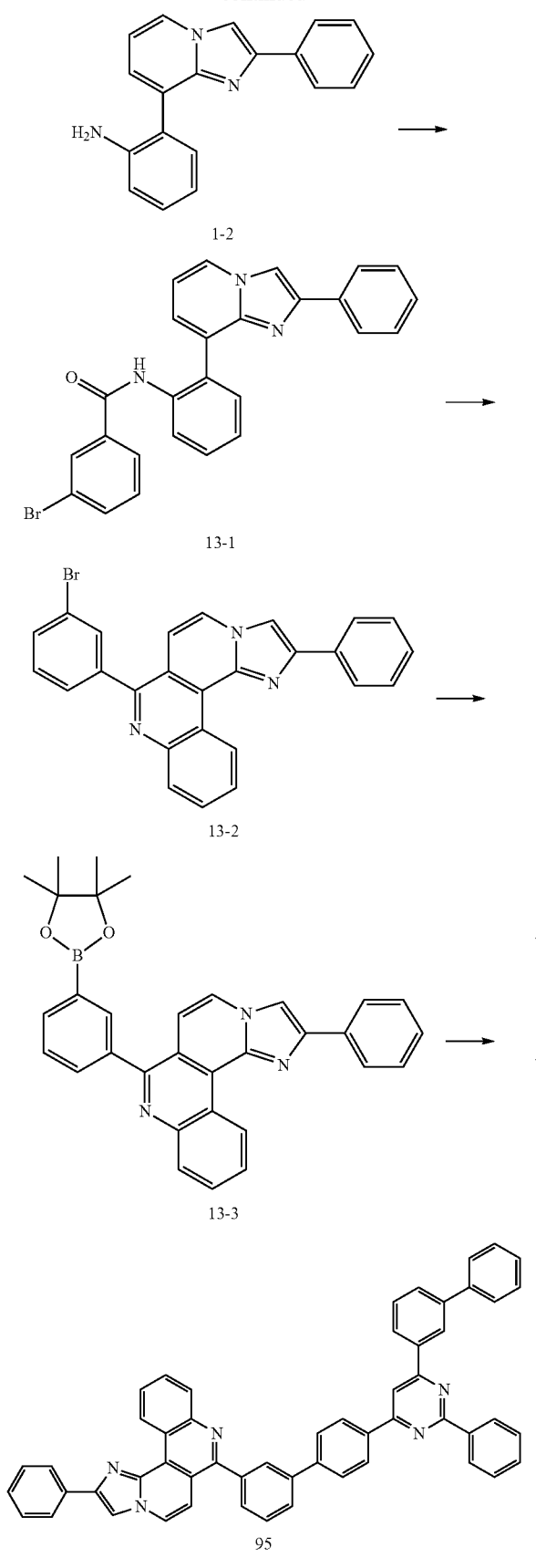
128
Preparation of Compound 95
Target Compound 95 was obtained in the same manner as in Preparation of Compound 28 of Preparation Example 5 except that 4-([1,1'-biphenyl]-3-yl)-6-(4-bromophenyl)-2-phenylpyrimidine was used instead of 5-(4-bromophenyl)-1,10-phenanthroline.
[Preparation Example 14] Preparation of Compound 115
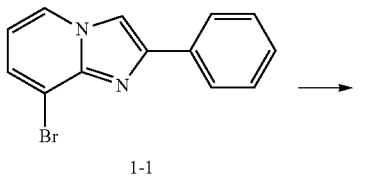
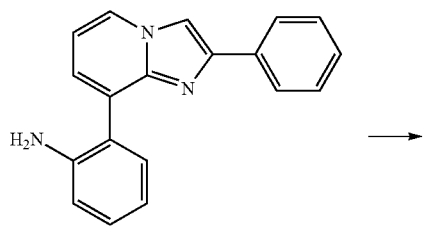
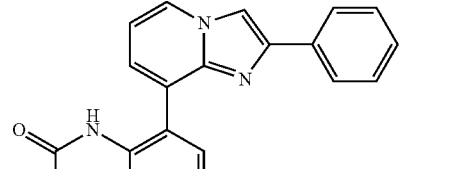
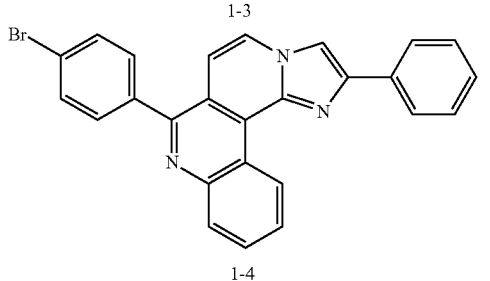

-continued
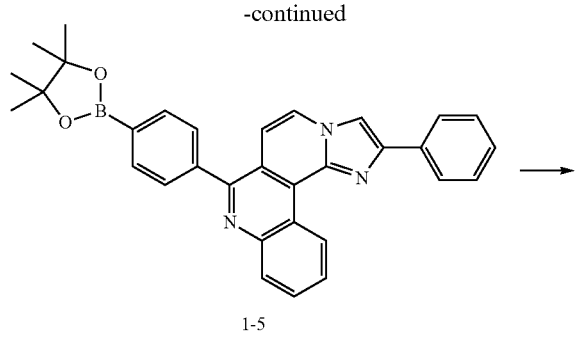
1-5
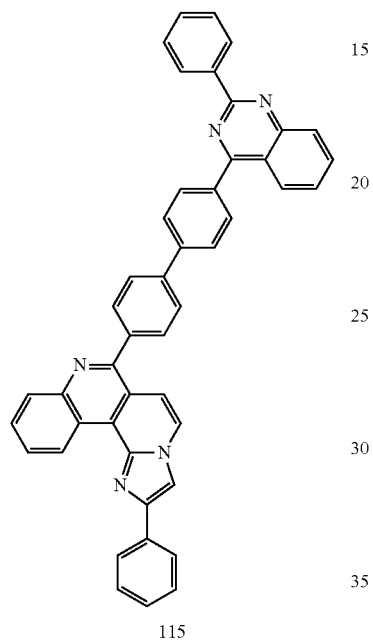
115
Preparation of Compound 115
Target Compound 115 was obtained in the same manner as in Preparation of Compound 51 of Preparation Example 6 except that 4-(4-bromophenyl)-2-phenylquinazoline was used instead of 2,2'-(4'-bromo-[1,1'-biphenyl]-3,5-diyl)dipyridine.
[Preparation Example 15] Preparation of Compound 120
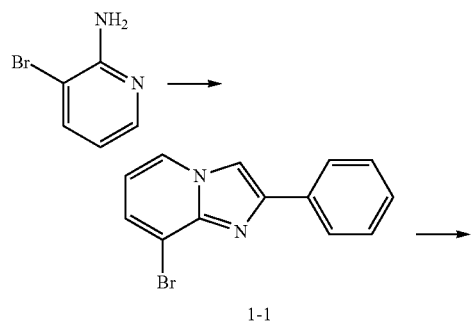
1-1
-continued
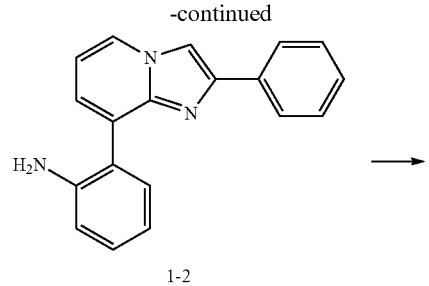
1-2
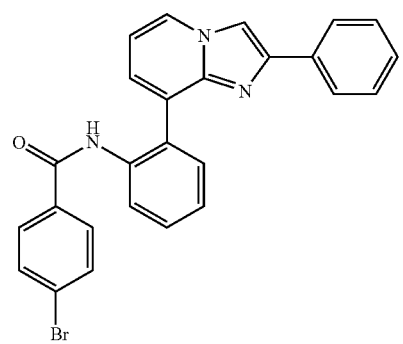
1-3
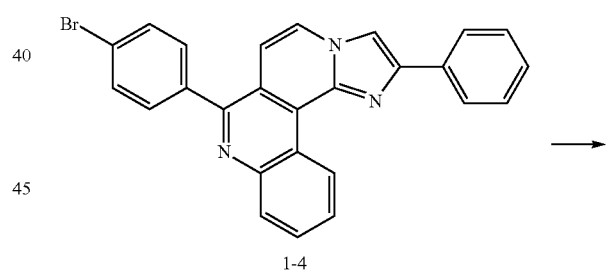
1-4
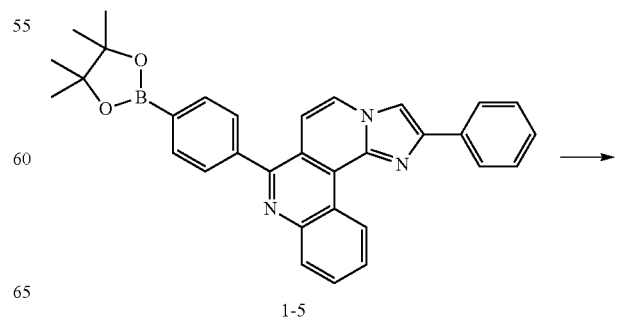
1-5

131
-continued
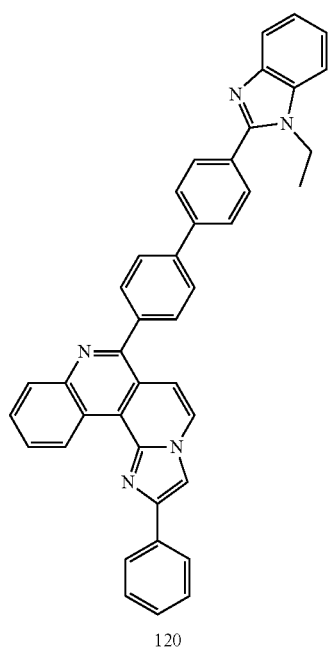 [SMILES: CCn1c(-c2ccc(-c3ccc(-c4nc5ccccc5c5c4ccn4cc(-c6ccccc6)nc54)cc3)cc2)nc2ccccc21]
120
Preparation of Compound 120
Target Compound 120 was obtained in the same manner as in Preparation of Compound 51 of Preparation Example 6 except that 2-(4-bromophenyl)-1-ethyl-1H-benzo[d]imidazole was used instead of 2,2'-(4'-bromo-[1,1'-biphenyl]-3,5-diyl)dipyridine.
[Preparation Example 16] Preparation of Compound 139
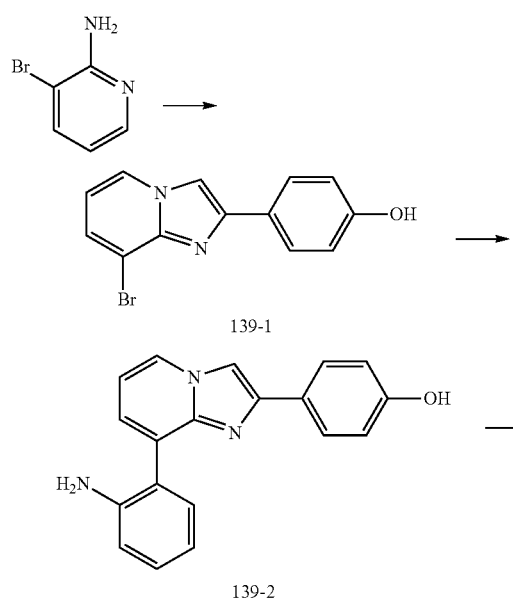
132
-continued
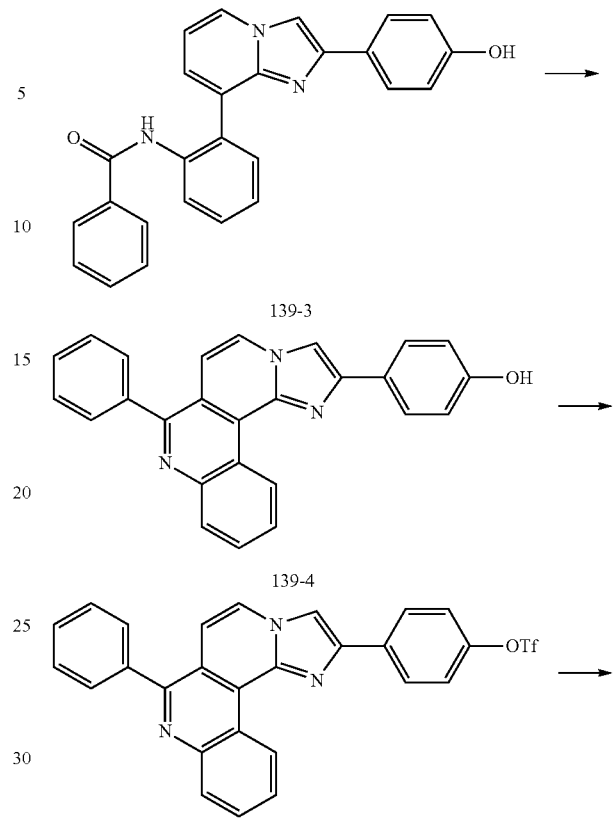
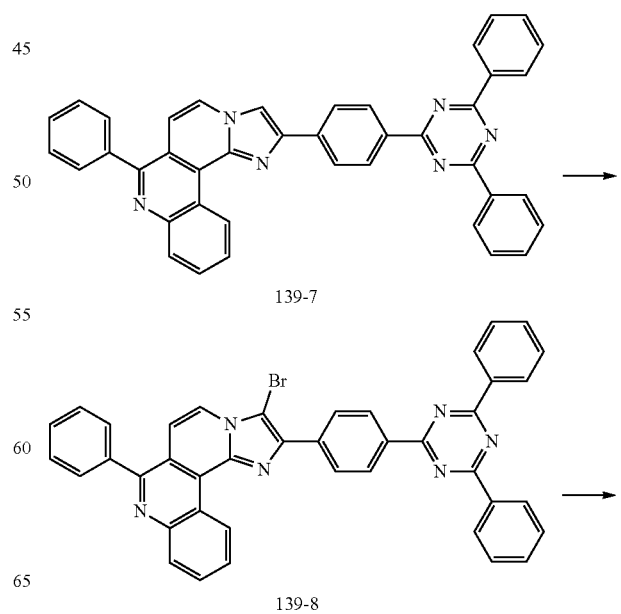

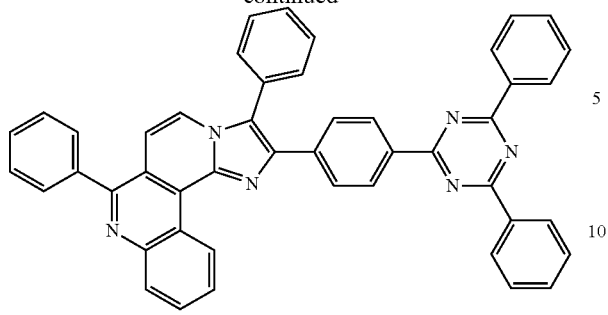

139

Preparation of Compound 139-1

After dissolving 2-amino-3-bromopyridine (1 eq.) in EtOH, 4-hydroxyphenacyl bromide (1.2 eq.) was added thereto, and the result was stirred under reflux. After the reaction was finished, the result was cooled to room temperature, and produced solids were filtered to obtain target Compound 139-1.

Preparation of Compound 139-2

After dissolving Compound 139-1 (1 eq.) in 1,4-dioxane/$H_2O$, 2-(4,4,5,5-tetramethyl-1,3,2-dioxaborolan-2-yl)aniline (1.2 eq.), $Pd(PPh_3)_4$ (0.05 eq.) and $K_2CO_3$ (3 eq.) were added thereto, and the result was stirred for 4 hours at 100° C. After the reaction was finished, the result was cooled to room temperature, and extracted with distilled water and EA. The organic layer was dried with $MgSO_4$, and then filtered and concentrated. The concentrated residue was purified by column chromatography using ethyl acetate and hexane as a developing solvent to obtain target Compound 139-2.

Preparation of Compound 139-3

After dissolving Compound 139-2 (1 eq.) in THF, TEA (3 eq.) and benzoyl chloride (1.5 eq.) were added thereto at 0° C., and the result was stirred for 1 hour at room temperature. After the reaction was finished, the result was extracted with distilled water and EA. The organic layer was dried with $MgSO_4$, and then filtered and concentrated. The concentrated residue was purified by column chromatography using ethyl acetate and hexane as a developing solvent to obtain target Compound 139-3.

Preparation of Compound 139-4

After dissolving Compound 139-3 (1 eq.) in nitrobenzene, $POCl_3$ (1.5 eq.) was added thereto, and the result was stirred for 6 hours at 150° C. After the reaction was finished, the result was neutralized at room temperature, and then extracted with distilled water and dichloromethane. The organic layer was dried with $MgSO_4$, and then filtered and concentrated. The concentrated residue was stirred with ethyl acetate, and then filtered to obtain target Compound 139-4.

Preparation of Compound 139-5

After dissolving Compound 139-4 (14.0 g, 37.7 mmol) in dichloromethane, pyridine (1.5 eq.) was added thereto, and then triflic anhydride was added dropwise thereto at 0° C. After that, the result was stirred for 5 hours at room temperature. After the reaction was completed, the reaction solution was passed through silica, and, after removing the solvent of the filtrate using a rotary evaporator, purified by column chromatography using dichloromethane and methanol as a developing solvent to obtain target Compound 139-5.

Preparation of Compound 139-6

After dissolving Compound 139-5 (1 eq.) in 1,4-dioxane, bis(pinacolato)diboron, $Pd(dppf)Cl_2$ and potassium acetate were added thereto, and the result was stirred for 2 hours at 110° C. After the reaction was completed, the result was extracted with distilled water and EA. The organic layer was dried with anhydrous $MgSO_4$, and, after removing the solvent using a rotary evaporator, passed through silica gel to obtain target Compound 139-6.

Preparation of Compound 139-7

After adding 2-bromo-4,6-diphenyl-1,3,5-triazine (1.2 eq.), $Pd(PPh_3)_4$ (0.05 eq.), $K_2CO_3$ (3.0 eq.) and toluene/EtOH/$H_2O$ to Compound 139-6 (1 eq.), the result was stirred for 6 hours at 110° C. After the reaction was completed, the result was cooled to room temperature, and extracted with distilled water and EA. The organic layer was dried with anhydrous $MgSO_4$, and, after removing the solvent using a rotary evaporator, purified by column chromatography using dichloromethane and hexane as a developing solvent to obtain target Compound 139-7.

Preparation of Compound 139-8

After dissolving Compound 139-7 (1 eq.) in ACN, N-bromosuccimide (1 eq.) was added thereto, and the result was stirred for 1 hour at room temperature. After the reaction was finished, produced solids were washed with ACN, and target Compound 139-8 was obtained.

Preparation of Compound 139

After adding phenylboronic acid (1.2 eq.), $Pd(PPh_3)_4$ (0.05 eq.), $K_2CO_3$ (3.0 eq.) and toluene/EtOH/$H_2O$ to Compound 139-8 (1 eq.), the result was stirred for 6 hours at 110° C. After the reaction was completed, the result was cooled to room temperature, and extracted with distilled water and EA. The organic layer was dried with anhydrous $MgSO_4$, and, after removing the solvent using a rotary evaporator, purified by column chromatography using dichloromethane and hexane as a developing solvent to obtain target Compound 139.

[Preparation Example 17] Preparation of Compound 142

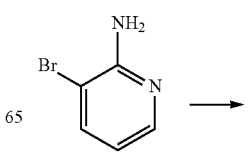

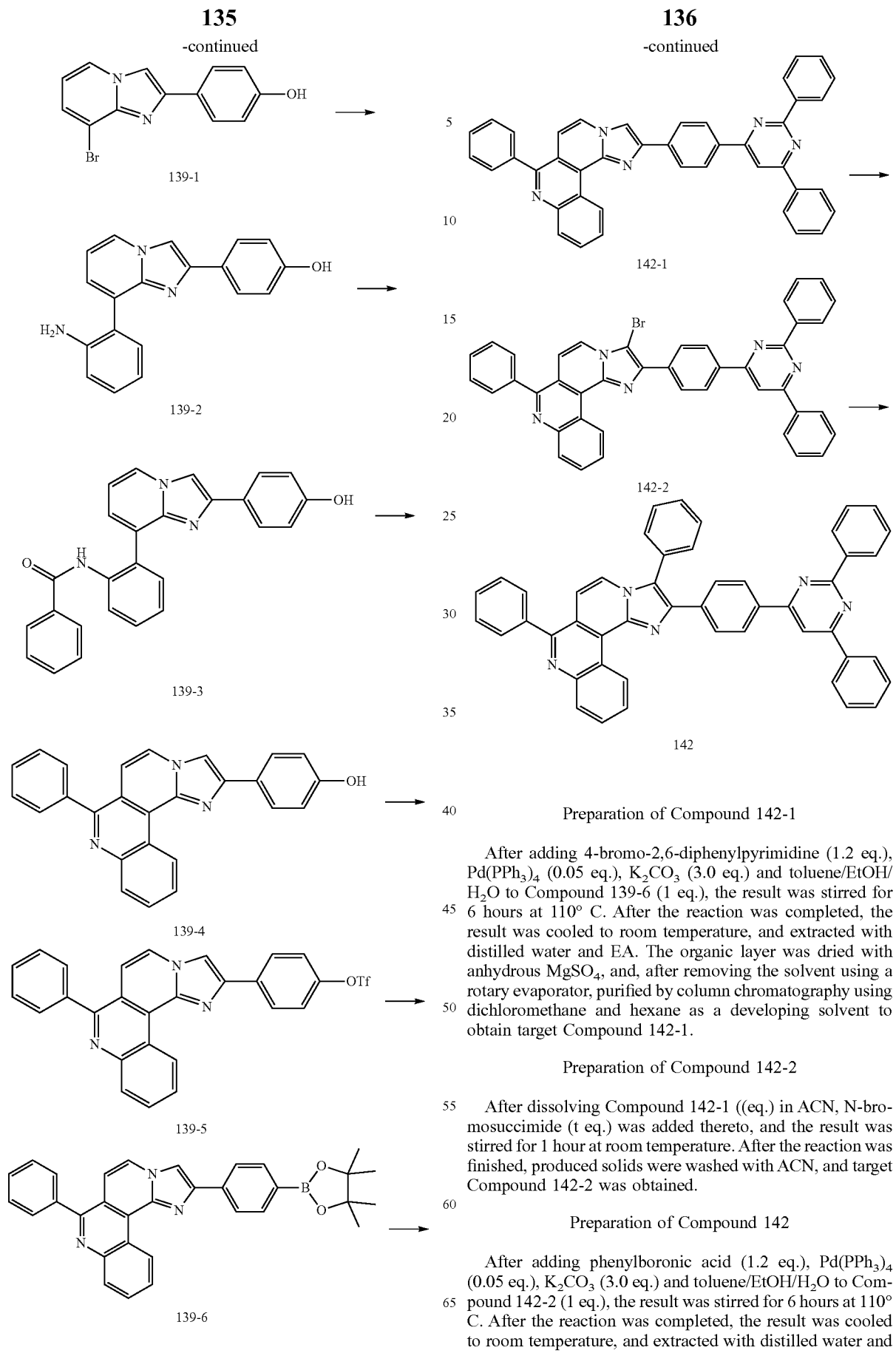

Preparation of Compound 142-1

After adding 4-bromo-2,6-diphenylpyrimidine (1.2 eq.), Pd(PPh$_3$)$_4$ (0.05 eq.), K$_2$CO$_3$ (3.0 eq.) and toluene/EtOH/H$_2$O to Compound 139-6 (1 eq.), the result was stirred for 6 hours at 110° C. After the reaction was completed, the result was cooled to room temperature, and extracted with distilled water and EA. The organic layer was dried with anhydrous MgSO$_4$, and, after removing the solvent using a rotary evaporator, purified by column chromatography using dichloromethane and hexane as a developing solvent to obtain target Compound 142-1.

Preparation of Compound 142-2

After dissolving Compound 142-1 ((eq.) in ACN, N-bromosuccimide (t eq.) was added thereto, and the result was stirred for 1 hour at room temperature. After the reaction was finished, produced solids were washed with ACN, and target Compound 142-2 was obtained.

Preparation of Compound 142

After adding phenylboronic acid (1.2 eq.), Pd(PPh$_3$)$_4$ (0.05 eq.), K$_2$CO$_3$ (3.0 eq.) and toluene/EtOH/H$_2$O to Compound 142-2 (1 eq.), the result was stirred for 6 hours at 110° C. After the reaction was completed, the result was cooled to room temperature, and extracted with distilled water and EA. The organic layer was dried with anhydrous MgSO₄, and, after removing the solvent using a rotary evaporator, purified by column chromatography using dichloromethane and hexane as a developing solvent to obtain target Compound 142.

[Preparation Example 18] Preparation of Compound 147

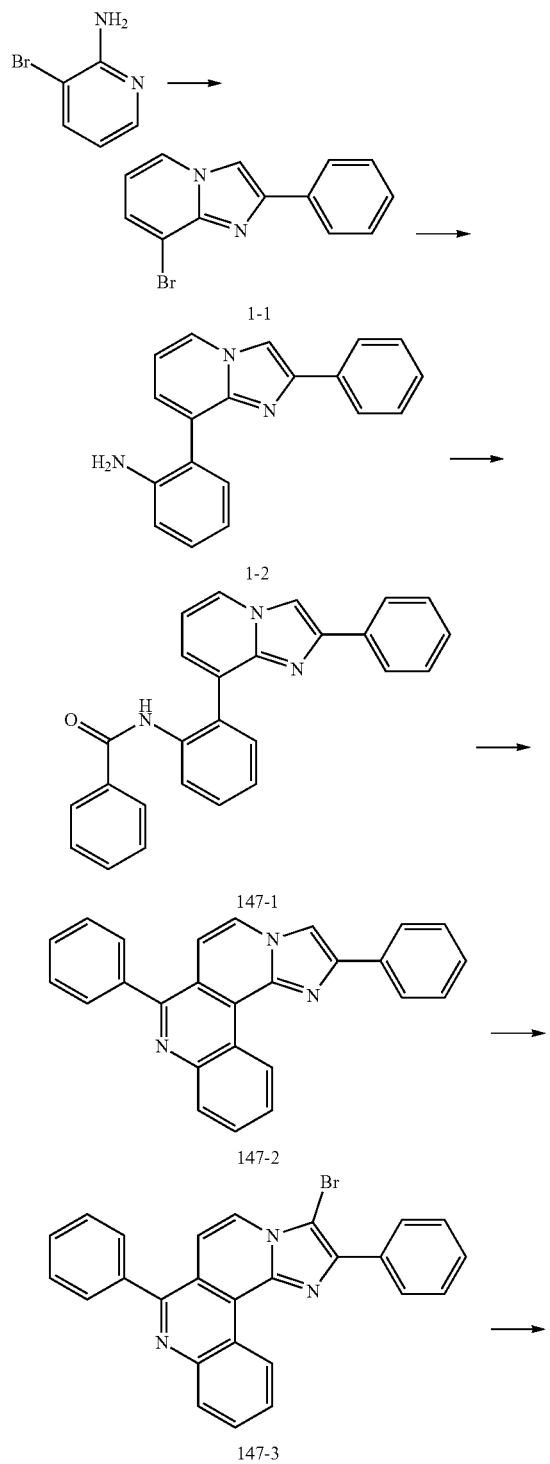

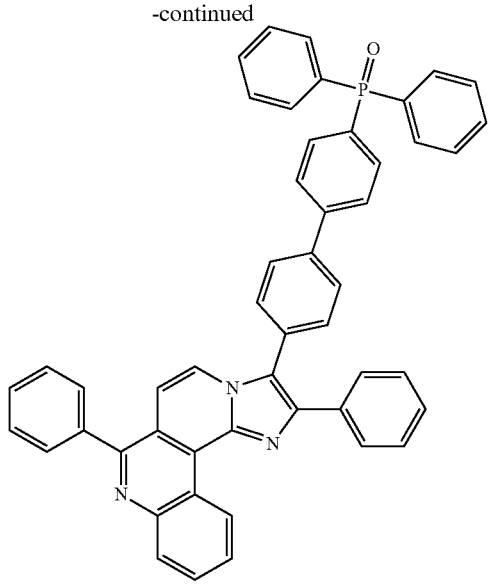

147

Preparation of Compound 147-1

After dissolving Compound 1-2 (20 g, 70.1 mmol, 1 eq.) in THF, TEA (21 ml, 210 mmol, 3 eq.) and bromobenzoyl chloride (14.7 g, 105 mmol, 1.5 eq.) were added thereto at 0° C., and the result was stirred for 1 hour at room temperature. After the reaction was finished, the result was extracted with distilled water and EA. The organic layer was dried with MgSO₄, and then filtered and concentrated. The concentrated residue was purified by column chromatography using ethyl acetate and hexane as a developing solvent to obtain target Compound 147-1 (25.7 g, 94%).

Preparation of Compound 147-2

After dissolving Compound 147-1 (25.7 g, 65.8 mmol, 1 eq.) in nitrobenzene, POCl₃ (15 mL, 98.7 mmol, 1.5 eq.) was added thereto, and the result was stirred for 6 hours at 150° C. After the reaction was finished, the result was neutralized at room temperature, and then extracted with distilled water and dichloromethane. The organic layer was dried with MgSO₄, and then filtered and concentrated. The concentrated residue was stirred with ethyl acetate, and then filtered to obtain target Compound 147-2 (20.5 g, 84%).

Preparation of Compound 147-3

After dissolving Compound 147-2 (20.5 g, 55.2 mmol, 1 eq.) in ACN, N-bromosuccimide (9.8 g, 55.2 mmol, 1 eq.) was added thereto, and the result was stirred for 1 hour at room temperature. After the reaction was finished, produced solids were washed with ACN, and target Compound 147-3 (23 g, 95%) was obtained.

Preparation of Compound 147

After adding diphenyl(4'-(4,4,5,5-tetramethyl-1,3,2-dioxaborolan-2-yl)-[1,1'-biphenyl]-4-yl)phosphine oxide (12.7 g, 26.6 mmol), Pd(PPh₃)₄ (1.11 mmol), K₂CO₃ (66.6 mmol) and toluene/EtOH/H₂O to Compound 147-3 (10 g, 22.2 mmol), the result was stirred for 6 hours at 110° C.

After the reaction was completed, the result was cooled to room temperature, and extracted with distilled water and EA. The organic layer was dried with anhydrous MgSO$_4$, and, after removing the solvent using a rotary evaporator, purified by column chromatography using dichloromethane and hexane as a developing solvent to obtain target Compound 147 (13.1 g, 82%).

[Preparation Example 19] Preparation of Compound 148

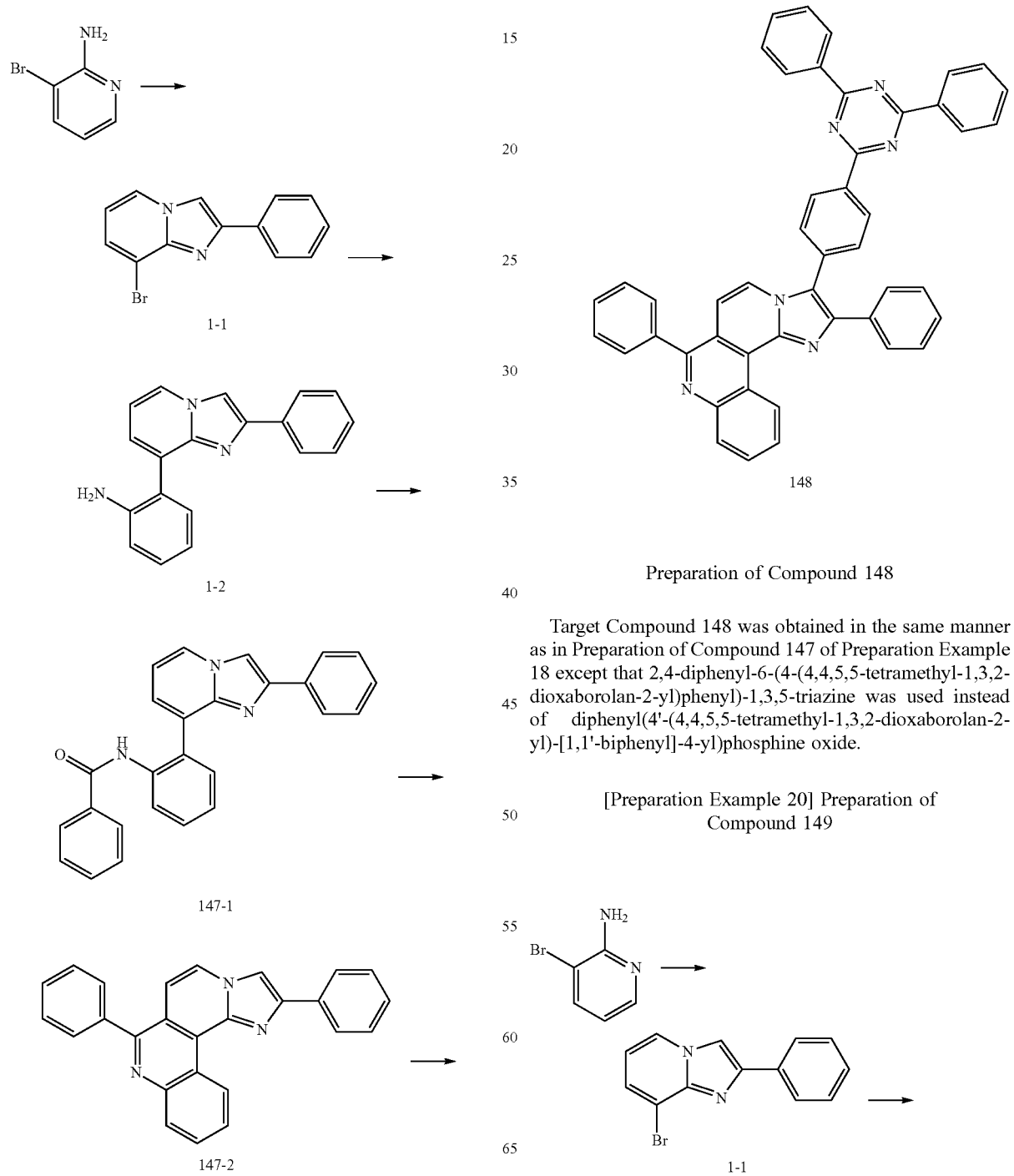

Preparation of Compound 148

Target Compound 148 was obtained in the same manner as in Preparation of Compound 147 of Preparation Example 18 except that 2,4-diphenyl-6-(4-(4,4,5,5-tetramethyl-1,3,2-dioxaborolan-2-yl)phenyl)-1,3,5-triazine was used instead of diphenyl(4'-(4,4,5,5-tetramethyl-1,3,2-dioxaborolan-2-yl)-[1,1'-biphenyl]-4-yl)phosphine oxide.

[Preparation Example 20] Preparation of Compound 149

141
-continued

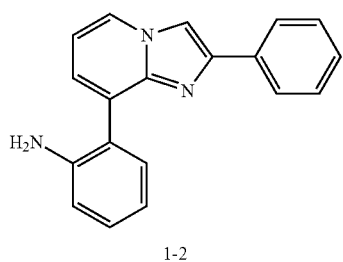
1-2

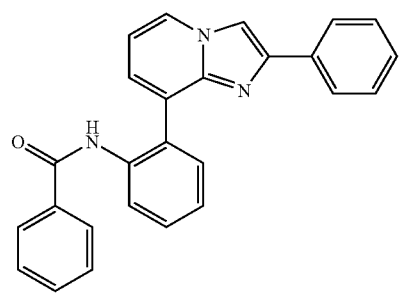
147-1

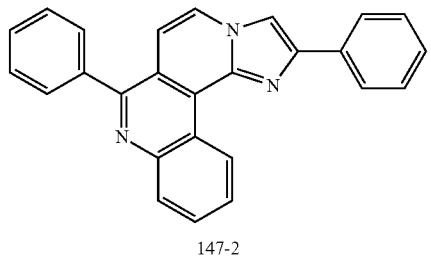
147-2

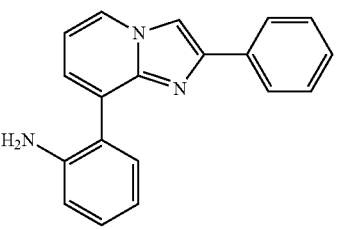
147-3

142
-continued

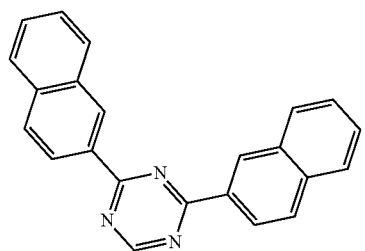
149

Preparation of Compound 149

Target Compound 149 was obtained in the same manner as in Preparation of Compound 147 of Preparation Example 18 except that 2,4-di(naphthalen-2-yl)-6-(4-(4,4,5,5-tetramethyl-1,3,2-dioxaborolan-2-yl)phenyl)-1,3,5-triazine was used instead of diphenyl(4'-(4,4,5,5-tetramethyl-1,3,2-dioxaborolan-2-yl)-[1,1'-biphenyl]-4-yl)phosphine oxide.

[Preparation Example 21] Preparation of Compound 157

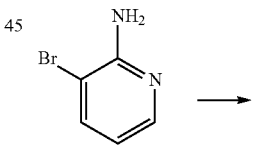

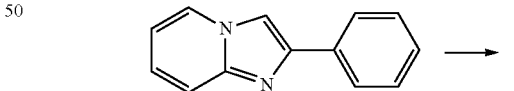
1-1

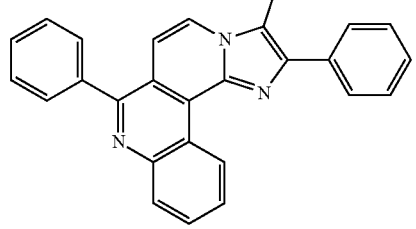
1-2

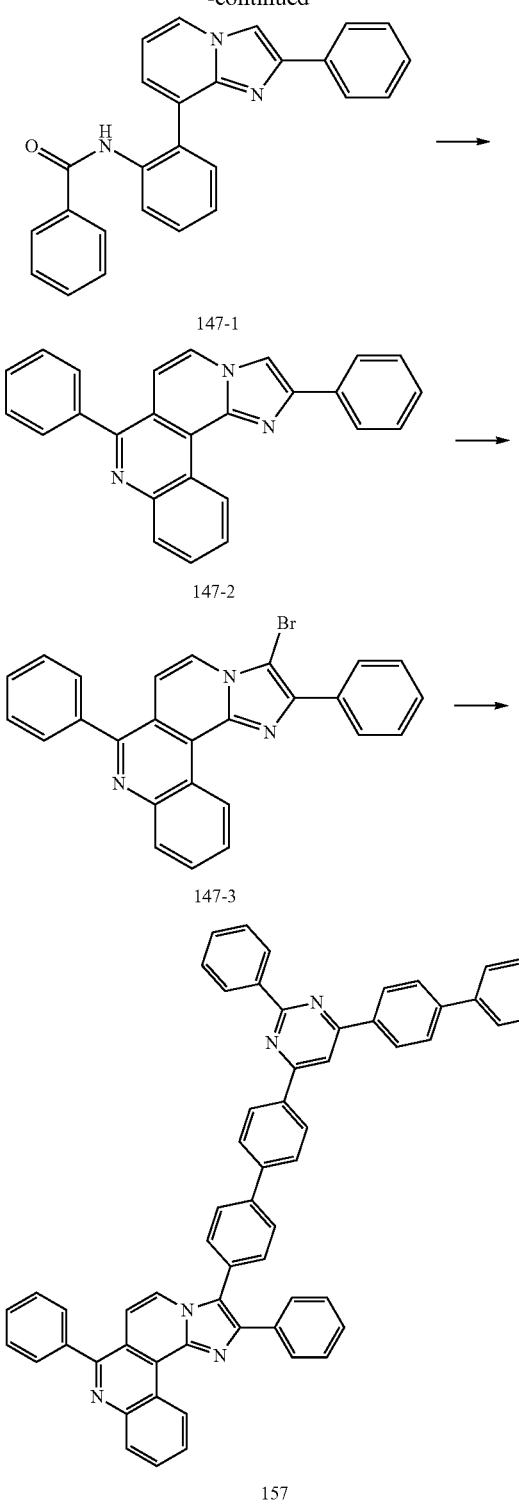
Preparation of Compound 157
Target Compound 157 was obtained in the same manner as in Preparation of Compound 147 of Preparation Example 18 except that 4-([1,1'-biphenyl]-4-yl)-2-phenyl-6-(4'-(4,4,5,5-tetramethyl-1,3,2-dioxaborolan-2-yl)-[1,1'-biphenyl]-4-yl)pyrimidine was used instead of diphenyl(4'-(4,4,5,5-tetramethyl-1,3,2-dioxaborolan-2-yl)-[1,1'-biphenyl]-4-yl)phosphine oxide.
[Preparation Example 22] Preparation of Compound 163
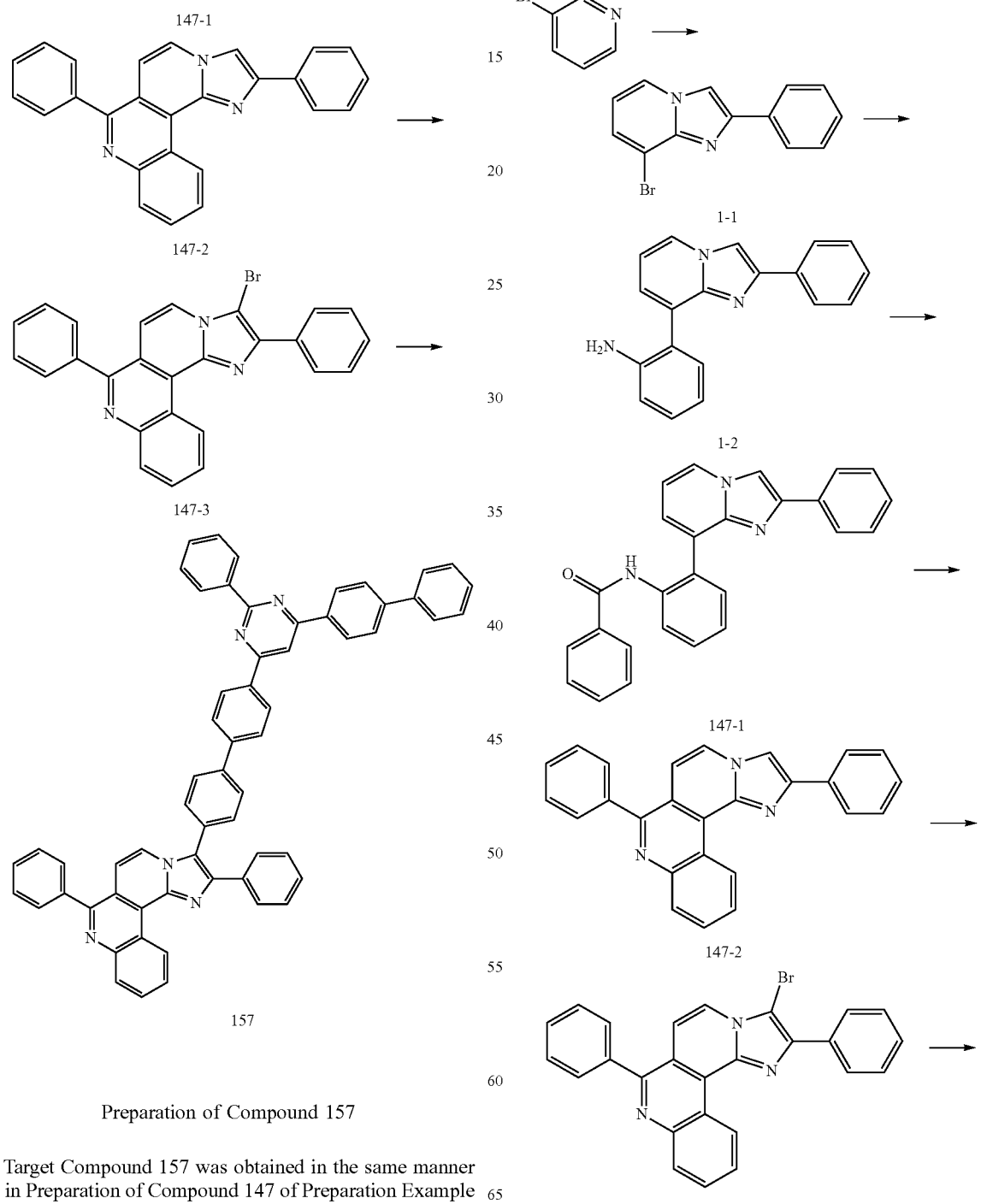

145
-continued

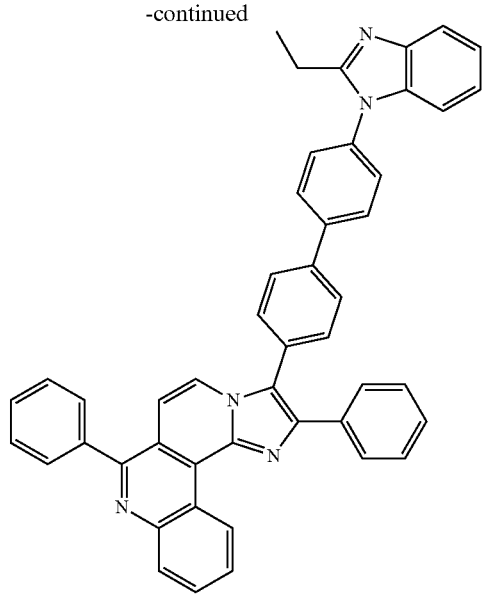

163

Preparation of Compound 163

Target Compound 163 was obtained in the same manner as in Preparation of Compound 147 of Preparation Example 18 except that 2-ethyl-1-(4'-(4,4,5,5-tetramethyl-1,3,2-dioxaborolan-2-yl)-[1,1'-biphenyl]-4-yl)-1H-benzo[d]imidazole was used instead of diphenyl(4'-(4,4,5,5-tetramethyl-1,3,2-dioxaborolan-2-yl)-[1,1'-biphenyl]-4-yl)phosphine oxide.

[Preparation Example 23] Preparation of Compound 175

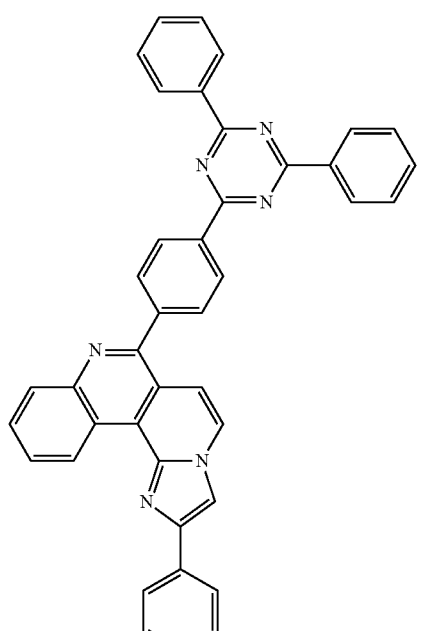

66

146
-continued

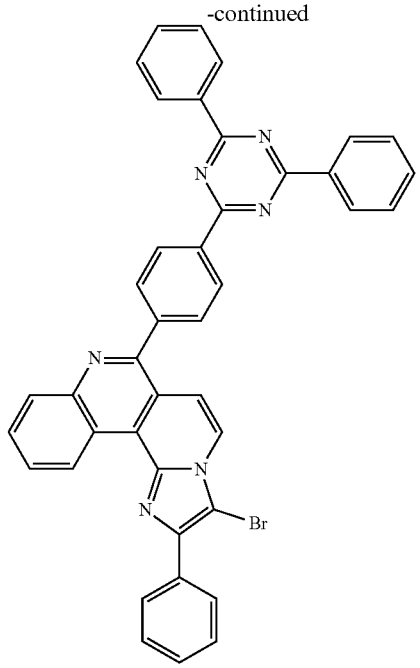

175-1

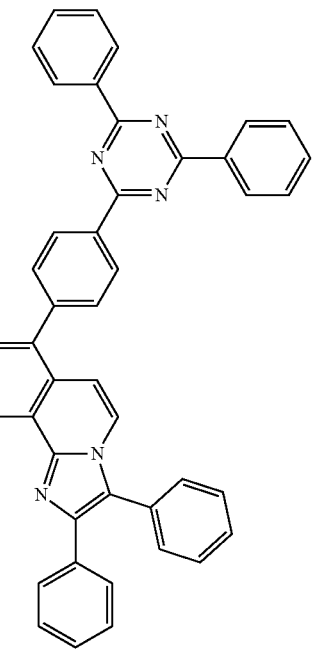

175

Preparation of Compound 175-1

After dissolving Compound 66 (10.0 g, 16.6 mmol, 1 eq.) in ACN, N-bromosuccimide (2.95 g, 16.6 mmol, 1 eq.) was added thereto, and the result was stirred for 1 hour at room temperature. After the reaction was finished, produced solids were washed with ACN, and target Compound 175-1 (10.5 g, 93%) was obtained.

Preparation of Compound 175

After adding phenylboronic acid (2.2 g, 18.8 mmol), Pd(PPh$_3$)$_4$ (0.021 g, 0.77 mmol), K$_2$CO$_3$ (6.4 g, 46.2 mmol)

and toluene/EtOH/H₂O to Compound 175-1 (10.5 g, 15.4 mmol), the result was stirred for 6 hours at 110° C. After the reaction was completed, the result was cooled to room temperature, and extracted with distilled water and EA. The organic layer was dried with anhydrous MgSO₄, and, after removing the solvent using a rotary evaporator, purified by column chromatography using dichloromethane and hexane as a developing solvent to obtain target Compound 175 (8.5 g, 82%).

[Preparation Example 24] Preparation of Compound 176

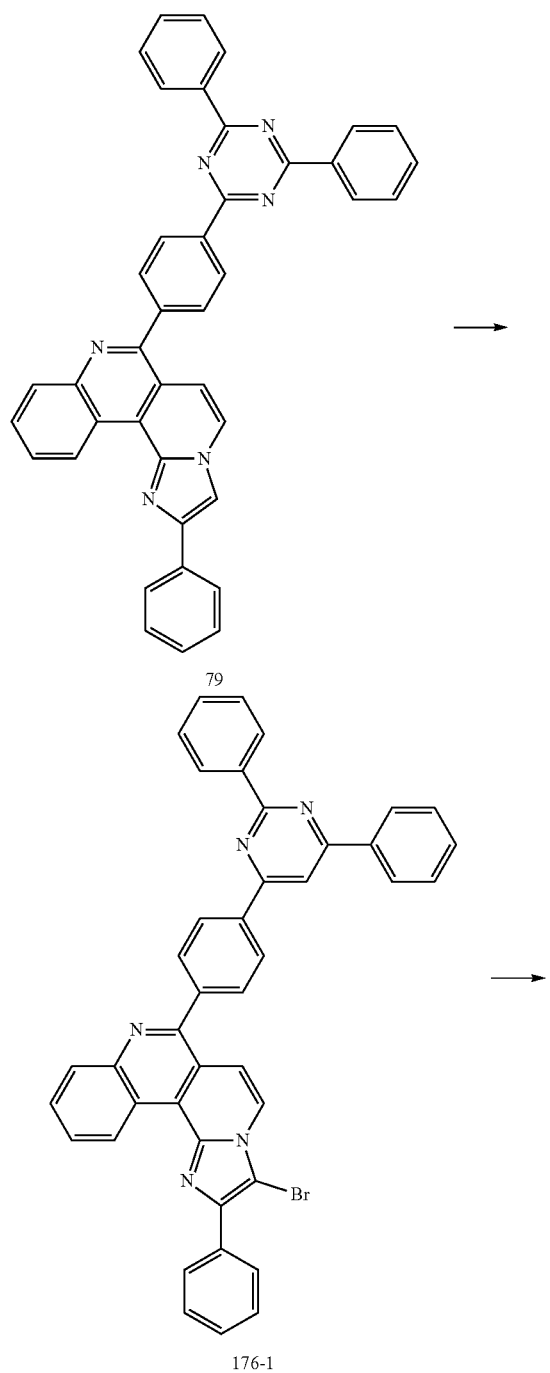

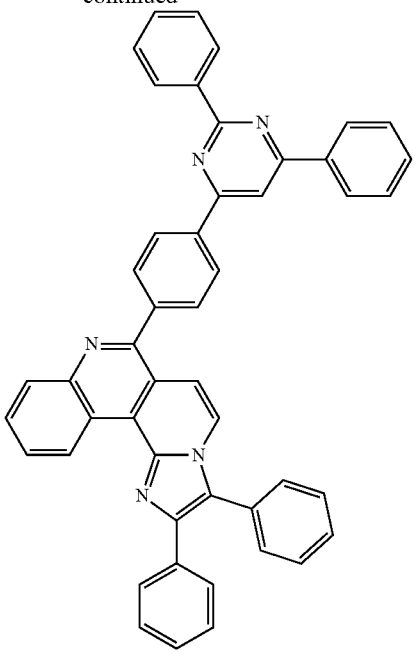

Preparation of Compound 176-1

After dissolving Compound 79 (10.0 g, 16.6 mmol, 1 eq.) in ACN, N-bromosuccimide (1 eq.) was added thereto, and the result was stirred for 1 hour at room temperature. After the reaction was finished, produced solids were washed with ACN, and target Compound 176-1 (10.1 g, 90%) was obtained.

Preparation of Compound 176

After adding phenylboronic acid (1.2 eq., 17.7 mmol), Pd(PPh₃)₄ (0.05 eq., 0.85 g, 0.74 mmol), K₂CO₃ (3.0 eq., 6.1 g, 44.4 mmol) and toluene/EtOH/H₂O to Compound 176-1 (10.1 g, 14.8 mmol, 1 eq.), the result was stirred for 6 hours at 110° C. After the reaction was completed, the result was cooled to room temperature, and extracted with distilled water and EA. The organic layer was dried with anhydrous MgSO₄, and, after removing the solvent using a rotary evaporator, purified by column chromatography using dichloromethane and hexane as a developing solvent to obtain target Compound 176 (8.0 g, 80%).

[Preparation Example 25] Preparation of Compound 181

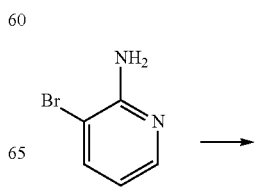

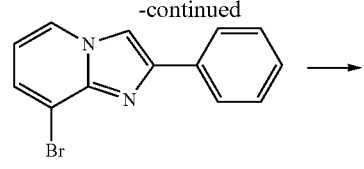
1-1
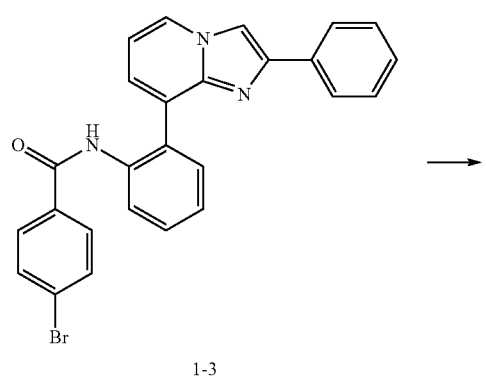
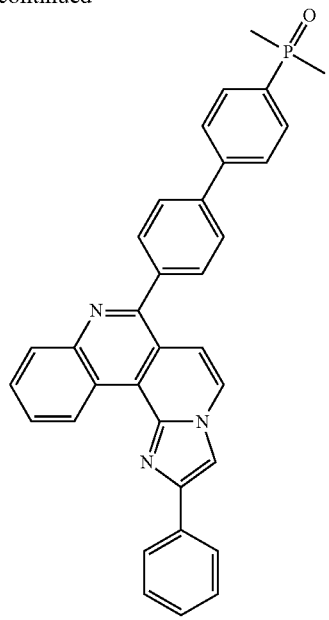
181
Preparation of Compound 181
Target Compound 181 was obtained in the same manner as in Preparation of Compound 51 of Preparation Example 6 except that (4-bromophenyl)dimethylphosphine oxide was used instead of 2,2'-(4'-bromo-[1,1'-biphenyl]-3,5-diyl)dipyridine.
[Preparation Example 26] Preparation of Compound 192
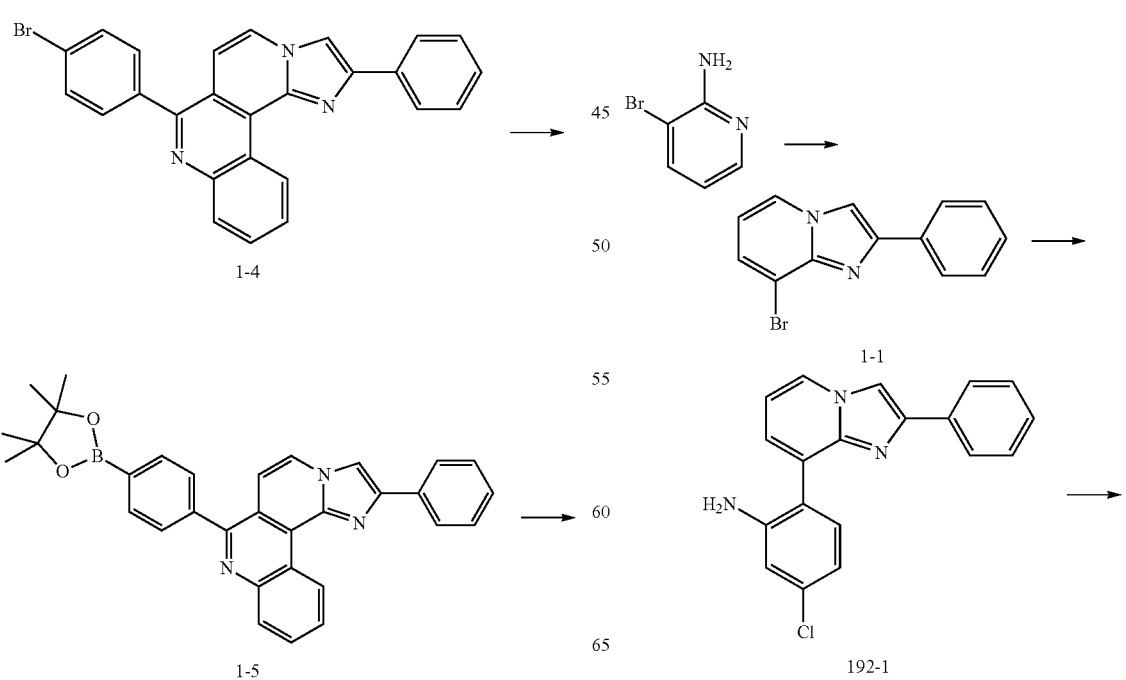

-continued

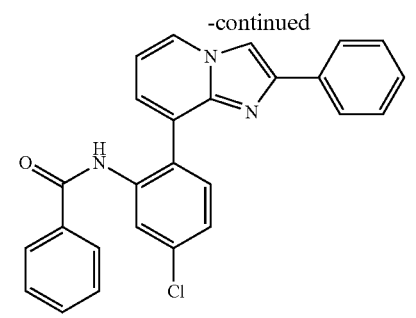
192-2

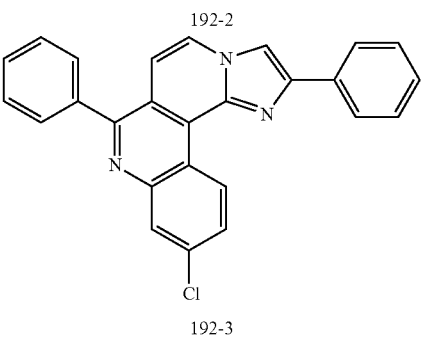
192-3

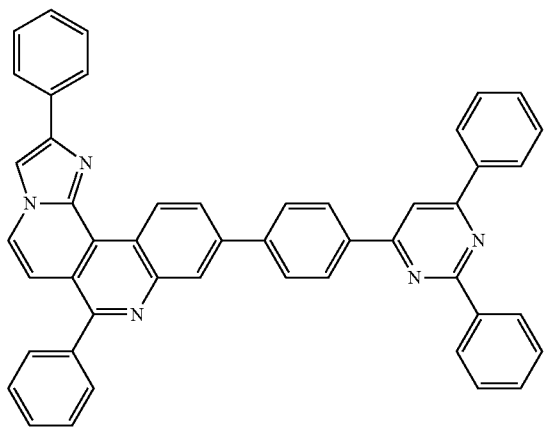
192

Preparation of Compound 192-1

After dissolving Compound 1-1 (100 g, 366.13 mmol, 1 eq.) in 1,4-dioxane/H₂O, 5-chloro-2-(4,4,5,5-tetramethyl-1,3,2-dioxaborolan-2-yl)aniline (111.4 g, 439.35 mmol, 1.2 eq.), Pd(PPh₃)₄ (21 g, 18.31 mmol, 0.05 eq.) and K₂CO₃ (151.8 g, 1098.4 mmol, 3 eq.) were added thereto, and the result was stirred for 3 hours at 100° C. After the reaction was finished, the result was cooled to room temperature, and extracted with distilled water and EA. The organic layer was dried with MgSO₄, and then filtered and concentrated. The concentrated residue was purified by column chromatography using ethyl acetate and hexane as a developing solvent to obtain target Compound 192-1 (103.1 g, 88%).

Preparation of Compound 192-2

After dissolving Compound 192-1 (92 g, 322.41 mmol, 1 eq.) in THF, TEA (135 ml, 967.23 mmol, 3 eq.) and benzoyl chloride (20.78 g, 81.85 mmol, 1.5 eq.) were added thereto at 0° C., and the result was stirred for 1 hour at room temperature. After the reaction was finished, the result was extracted with distilled water and EA. The organic layer was dried with MgSO₄, and then filtered and concentrated. The concentrated residue was purified by column chromatography using ethyl acetate and hexane as a developing solvent to obtain target Compound 192-2 (106.6 g, 78%).

Preparation of Compound 192-3

After dissolving Compound 192-2 (106.6 g, 251.47 mmol, 1 eq.) in nitrobenzene, POCl₃ (36.5 mL, 377.2 mmol, 1.5 eq.) was added thereto, and the result was stirred for 14 hours at 150° C. After the reaction was finished, the result was neutralized at room temperature, and then extracted with distilled water and dichloromethane. The organic layer was dried with MgSO₄, and then filtered and concentrated. The concentrated residue was stirred with ethyl acetate, and then filtered to obtain target Compound 192-3 (64.3 g, 63%).

Preparation of Compound 192

After adding 2,4-diphenyl-6-(4-(4,4,5,5-tetramethyl-1,3,2-dioxaborolan-2-yl)phenyl)pyrimidine (10.7 g, 24.6 mmol), Pd₂(dba)₃ (2.46 mmol), SPhps (4.92 mmol), K₂CO₃ (73.8 mmol) and 1,4-dioxane/H₂O to Compound 192-3 (10 g, 24.6 mmol), the result was stirred for 2 hours at 110° C. After the reaction was completed, the result was cooled to room temperature, and precipitated solids were filtered. After that, the result was purified by column chromatography using dichloromethane and hexane as a developing solvent to obtain target Compound 192 (12 g, 72%).

[Preparation Example 27] Preparation of Compound 199

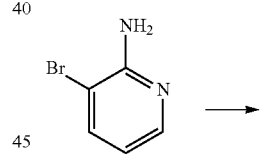

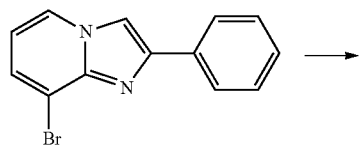
1-1

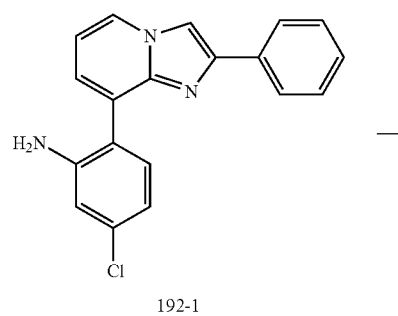
192-1

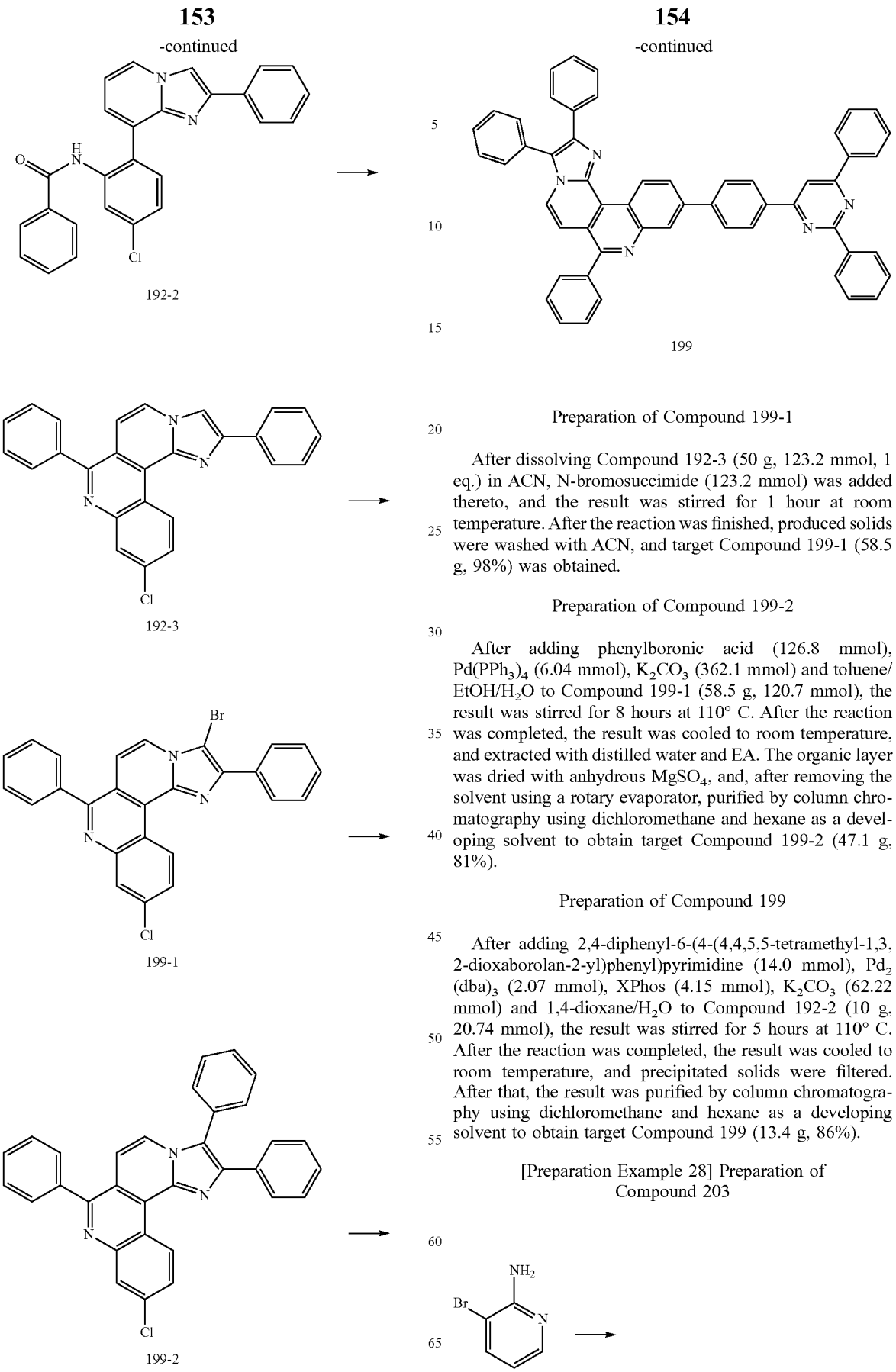

Preparation of Compound 199-1

After dissolving Compound 192-3 (50 g, 123.2 mmol, 1 eq.) in ACN, N-bromosuccimide (123.2 mmol) was added thereto, and the result was stirred for 1 hour at room temperature. After the reaction was finished, produced solids were washed with ACN, and target Compound 199-1 (58.5 g, 98%) was obtained.

Preparation of Compound 199-2

After adding phenylboronic acid (126.8 mmol), Pd(PPh$_3$)$_4$ (6.04 mmol), K$_2$CO$_3$ (362.1 mmol) and toluene/EtOH/H$_2$O to Compound 199-1 (58.5 g, 120.7 mmol), the result was stirred for 8 hours at 110° C. After the reaction was completed, the result was cooled to room temperature, and extracted with distilled water and EA. The organic layer was dried with anhydrous MgSO$_4$, and, after removing the solvent using a rotary evaporator, purified by column chromatography using dichloromethane and hexane as a developing solvent to obtain target Compound 199-2 (47.1 g, 81%).

Preparation of Compound 199

After adding 2,4-diphenyl-6-(4-(4,4,5,5-tetramethyl-1,3,2-dioxaborolan-2-yl)phenyl)pyrimidine (14.0 mmol), Pd$_2$(dba)$_3$ (2.07 mmol), XPhos (4.15 mmol), K$_2$CO$_3$ (62.22 mmol) and 1,4-dioxane/H$_2$O to Compound 192-2 (10 g, 20.74 mmol), the result was stirred for 5 hours at 110° C. After the reaction was completed, the result was cooled to room temperature, and precipitated solids were filtered. After that, the result was purified by column chromatography using dichloromethane and hexane as a developing solvent to obtain target Compound 199 (13.4 g, 86%).

[Preparation Example 28] Preparation of Compound 203

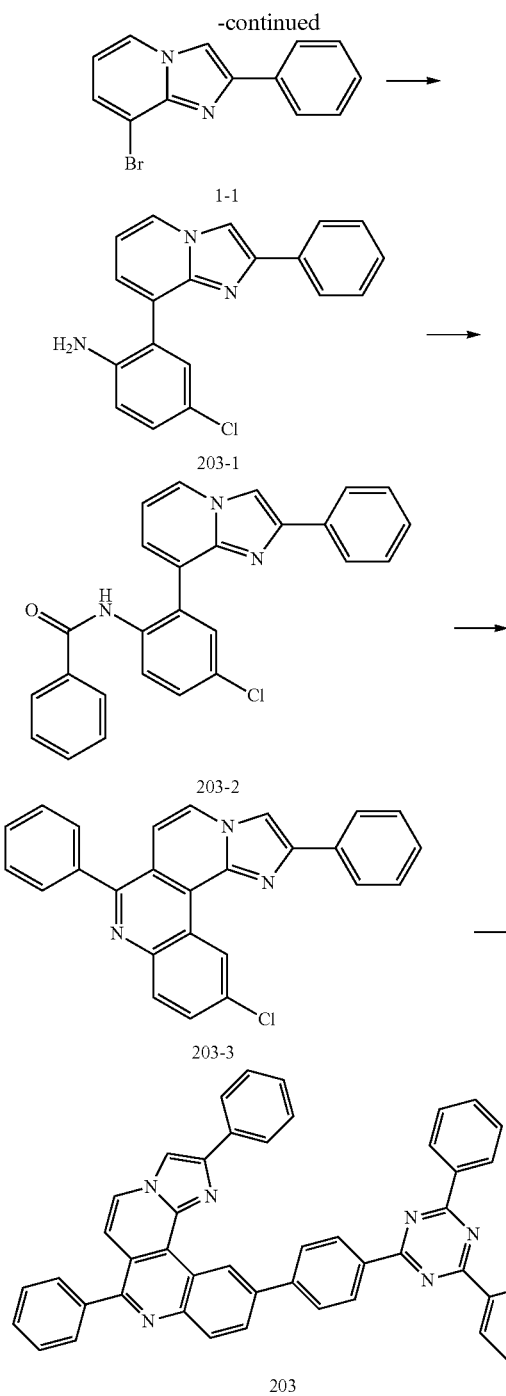

Preparation of Compound 203-1

After dissolving Compound 1-1 (100 g, 366.13 mmol, 1 eq.) in 1,4-dioxane/H₂O, 4-chloro-2-(4,4,5,5-tetramethyl-1,3,2-dioxaborolan-2-yl)aniline (111.4 g, 439.35 mmol), Pd(PPh₃)₄ (18.31 mmol) and K₂CO₃ (1098.4 mmol) were added thereto, and the result was stirred for 5 hours at 100° C. After the reaction was finished, the result was cooled to room temperature, and extracted with distilled water and EA. The organic layer was dried with MgSO₄, and then filtered and concentrated. The concentrated residue was purified by column chromatography using ethyl acetate and hexane as a developing solvent to obtain target Compound 203-1 (95.8 g, 82%).

Preparation of Compound 203-2

After dissolving Compound 203-1 (95.8 g, 300.22 mmol, 1 eq.) in THF, TEA (900.66 mmol) and benzoyl chloride (450.33 mmol) were added thereto at 0° C., and the result was stirred for 1 hour at room temperature. After the reaction was finished, the result was extracted with distilled water and EA. The organic layer was dried with MgSO₄, and then filtered and concentrated. The concentrated residue was purified by column chromatography using ethyl acetate and hexane as a developing solvent to obtain target Compound 203-2 (110.7 g, 87%).

Preparation of Compound 203-3

After dissolving Compound 203-2 (110.7 g, 261.19 mmol, 1 eq.) in nitrobenzene, POCl₃ (391.79 mmol) was added thereto, and the result was stirred for 17 hours at 150° C. After the reaction was finished, the result was neutralized at room temperature, and then extracted with distilled water and dichloromethane. The organic layer was dried with MgSO₄, and then filtered and concentrated. The concentrated residue was stirred with ethyl acetate, and then filtered to obtain target Compound 203-3 (54.1 g, 51%).

Preparation of Compound 203

After adding 2,4-diphenyl-6-(4-(4,4,5,5-tetramethyl-1,3,2-dioxaborolan-2-yl)phenyl)-1,3,5-triazine (24.6 mmol), Pd₂(dba)₃ (2.46 mmol), Xphos (4.92 mmol), K₂CO₃ (73.8 mmol) and 1,4-dioxane/H₂O to Compound 203-3 (10 g, 24.6 mmol), the result was stirred for 4 hours at 110° C. After the reaction was completed, the result was cooled to room temperature, and precipitated solids were filtered. After that, the result was purified by column chromatography using dichloromethane and hexane as a developing solvent to obtain target Compound 203 (12.9 g, 77%).

[Preparation Example 29] Preparation of Compound 212

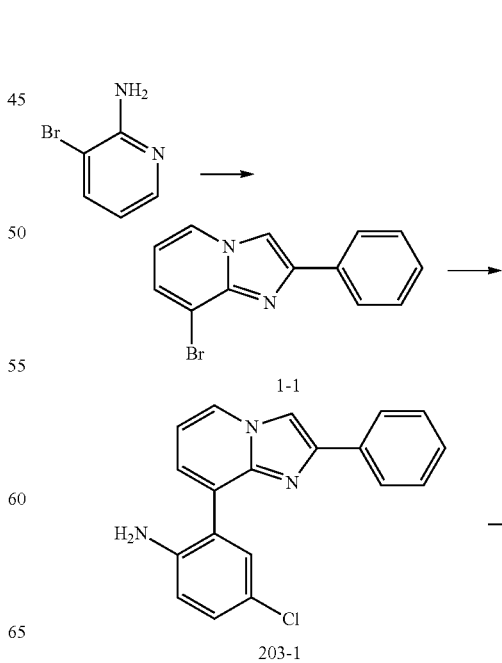

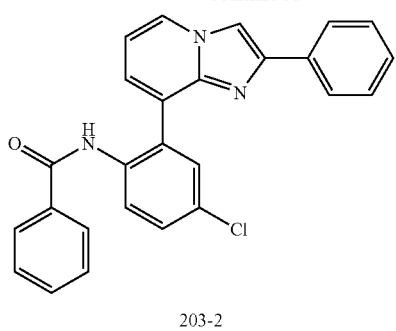

203-2

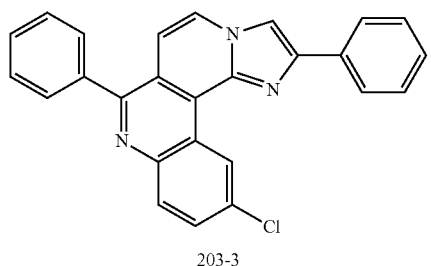

203-3

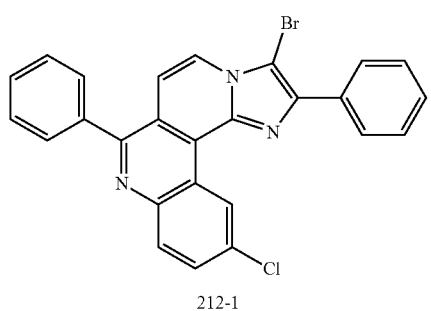

212-1

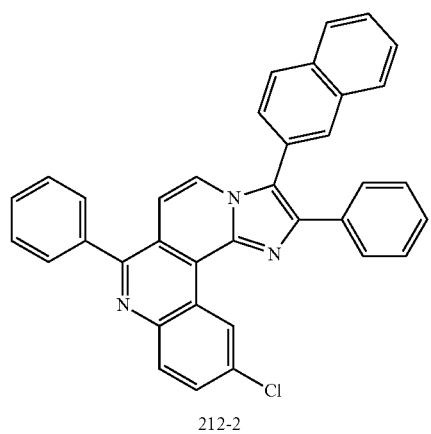

212-2

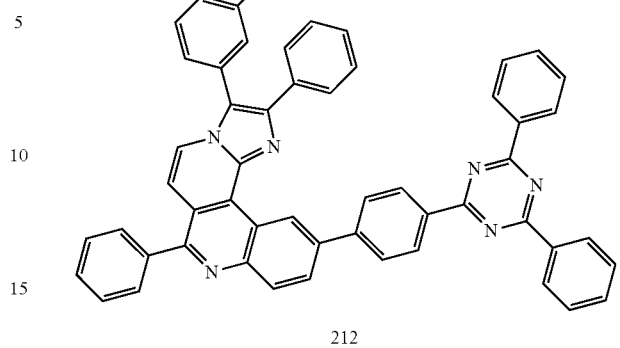

212

Preparation of Compound 212-1

After dissolving Compound 203-3 (50 g, 123.2 mmol, 1 eq.) in ACN, N-bromosuccimide (123.2 mmol) was added thereto, and the result was stirred for 1 hour at room temperature. After the reaction was finished, produced solids were washed with ACN, and target Compound 212-1 (54.9 g, 92%) was obtained.

Preparation of Compound 212-2

After adding naphthalen-2-ylboronic acid (124.6 mmol), $Pd(PPh_3)_4$ (5.67 mmol), $K_2CO_3$ (339.3 mmol) and toluene/EtOH/$H_2O$ to Compound 212-1 (54.9 g, 113.3 mmol), the result was stirred for 4 hours at 110° C. After the reaction was completed, the result was cooled to room temperature, and extracted with distilled water and EA. The organic layer was dried with anhydrous $MgSO_4$, and, after removing the solvent using a rotary evaporator, purified by column chromatography using dichloromethane and hexane as a developing solvent to obtain target Compound 212-2 (50.6 g, 84%).

Preparation of Compound 212

After adding 2,4-diphenyl-6-(4-(4,4,5,5-tetramethyl-1,3,2-dioxaborolan-2-yl)phenyl)-1,3,5-triazine (20.68 mmol), $Pd_2(dba)_3$ (1.88 mmol), XPhos (3.76 mmol), $K_2CO_3$ (56.4 mmol) and 1,4-dioxane/$H_2O$ to Compound 212-2 (10 g, 18.80 mmol), the result was stirred for 3 hours at 110° C. After the reaction was completed, the result was cooled to room temperature, and precipitated solids were filtered. After that, the result was purified by column chromatography using dichloromethane and hexane as a developing solvent to obtain target Compound 212 (11.5 g, 76%).

Compounds other than the compounds described in Preparation Examples 1 to 29 were also prepared in the same manner as in the methods for preparing the compounds described in Preparation Examples 1 to 29, and the synthesis identification results are shown in the following Table 1 and Table 2.

TABLE 1

| NO | ¹H NMR (CDCl₃, 300 Mz) |
|---|---|
| 1 | 8.80-8.69(7H, m), 8.45(1H, d), 8.37(1H, s), 8.20(1H, d), 8.14(3H, d), 7.96-7.83(8H, m), 7.69(1H, t), 7.56-7.49(4H, m), 7.29(1H, d) |
| 2 | 8.75-8.69(7H, m), 8.37(1H, s), 8.33(2H, d), 8.20(1H, d), 8.14(3H, d), 7.96-7.83(8H, m), 7.69(1H, t), 7.55-7.49(6H, m), 7.29(2H, d) |
| 3 | 8.80-8.69(7H, m), 8.45(1H, d), 8.37(1H, s), 8.20(1H, d), 8.14(3H, d), 7.96-7.78(4H, m), 7.69(1H, t), 7.56-7.49(4H, m), 7.29(1H, d) |
| 4 | 8.75-8.69(7H, m), 8.37(1H, s), 8.33(2H, d), 8.20(1H, d), 8.14(3H, d), 7.96-7.78(4H, m), 7.69(1H, t), 7.55-7.49(6H, m), 7.29(2H, d) |
| 12 | 8.80-8.69(5H, m), 8.45(1H, d), 8.37-8.33(3H, m), 8.20(1H, d), 8.14(3H, d), 7.96-7.49(13H, m), 7.29(1H, d) |
| 13 | 8.75-8.69(5H, m), 8.37-8.33(5H, m), 8.20(1H, d), 8.14(3H, d), 7.96-7.49(15H, m), 7.29(2H, d) |
| 16 | 8.80-8.67(5H, m), 8.50(1H, d), 8.44(1H, d), 8.37(1H, s), 8.14(3H, d), 7.96(1H, d), 7.85-7.78(4H, m), 7.62-7.49(6H, m), 7.32(1H, s), 7.25(4H, s) |
| 17 | 8.75-8.69(5H, m), 8.37(1H, s), 8.33(4H, d), 8.14(3H, d), 7.96(1H, d), 7.85-7.78(4H, m), 7.69(1H, t), 7.55-7.49(9H, m), 7.33-7.22(7H, m) |
| 28 | 8.80(1H, d), 8.75(1H, d), 8.67(1H, d), 8.50(1H, d), 8.44(1H, d), 8.37(1H, s), 8.33(2H, m), 8.14(3H, d), 7.83-7.49(10H, m), 7.32(1H, s), 7.25(4H, s) |
| 44 | 9.02(1H, d), 8.95(1H, d), 8.87(1H, d), 8.80(1H, d), 8.75(1H, d), 8.45(1H, d), 8.37-8.33(3H, m), 8.14-8.06(4H, m), 7.96(1H, d), 7.84-7.46(13H, m), 7.15(1H, d) |
| 47 | 9.18(1H, d), 8.92(2H, d), 8.78-8.69(6H, m), 8.55(1H, d), 8.37(1H, s), 8.14(3H, d), 7.96(1H, d), 7.83-7.69(4H, m), 7.56-7.49(4H, m), 7.37(1H, t), 7.23(1H, t), 6.88(1H, t) |
| 51 | 8.82(1H, s), 8.75(1H, d), 8.69(2H, d), 8.43(2H, s), 8.37(3H, m), 8.14(3H, d), 7.96(1H, d), 7.85-7.78(4H, m), 7.69(1H, t), 7.50-7.49(3H, m), 7.38(1H, t), 7.25(4H, s), 7.14(2H, d), 6.90(2H, t) |
| 60 | 8.99(1H, s), 8.75(1H, d), 8.69(2H, d), 8.42(1H, d), 8.37(1H, s), 8.20-7.98(12H, m), 7.85-7.78(4H, m), 7.69-7.38(15H, m) |
| 62 | 8.75(1H, d), 8.37-8.36(3H, m), 8.14(3H, d), 7.96(3H, d), 7.83-7.69(7H, m), 7.51-7.49(9H, m) |
| 63 | 8.75(1H, d), 8.69(2H, d), 8.37(1H, d), 8.14(3H, d), 7.97-7.96(5H, m), 7.85-7.69(9H, m), 7.51-7.49(9H, m) |
| 65 | 8.75(1H, d), 8.69(2H, d), 8.55(2H, d), 8.37(1H, s), 8.19-8.14(7H, m), 7.96-7.94(3H, m), 7.85-7.78(4H, m), 7.69(1H, t), 7.60-7.49(8H, m), 7.35(2H, t), 7.20-7.16(4H, m) |
| 66 | 8.75(1H, d), 8.69(2H, d), 8.37-8.36(5H, m), 8.14(3H, d), 7.96(2H, d), 7.83-7.78(2H, m), 7.69(1H, t), 7.50-7.49(9H, m) |
| 68 | 9.09(2H, s), 8.75(1H, d), 8.69(2H, d), 8.49(2H, d), 8.37(1H, s), 8.16-7.96(12H, m), 7.83-7.78(2H, m), 7.69-7.49(8H, m) |
| 69 | 8.75(1H, d), 8.69(2H, d), 8.37(1H, s), 8.36(4H, d), 8.14(3H, d), 7.96(3H, d), 7.85-7.78(4H, m), 7.69(1H, t), 7.50-7.49(9H, m), 7.25(2H, d) |
| 79 | 8.75(1H, d), 8.69(2H, d), 8.37-8.30(5H, m), 8.14(3H, d), 7.96-7.94(3H, m), 7.83-7.78(2H, m), 7.69(1H, t), 7.55-7.49(9H, m) |
| 84 | 8.75(1H, d), 8.69(2H, d), 8.37-8.30(7H, m), 8.14(3H, d), 7.96-7.75(7H, m), 7.85-7.75(7H, m), 7.50-7.41(9H, m) |
| 93 | 8.75(1H, d), 8.37-8.33(7H, m), 8.14(3H, d), 7.96(3H, d), 7.83-7.61(5H, m), 7.50-7.49(9H, m), 7.25(2H, d) |
| 95 | 8.75(1H, d), 8.37-8.30(7H, m), 8.23(1H, s), 8.14(3H, d), 7.96-7.94(3H, m), 7.85-7.61(11H, m), 7.50-7.41(9H, m) |
| 98 | 8.75(1H, d), 8.69(2H, d), 8.37(1H, s), 8.14(3H, d), 8.13(1H, d), 7.96(3H, d), 7.84-7.49(14H, m) |
| 106 | 8.75(1H, d), 8.69(2H, d), 8.37(1H, s), 8.35(2H, d), 8.14(3H, d), 7.96(1H, d), 7.83-7.78(6H, m), 7.69-7.65(5H, m), 7.50-7.49(8H, m), 7.25(2H, d) |
| 115 | 8.75(1H, d), 8.69(2H, d), 8.37-8.30(5H, m), 8.14-8.13(4H, m), 7.96(1H, d), 7.85-7.78(8H, m), 7.69(1H, t), 7.58-7.49(7H, m) |
| 120 | 8.75(1H, d), 8.69(2H, d), 8.37(1H, s), 8.14(3H, d), 7.96(3H, d), 7.85-7.64(7H, m), 7.50-7.49(3H, m), 7.27-7.25(3H, m), 4.12(2H, q), 1.31(3H, t) |
| 131 | 8.75(1H, d), 8.37(1H, s), 8.33(2H, m), 8.14-8.13(4H, m), 7.96(3H, d), 7.83-7.49(16H, m), 7.25(2H, d) |
| 142 | 8.85(1H, s), 8.75(1H, d), 8.37-8.30(7H, m), 8.14(1H, d), 8.06-7.94(6H, m), 7.84-7.78(4H, m), 7.69-7.49(12H, m) |
| 147 | 8.75(1H, d), 8.30(2H, d), 8.19(2H, d), 8.14(1H, d), 7.97-7.96(5H, m), 7.85-7.65(11H, m), 7.51-7.47(10H, m), 7.28(2H, t) |
| 148 | 8.75(1H, d), 8.36-8.30(6H, m), 8.19(2H, d), 8.14(1H, d), 7.96(3H, d), 7.83-7.78(2H, m), 7.69-7.65(3H, m), 7.50-7.47(10H, m), 7.28(2H, t) |
| 149 | 9.09(2H, s), 8.75(1H, d), 8.49(2H, d), 8.30(2H, d), 8.19-7.96(12H, m), 7.83-7.78(2H, m), 7.69-7.47(11H, m), 7.28(2H, t) |
| 157 | 8.75(1H, s), 8.35-8.14(12H, m), 7.96(1H, d), 7.85-7.65(13H, m), 7.50-7.41(10H, m), 7.28(2H, t) |
| 163 | 8.75(1H, d), 8.56(1H, d), 8.30(2H, d), 8.19-8.14(3H, m), 7.96(1H, d), 7.85-7.65(11H, m), 7.54-7.47(5H, m), 7.28-7.21(4H, m), 2.58(2H, q), 1.30(3H, t) |
| 172 | 8.75(1H, d), 8.19(2H, d), 8.14(1H, d), 7.96(1H, d), 7.84-7.78(4H, m), 7.69-7.65(3H, m), 7.53-7.47(7H, m), 7.28(2H, t) |
| 175 | 8.75(1H, d), 8.69(2H, d), 8.36(4H, d), 8.14(1H, d), 7.96(3H, m), 7.84-7.78(4H, m), 7.69(1H, t), 7.53-7.47(12H, m), 7.28(2H, t) |
| 176 | 8.75(1H, d), 8.69(2H, d), 8.35-8.30(4H, m), 8.23(1H, s), 8.14(1H, d), 7.96-7.94(3H, m), 7.84-7.78(4H, m), 7.69(1H, t), 7.55-7.47(12H, m), 7.28(2H, t) |
| 183 | 8.85(1H, s), 8.75(1H, d), 8.37(2H, m), 8.14(3H, m), 7.99-7.93(4H, m), 7.83-7.78(2H, m), 7.69-7.63(2H, m), 7.50(3H, m), 2.06(6H, d) |
| 192 | 8.75(d, 1H), 8.39-8.14(m, 12H), 7.94-7.78(m, 6H), 7.65(t, 2H), 7.55-7.49(m, 10H) |
| 199 | 8.75(d, 1H), 8.39-8.19(m, 9H), 7.94-7.78(m, 8H), 7.65(t, 2H), 7.55-7.47(m, 13H), 7.28(t, 2H) |
| 203 | 8.75(d, 1H), 8.37-8.33(m, 6H), 8.19-8.14(m, 4H), 8.07(d, 1H), 7.96(d, 2H), 7.88(s, 1H), 7.78(d, 1H), 7.65(t, 2H), 7.50-7.49(m, 10H), 7.25(d, 2H) |
| 212 | 8.75(d, 1H), 8.46(s, 1H), 8.36-8.33(m, 5H), 8.19(d, 2H), 8.07-7.96(m, 7H), 7.88(s, 1H), 7.78(d, 1H), 7.65-7.47(m, 14H), 7.28-7.25(m, 4H) |

TABLE 2

| Compound | FD-MS | Compound | FD-MS |
|---|---|---|---|
| 1 | m/z = 625.73(C44H27N5 = 625.23) | 2 | m/z = 701.83(C50H31N5 = 701.26) |
| 3 | m/z = 549.64(C38H23N5 = 549.20) | 4 | m/z = 625.73(C44H27N5 = 625.23) |
| 5 | m/z = 674.81(C49H30N4 = 674.25) | 6 | m/z = 675.79(C48H29N5 = 675.24) |
| 7 | m/z = 676.78(C47H28N6 = 676.24) | 8 | m/z = 676.78(C47H28N6 = 676.24) |
| 9 | m/z = 725.86(C52H31N5 = 725.26) | 10 | m/z = 725.86(C52H31N5 = 725.26) |
| 11 | m/z = 740.87(C52H32N6 = 740.27) | 12 | m/z = 625.73(C44H27N5 = 625.23) |
| 13 | m/z = 701.83(C50H31N5 = 701.26) | 14 | m/z = 675.79(C48H29N5 = 675.24) |
| 15 | m/z = 676.78(C47H28N6 = 676.24) | 16 | m/z = 625.73(C44H27N5 = 625.23) |
| 17 | m/z = 777.93(C56H35N5 = 777.29) | 18 | m/z = 701.83(C50H31N5 = 701.26) |
| 19 | m/z = 777.93(C56H35N5 = 777.29) | 20 | m/z = 675.79(C48H29N5 = 675.24) |
| 21 | m/z = 675.79(C48H29N5 = 675.24) | 22 | m/z = 676.78(C47H28N6 = 676.24) |
| 23 | m/z = 676.78(C47H28N6 = 676.24) | 24 | m/z = 725.86(C52H31N5 = 725.26) |
| 25 | m/z = 725.86(C52H31N5 = 725.26) | 26 | m/z = 725.86(C52H31N5 = 725.26) |

TABLE 2-continued

| Compound | FD-MS | Compound | FD-MS |
|---|---|---|---|
| 27 | m/z = 751.89(C54H33N5 = 751.27) | 28 | m/z = 625.73(C44H27N5 = 625.23) |
| 29 | m/z = 675.79(C48H29N5 = 675.24) | 30 | m/z = 675.79(C48H29N5 = 675.24) |
| 31 | m/z = 625.73(C44H27N5 = 625.23) | 32 | m/z = 626.72(C43H26N6 = 626.22) |
| 33 | m/z = 626.72(C43H26N6 = 626.22) | 34 | m/z = 626.72(C43H26N6 = 626.22) |
| 35 | m/z = 675.79(C48H29N5 = 675.24) | 36 | m/z = 675.79(C48H29N5 = 675.24) |
| 37 | m/z = 676.78(C47H28N6 = 676.24) | 38 | m/z = 676.78(C47H28N6 = 676.24) |
| 39 | m/z = 725.86(C52H31N5 = 725.26) | 40 | m/z = 725.86(C52H31N5 = 725.26) |
| 41 | m/z = 725.86(C52H31N5 = 725.26) | 42 | m/z = 751.89(C54H33N5 = 751.27) |
| 43 | m/z = 625.73(C44H27N5 = 625.23) | 44 | m/z = 675.79(C48H29N5 = 675.24) |
| 45 | m/z = 626.72(C43H26N6 = 626.22) | 46 | m/z = 601.71(C42H27N5 = 601.23) |
| 47 | m/z = 602.70(C41H26N6 = 602.22) | 48 | m/z = 751.89(C54H33N5 = 751.27) |
| 49 | m/z = 701.83(C50H31N5 = 701.26) | 50 | m/z = 652.76(C45H28N6 = 652.24) |
| 51 | m/z = 677.81(C48H31N5 = 677.26) | 52 | m/z = 678.80(C47H30N6 = 678.25) |
| 53 | m/z = 728.86(C51H32N6 = 728.27) | 54 | m/z = 827.99(C60H37N5 = 827.30) |
| 55 | m/z = 651.77(C46H29N5 = 651.24) | 56 | m/z = 701.83(C50H31N5 = 701.26) |
| 57 | m/z = 777.93(C56H35N5 = 777.29) | 58 | m/z = 673.82(C50H31N3 = 673.25) |
| 59 | m/z = 623.76(C46H29N3 = 623.24) | 60 | m/z = 799.98(C60H37N3 = 799.30) |
| 61 | m/z = 547.66(C40H25N3 = 547.20) | 62 | m/z = 571.62(C38H26N3OP = 571.18) |
| 63 | m/z = 647.72(C44H30N3OP = 647.21) | 64 | m/z = 697.78(C48H32N3OP = 697.23) |
| 65 | m/z = 777.93(C56H35N5 = 777.29) | 66 | m/z = 602.70(C41H26N6 = 602.22) |
| 67 | m/z = 604.68(C39H24N8 = 604.21) | 68 | m/z = 702.82(C49H30N6 = 702.25) |
| 69 | m/z = 678.80(C47H30N6 = 678.25) | 70 | m/z = 728.86(C51H32N6 = 728.27) |
| 71 | m/z = 601.71(C42H27N5 = 601.23) | 72 | m/z = 603.69(C40H25N7 = 603.22) |
| 73 | m/z = 701.83(C50H31N5 = 701.26) | 74 | m/z = 677.81(C48H31N5 = 677.26) |
| 75 | m/z = 753.91(C54H35N5 = 753.29) | 76 | m/z = 777.93(C56H35N5 = 777.29) |
| 77 | m/z = 677.81(C48H31N5 = 677.26) | 78 | m/z = 830.01(C60H39N5 = 829.32) |
| 79 | m/z = 601.71(C42H27N5 = 601.23) | 80 | m/z = 753.91(C54H35N5 = 753.29) |
| 81 | m/z = 727.87(C52H33N5 = 727.27) | 82 | m/z = 603.69(C40H25N7 = 603.22) |
| 83 | m/z = 701.83(C50H31N5 = 701.26) | 84 | m/z = 677.81(C48H31N5 = 677.26) |
| 85 | m/z = 753.91(C54H35N5 = 753.29) | 86 | m/z = 677.81(C48H31N5 = 677.26) |
| 87 | m/z = 777.93(C56H35N5 = 777.29) | 88 | m/z = 830.01(C60H39N5 = 829.32) |
| 89 | m/z = 753.91(C54H35N5 = 753.29) | 90 | m/z = 803.97(C58H37N5 = 803.30) |
| 91 | m/z = 647.72(C44H30N3OP = 647.21) | 92 | m/z = 777.93(C56H35N5 = 777.29 |
| 93 | m/z = 678.80(C47H30N6 = 678.25) | 94 | m/z = 677.81(C48H31N5 = 677.26) |
| 95 | m/z = 753.91(C54H35N5 = 753.29) | 96 | m/z = 830.01(C60H39N5 = 829.32) |
| 97 | m/z = 651.77(C46H29N5 = 651.24) | 98 | m/z = 575.67(C40H25N5 = 575.21) |
| 99 | m/z = 727.87(C52H33N5 = 727.27) | 100 | m/z = 625.73(C44H27N5 = 625.23) |
| 101 | m/z = 727.87(C52H33N5 = 727.27) | 102 | m/z = 701.83(C50H31N5 = 701.26 |
| 103 | m/z = 727.87(C52H33N5 = 727.27) | 104 | m/z = 651.77(C46H29N5 = 651.24) |
| 105 | m/z = 701.83(C50H31N5 = 701.26 | 106 | m/z = 677.81(C48H31N5 = 677.26) |
| 107 | m/z = 830.01(C60H39N5 = 829.32) | 108 | m/z = 777.93(C56H35N5 = 777.29) |
| 109 | m/z = 753.91(C54H35N5 = 753.29) | 110 | m/z = 727.87(C52H33N5 = 727.27) |
| 111 | m/z = 727.87(C52H33N5 = 727.27) | 112 | m/z = 575.67(C40H25N5 = 575.21) |
| 113 | m/z = 651.77(C46H29N5 = 651.24) | 114 | m/z = 651.77(C46H29N5 = 651.24) |
| 115 | m/z = 651.77(C46H29N5 = 651.24) | 116 | m/z = 727.87(C52H33N5 = 727.27) |
| 117 | m/z = 563.66(C39H25N5 = 563.21) | 118 | m/z = 563.66(C39H25N5 = 563.21) |
| 119 | m/z = 563.66(C39H25N5 = 563.21) | 120 | m/z = 591.72(C41H29N5 = 591.24) |
| 121 | m/z = 639.76(C45H29N5 = 639.24) | 122 | m/z = 591.72(C41H29N5 = 591.24) |
| 123 | m/z = 639.76(C45H29N5 = 639.24) | 124 | m/z = 591.72(C41H29N5 = 591.24) |
| 125 | m/z = 515.62(C35H25N5 = 515.21) | 126 | m/z = 580.71(C39H24N4S = 580.17) |
| 127 | m/z = 580.71(C39H24N4S = 580.17) | 128 | m/z = 580.71(C39H24N4S = 580.17) |
| 129 | m/z = 630.77(C43H26N4S = 630.19) | 130 | m/z = 727.87(C52H33N5 = 727.27) |
| 131 | m/z = 651.77(C46H29N5 = 651.24) | 132 | m/z = 651.77(C46H29N5 = 651.24) |
| 133 | m/z = 563.66(C39H25N5 = 563.21) | 134 | m/z = 591.72(C41H29N5 = 591.24) |
| 135 | m/z = 591.72(C41H29N5 = 591.24) | 136 | m/z = 580.71(C39H24N4S = 580.17) |
| 137 | m/z = 639.76(C45H29N5 = 639.24) | 138 | m/z = 630.77(C43H26N4S = 630.19) |
| 139 | m/z = 678.80(C47H30N6 = 678.25) | 140 | m/z = 728.86(C51H32N6 = 728.27) |
| 141 | m/z = 778.92(C55H34N6 = 778.28) | 142 | m/z = 727.87(C52H33N5 = 727.27) |
| 143 | m/z = 804.96(C57H36N6 = 804.30) | 144 | m/z = 803.97(C58H37N5 = 803.30) |
| 145 | m/z = 749.92(C56H35N3 = 749.28) | 146 | m/z = 647.72(C44H30N3OP = 647.21) |
| 147 | m/z = 723.82(C50H34N3OP = 723.24) | 148 | m/z = 678.80(C47H30N6 = 678.25) |
| 149 | m/z = 778.92(C55H34N6 = 778.28 | 150 | m/z = 754.90(C53H34N6 = 754.28) |
| 151 | m/z = 677.81(C48H31N5 = 677.26) | 152 | m/z = 777.93(C56H35N5 = 777.29) |
| 153 | m/z = 677.81(C48H31N5 = 677.26) | 154 | m/z = 753.91(C54H35N5 = 753.29) |
| 155 | m/z = 854.03(C62H39N5 = 853.32) | 156 | m/z = 906.11(C66H43N5 = 905.35) |
| 157 | m/z = 830.01(C60H39N5 = 829.32) | 158 | m/z = 830.01(C60H39N5 = 829.32) |
| 159 | m/z = 803.97(C58H37N5 = 803.30) | 160 | m/z = 753.91(C54H35N5 = 753.29) |
| 161 | m/z = 639.76(C45H29N5 = 639.24) | 162 | m/z = 667.82(C47H33N5 = 667.27) |
| 163 | m/z = 667.82(C47H33N5 = 667.27) | 164 | m/z = 715.86(C51H33N5 = 715.27) |
| 165 | m/z = 723.82(C50H34N3OP = 723.24) | 166 | m/z = 754.90(C53H34N6 = 754.28) |
| 167 | m/z = 753.91(C54H35N5 = 753.29) | 168 | m/z = 854.03(C62H39N5 = 853.32) |
| 169 | m/z = 830.01(C60H39N5 = 829.32) | 170 | m/z = 830.01(C60H39N5 = 829.32) |

TABLE 2-continued

| Compound | FD-MS | Compound | FD-MS |
|---|---|---|---|
| 171 | m/z = 667.82(C47H33N5 = 667.27) | 172 | m/z = 447.54(C32H21N3 = 447.17) |
| 173 | m/z = 497.60(C36H23N3 = 497.19) | 174 | m/z = 497.60(C36H23N3 = 497.19) |
| 175 | m/z = 678.80(C47H30N6 = 678.25) | 176 | m/z = 677.81(C48H31N5 = 677.26) |
| 177 | m/z = 753.89(C54H35N5 = 753.29) | 178 | m/z = 778.92(C55H34N6 = 778.28) |
| 179 | m/z = 830.97(C59H38N6 = 830.32) | 180 | m/z = 753.89(C54H35N5 = 753.29) |
| 181 | m/z = 523.58(C34H26N3OP = 523.18) | 182 | m/z = 573.64(C38H28N3OP = 573.20) |
| 183 | m/z = 497.54(C32H24N3OP = 497.17) | 184 | m/z = 766.91(C54H34N6 = 766.28) |
| 185 | m/z = 767.90(C53H33N7 = 767.28) | 186 | m/z = 767.90(C53H33N7 = 767.28) |
| 187 | m/z = 753.91(C54H35N5 = 753.29) | 188 | m/z = 754.90(C53H34N6 = 754.28) |
| 189 | m/z = 753.91(C54H35N5 = 753.29) | 190 | m/z = 447.54(C32H21N3 = 447.17) |
| 191 | m/z = 678.80(C47H30N6 = 678.25) | 192 | m/z = 677.81(C48H31N5 = 677.26) |
| 193 | m/z = 843.99(C59H37N7 = 843.31) | 194 | m/z = 843.01(C60H38N6 = 842.32) |
| 195 | m/z = 777.93(C56H35N5 = 777.29) | 196 | m/z = 647.72(C44H30N3OP = 647.21) |
| 197 | m/z = 775.95(C58H37N3 = 775.30) | 198 | m/z = 701.83(C50H31N5 = 701.26) |
| 199 | m/z = 753.91(C54H35N5 = 753.29) | 200 | m/z = 804.96(C57H36N6 = 804.30) |
| 201 | m/z = 753.91(C54H35N5 = 753.29) | 202 | m/z = 447.54(C32H21N3 = 447.17) |
| 203 | m/z = 678.80(C47H30N6 = 678.25) | 204 | m/z = 677.81(C48H31N5 = 677.26) |
| 205 | m/z = 843.99(C59H37N7 = 843.31) | 206 | m/z = 843.01(C60H38N6 = 842.32) |
| 207 | m/z = 777.93(C56H35N5 = 777.29) | 208 | m/z = 647.72(C44H30N3OP = 647.21) |
| 209 | m/z = 775.95(C58H37N3 = 775.30) | 210 | m/z = 701.83(C50H31N5 = 701.26) |
| 211 | m/z = 753.91(C54H35N5 = 753.29) | 212 | m/z = 804.96(C57H36N6 = 804.30) |
| 213 | m/z = 753.91(C54H35N5 = 753.29) | 214 | m/z = 447.54(C32H21N3 = 447.17) |
| 215 | m/z = 678.80(C47H30N6 = 678.25) | 216 | m/z = 677.81(C48H31N5 = 677.26) |
| 217 | m/z = 843.99(C59H37N7 = 843.31) | 218 | m/z = 843.01(C60H38N6 = 842.32) |
| 219 | m/z = 777.93(C56H35N5 = 777.29) | 220 | m/z = 647.72(C44H30N3OP = 647.21) |
| 221 | m/z = 775.95(C58H37N3 = 775.30) | 222 | m/z = 701.83(C50H31N5 = 701.26) |
| 223 | m/z = 753.91(C54H35N5 = 753.29) | 224 | m/z = 804.96(C57H36N6 = 804.30) |
| 225 | m/z = 753.91(C54H35N5 = 753.29) | | |

EXPERIMENTAL EXAMPLE

Experimental Example 1

1) Manufacture of Organic Light Emitting Device

A glass substrate on which indium tin oxide (ITO) was coated as a thin film to a thickness of 1500 Å was cleaned with distilled water ultrasonic waves. After the cleaning with distilled water was finished, the substrate was ultrasonic cleaned with solvents such as acetone, methanol and isopropyl alcohol, then dried, and ultraviolet ozone (UVO) treated for 5 minutes using UV in an ultraviolet (UV) cleaner. After that, the substrate was transferred to a plasma cleaner (PT), and after conducting plasma treatment under vacuum for ITO work function and residual film removal, the substrate was transferred to a thermal deposition apparatus for organic deposition. On the transparent ITO electrode (anode), organic materials were formed in a single stack structure. As a hole injection layer, HAT-CN was deposited to a thickness of 50 Å, and subsequently, as a hole transfer layer, NPD doped with DNTPD in 10% or less was deposited to a thickness of 1500 Å, and TCTA was continuously deposited to a thickness of 200 Å. Subsequently, a light emitting layer comprising a t-Bu-perylene dopant in an ADN host was formed to a thickness of 250 Å. Subsequently, Alq$_3$, an electron transfer layer, was formed as a film to a thickness of 250 Å, and as an N-type charge generation layer, a compound described in the following Table 3 was doped with lithium, an alkali metal, and formed as a film to a thickness of 100 Å. Al, a cathode, was formed as a film to a thickness of 1,000 Å, and as a result, an organic light emitting device was manufactured.

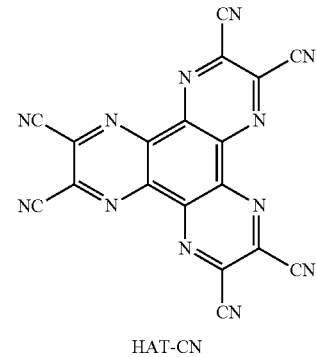

HAT-CN

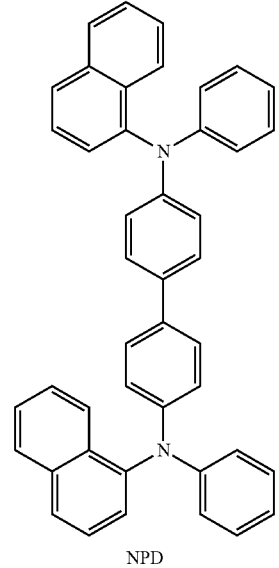

NPD

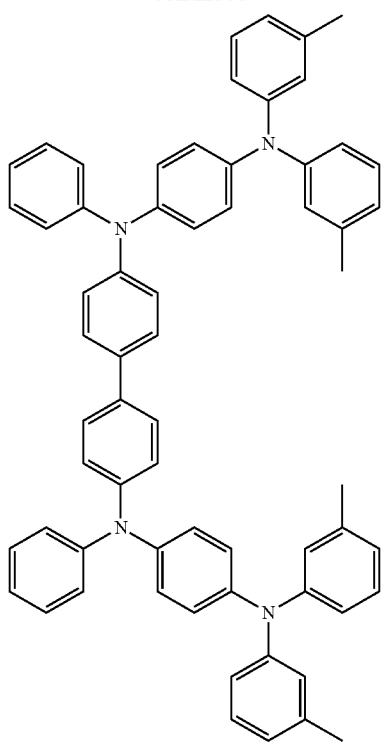

DNTPD

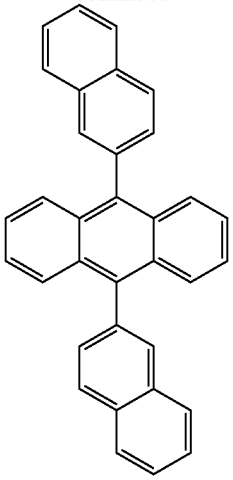

ADN

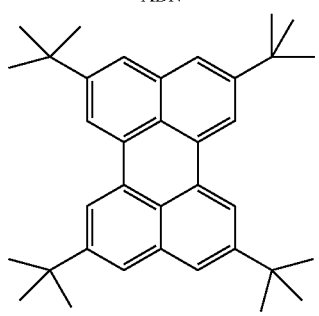

t-Bu-Perylene

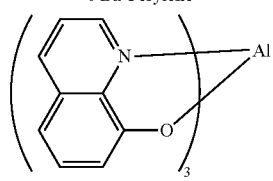

Alq3

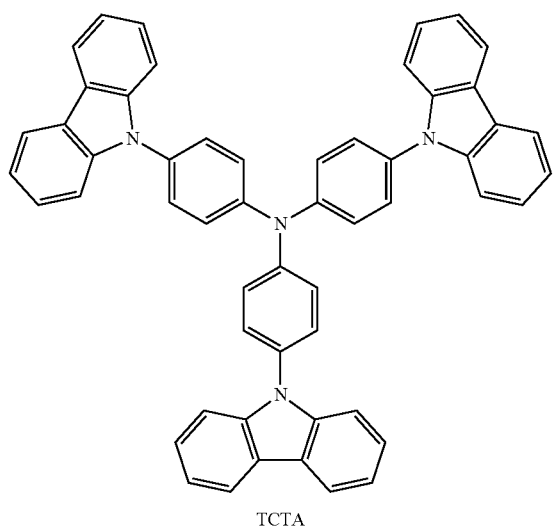

TCTA

2) Driving Voltage and Light Emission Efficiency of Organic Light Emitting Device For the organic light emitting devices manufactured as above, electroluminescent light emission (EL) properties were measured using M7000 manufactured by McScience Inc., and with the measurement results, T95 when standard luminance was 750 cd/m$^2$ was measured using a lifetime measurement system (M6000) manufactured by McScience Inc. Results of measuring driving voltage, light emission efficiency, external quantum efficiency and color coordinate (CIE) of the blue organic electroluminescent devices manufactured according to the present disclosure are as shown in Table 3.

TABLE 3

| | Compound | Driving Voltage (V) | Light Emission Efficiency (cd/A) | CIE (x, y) | Lifetime (T95) |
|---|---|---|---|---|---|
| Example 1 | 1 | 4.53 | 7.21 | (0.134, 0.104) | 43 |
| Example 2 | 2 | 4.18 | 7.13 | (0.134, 0.104) | 45 |
| Example 3 | 3 | 4.27 | 7.30 | (0.134, 0.105) | 39 |
| Example 4 | 4 | 4.21 | 6.98 | (0.134, 0.103) | 41 |

TABLE 3-continued

| | Compound | Driving Voltage (V) | Light Emission Efficiency (cd/A) | CIE (x, y) | Lifetime (T95) |
|---|---|---|---|---|---|
| Example 5 | 12 | 4.97 | 6.56 | (0.134, 0.101) | 37 |
| Example 6 | 13 | 4.57 | 7.00 | (0.134, 0.101) | 44 |
| Example 7 | 16 | 5.12 | 6.48 | (0.133, 0.102) | 34 |
| Example 8 | 17 | 4.32 | 7.11 | (0.134, 0.100) | 42 |
| Example 9 | 28 | 5.11 | 6.42 | (0.133, 0.101) | 30 |
| Example 10 | 44 | 5.27 | 6.55 | (0.134, 0.101) | 28 |
| Example 11 | 47 | 5.68 | 6.42 | (0.134, 0.101) | 32 |
| Example 12 | 51 | 5.88 | 6.30 | (0.134, 0,101) | 30 |
| Example 13 | 60 | 5.14 | 6.51 | (0.133, 0.101) | 28 |
| Example 14 | 62 | 5.89 | 6.18 | (0.133, 0.102) | 80 |
| Example 15 | 63 | 5.90 | 6.11 | (0.134, 0.100) | 78 |
| Example 16 | 65 | 5.28 | 6.78 | (0.133, 0.101) | 27 |
| Example 17 | 66 | 5.44 | 6.37 | (0.134, 0.101) | 26 |
| Example 18 | 68 | 5.68 | 6.32 | (0.133, 0.100) | 37 |
| Example 19 | 69 | 5.40 | 6.48 | (0.134, 0.100) | 25 |
| Example 20 | 79 | 5.38 | 6.50 | (0.133, 0.101) | 28 |
| Example 21 | 84 | 5.33 | 6.48 | (0.134, 0.101) | 28 |
| Example 22 | 93 | 5.36 | 6.54 | (0.134, 0.099) | 27 |
| Example 23 | 95 | 5.34 | 6.55 | (0.134, 0.101) | 30 |
| Example 24 | 98 | 5.68 | 6.43 | (0.133, 0.101) | 31 |
| Example 25 | 106 | 5.44 | 6.40 | (0.134, 0.102) | 33 |
| Example 26 | 115 | 5.67 | 6.39 | (0.134, 0.101) | 35 |
| Example 27 | 120 | 4.87 | 5.99 | (0.132, 0.101) | 29 |
| Example 28 | 131 | 5.68 | 6.47 | (0.134, 0.103) | 31 |
| Example 29 | 139 | 5.68 | 6.50 | (0.134, 0.101) | 34 |
| Example 30 | 142 | 5.66 | 6.77 | (0.133, 0.102) | 29 |
| Example 31 | 147 | 5.73 | 6.41 | (0.133, 0.101) | 54 |
| Example 32 | 148 | 5.64 | 6.40 | (0.134, 0.100) | 32 |
| Example 33 | 149 | 5.71 | 6.52 | (0.134, 0.101) | 33 |
| Example 34 | 157 | 5.68 | 6.55 | (0.133, 0.100) | 30 |
| Example 35 | 163 | 5.70 | 6.40 | (0.133, 0.101) | 30 |
| Example 36 | 172 | 5.23 | 6.33 | (0.133, 0.101) | 31 |
| Example 37 | 175 | 5.78 | 6.44 | (0.133, 0.101) | 37 |
| Example 38 | 176 | 5.73 | 6.62 | (0.133, 0.099) | 31 |
| Example 39 | 183 | 5.22 | 6.38 | (0.134, 0.101) | 67 |
| Example 40 | 192 | 5.11 | 6.52 | (0.133, 0.101) | 30 |
| Example 41 | 199 | 5.27 | 6.55 | (0.134, 0.101) | 28 |
| Example 42 | 203 | 5.68 | 6.40 | (0.134, 0.101) | 36 |
| Example 43 | 212 | 5.88 | 6.34 | (0.134, 0.101) | 37 |
| Comparative Example 1-1 | Bphen | 5.82 | 6.23 | (0.134, 0.110) | 27 |
| Comparative Example 1-2 | BBQB | 5.80 | 6.32 | (0.134, 0.111) | 29 |
| Comparative Example 1-3 | TBQB | 5.84 | 6.39 | (0.134, 0.111) | 25 |
| Comparative Example 1-4 | E2 | 5.96 | 6.38 | (0.134, 0.106) | 16 |
| Comparative Example 1-5 | E3 | 5.82 | 6.40 | (0.133, 0.109) | 12 |

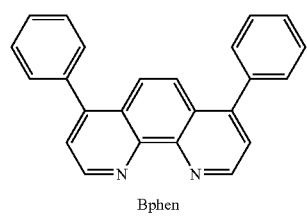 [SMILES: c1ccc(-c2ccnc3c2ccc2c(-c4ccccc4)ccnc23)cc1]

Bphen

BBQB

TBQB

E2

E3

As seen from the results of Table 3, the organic light emitting device using the charge generation layer material of the blue organic light emitting device of the present disclosure had lower driving voltage and improved light emission efficiency compared to the comparative examples. Particularly, it was identified that Compounds 1, 2, 3, 4, 13 and 17 were significantly superior in all aspects of driving, efficiency and lifetime.

Such a result is considered to be due to the fact that the compound of the present disclosure used as an N-type charge generation layer formed with the disclosed skeleton having proper length and strength, and flatness and a proper hetero-compound capable of binding to metals forms a gap state in the N-type charge generation layer by doping an alkali metal or an alkaline earth metal, and electrons produced from a P-type charge generation layer are readily injected into an electron transfer layer through the gap state produced in the N-type charge generation layer. Accordingly, the P-type charge generation layer may favorably inject and transfer electrons to the N-type charge generation layer, and as a result, driving voltage was lowered, and efficiency and lifetime were improved in the organic light emitting device.

Experimental Example 2

1) Manufacture of Organic Light Emitting Device

A glass substrate on which ITO was coated as a thin film to a thickness of 1500 Å was cleaned with distilled water ultrasonic waves. After the cleaning with distilled water was finished, the substrate was ultrasonic cleaned with solvents such as acetone, methanol and isopropyl alcohol, then dried, and UVO treated for 5 minutes using UV in a UV cleaner. After that, the substrate was transferred to a plasma cleaner (PT), and plasma treatment was performed under vacuum for ITO work function and residual film removal, and the substrate was transferred to a thermal deposition apparatus for organic deposition.

On the transparent ITO electrode (anode), organic materials were formed in a 2-stack white organic light emitting device (WOLED) structure. As for the first stack, TAPC was thermal vacuum deposited to a thickness of 300 Å to form a hole transfer layer. After forming the hole transfer layer, a light emitting layer was thermal vacuum deposited thereon as follows. As the light emitting layer, TCzl, a host, was 8% doped with FIrpic, a blue phosphorescent dopant, and deposited to 300 Å. After forming an electron transfer layer to 400 Å using TmPyPB, the compound described in the following Table 4 was 20% doped with $Cs_2CO_3$ to form a charge generation layer to 100 Å. As for the second stack, $MoO_3$ was thermal vacuum deposited to a thickness of 50 Å to form a hole injection layer. A hole transfer layer, a common layer, was formed to 100 Å by 20% doping $MoO_3$ to TAPC and then depositing TAPC to 300 Å. A light emitting layer was formed by 8% doping Ir(ppy)$_3$, a green phosphorescent dopant, to TCzl, a host, and depositing the result to 300 Å, and then an electron transfer layer was formed to 600 Å using TmPyPB. Lastly, an electron injection layer was formed on the electron transfer layer by depositing lithium fluoride (LiF) to a thickness of 10 Å, and then a cathode was formed on the electron injection layer by depositing an aluminum (Al) cathode to a thickness of 1,200 Å, and as a result, an organic light emitting device was manufactured.

Meanwhile, all the organic compounds required to manufacture the OLED were vacuum sublimation purified under $10^{-6}$ torr to $10^{-8}$ torr for each material to be used in the OLED manufacture.

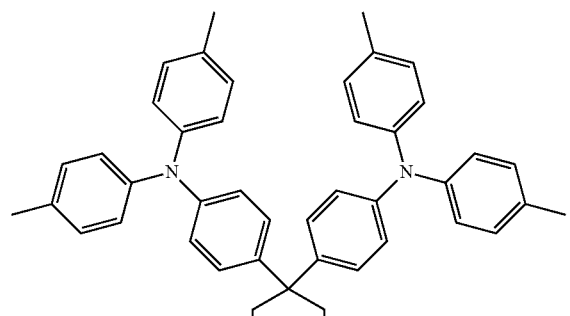

TAPC

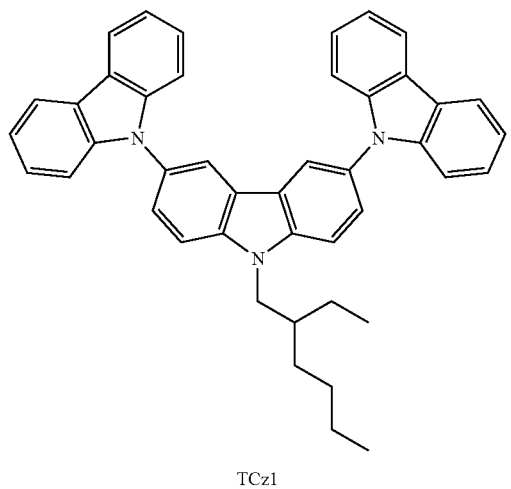

TCz1

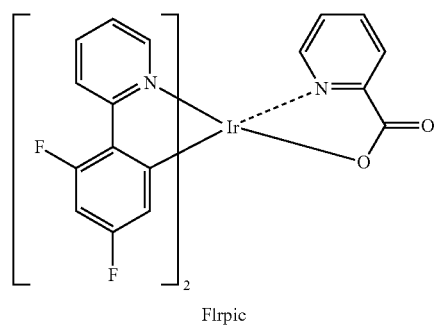

FIrpic

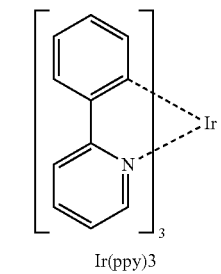

Ir(ppy)3

-continued

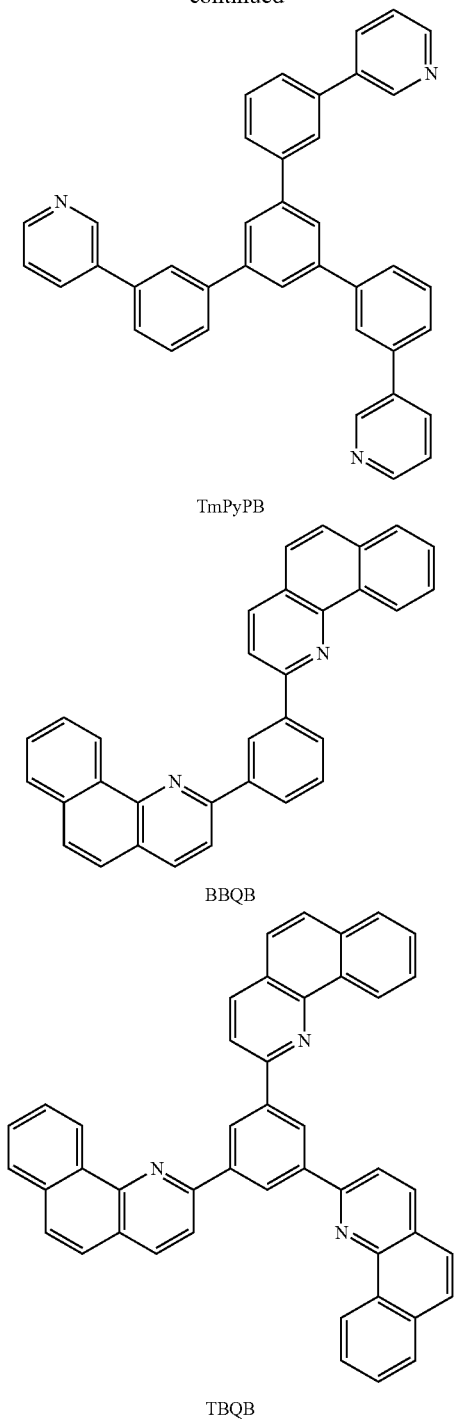

TmPyPB

BBQB

TBQB

2) Driving Voltage and Light Emission Efficiency of Organic Light Emitting Device For the organic light emitting devices manufactured as above, electroluminescent light emission (EL) properties were measured using M7000 manufactured by McScience Inc., and with the measurement results, T95 when standard luminance was 3,500 cd/m² was measured using a lifetime measurement system (M6000) manufactured by McScience Inc. Results of measuring driving voltage, light emission efficiency, external quantum efficiency and color coordinate (CIE) of the white organic electroluminescent devices manufactured according to the present disclosure are as shown in Table 4.

TABLE 4

| | Compound | Driving Voltage (V) | Light Emission Efficiency (cd/A) | CIE (x, y) | Lifetime (T95) |
|---|---|---|---|---|---|
| Example 44 | 1 | 7.23 | 68.95 | (0.218, 0.427) | 35 |
| Example 45 | 2 | 7.02 | 69.45 | (0.220, 0.431) | 49 |
| Example 46 | 3 | 7.07 | 64.88 | (0.200, 0.421) | 32 |
| Example 47 | 4 | 7.11 | 67.23 | (0.205, 0.411) | 40 |
| Example 48 | 12 | 7.65 | 63.21 | (0.221, 0.434) | 33 |
| Example 49 | 13 | 7.01 | 69.82 | (0.220, 0.440) | 43 |
| Example 50 | 16 | 7.67 | 58.98 | (0.219, 0.411) | 35 |
| Example 51 | 17 | 7.10 | 69.45 | (0.219, 0.429) | 40 |
| Example 52 | 28 | 7.66 | 59.22 | (0.215, 0.411) | 30 |
| Example 53 | 44 | 7.77 | 60.94 | (0.211, 0.419) | 32 |
| Example 54 | 47 | 8.24 | 58.26 | (0.209, 0.419) | 31 |
| Example 55 | 51 | 8.01 | 59.11 | (0.207, 0.409) | 33 |
| Example 56 | 60 | 7.40 | 63.66 | (0,208, 0.415) | 29 |
| Example 57 | 62 | 8.06 | 58.03 | (0.208, 0.412) | 52 |
| Example 58 | 63 | 8.24 | 57.98 | (0.208, 0.411) | 56 |
| Example 59 | 65 | 7.96 | 60.77 | (0.208, 0.412) | 27 |
| Example 60 | 66 | 7.88 | 61.29 | (0.209, 0.412) | 30 |
| Example 61 | 68 | 8.13 | 59.01 | (0.207, 0.411) | 49 |
| Example 62 | 69 | 8.00 | 59.13 | (0.231, 0.440) | 34 |
| Example 63 | 79 | 7.82 | 63.22 | (0.232, 0.422) | 26 |
| Example 64 | 84 | 7.99 | 63.88 | (0.230, 0.420) | 30 |
| Example 65 | 93 | 8.25 | 61.12 | (0.223, 0.433) | 36 |
| Example 66 | 95 | 7.76 | 63.47 | (0.222, 0.435) | 31 |
| Example 67 | 98 | 8.22 | 60.84 | (0.218, 0.421) | 30 |
| Example 68 | 106 | 8.37 | 59.91 | (0.220, 0.421) | 30 |
| Example 69 | 115 | 8.25 | 62.56 | (0.224, 0.429) | 32 |
| Example 70 | 120 | 7.55 | 60.99 | (0.215, 0.422) | 27 |
| Example 71 | 131 | 8.33 | 61.11 | (0,214, 0.420) | 33 |
| Example 72 | 139 | 7.74 | 63.32 | (0.230, 0.439) | 37 |
| Example 73 | 142 | 7.71 | 65.97 | (0.208, 0.412) | 29 |
| Example 74 | 147 | 8.52 | 57.04 | (0.231, 0.418) | 70 |
| Example 75 | 148 | 7.78 | 60.01 | (0.208, 0.412) | 32 |
| Example 76 | 149 | 8.01 | 59.97 | (0.209, 0.411) | 41 |
| Example 77 | 157 | 7.71 | 64.37 | (0.208, 0.412) | 30 |
| Example 78 | 163 | 7.82 | 54.67 | (0.233, 0.419) | 30 |
| Example 79 | 172 | 7.54 | 63.58 | (0.208, 0.412) | 31 |
| Example 80 | 175 | 7.88 | 59.36 | (0.207, 0.417) | 37 |
| Example 81 | 176 | 7.71 | 62.03 | (0.220, 0.412) | 29 |
| Example 82 | 183 | 8.38 | 59.80 | (0.231, 0.423) | 71 |
| Example 83 | 192 | 7.91 | 60.22 | (0.215, 0.411) | 28 |
| Example 84 | 199 | 7.97 | 60.94 | (0.211, 0.419) | 31 |
| Example 85 | 203 | 8.24 | 58.26 | (0.209, 0.419) | 35 |
| Example 86 | 212 | 8.01 | 59.11 | (0.207, 0.409) | 37 |
| Comparative Example 2-1 | TmPyPB | 8.57 | 57.61 | (0.212, 0.433) | 24 |
| Comparative Example 2-2 | BBQB | 8.43 | 58.11 | (0.220, 0.429) | 27 |
| Comparative Example 2-3 | TBQB | 8.47 | 58.90 | (0.222, 0.430) | 28 |

As seen from the results of Table 4, the organic light emitting device using the charge generation layer material of the 2-stack white organic light emitting device of the present disclosure had lower driving voltage and improved light emission efficiency compared to the comparative examples. Particularly, it was identified that Compounds 1, 2, 3, 4, 13 and 17 were significantly superior in all aspects of driving, efficiency and lifetime.

Such a result is considered to be due to the fact that the compound of the present disclosure used as an N-type charge generation layer formed with the disclosed skeleton having proper length and strength, and flatness and a proper hetero-compound capable of binding to metals forms a gap state in the N-type charge generation layer by doping an alkali metal or an alkaline earth metal, and electrons produced from a P-type charge generation layer are readily injected into an electron transfer layer through the gap state produced in the N-type charge generation layer. Accordingly, the P-type charge generation layer may favorably inject and transfer electrons to the N-type charge generation layer, and as a result, driving voltage was lowered, and efficiency and lifetime were improved in the organic light emitting device.

Experimental Example 3

1) Manufacture of Organic Light Emitting Device

A transparent ITO electrode thin film obtained from glass for an OLED (manufactured by Samsung-Corning Co., Ltd.) was ultrasonic cleaned using trichloroethylene, acetone, ethanol and distilled water consecutively for 5 minutes each, stored in isopropanol, and used.

Next, an ITO substrate was installed in a substrate folder of a vacuum deposition apparatus, and the following 4,4', 4"-tris(N,N-(2-naphthyl)-phenylamino)triphenylamine (2-TNATA) was introduced to a cell in the vacuum deposition apparatus.

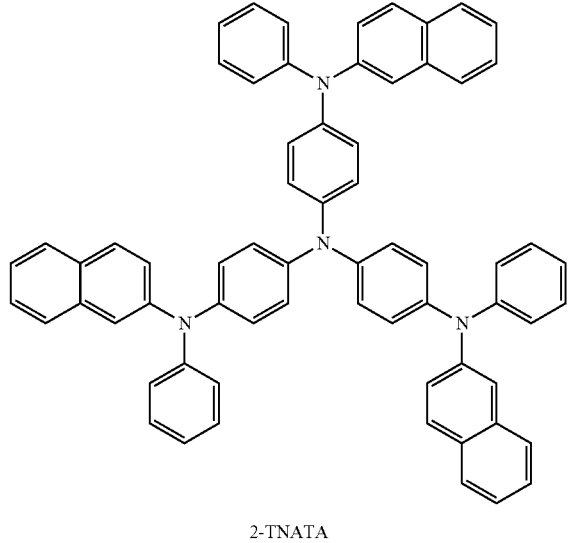 [SMILES: c1ccc(N(c2ccc(N(c3ccc(N(c4ccccc4)c4ccc5ccccc5c4)cc3)c3ccc(N(c4ccccc4)c4ccc5ccccc5c4)cc3)cc2)c2ccc3ccccc3c2)cc1]

2-TNATA

Subsequently, the chamber was evacuated until the degree of vacuum therein reached $10^{-6}$ torr, and then 2-TNATA was evaporated by applying a current to the cell to deposit a hole injection layer having a thickness of 600 Å on the ITO substrate.

To another cell of the vacuum deposition apparatus, the following N,N'-bis(α-naphthyl)-N,N'-diphenyl-4,4'-diamine (NPB) was introduced, and evaporated by applying a current to the cell to deposit a hole transfer layer having a thickness of 300 Å on the hole injection layer.

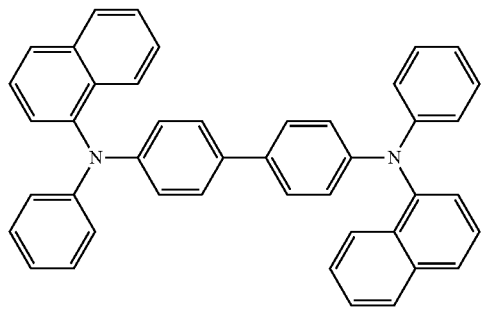

NPB

After forming the hole injection layer and the hole transfer layer as above, a blue light emitting material having a structure as below was deposited thereon as a light emitting layer. Specifically, in one side cell in the vacuum deposition apparatus, H1, a blue light emitting host material, was vacuum deposited to a thickness of 200 Å, and D1, a blue light emitting dopant material, was vacuum deposited thereon by 5% with respect to the host material.

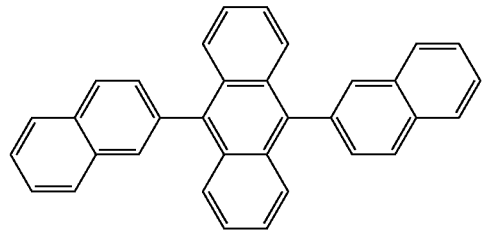

H1

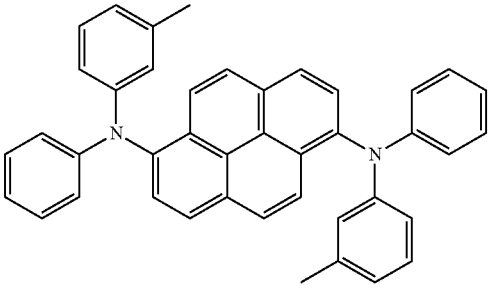

D1

Subsequently, a compound of the following Table 5 was deposited to a thickness of 300 Å as an electron transfer layer.

As an electron injection layer, lithium fluoride (LiF) was deposited to a thickness of 10 Å, and an Al cathode was employed to a thickness of 1,000 Å, and as a result, an OLED was manufactured.

Meanwhile, all the organic compounds required to manufacture the OLED were vacuum sublimation purified under $10^{-6}$ torr to $10^{-8}$ torr by each material to be used in the OLED manufacture.

2) Driving Voltage and Light Emission Efficiency of Organic Light Emitting Device For the organic light emitting devices manufactured as above, electroluminescent light emission (EL) properties were measured using M7000 manufactured by McScience Inc., and with the measurement results, T95 when standard luminance was 700 cd/m$^2$ was measured using a lifetime measurement system (M6000) manufactured by McScience Inc. Results of measuring driving voltage, light emission efficiency, external quantum efficiency and color coordinate (CIE) of the blue organic electroluminescent devices manufactured according to the present disclosure are as shown in Table 5.

TABLE 5

| Compound | Driving Voltage (V) | Light Emission Efficiency (cd/A) | CIE (x, y) | Lifetime (T95) |
| --- | --- | --- | --- | --- |
| Example 87 | 1 | 5.50 | 6.32 | (0.134, 0.101) | 33 |
| Example 88 | 2 | 5.44 | 6.44 | (0.134, 0.102) | 32 |
| Example 89 | 3 | 5.34 | 6.38 | (0.134, 0.101) | 31 |
| Example 90 | 4 | 5.38 | 6.20 | (0.134, 0.103) | 35 |
| Example 91 | 12 | 5.60 | 6.12 | (0.134, 0.102) | 34 |
| Example 92 | 13 | 5.45 | 6.01 | (0.134, 0.101) | 33 |
| Example 93 | 16 | 5.44 | 6.22 | (0.134, 0.102) | 30 |
| Example 94 | 17 | 5.46 | 6.18 | (0.134, 0.101) | 29 |
| Example 95 | 28 | 5.40 | 6.13 | (0.134, 0.101) | 31 |
| Example 96 | 44 | 5.44 | 6.30 | (0.134, 0.100) | 32 |
| Example 97 | 47 | 5.37 | 6.35 | (0.134, 0.101) | 32 |
| Example 98 | 51 | 5.38 | 6.41 | (0.134, 0.100) | 30 |
| Example 99 | 60 | 4.81 | 6.93 | (0.134, 0.100) | 30 |
| Example 100 | 62 | 5.48 | 6.21 | (0.134, 0.100) | 87 |
| Example 101 | 63 | 5.47 | 6.28 | (0.134, 0.100) | 79 |
| Example 102 | 65 | 4.45 | 6.98 | (0.134, 0.102) | 42 |
| Example 103 | 66 | 4.52 | 6.63 | (0.134, 0.102) | 44 |
| Example 104 | 68 | 5.12 | 6.20 | (0.134, 0.101) | 40 |
| Example 105 | 69 | 4.39 | 6.87 | (0.134, 0.102) | 43 |
| Example 106 | 79 | 4.71 | 6.48 | (0.134, 0.100) | 34 |
| Example 107 | 84 | 4.38 | 7.00 | (0.134, 0.103) | 39 |
| Example 108 | 93 | 5.34 | 6.31 | (0.134, 0.100) | 36 |
| Example 109 | 95 | 5.40 | 6.36 | (0.134, 0.102) | 32 |
| Example 110 | 98 | 5.42 | 6.26 | (0.134, 0.101) | 32 |
| Example 111 | 106 | 5.39 | 6.19 | (0.134, 0.100) | 31 |
| Example 112 | 115 | 5.55 | 6.27 | (0.134, 0.102) | 31 |
| Example 113 | 120 | 4.98 | 6.20 | (0.134, 0.103) | 30 |
| Example 114 | 131 | 5.41 | 6.19 | (0.134, 0.100) | 32 |
| Example 115 | 139 | 5.22 | 6.28 | (0.134, 0.103) | 36 |
| Example 116 | 142 | 5.19 | 6.41 | (0.134, 0.102) | 33 |
| Example 117 | 147 | 5.43 | 6.17 | (0.134, 0.100) | 62 |
| Example 118 | 148 | 4.94 | 6.85 | (0.134, 0.099) | 40 |
| Example 119 | 149 | 4.51 | 6.97 | (0.134, 0.102) | 42 |
| Example 120 | 157 | 4.45 | 7.03 | (0.134, 0.100) | 39 |
| Example 121 | 163 | 5.00 | 6.21 | (0.134, 0.103) | 32 |
| Example 122 | 172 | 4.93 | 6.35 | (0.134, 0.101) | 35 |
| Example 123 | 175 | 4.50 | 6.92 | (0.134, 0.104) | 41 |
| Example 124 | 176 | 5.03 | 6.27 | (0.134, 0.100) | 35 |
| Example 125 | 183 | 5.11 | 6.22 | (0.134, 0.103) | 36 |
| Example 126 | 192 | 5.01 | 6.98 | (0.134, 0.100) | 31 |
| Example 127 | 199 | 4.98 | 7.10 | (0.134, 0.103) | 33 |
| Example 128 | 203 | 5.34 | 6.21 | (0.134, 0.100) | 36 |
| Example 129 | 212 | 5.40 | 6.36 | (0.134, 0.102) | 39 |
| Comparative Example 3-1 | E1 | 5.56 | 5.91 | (0.134, 0.100) | 28 |
| Comparative Example 3-2 | BBQB | 5.50 | 6.10 | (0.134, 0.101) | 30 |
| Comparative Example 3-3 | TBQB | 5.51 | 6.15 | (0.134, 0.102) | 29 |
| Comparative Example 3-4 | E2 | 5.48 | 6.14 | (0.133, 0.108) | 15 |
| Comparative Example 3-5 | E3 | 5.53 | 5.99 | (0.134, 0.102) | 11 |

E1

BBQB

TBQB

E2

TABLE 5-continued

| Compound | Driving Voltage (V) | Light Emission Efficiency (cd/A) | CIE (x, y) | Lifetime (T95) |
|---|---|---|---|---|

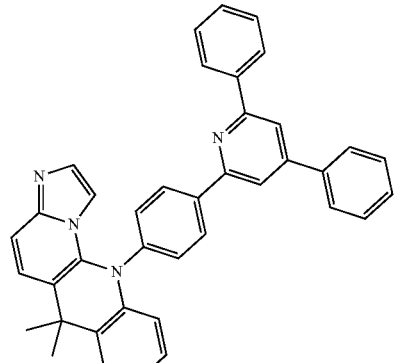

E3

As seen from the results of Table 5, the organic light emitting device using the electron transfer layer material of the blue organic light emitting device of the present disclosure had a lower driving voltage and significantly improved light emission efficiency and lifetime compared to the comparative examples. Particularly, it was identified that Compounds 65, 66, 69, 84, 149, 157 and 175 were superior in all aspects of driving, efficiency and lifetime.

Such a result is considered to be due to the fact that, when using the disclosed compound having proper length and strength, and flatness as an electron transfer layer, a compound in an excited state is made by receiving electrons under a specific condition, and particularly when a hetero-skeleton site of the compound is formed in an excited state, excited energy moves to a stable state before the excited hetero-skeleton site goes through other reactions, and a relatively stabilized compound is capable of efficiently transferring electrons without the compound being decomposed or destroyed. For reference, those that are stable when excited are considered to be aryl or acene-based compounds or polycyclic hetero-compounds. Accordingly, it is considered that excellent results in all aspects of driving, efficiency and lifetime were obtained by the compound of the present disclosure, enhancing electron-transfer properties or improved stability.

The invention claimed is:

1. A heterocyclic compound represented by the following Chemical Formula 1:

[Chemical Formula 1]

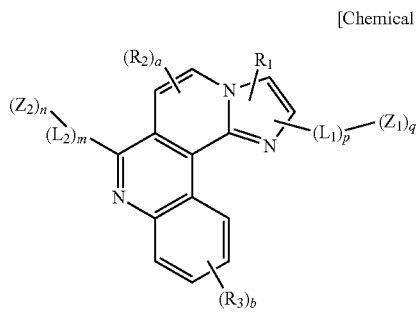

wherein, in Chemical Formula 1,
$L_1$ and $L_2$ are the same as or different from each other, and each independently a direct bond; a substituted or unsubstituted arylene group; or a substituted or unsubstituted heteroarylene group;
$Z_1$ and $Z_2$ are the same as or different from each other, and each independently a substituted or unsubstituted alkyl group; a substituted or unsubstituted aryl group; a substituted or unsubstituted heteroaryl group; —SiRR'R"; or —P(=O)RR';
$R_1$ to $R_3$ are the same as or different from each other, and each independently selected from the group consisting of hydrogen; deuterium; a substituted or unsubstituted alkyl group; a substituted or unsubstituted aryl group; a substituted or unsubstituted heteroaryl group; —SiRR'R"; and —P(=O)RR';
R, R' and R" are the same as or different from each other, and each independently hydrogen; a substituted or unsubstituted alkyl group; a substituted or unsubstituted aryl group; or a substituted or unsubstituted heteroaryl group;
m, p, n and q are each an integer of 1 to 5;
a is an integer of 0 to 2;
b is an integer of 0 to 4;
when m, p, n, q and b are an integer of 2 or greater, substituents in the parentheses are the same as or different from each other; and
when a is an integer of 2, substituents in the parentheses are the same as or different from each other,
wherein the "substituted or unsubstituted" means being substituted with one or more substituents selected from the group consisting of C1 to C60 linear or branched alkyl; C6 to C60 monocyclic or polycyclic aryl; C2 to C60 monocyclic or polycyclic heteroaryl; —SiRR'R"; and —P(=O)RR'; and
R, R' and R" have the same definitions as in Chemical Formula 1.

2. The heterocyclic compound of claim 1, wherein Chemical Formula 1 is represented by the following Chemical Formula 2 or Chemical Formula 3:

[Chemical Formula 2]

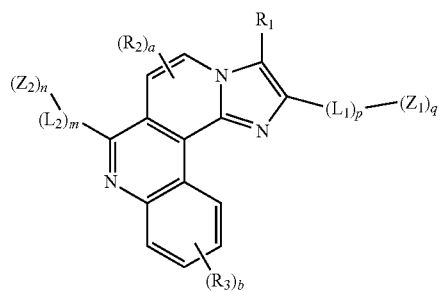

[Chemical Formula 3]

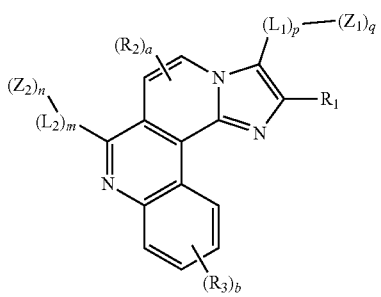

in Chemical Formulae 2 and 3, $L_1$, $L_2$, $Z_1$, $Z_2$, $R_1$ to $R_3$, a, b, m, n, p and q have the same definitions as in Chemical Formula 1.

3. The heterocyclic compound of claim 1, wherein Chemical Formula 1 is represented by any one of the following Chemical Formulae 4 to 9:

[Chemical Formula 4]

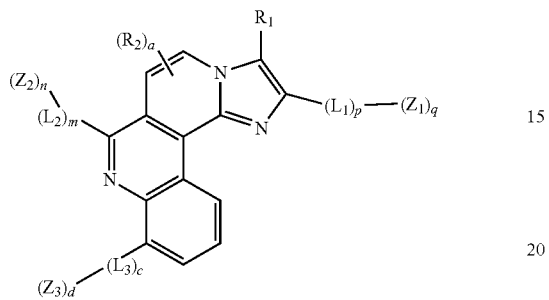

[Chemical Formula 5]

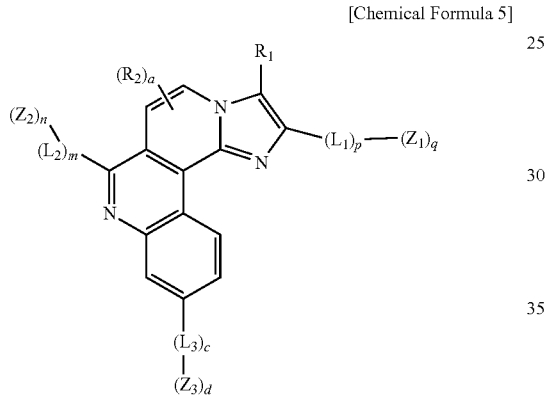

[Chemical Formula 6]

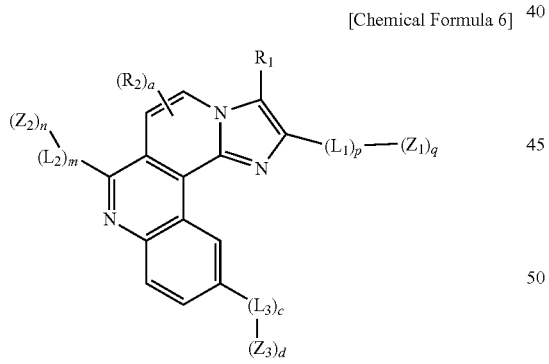

[Chemical Formula 7]

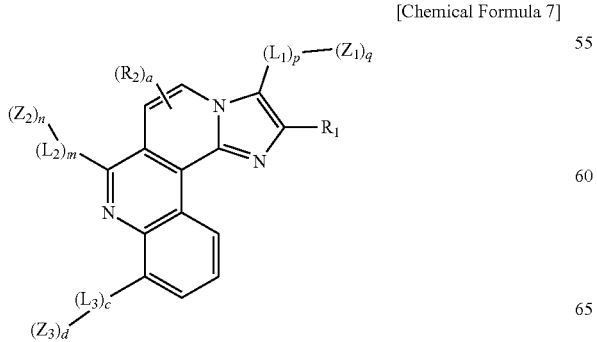

[Chemical Formula 8]

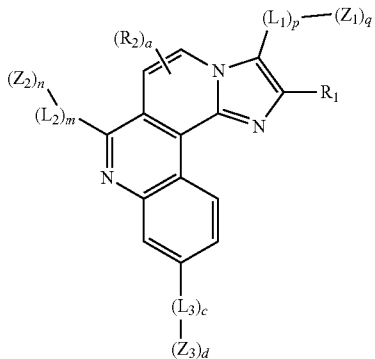

[Chemical Formula 9]

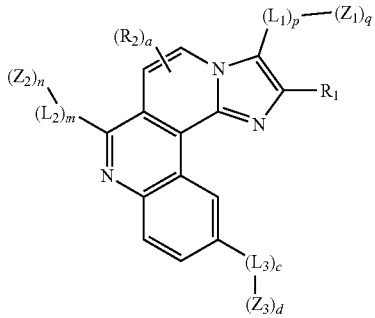

in Chemical Formulae 4 to 9, $L_1$, $L_2$, $Z_1$, $Z_2$, $R_1$, $R_2$, a, m, n, p and q have the same definitions as in Chemical Formula 1;

$L_3$ is a direct bond; a substituted or unsubstituted arylene group; or a substituted or unsubstituted heteroarylene group;

$Z_3$ is hydrogen; a substituted or unsubstituted alkyl group; a substituted or unsubstituted aryl group; a substituted or unsubstituted heteroaryl group; or —P(=O)RR';

c is an integer of 0 to 3;

d is an integer of 1 to 5; and

R and R' have the same definitions as in Chemical Formula 1.

4. The heterocyclic compound of claim 1, wherein $R_1$ is hydrogen; or a substituted or unsubstituted aryl group;

$R_2$ is hydrogen;

$R_3$ is hydrogen; a substituted or unsubstituted alkyl group; a substituted or unsubstituted aryl group; a substituted or unsubstituted heteroaryl group; or —P(=O)RR'; and R and R' have the same definitions as in Chemical Formula 1.

5. The heterocyclic compound of claim 1, wherein Chemical Formula 1 is represented by any one of the following compounds:

181
1
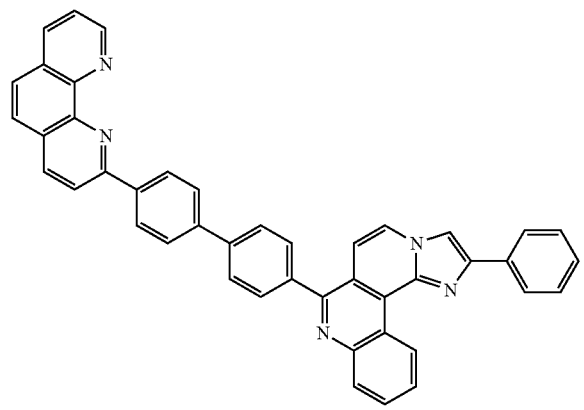
2
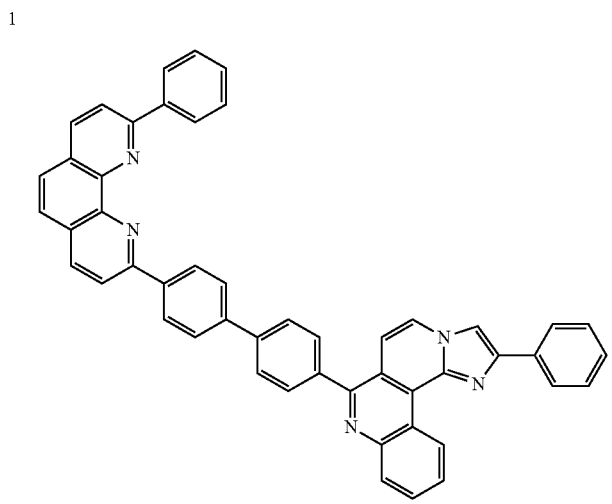
3
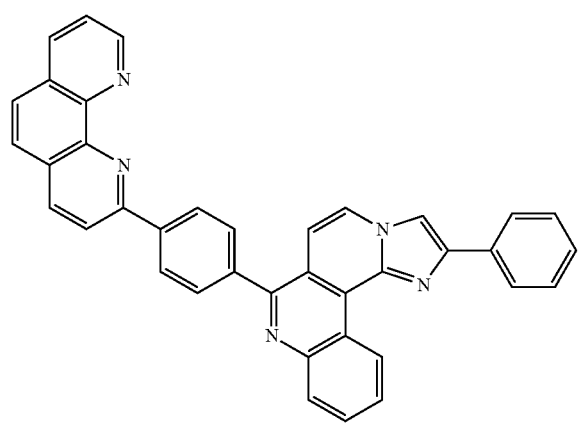
182
4
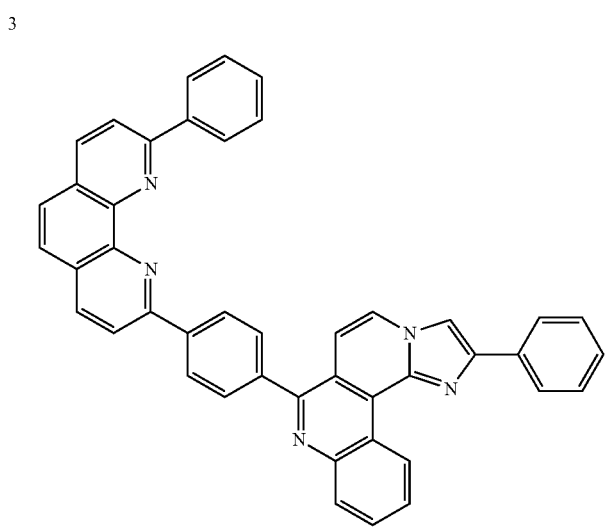
5
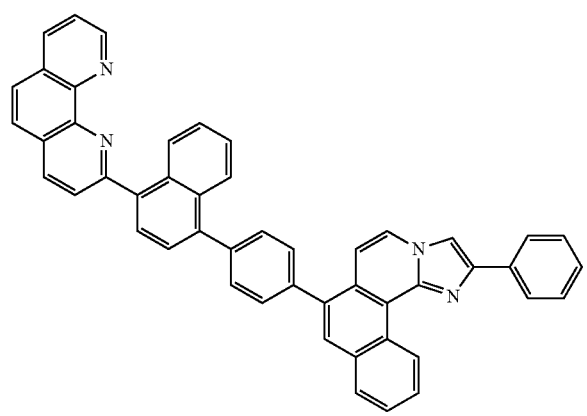
6
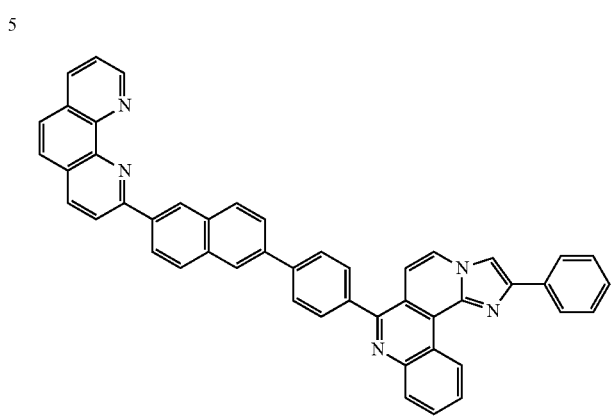

7
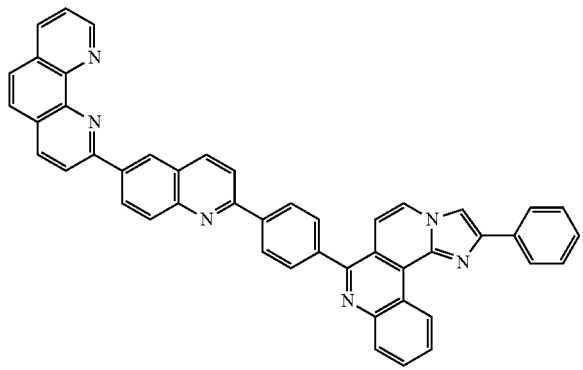
8
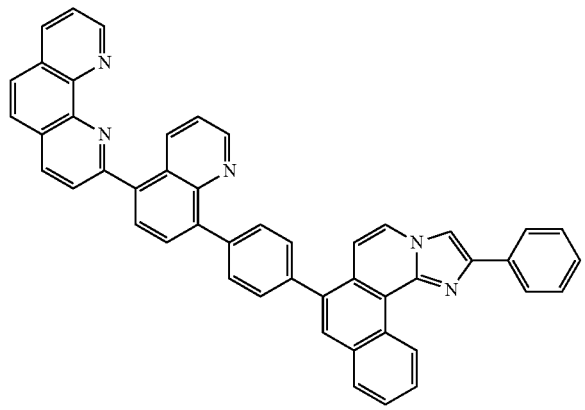
9
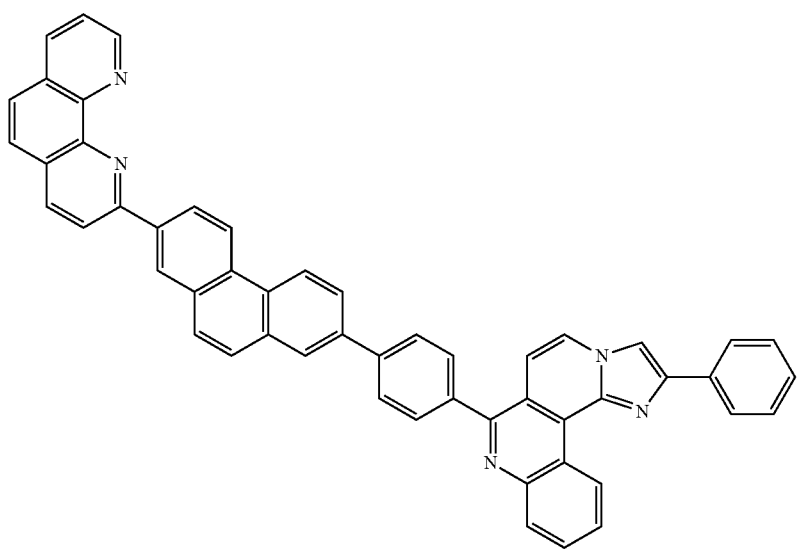
10
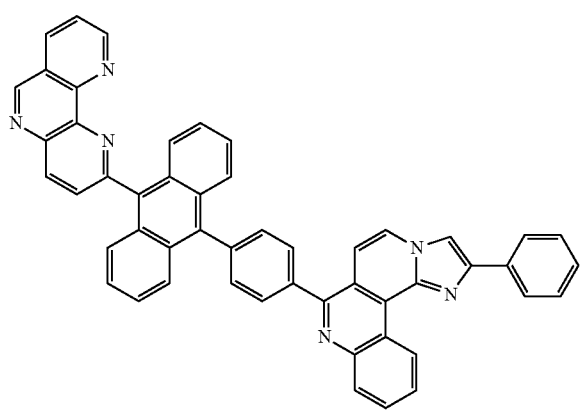

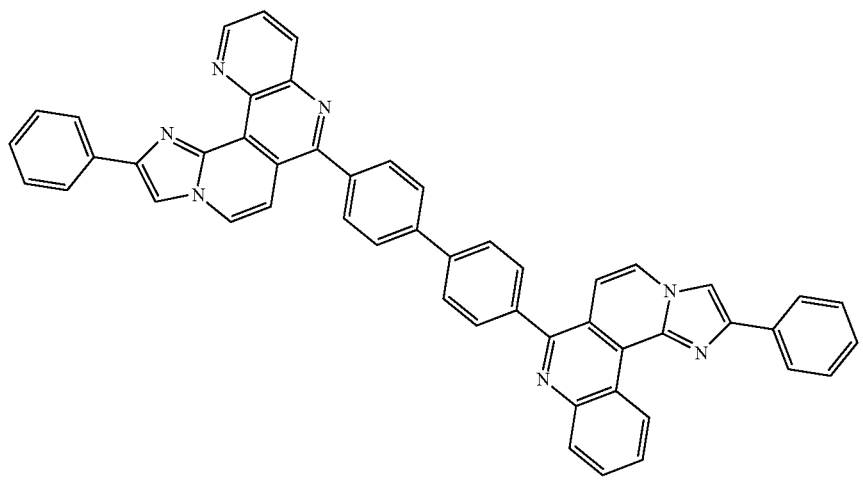
11
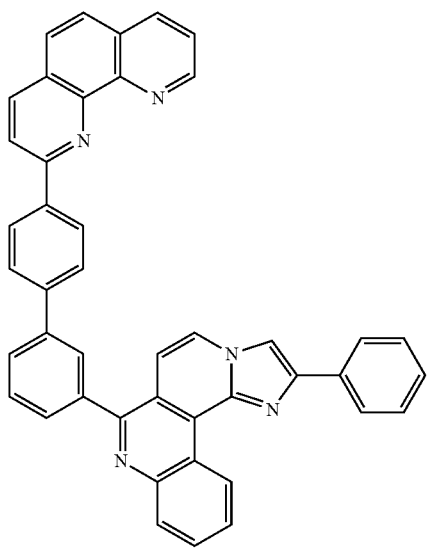
12
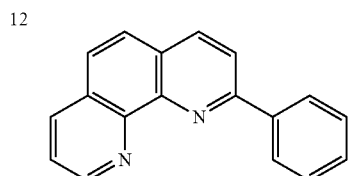
13
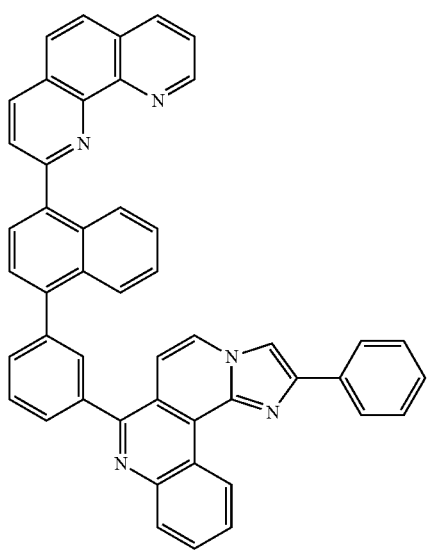
14
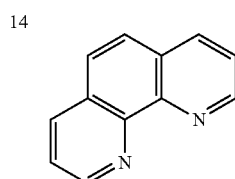
15

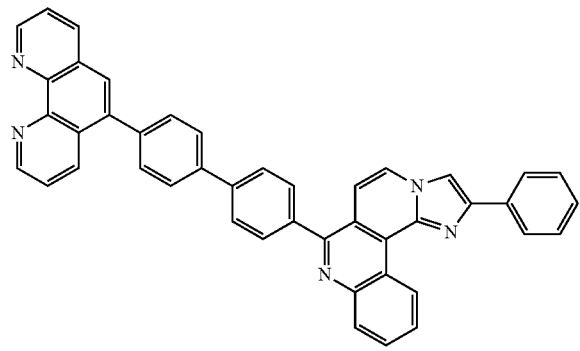
16
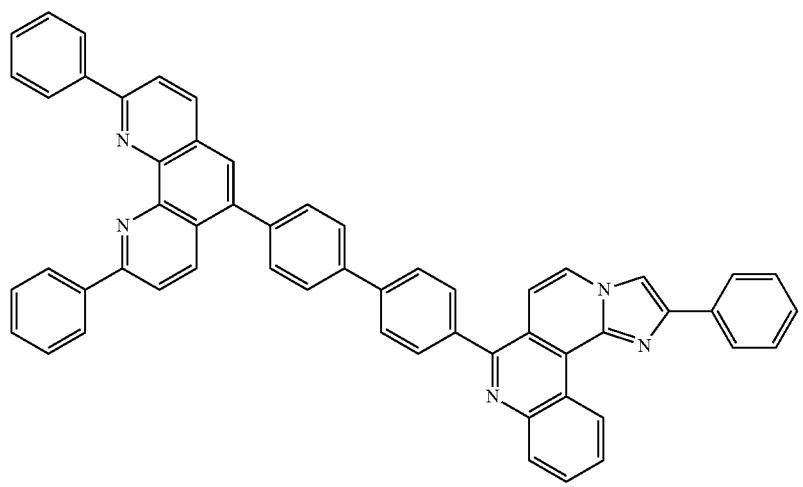
17
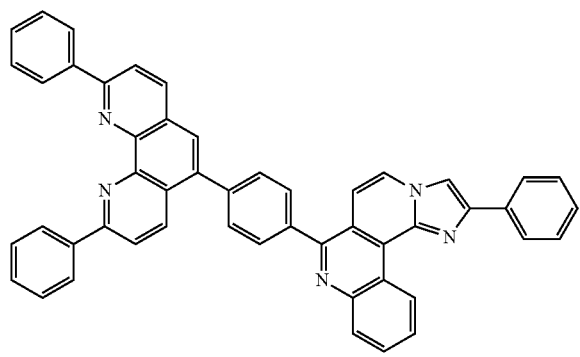
18
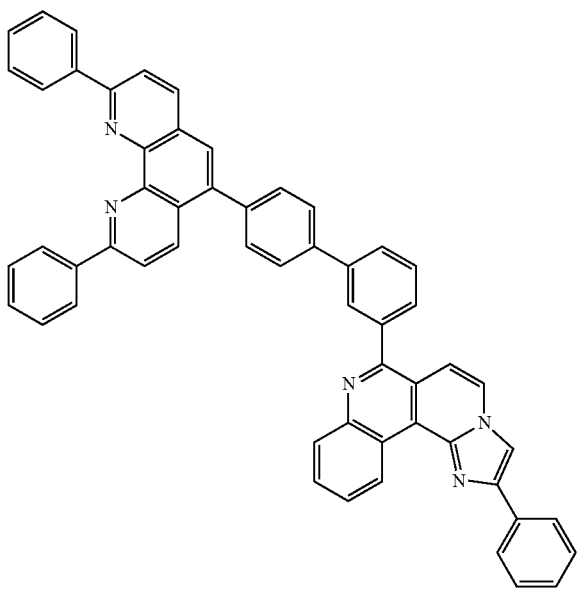
19

-continued
20
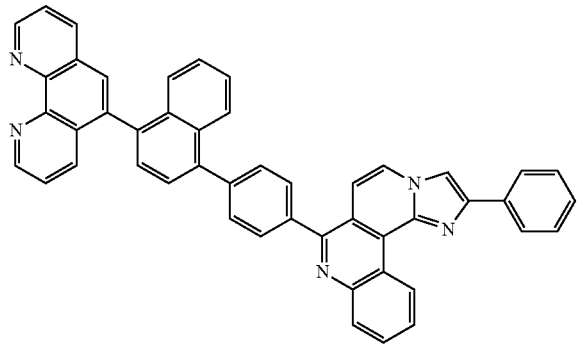
21
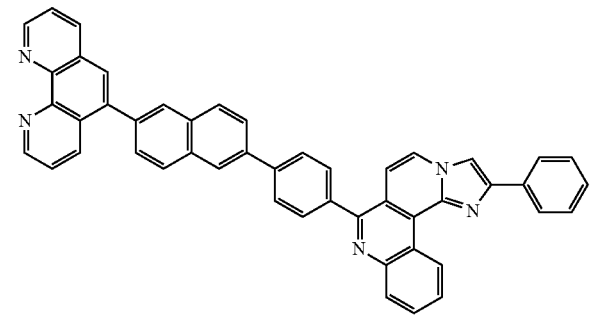
22
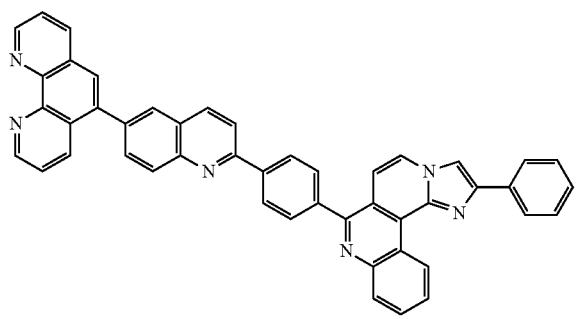
23
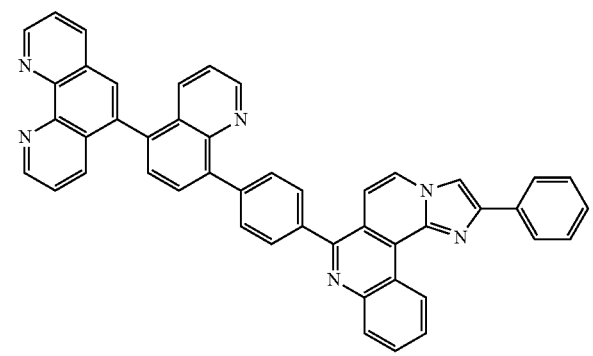
24
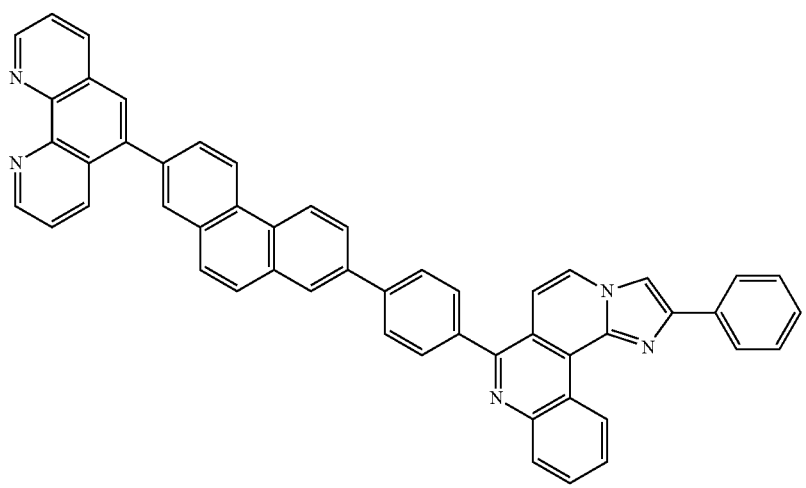

-continued
25
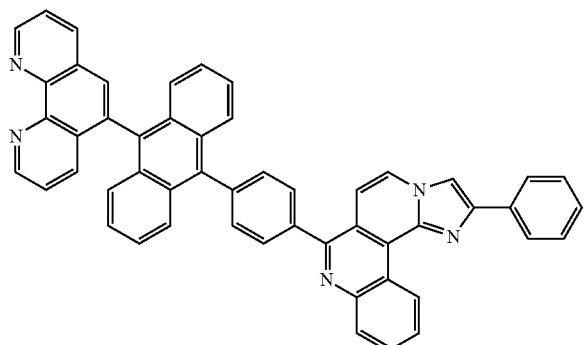
26
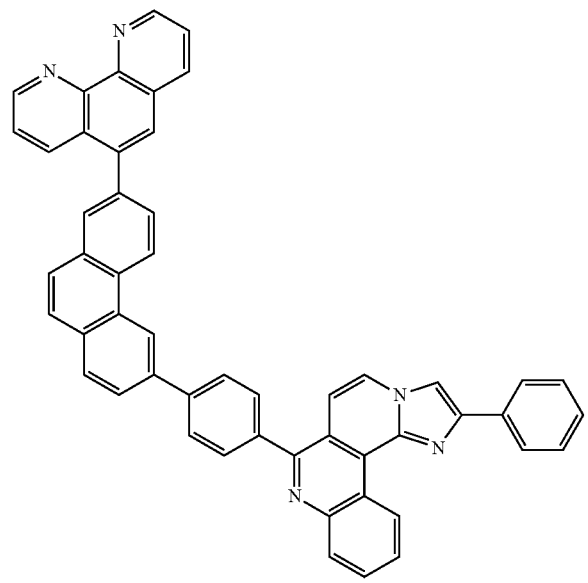
27
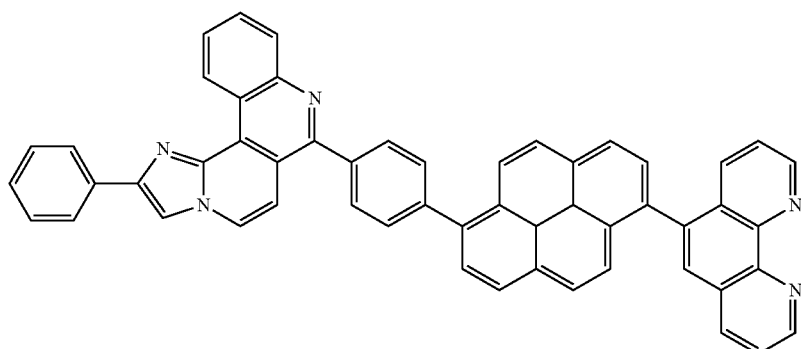
28
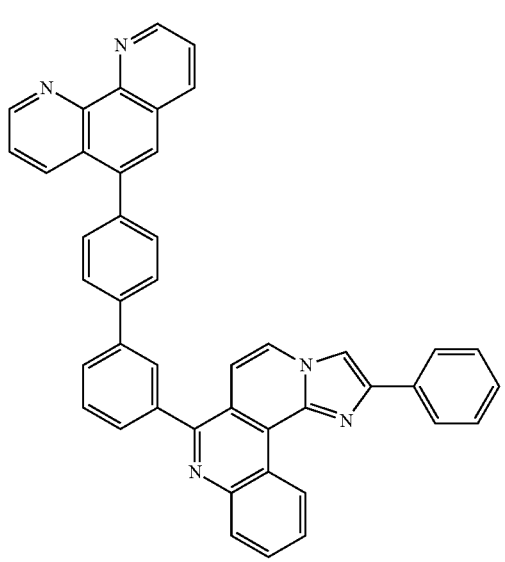
29
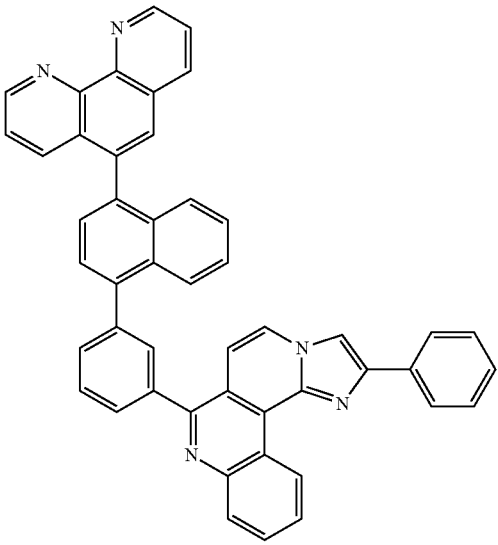

193
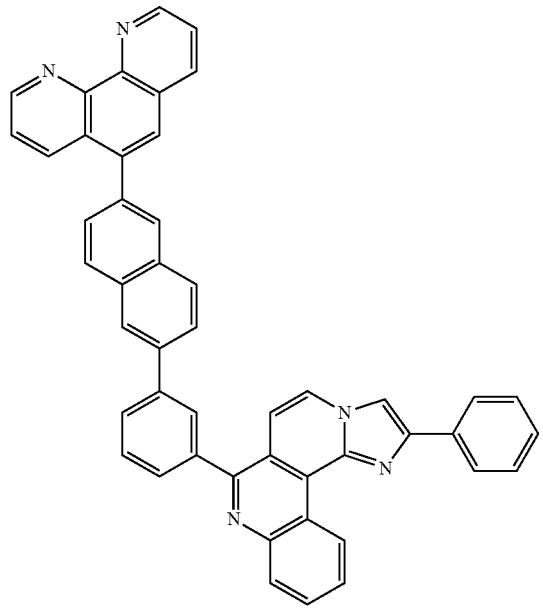
30
194
-continued
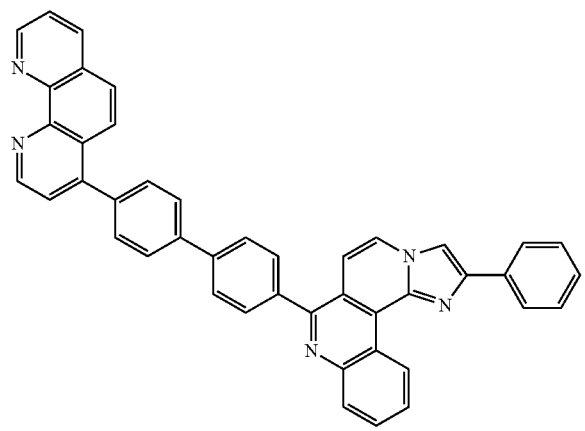
31
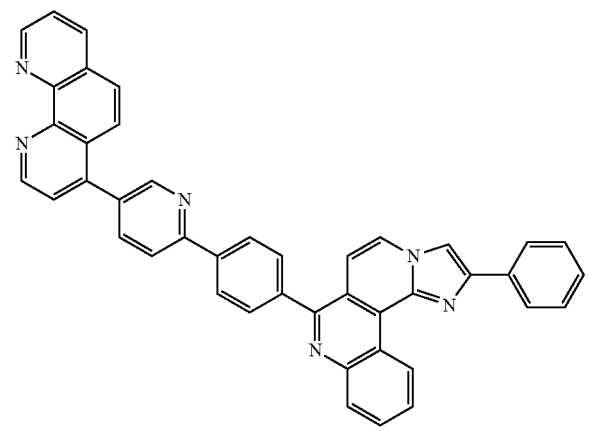
32
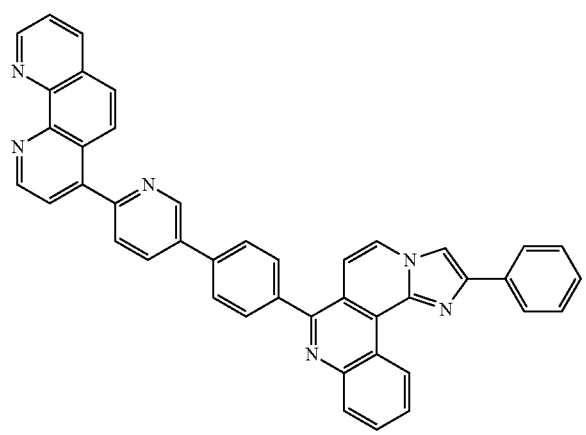
33
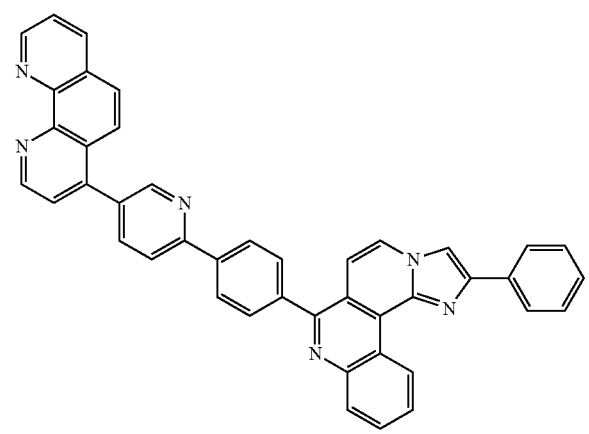
34

35
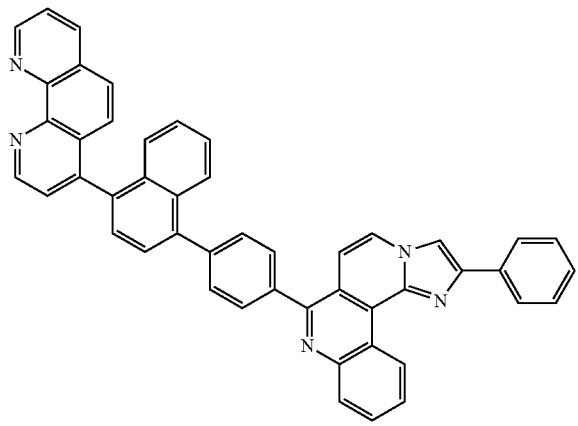
36
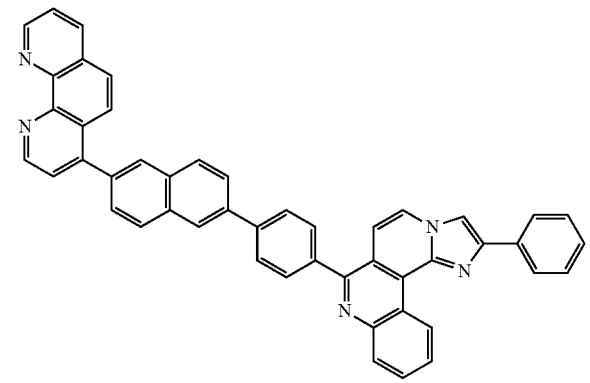
37
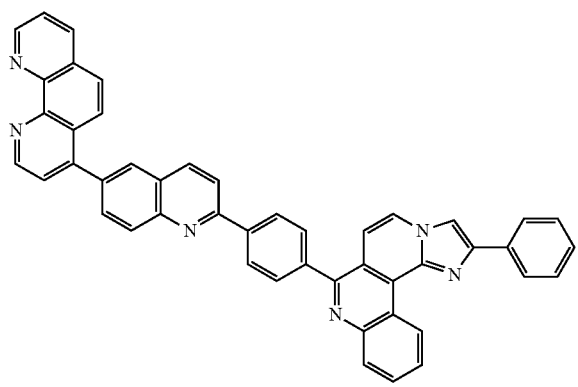
38
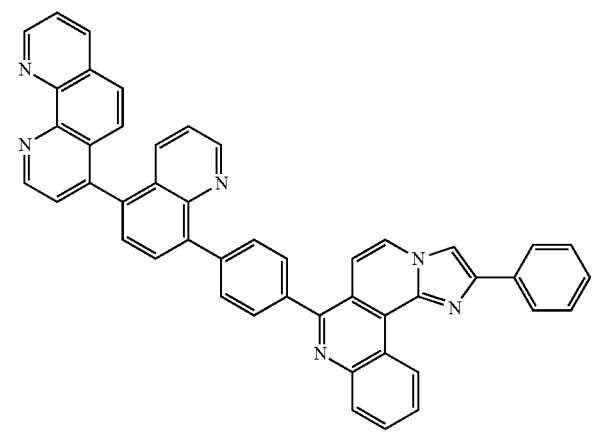
39
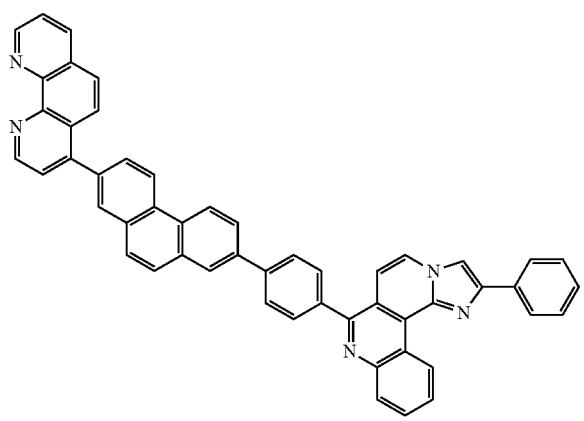
40
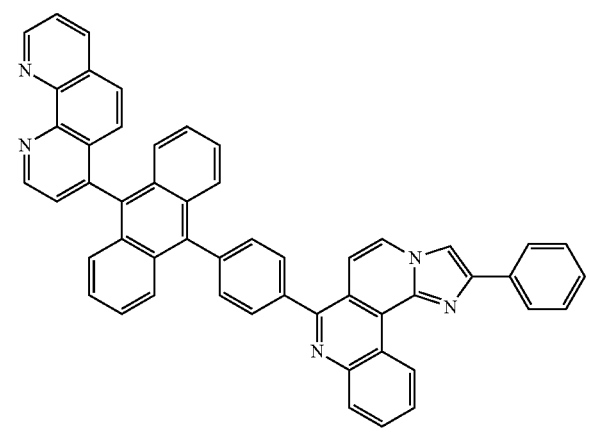

41
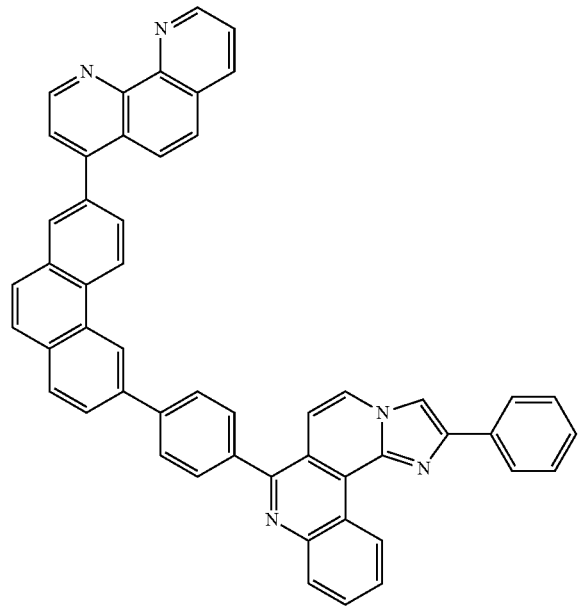
42
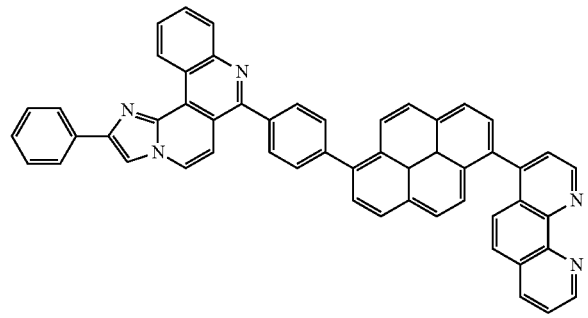
43
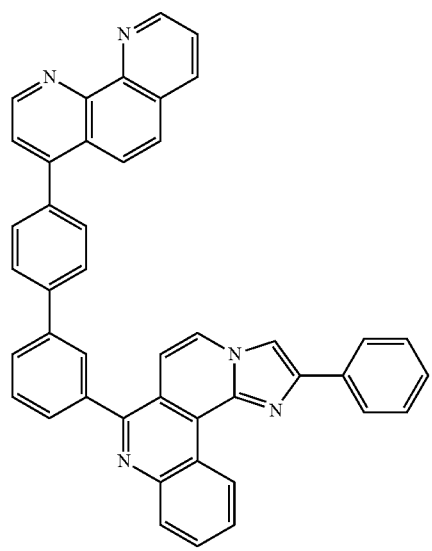
44
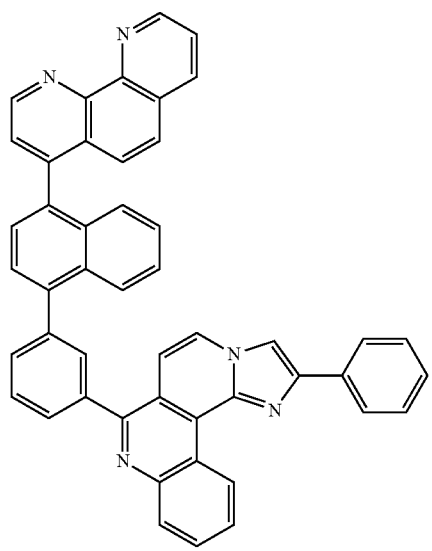

-continued
45
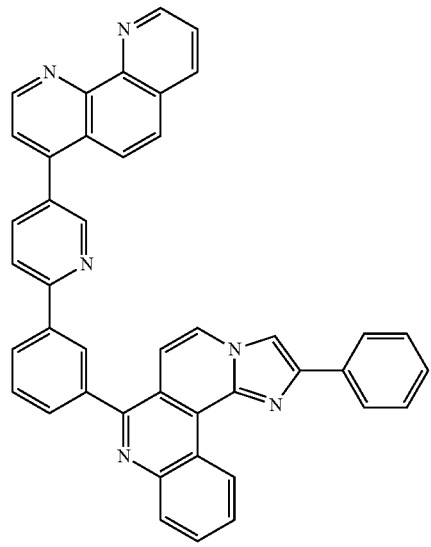
46
47
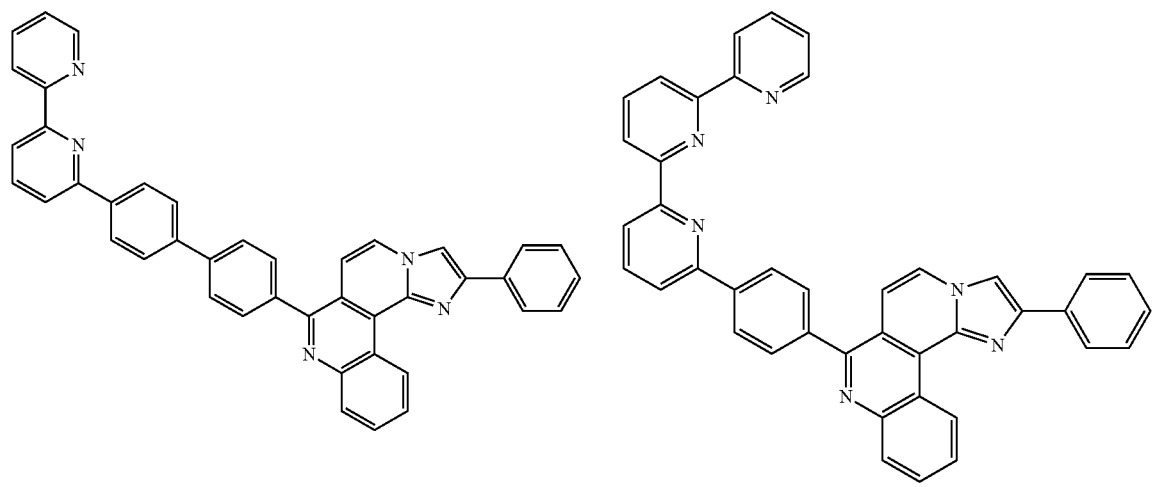
48
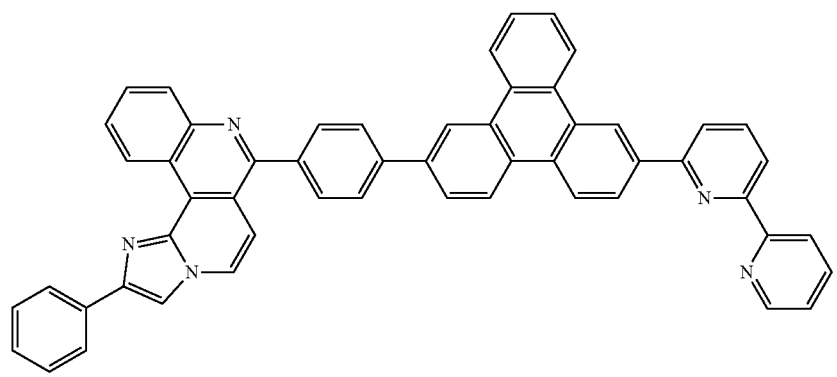

-continued
49
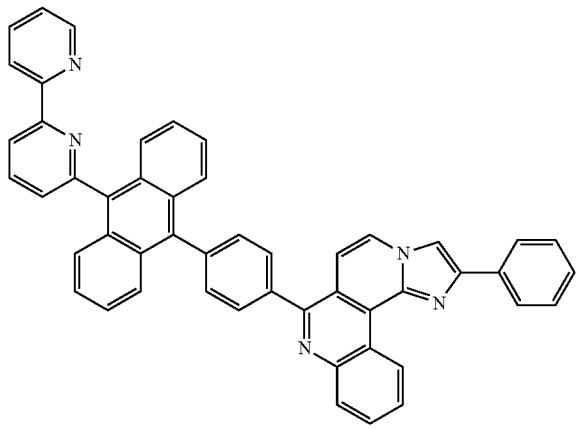
50
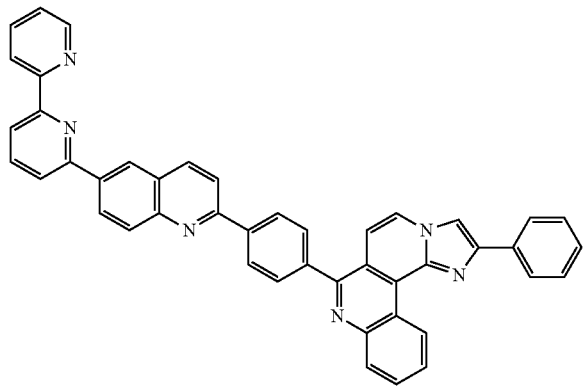
51
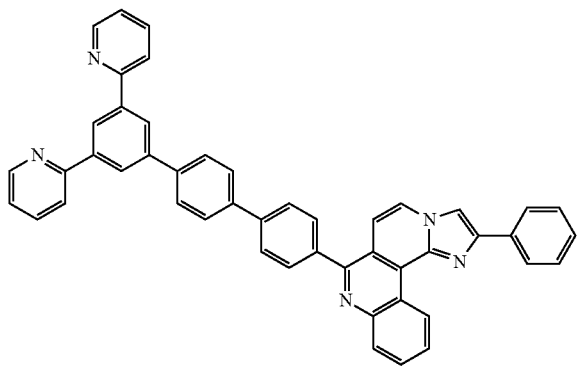
52
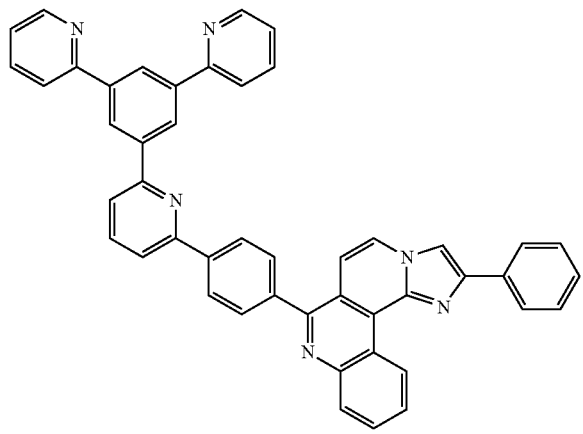
53
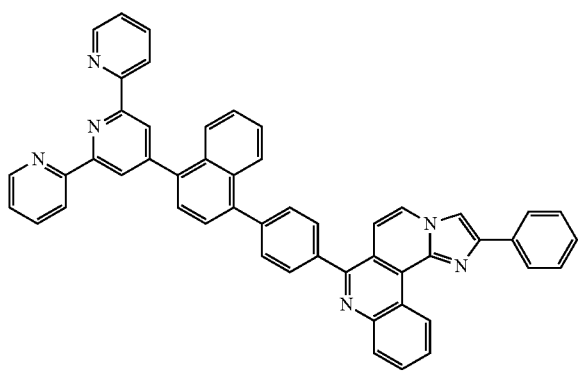
54
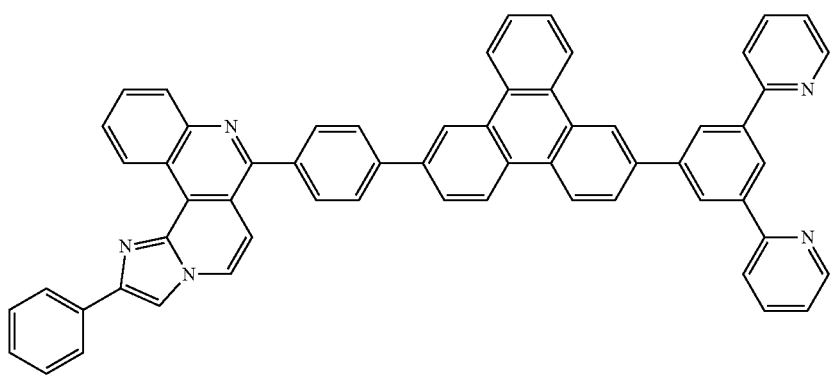

-continued
55
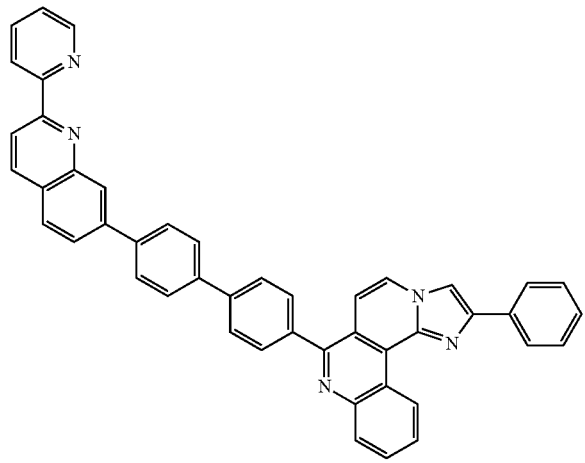
56
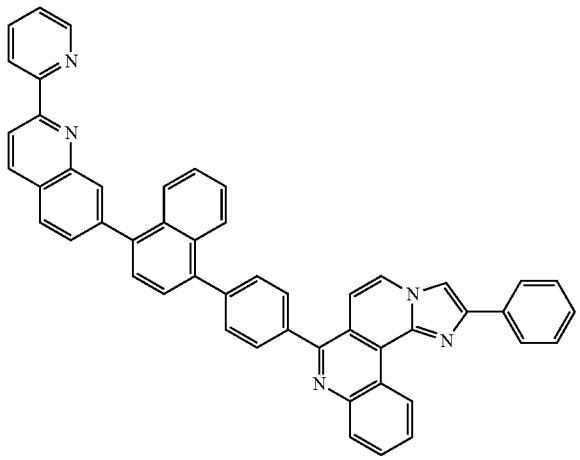
57
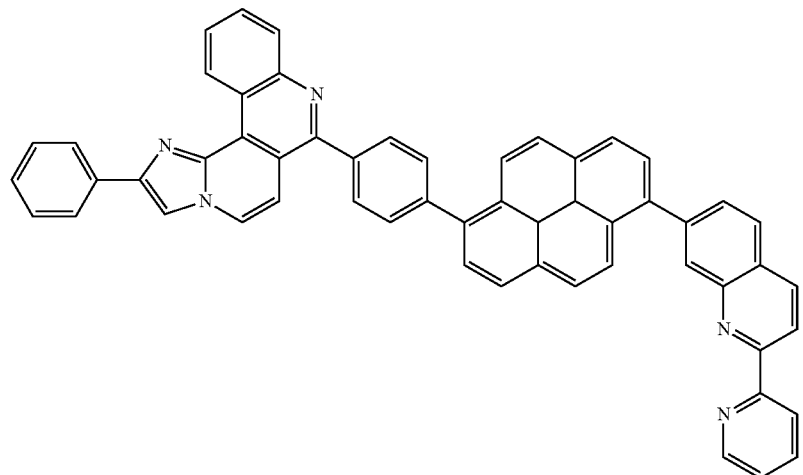
58
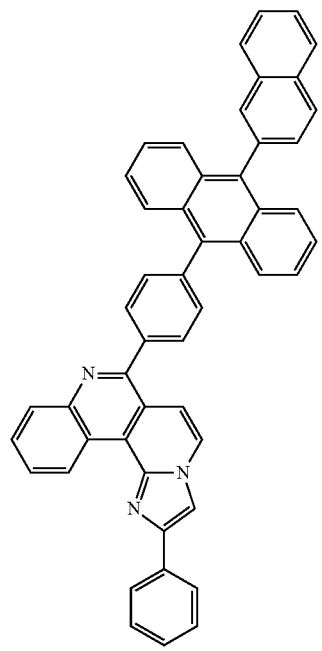
59
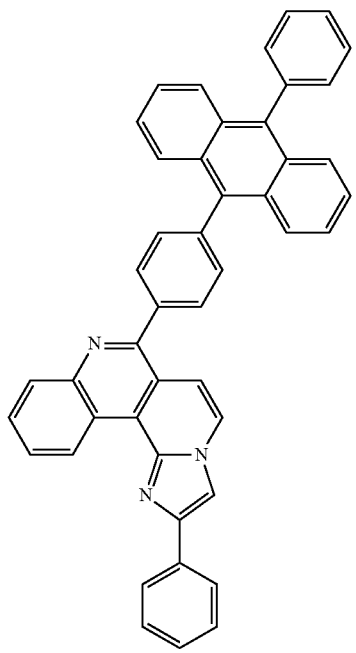

60
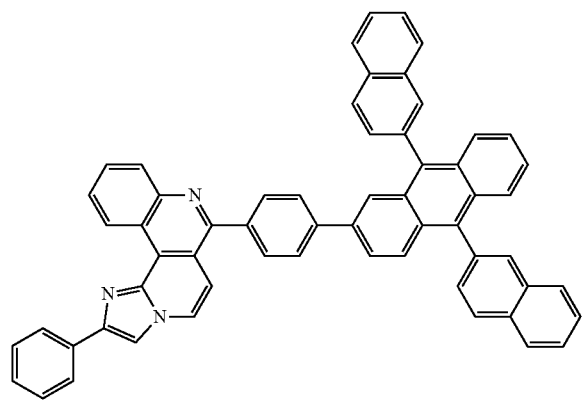
61
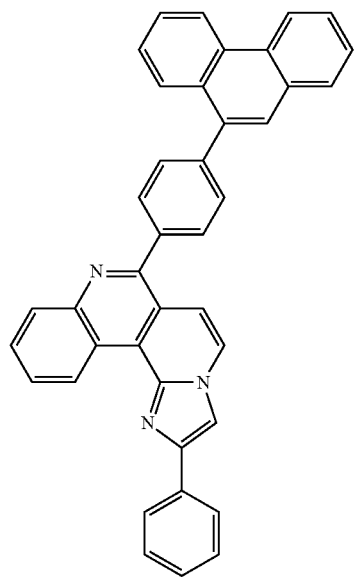
62
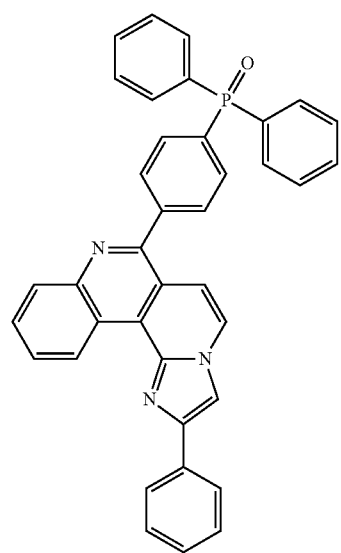
63
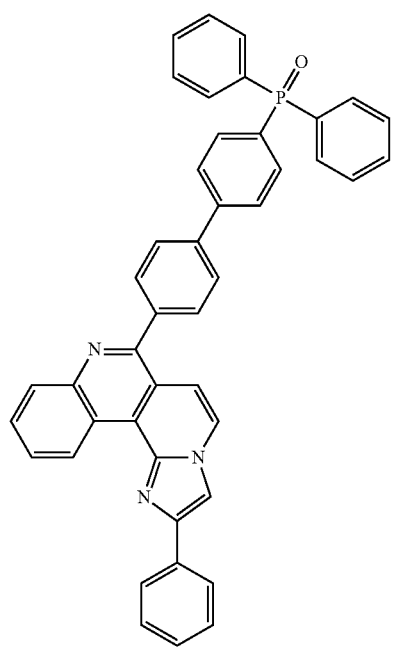

207 208
-continued
64
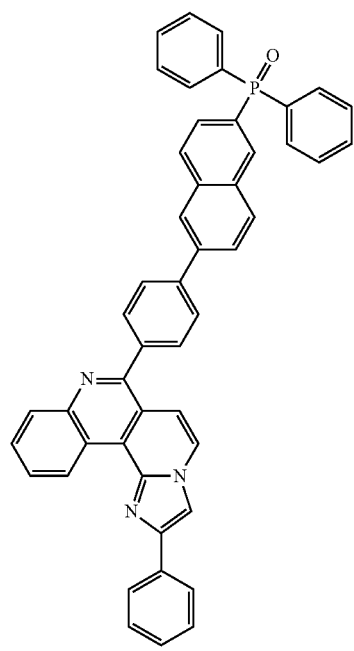
65
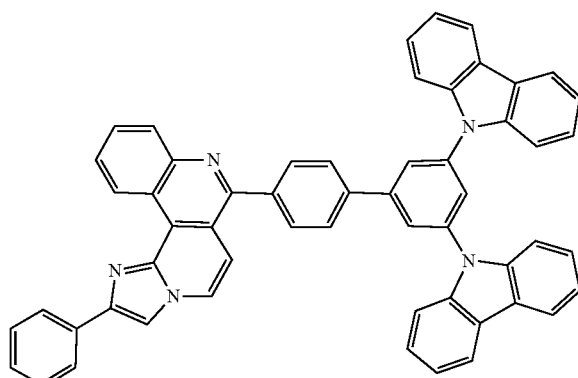
66
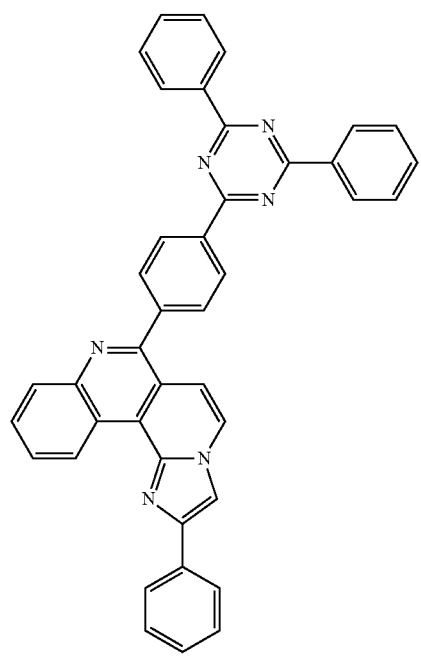
67
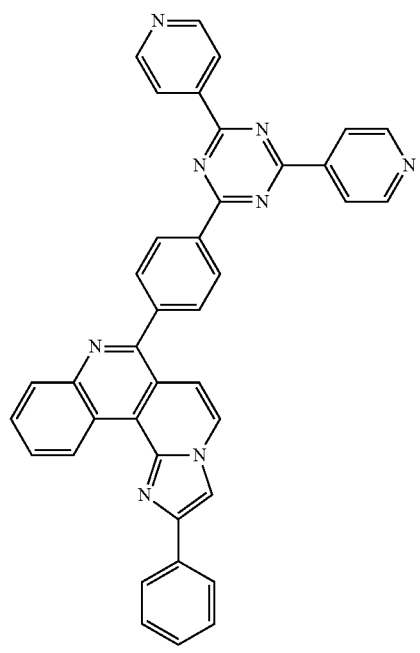

209
-continued
210
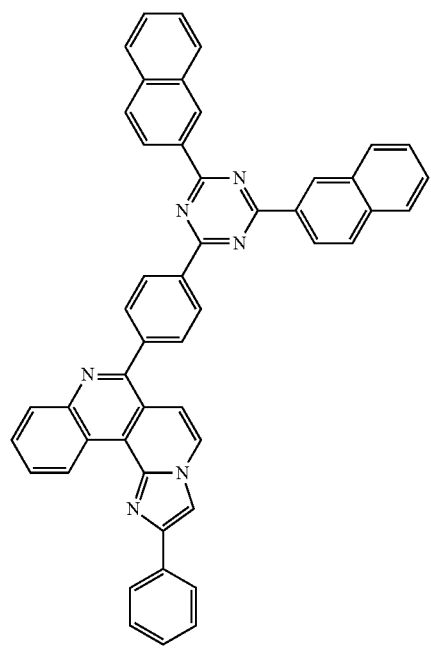
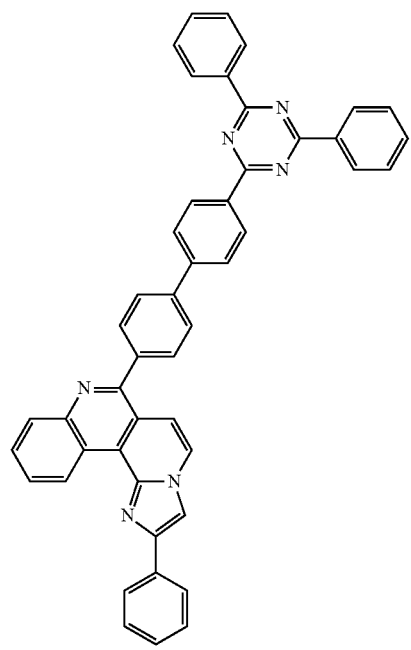
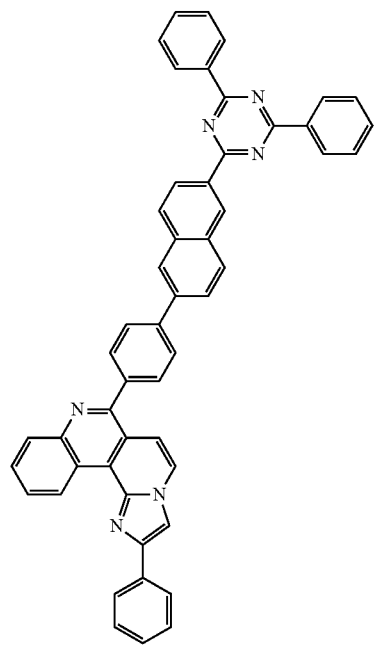
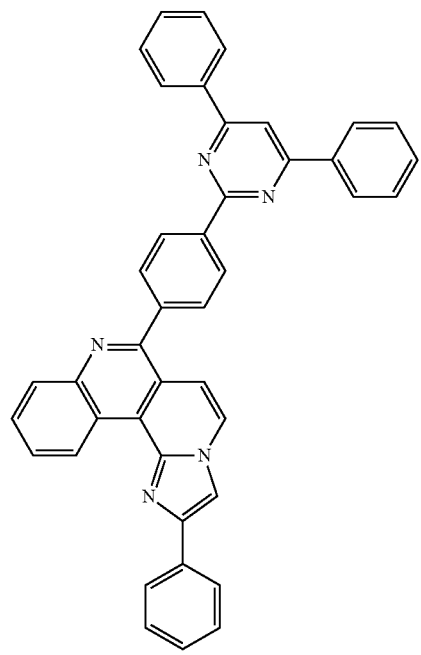

-continued
211
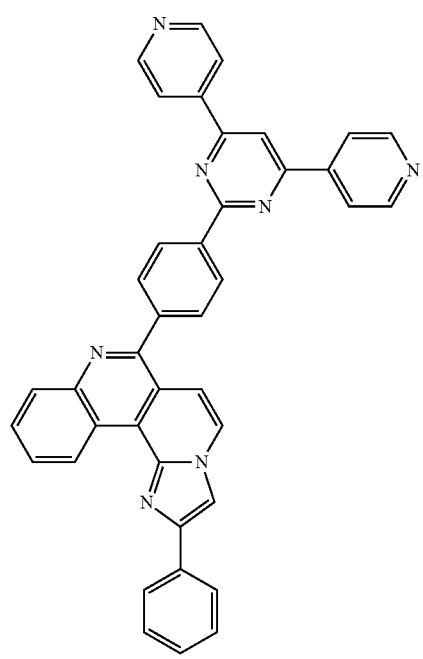
212
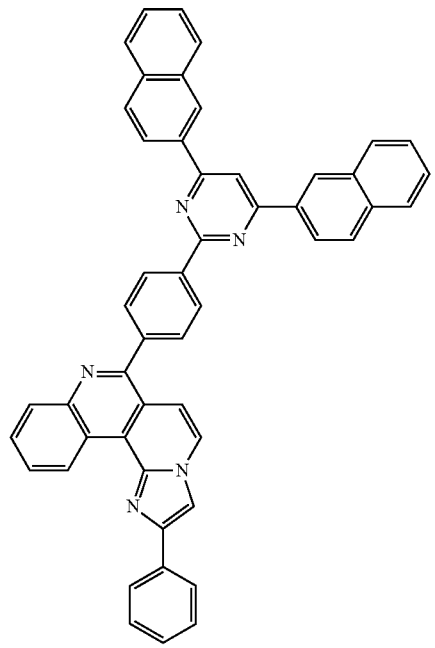
74
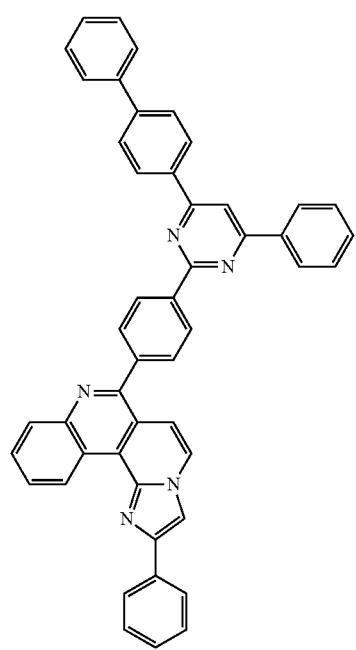
75
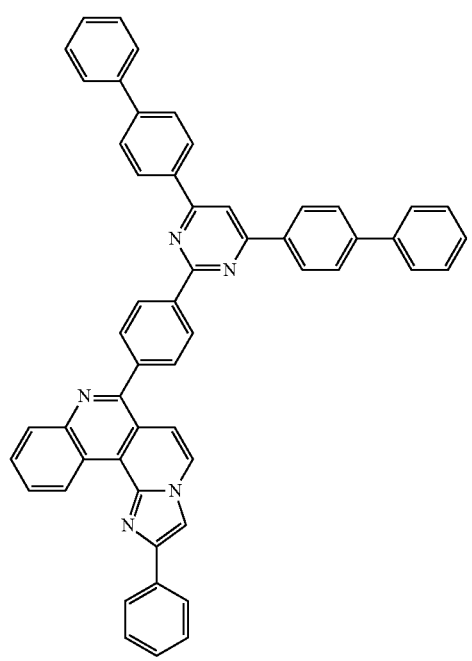

-continued
76
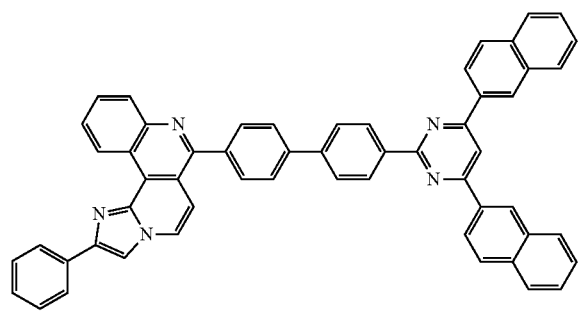
77
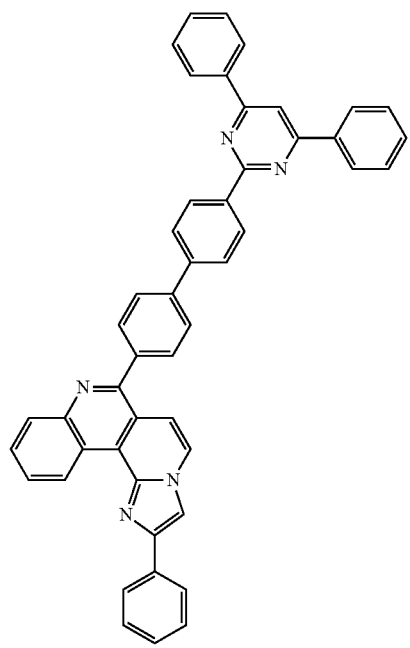
78
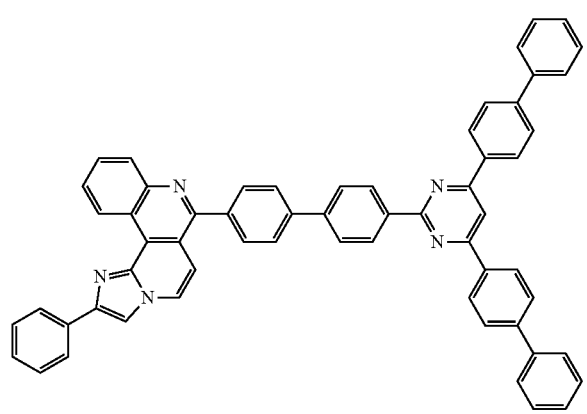
79
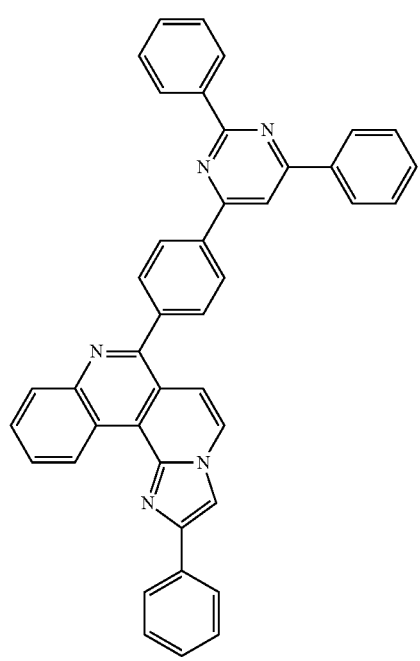

215
216
-continued
80
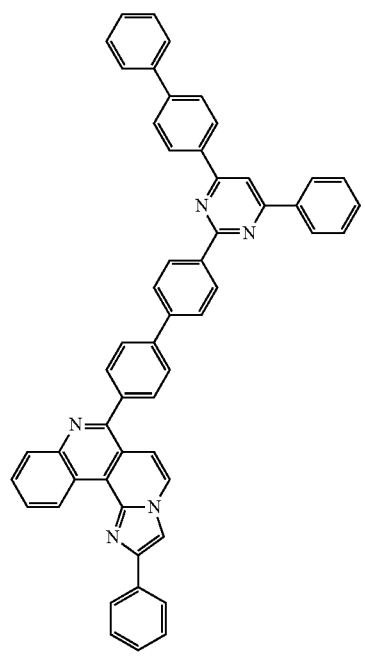
81
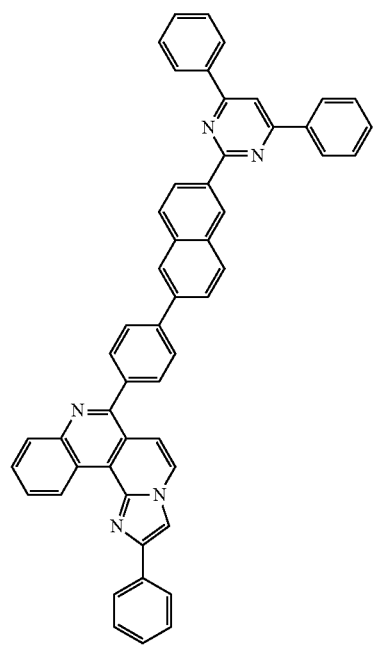
82
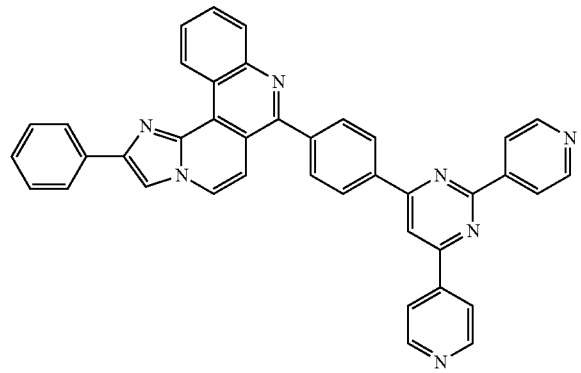
83
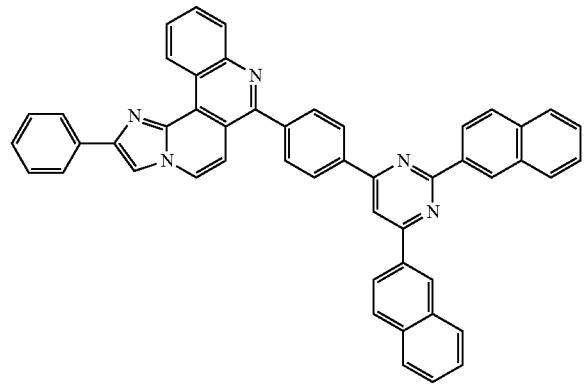
84
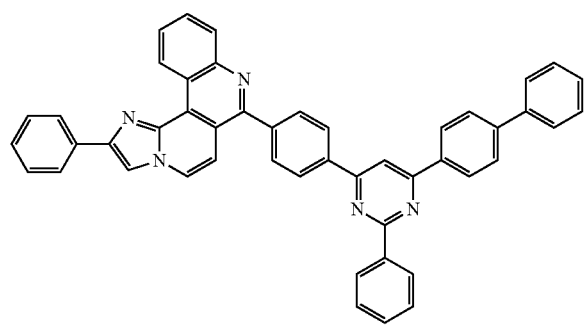
85
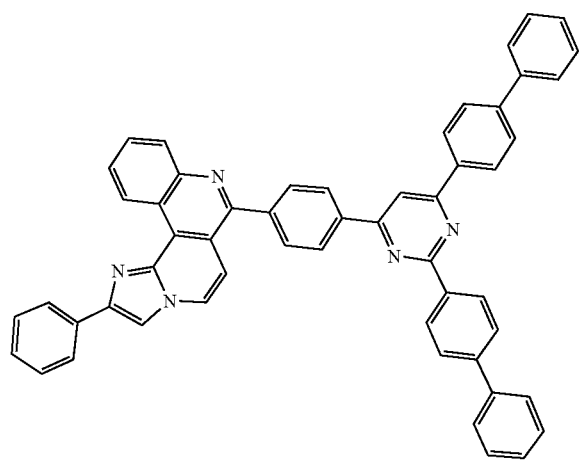

-continued
86
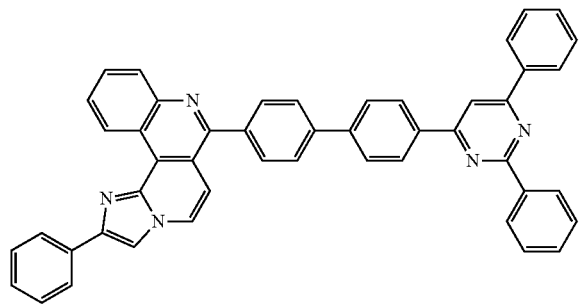
87
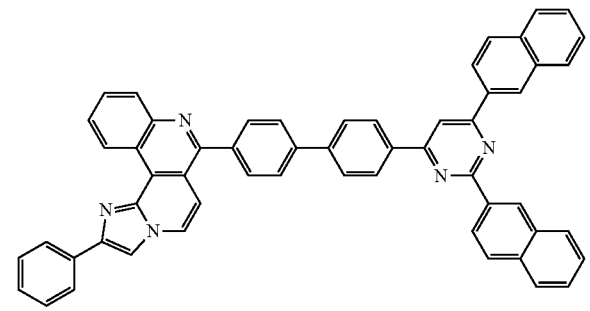
88
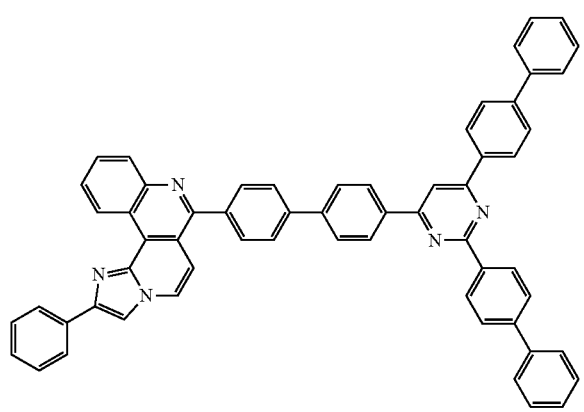
89
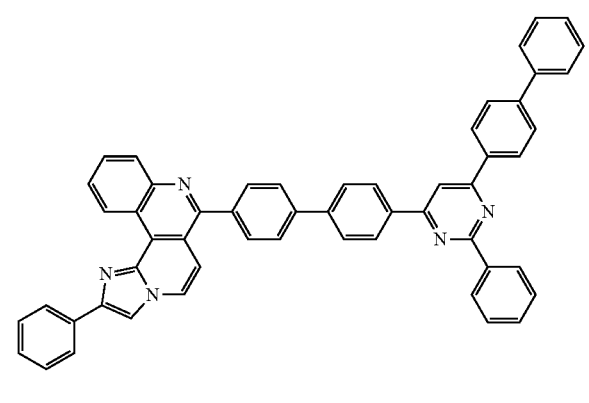
90
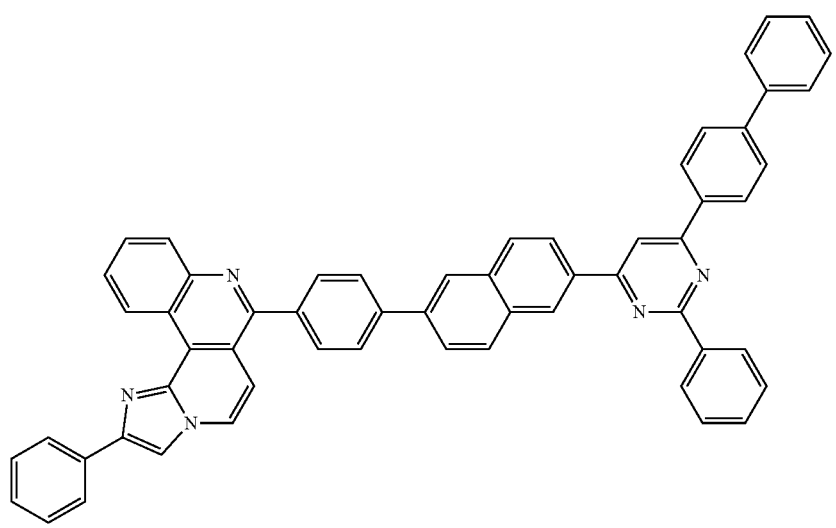
91
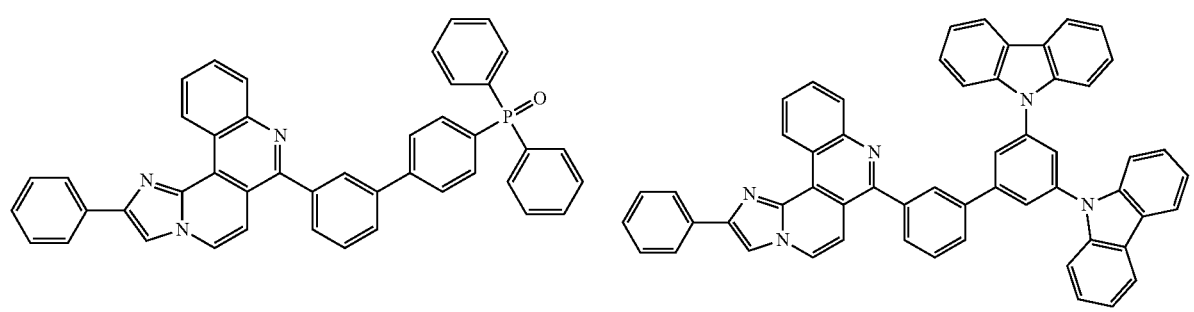
92
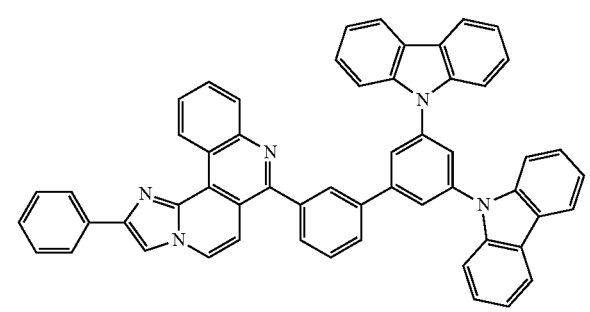

93
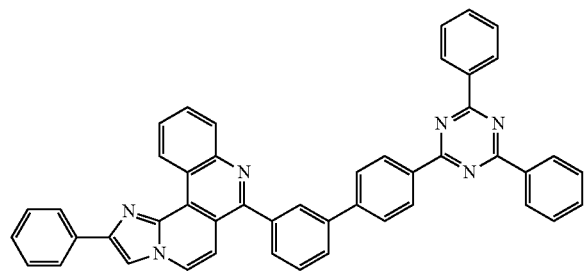
94
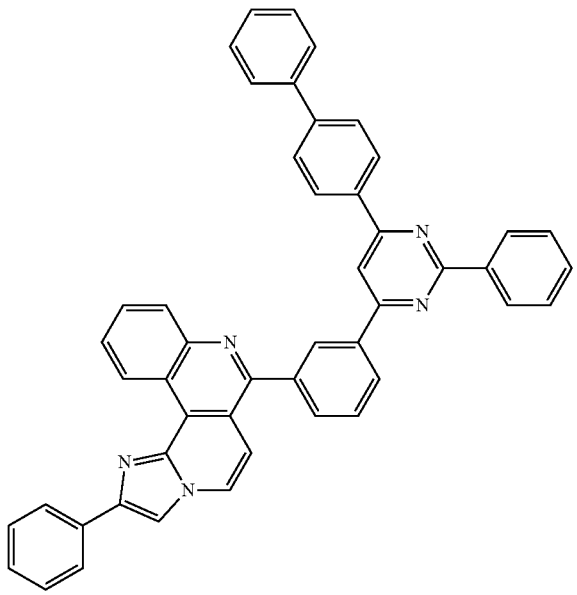
95
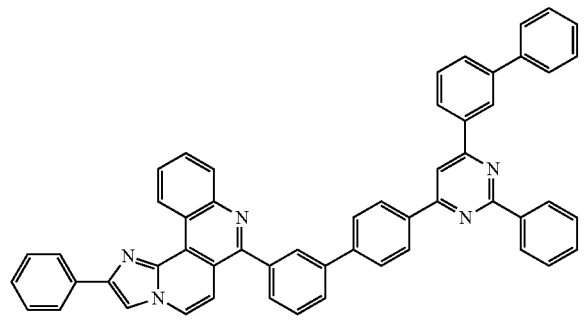
96
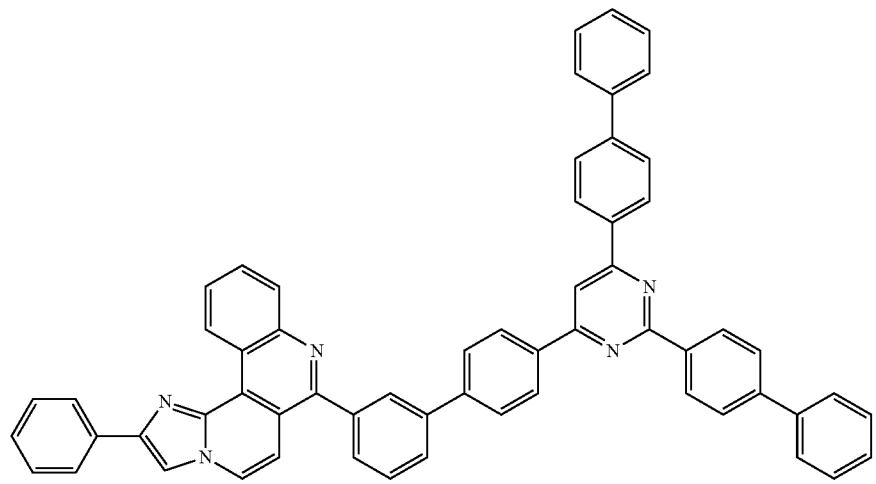

221
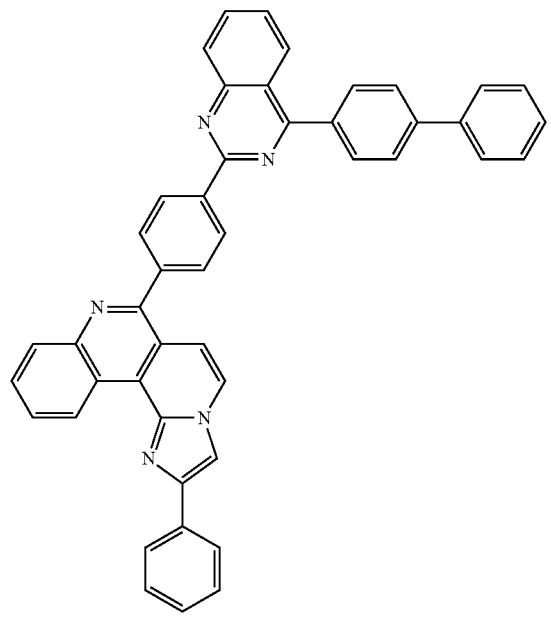
97
222
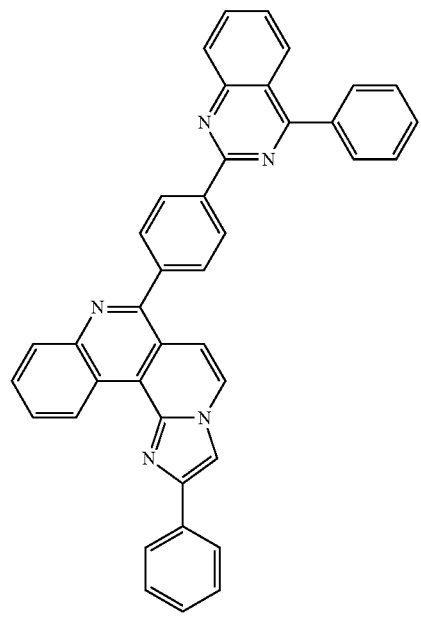
98
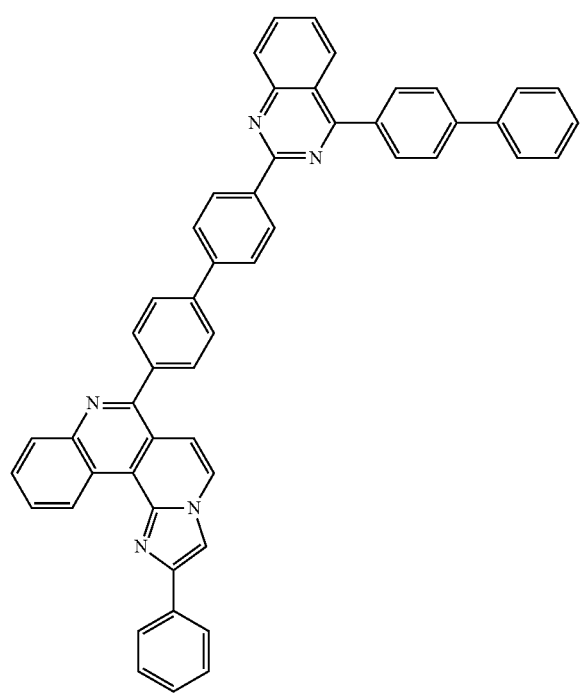
99
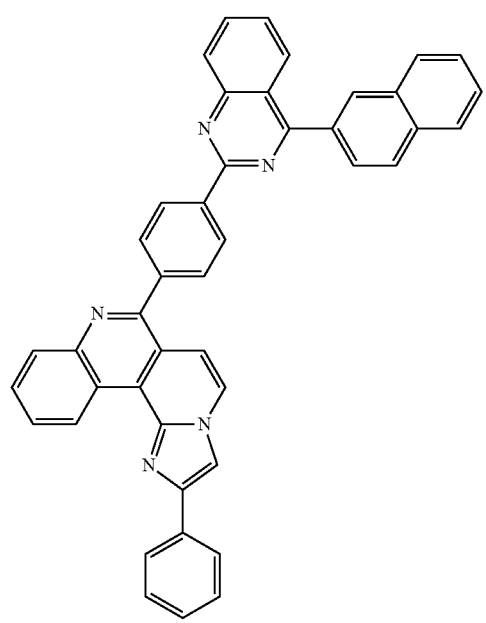
100

-continued
101
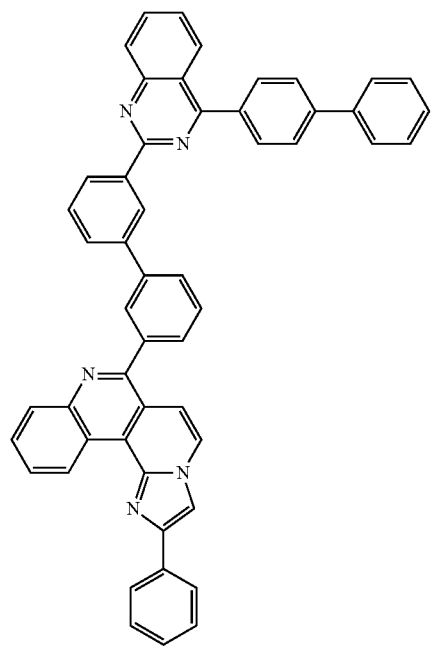
102
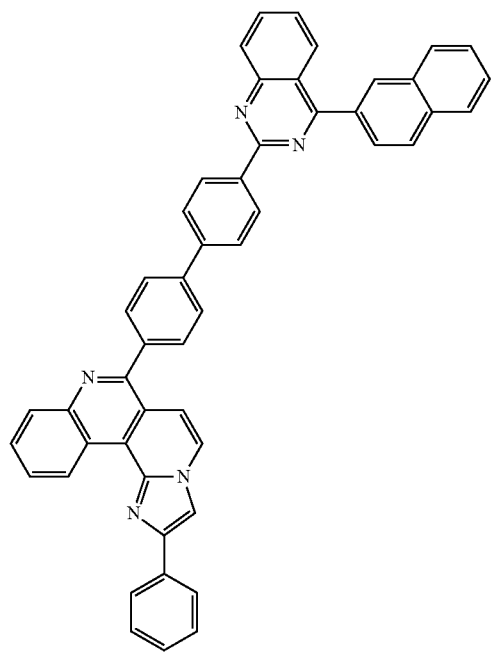
103
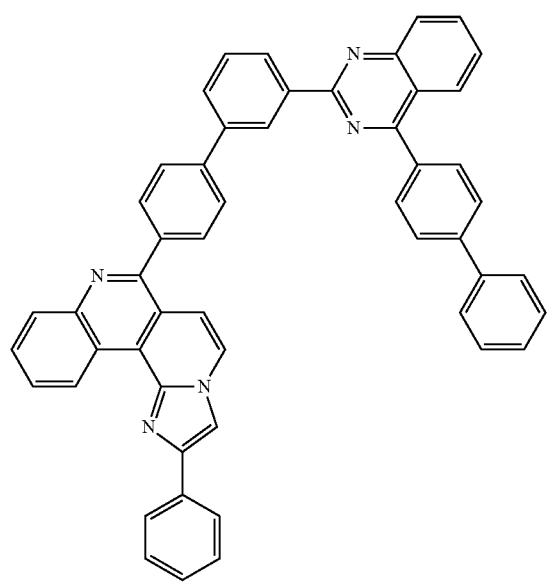
104
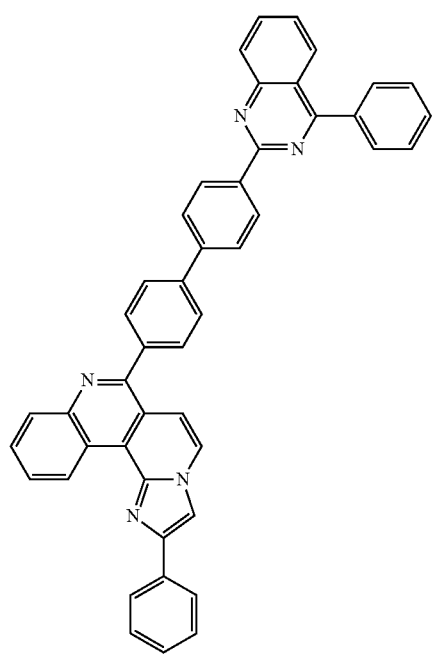

-continued
105
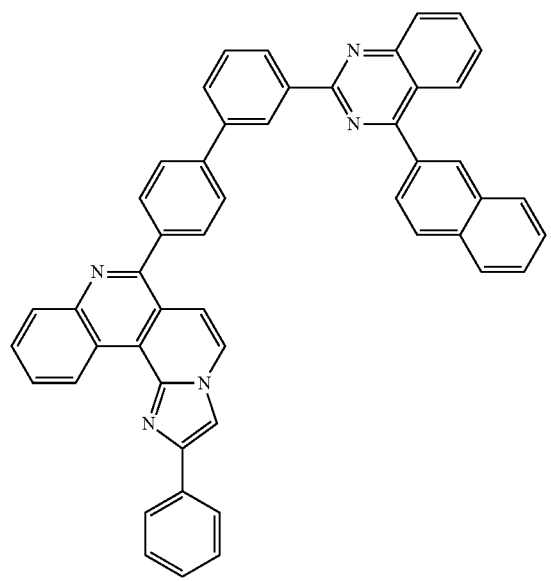
106
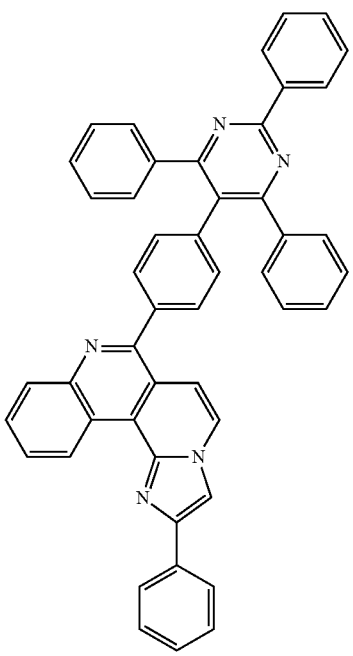
107
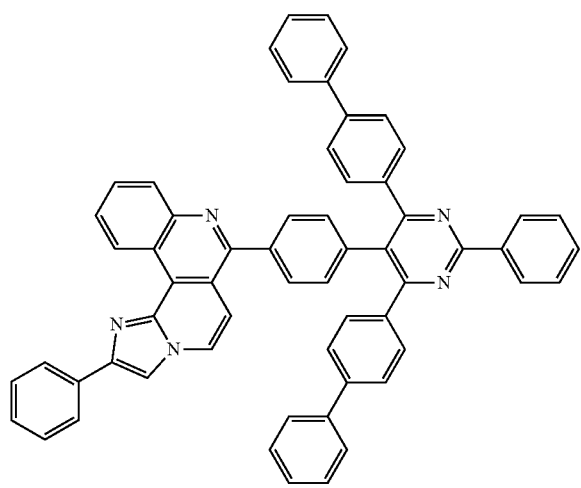
108
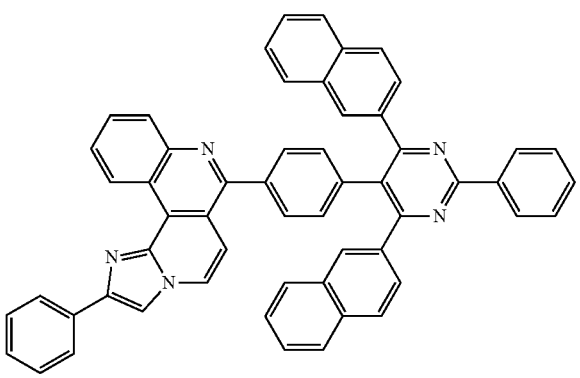

-continued
109
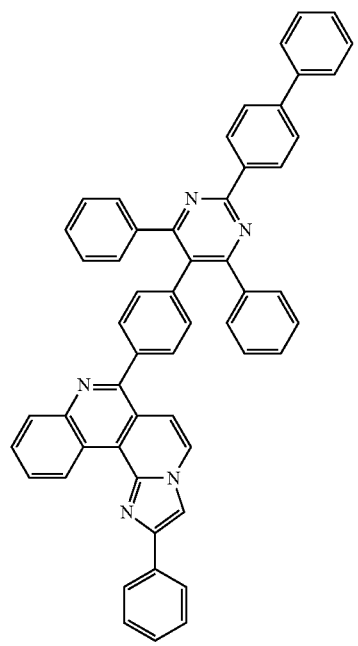
110
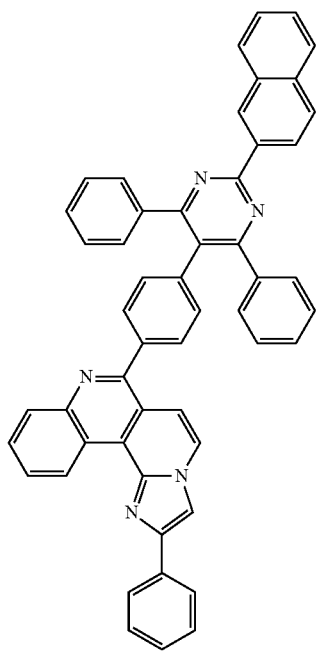
111
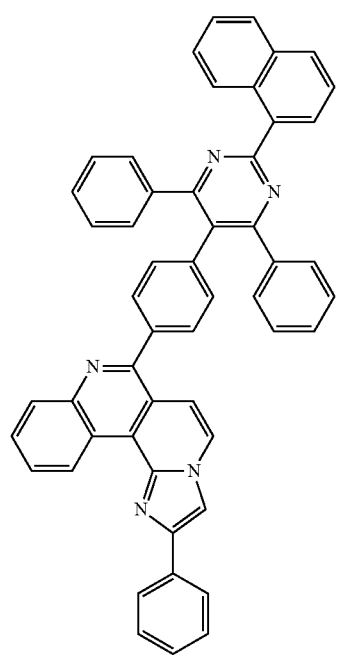
112
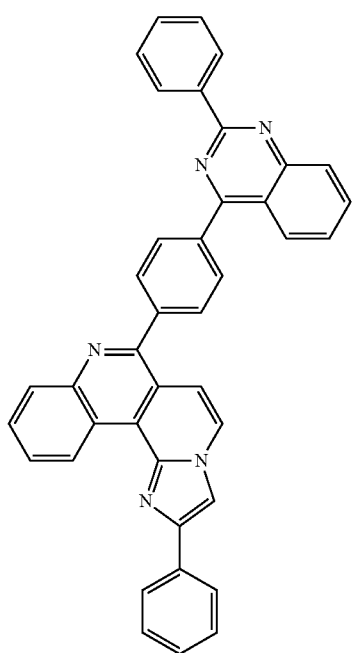

-continued
113 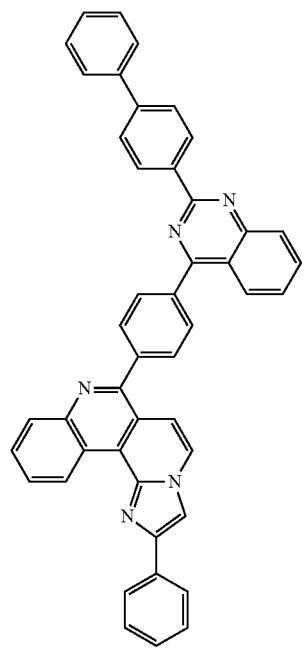
114 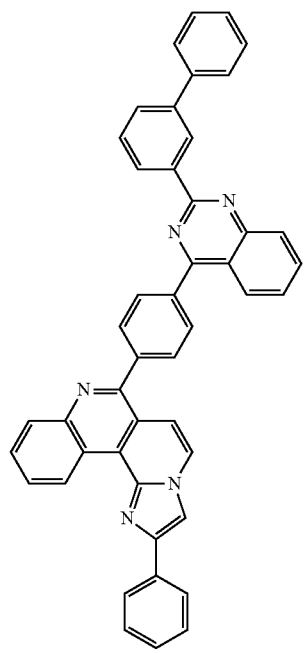
115 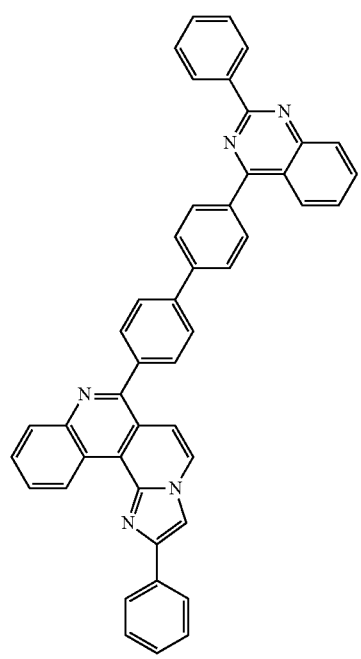
116 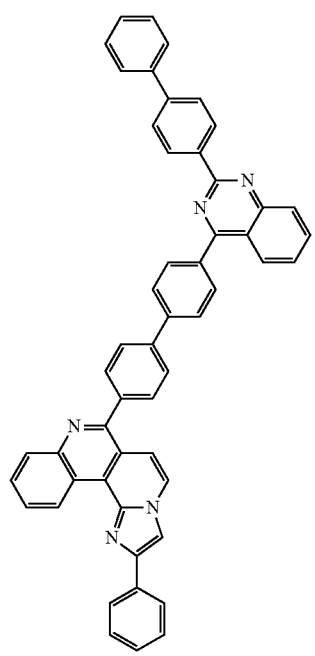

-continued
117
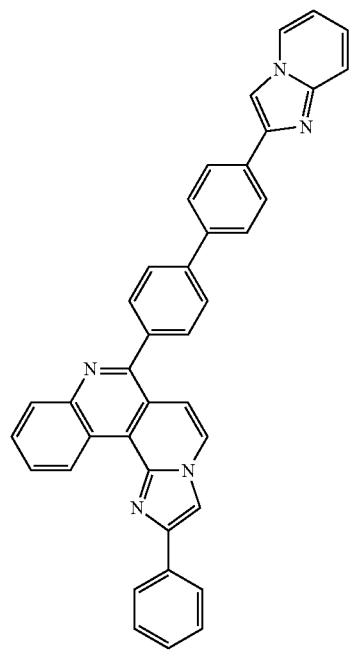
118
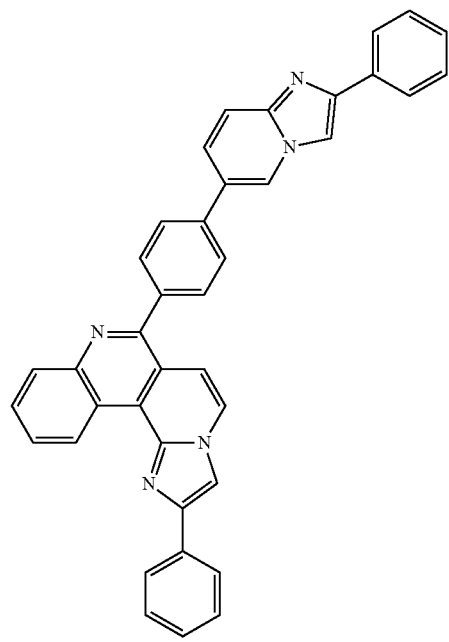
119
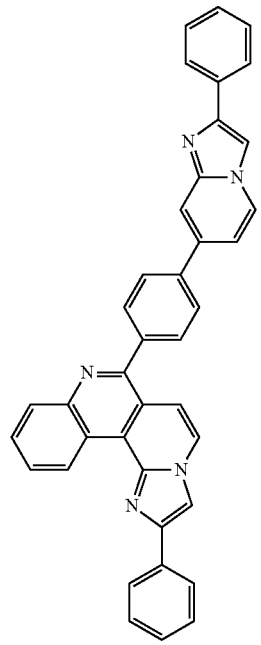
120
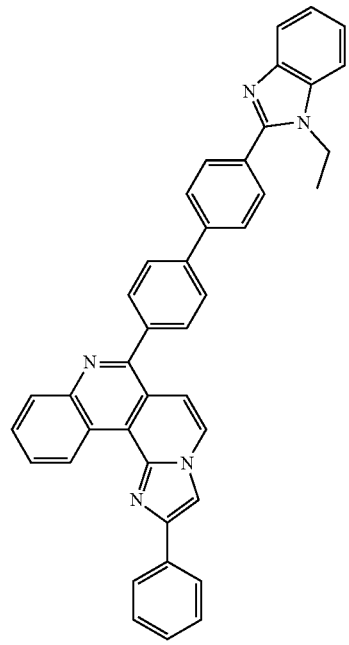

-continued
121
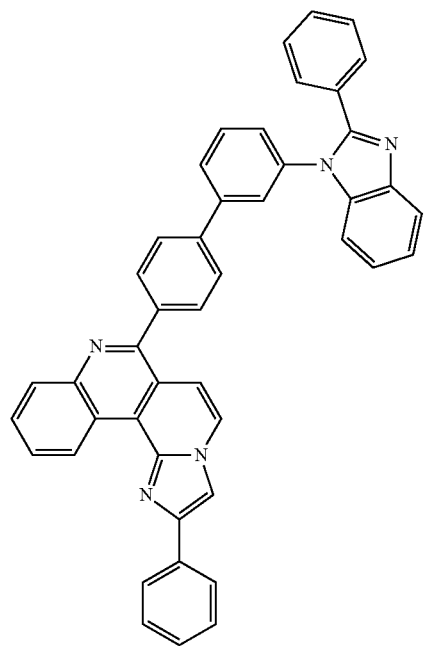
122
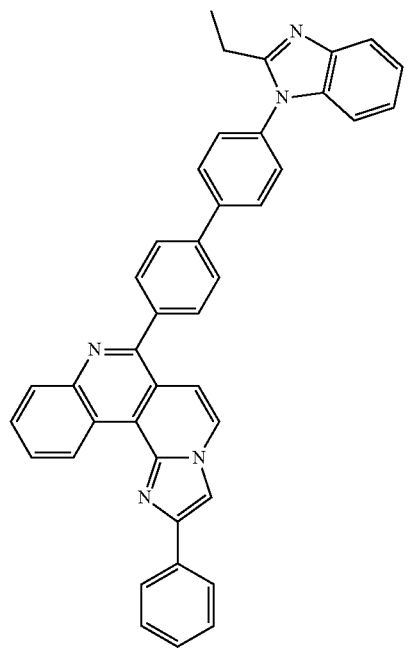
123
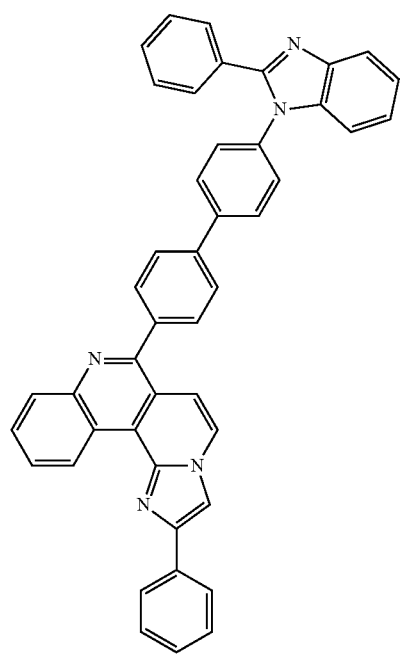
124
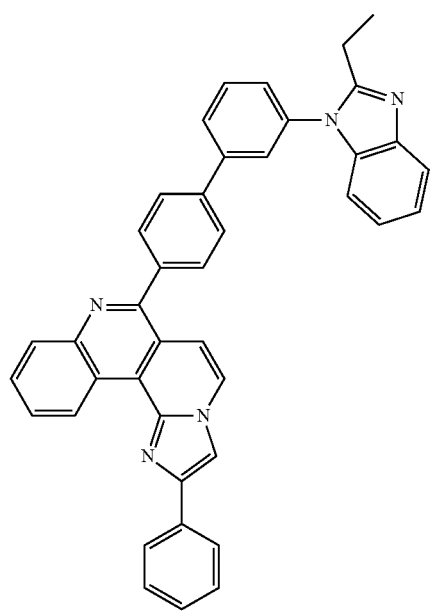

-continued
125
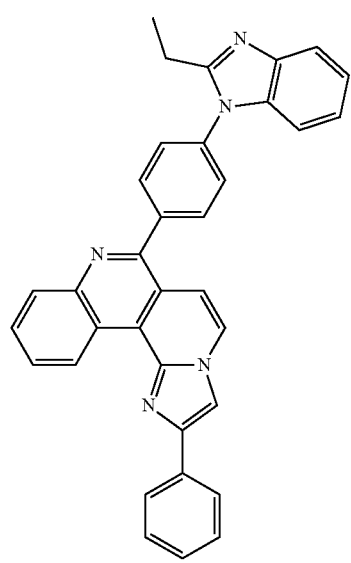
126
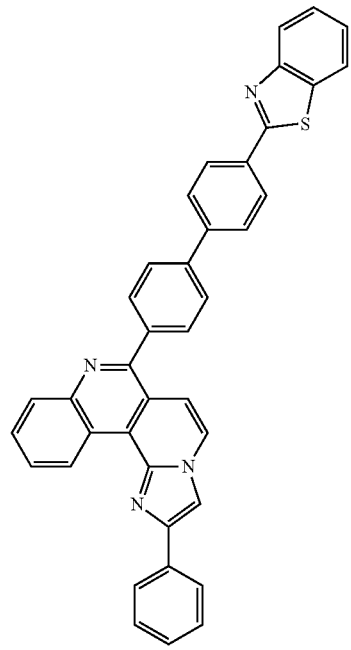
127
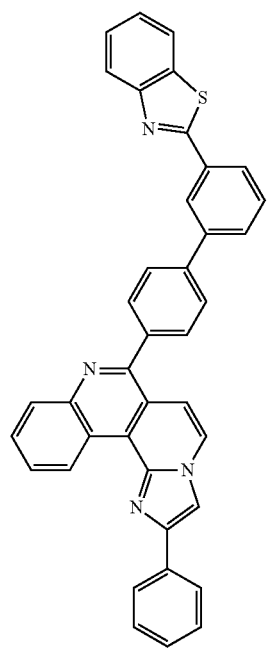
128
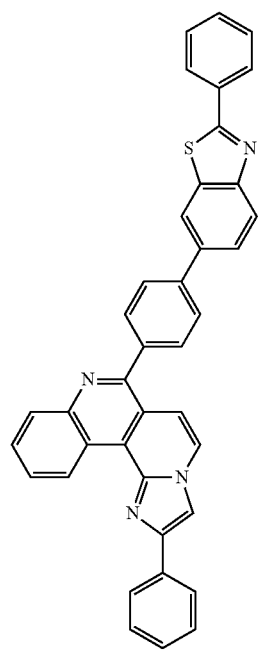

-continued
129
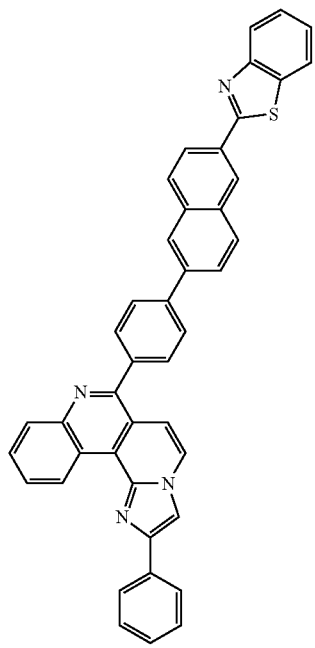
130
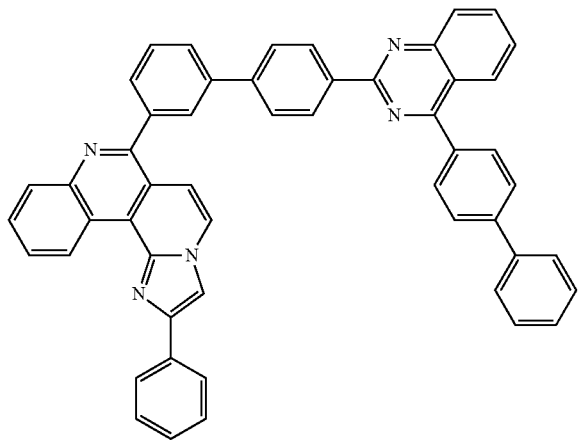
131
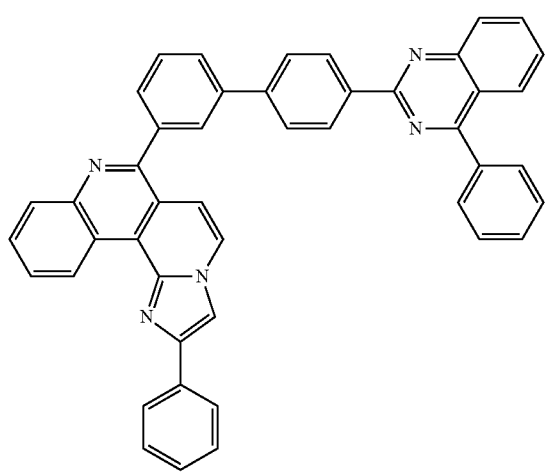
132
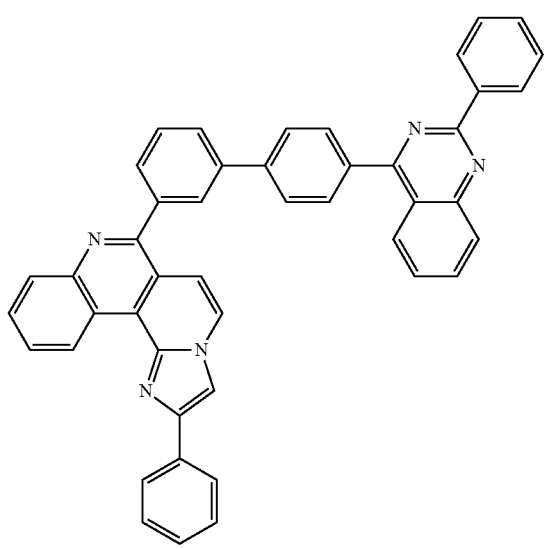
133
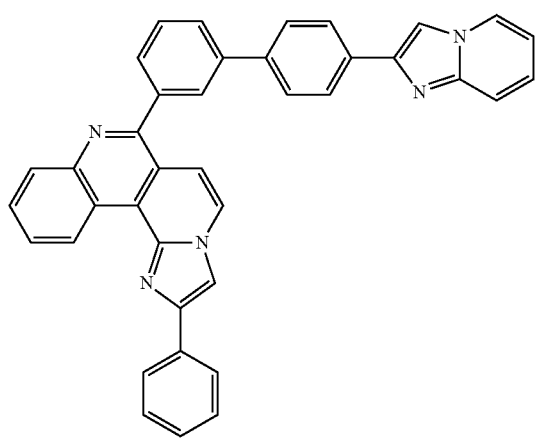
134
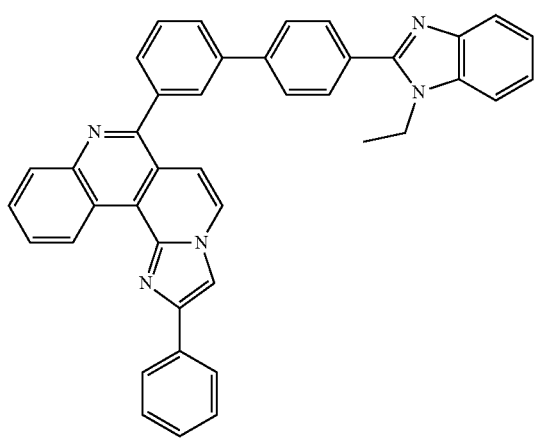

-continued
135
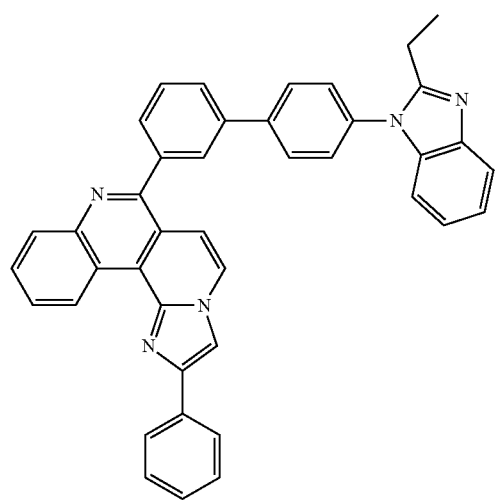
136
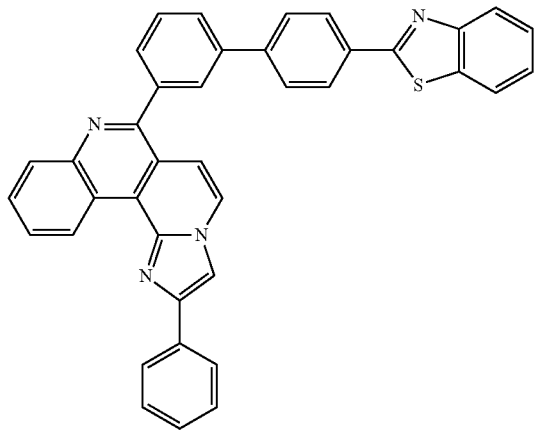
137
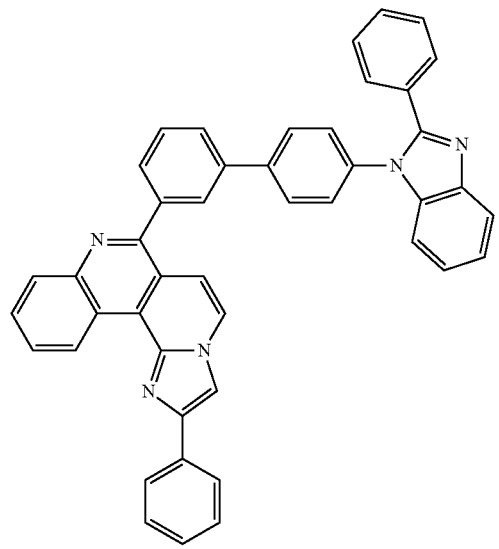
138
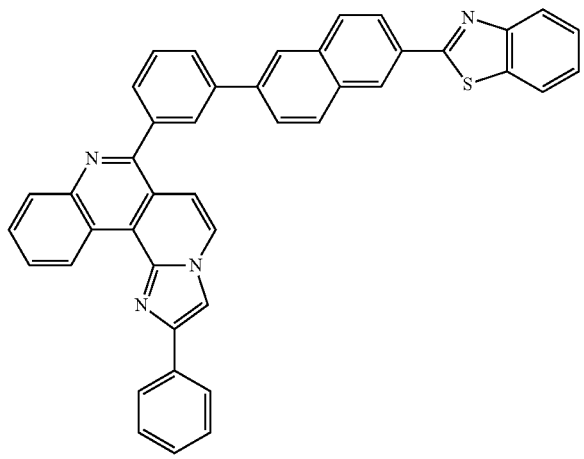

-continued
139
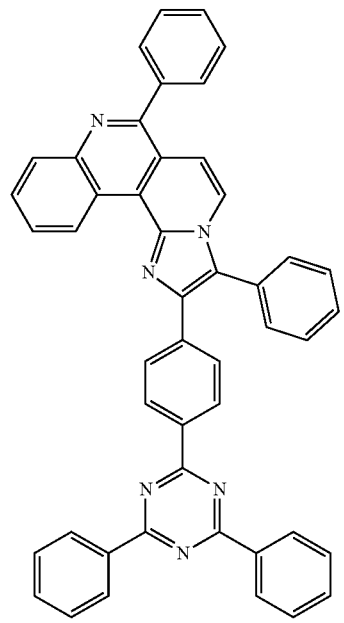
140
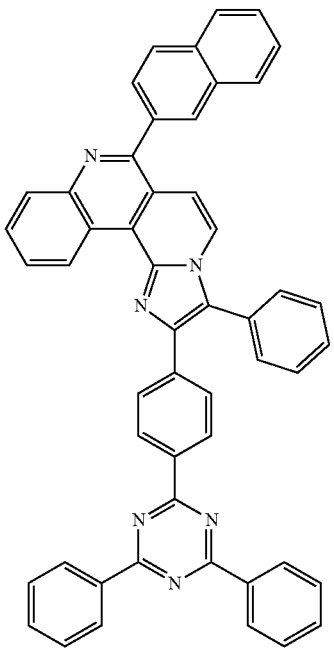
141
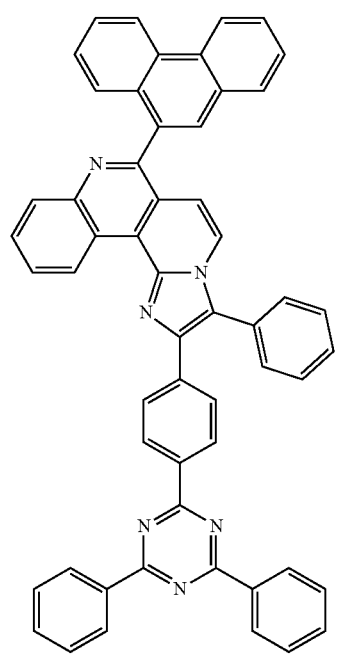
142
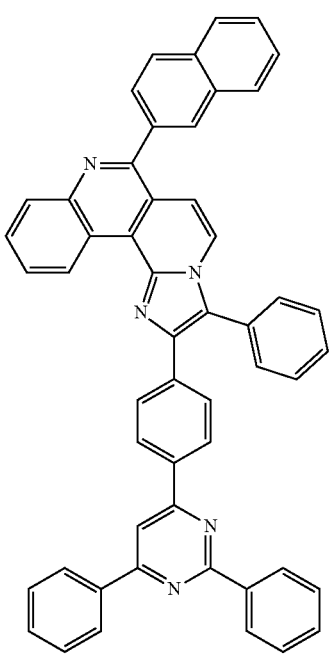

-continued
143
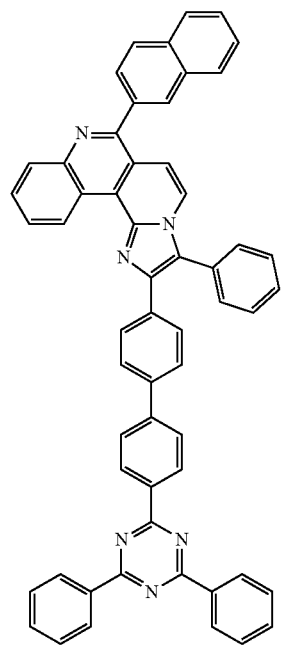
144
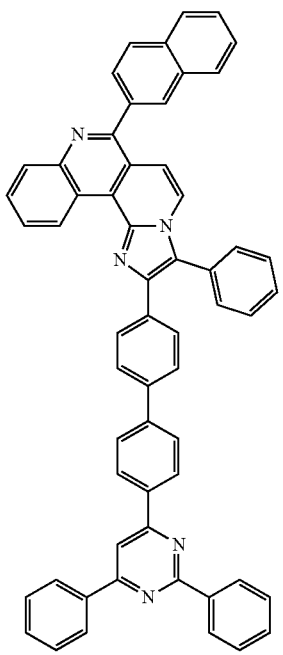
145
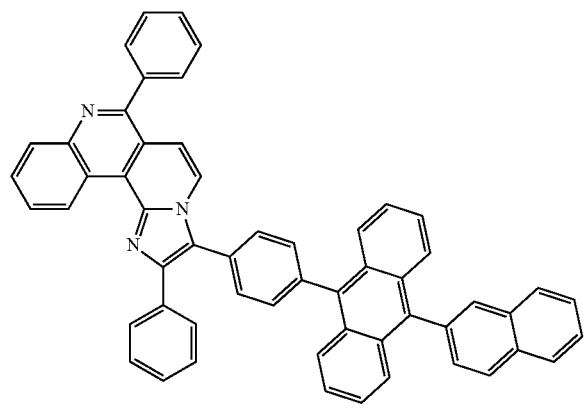
146
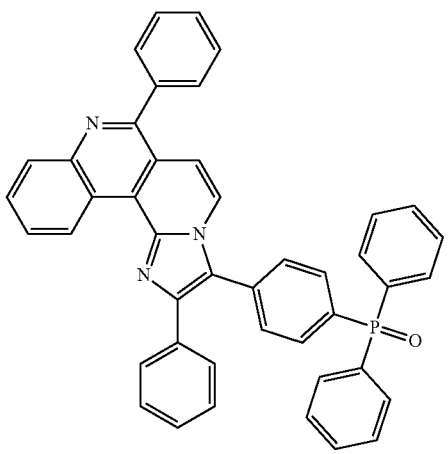
147
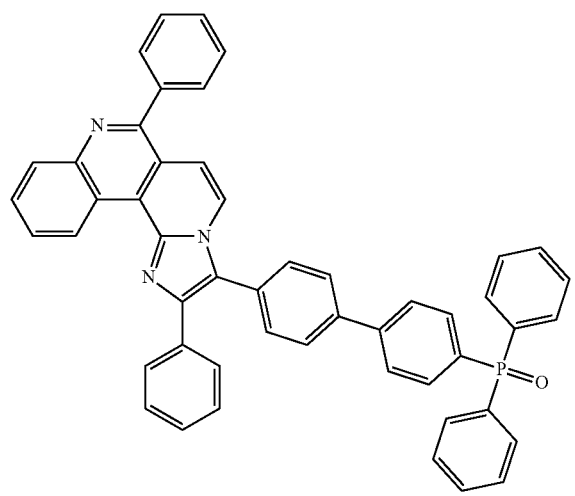
148
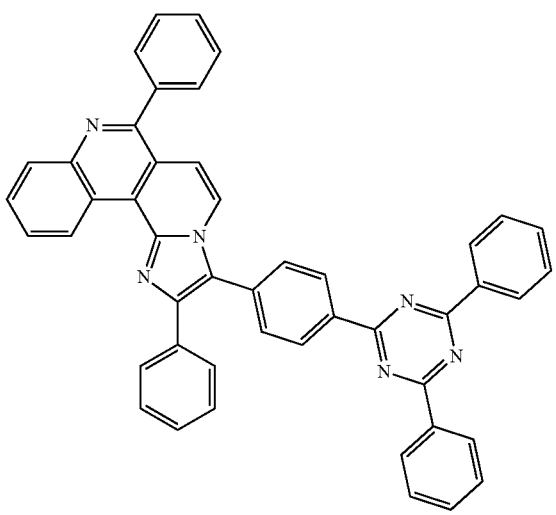

149
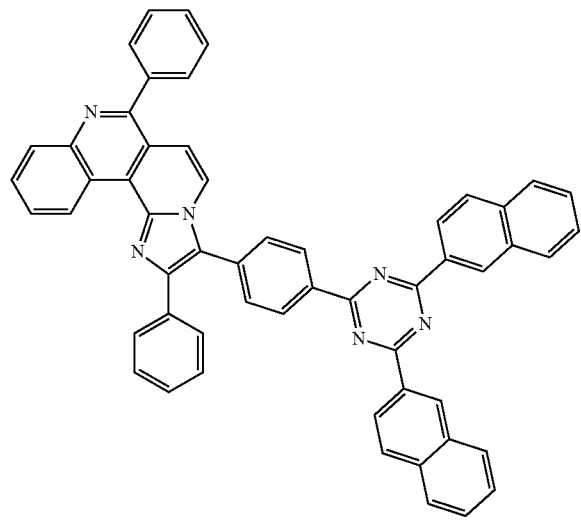
150
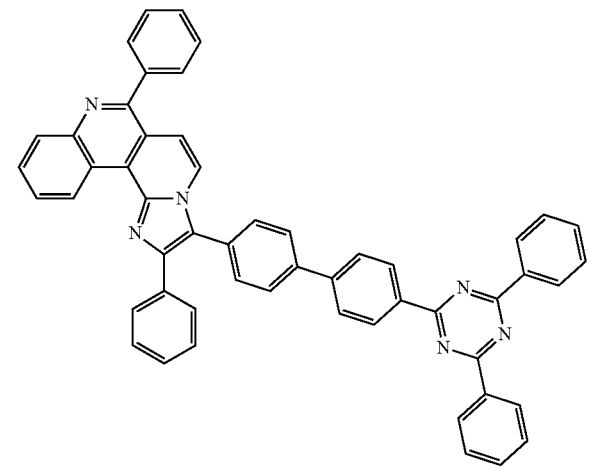
151
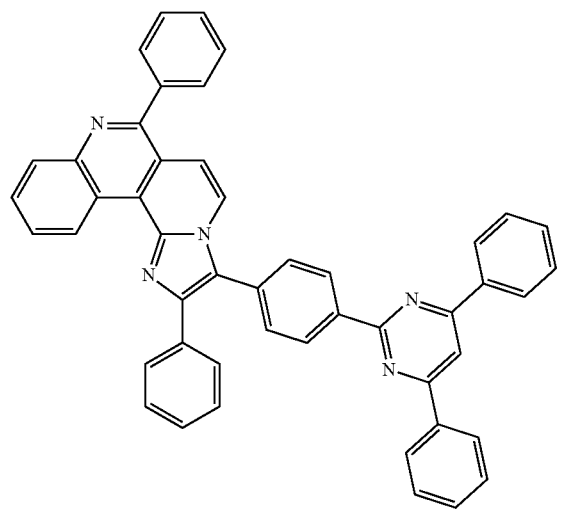
152
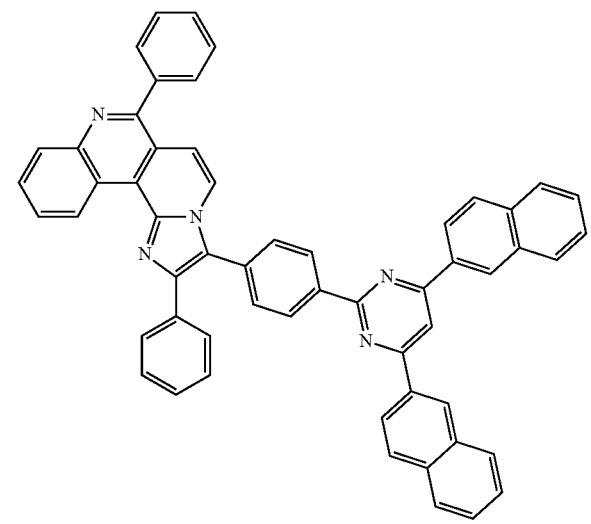
153
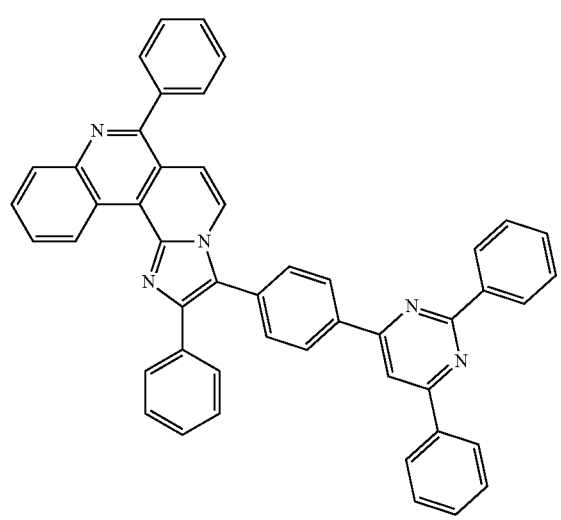
154
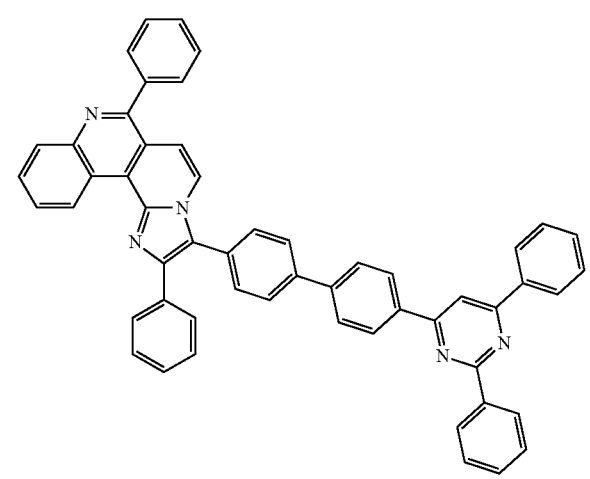

-continued
155
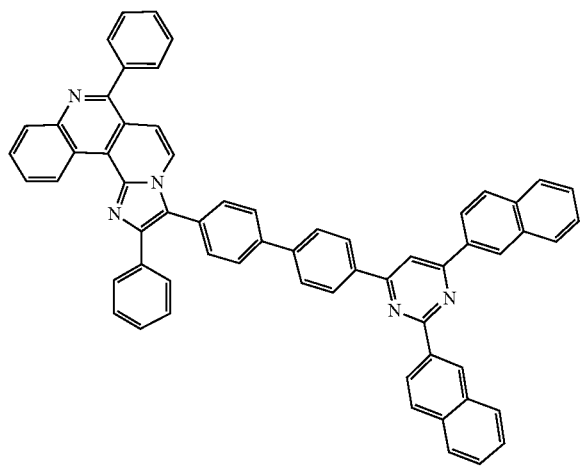
156
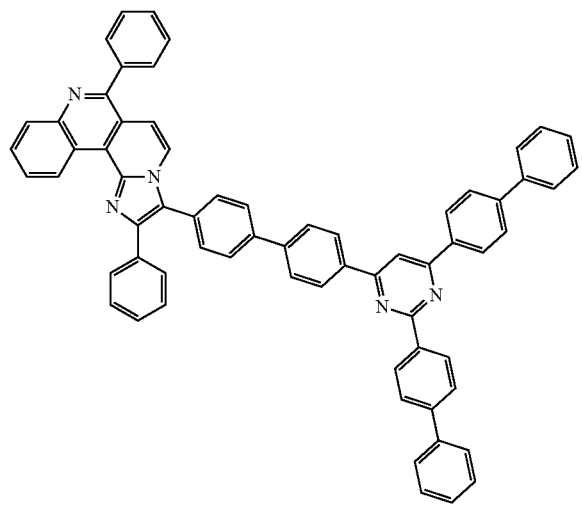
157
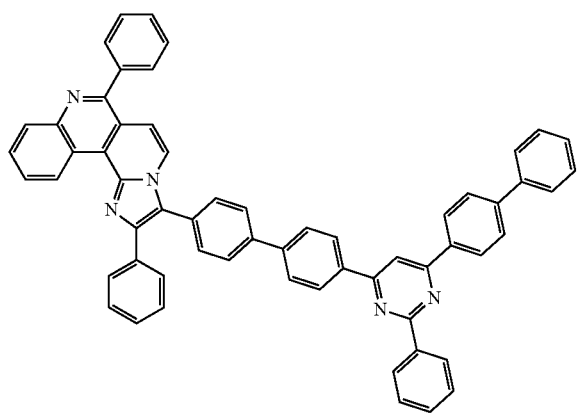
158
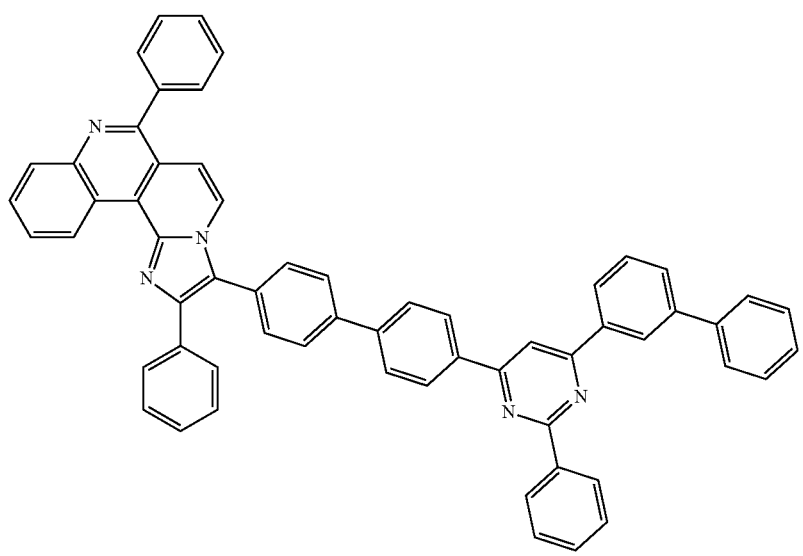

-continued
159
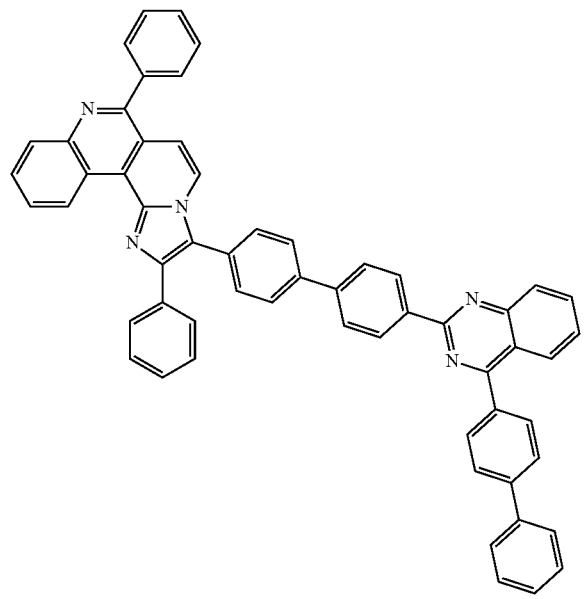
160
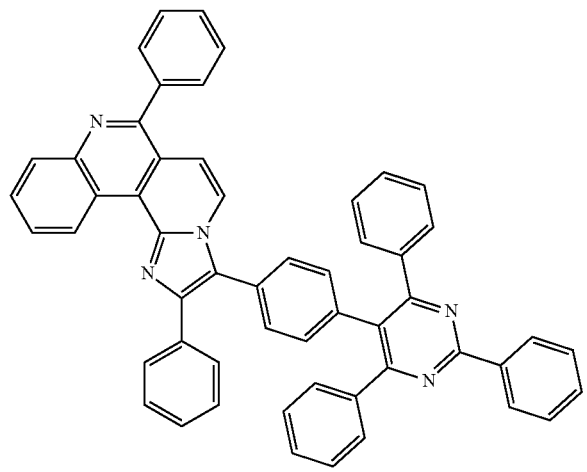
161
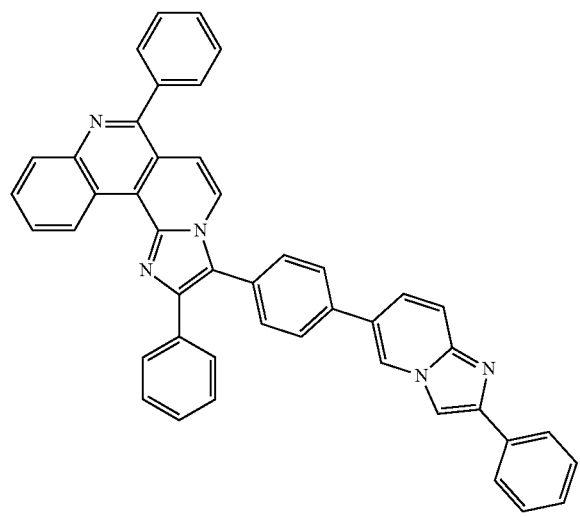
162
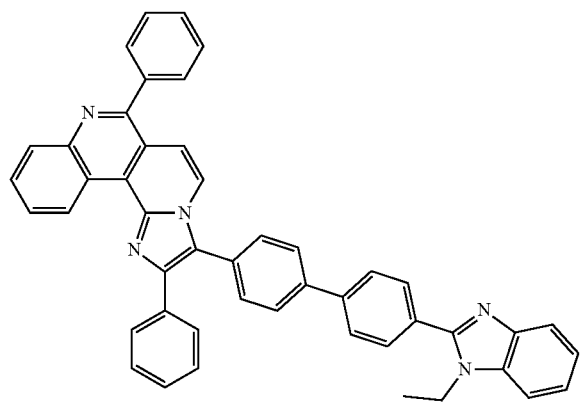
163
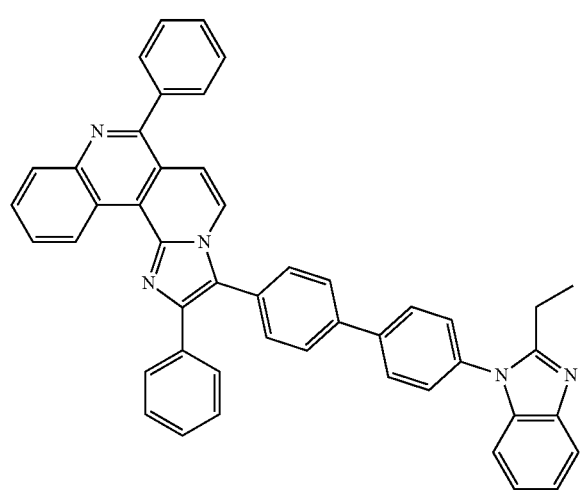
164
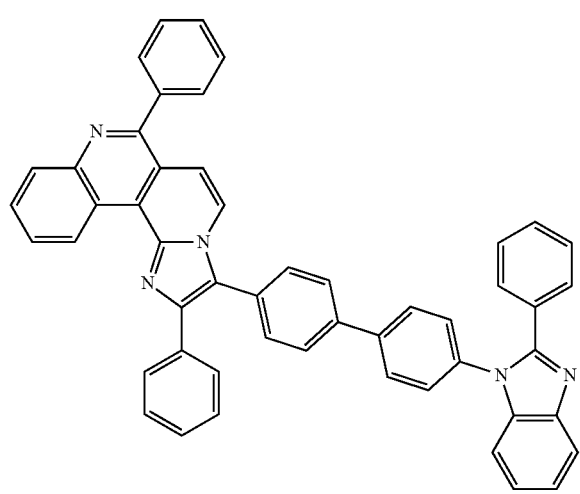

-continued
165
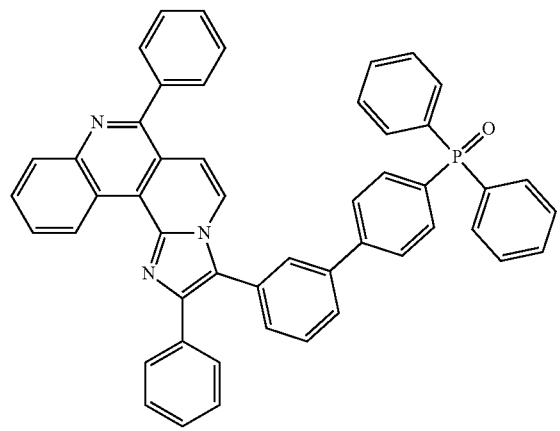
166
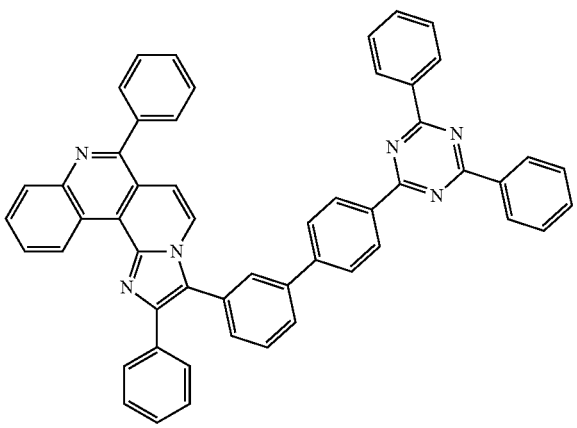
167
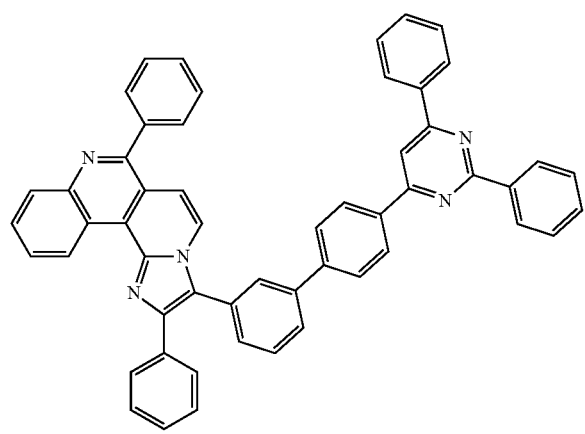
168
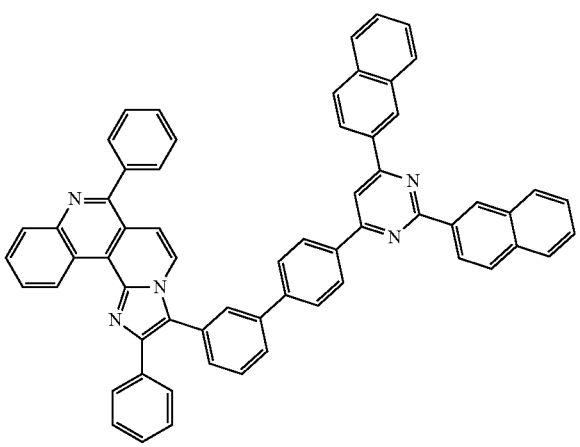
169
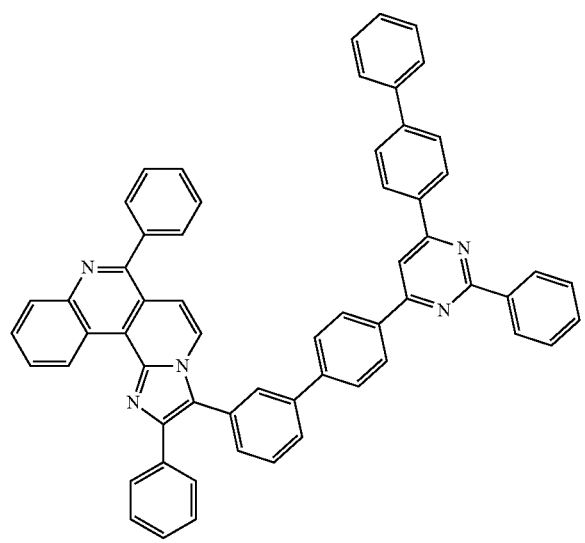
170
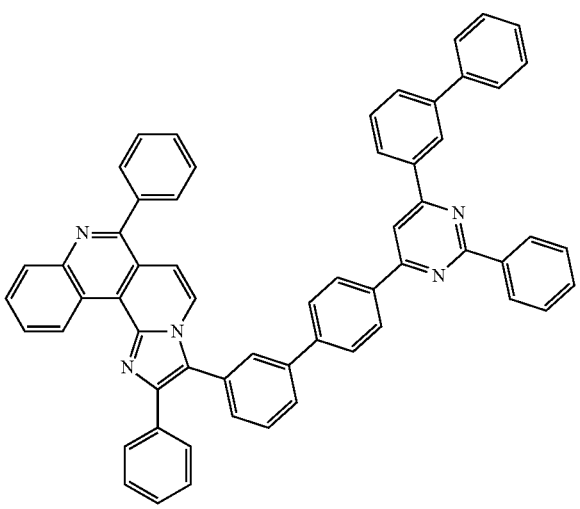

-continued
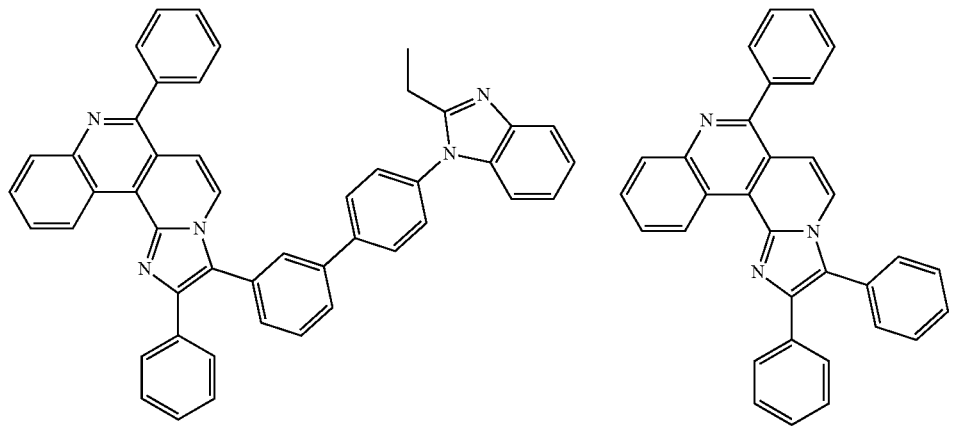
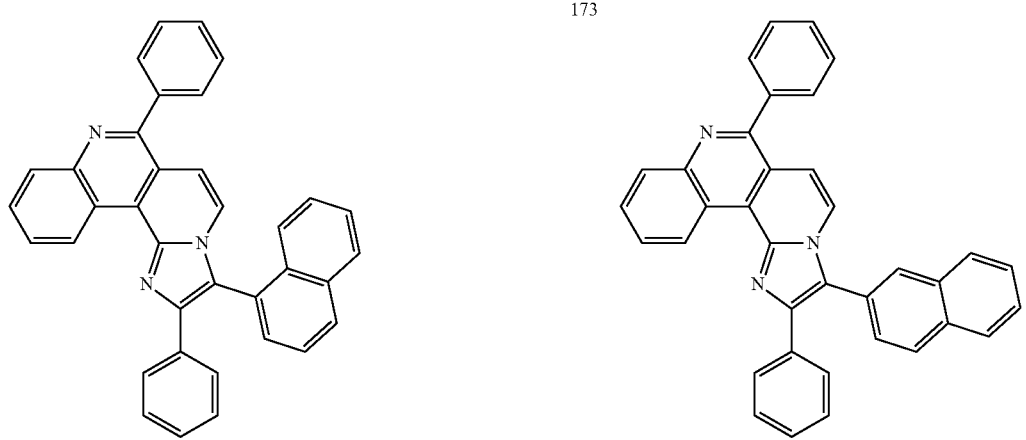
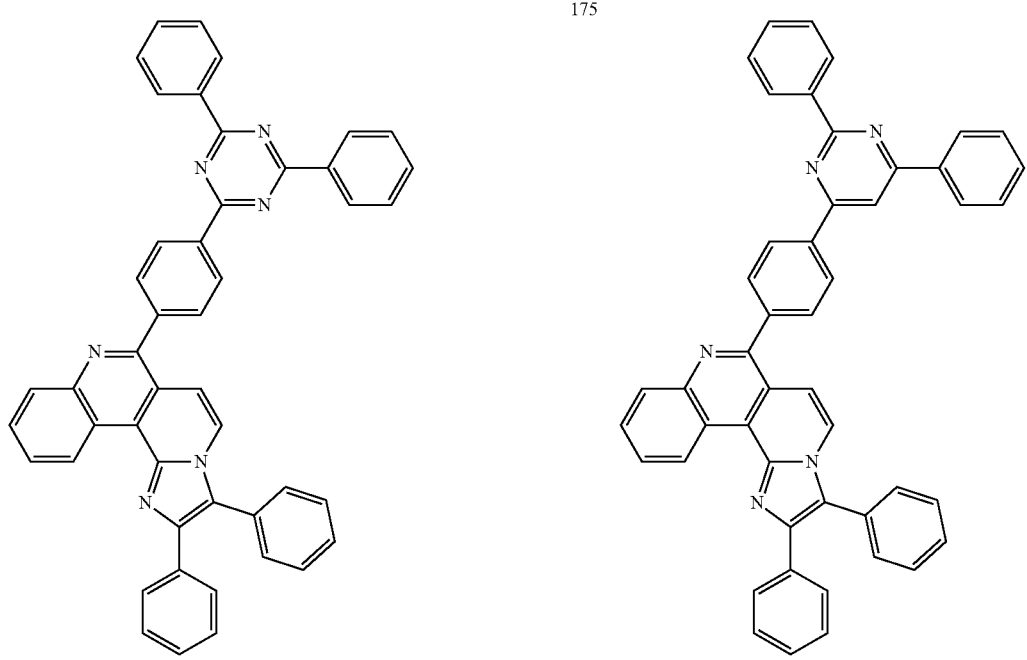

177
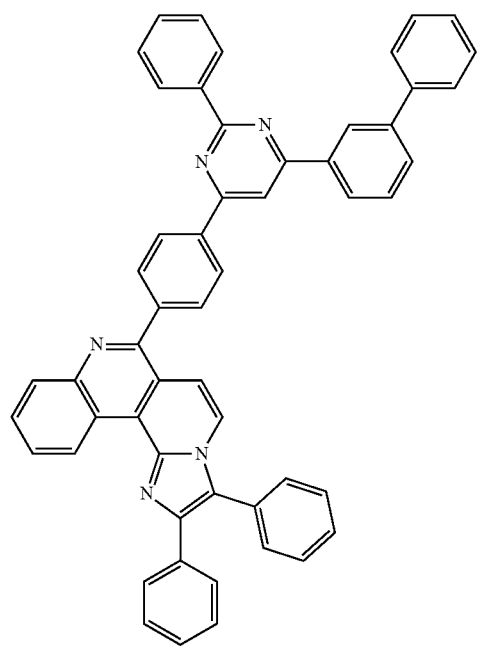
178
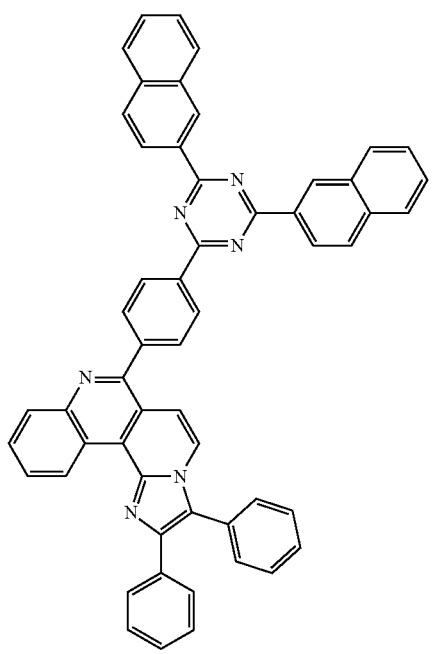
179
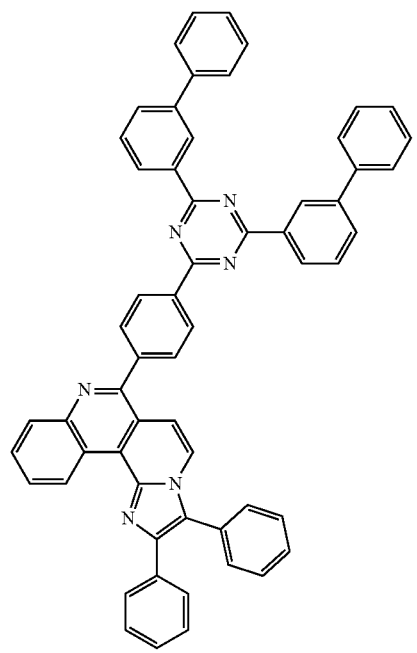
180
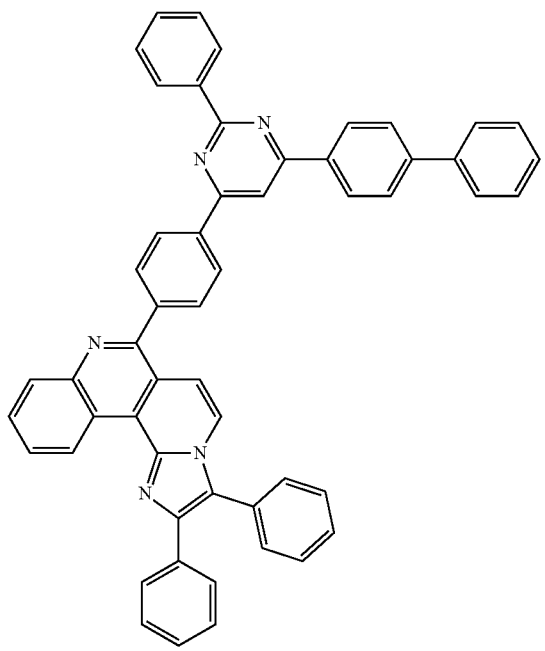

-continued
181
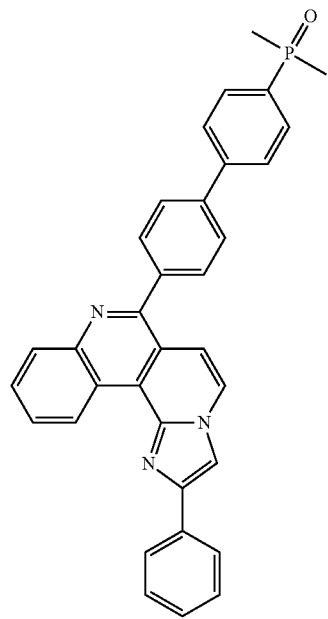
182
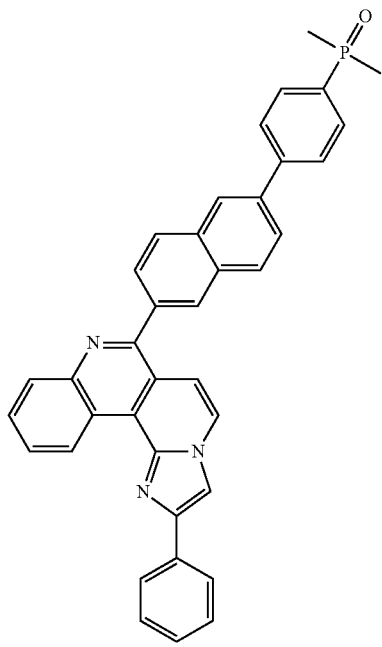
183
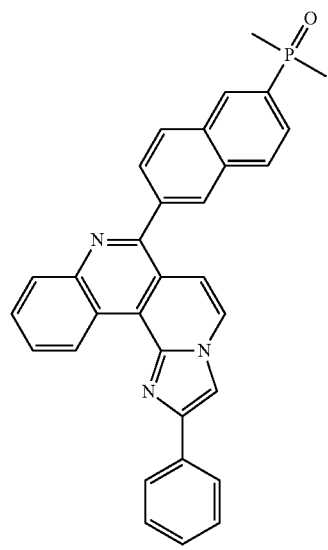
184
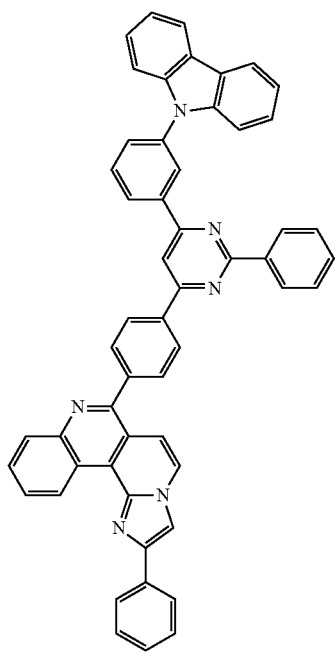

-continued
185
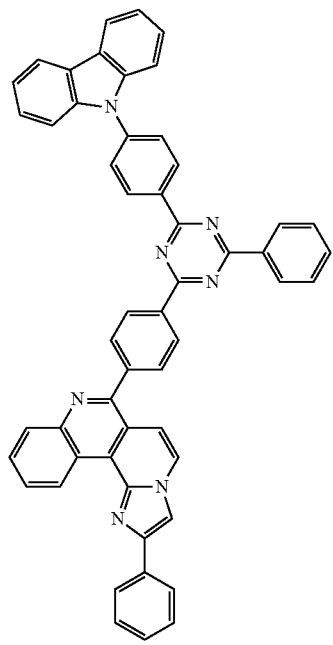
186
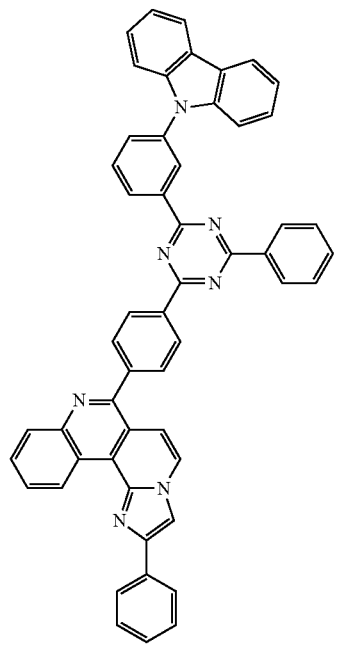
187
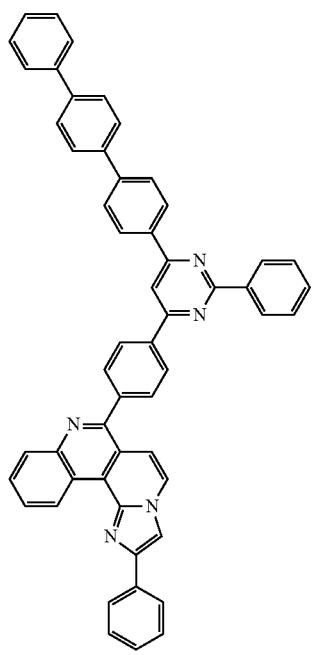
188
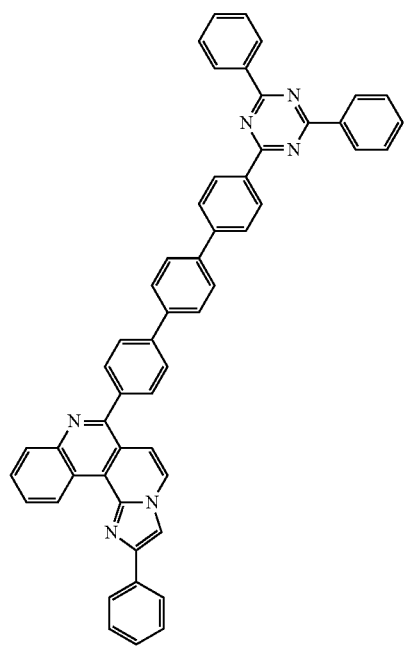

-continued
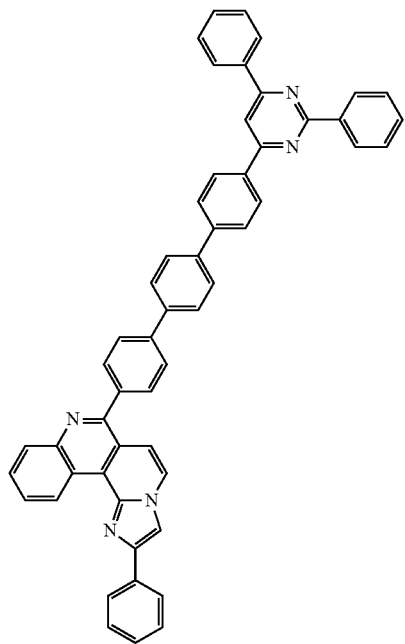
189
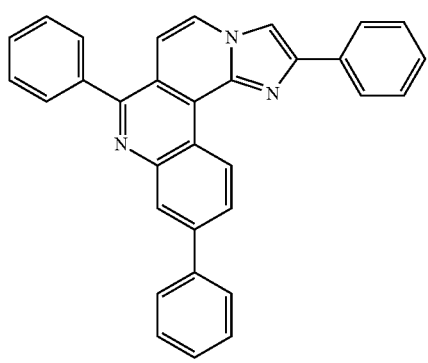
190
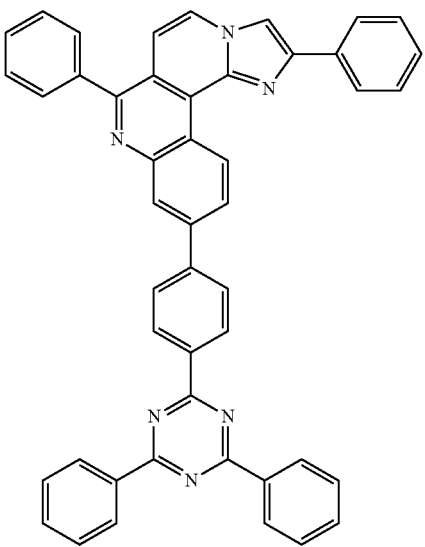
191

-continued
263
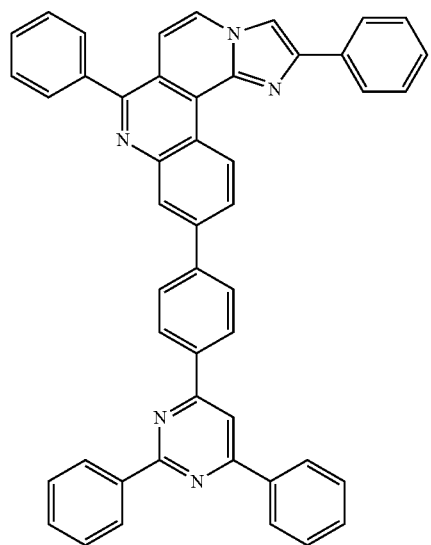
264
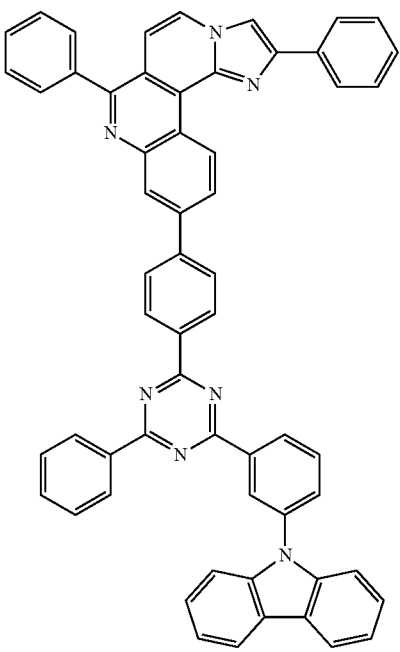
192
193
194
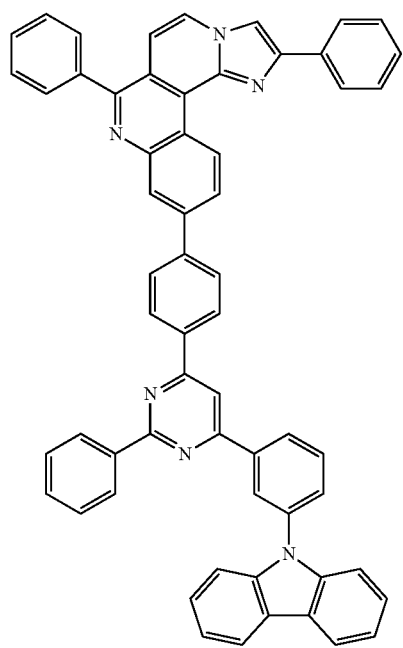
195
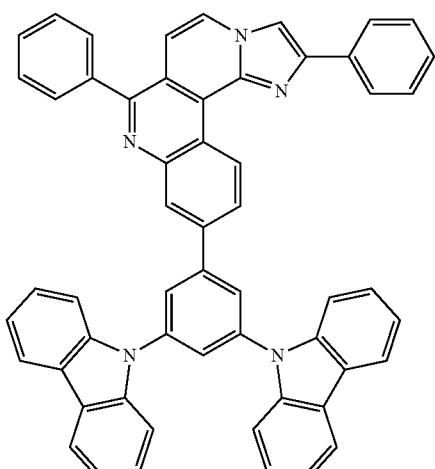

-continued
196 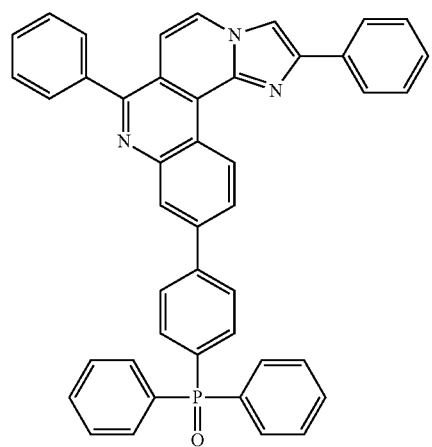
197 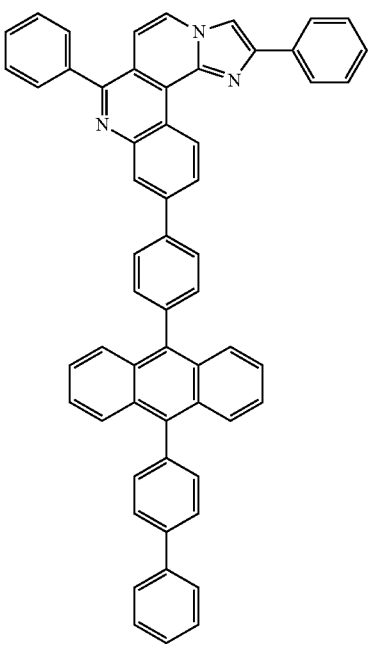
198 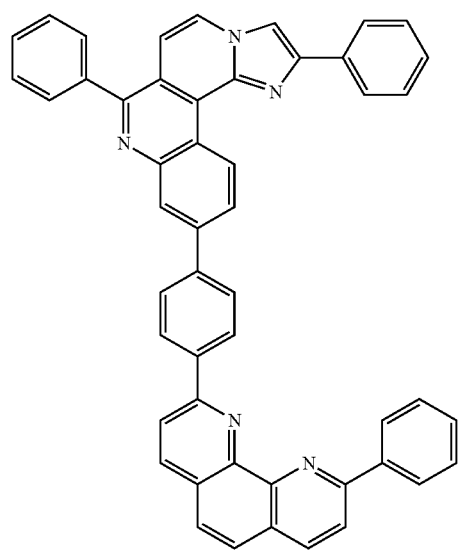
199 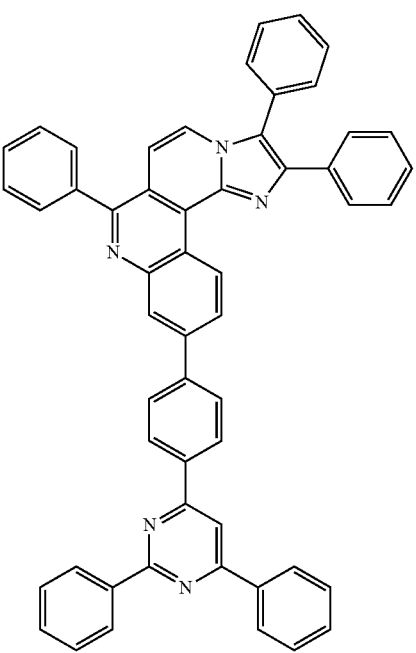

-continued
200
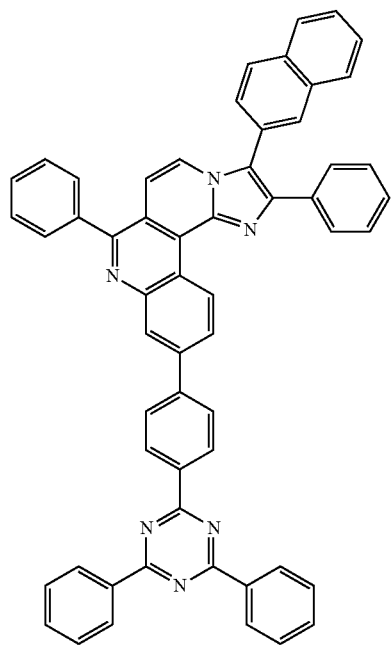
201
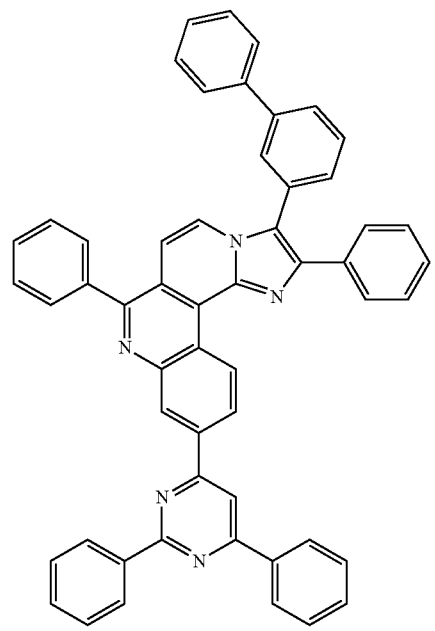
202
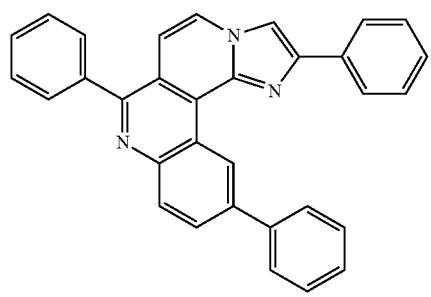
203
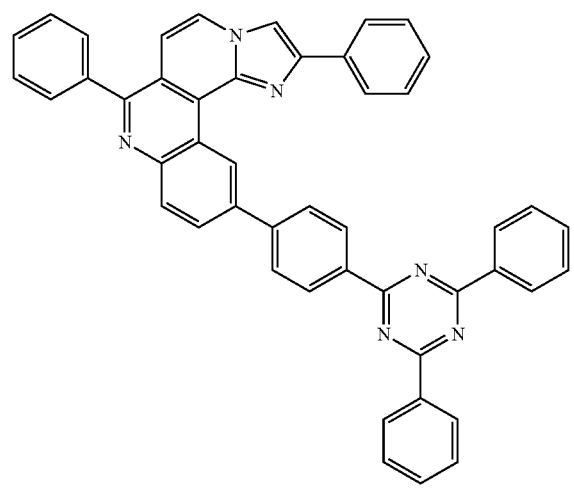
204
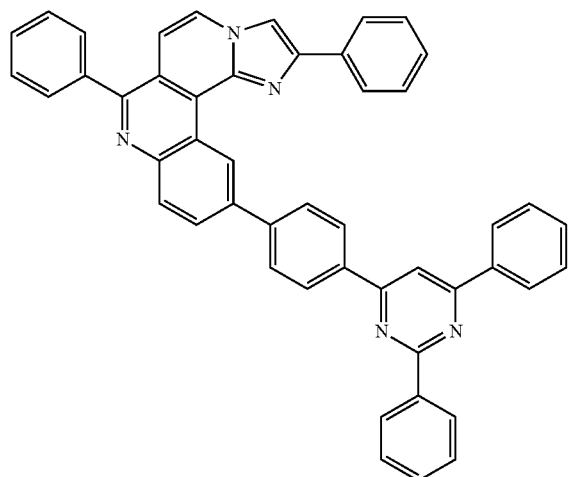
205
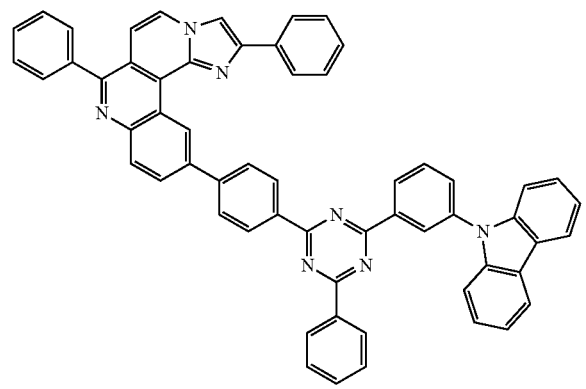

-continued
206
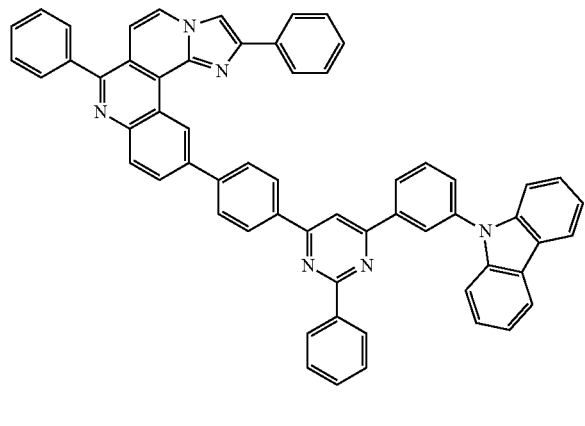
207
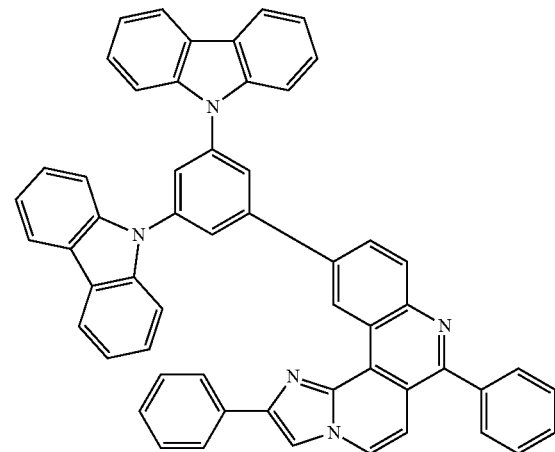
208
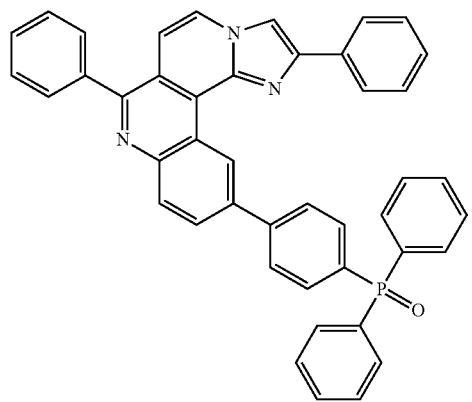
209
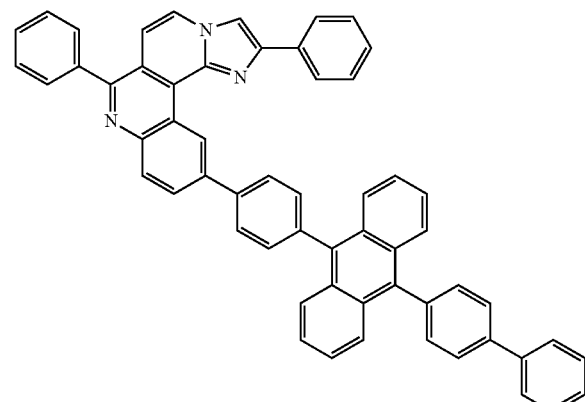
210
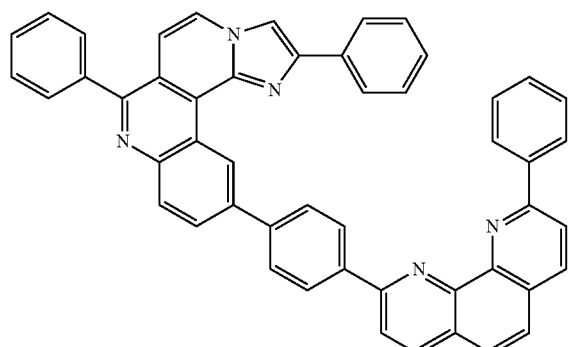
211
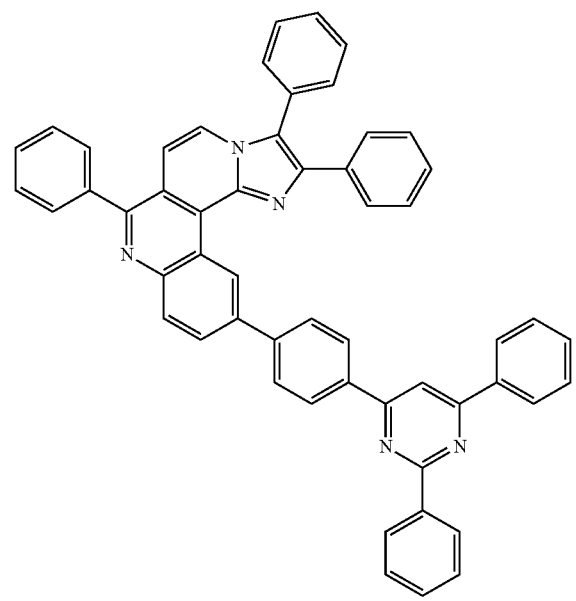

212
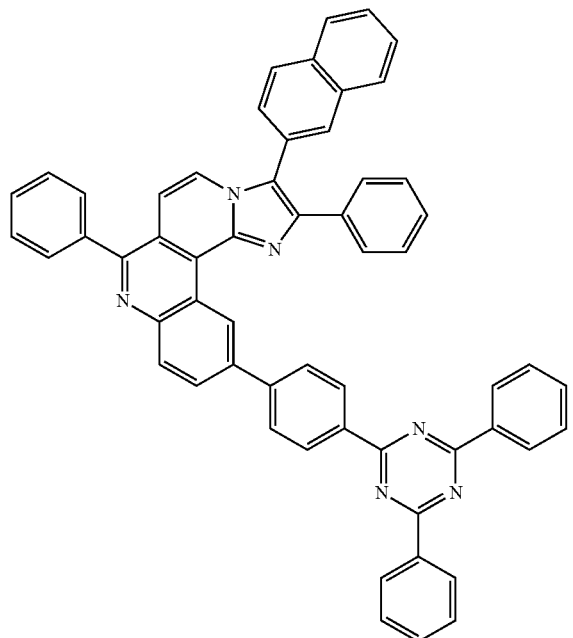
213
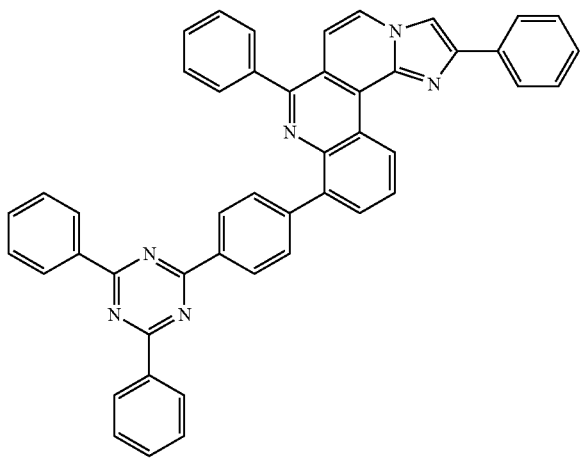
214
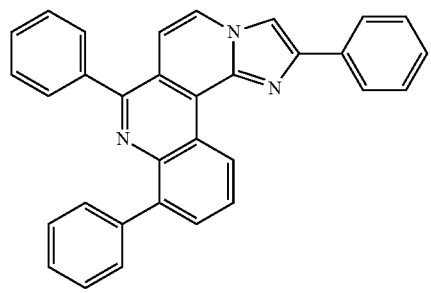
215
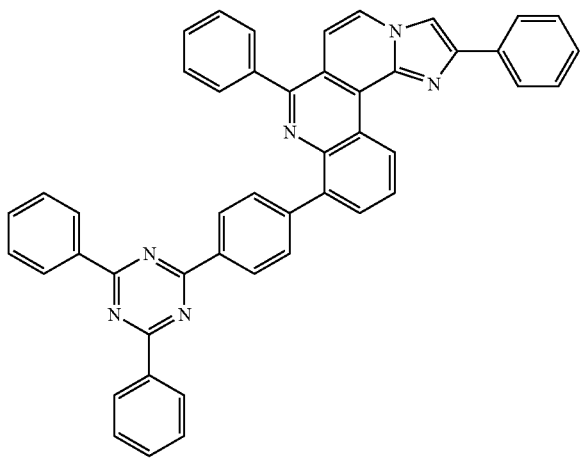
216
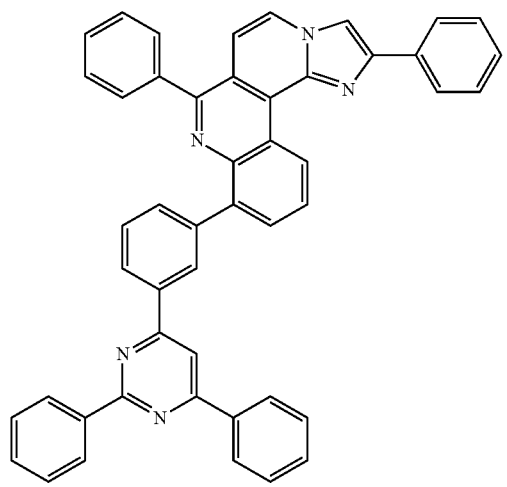

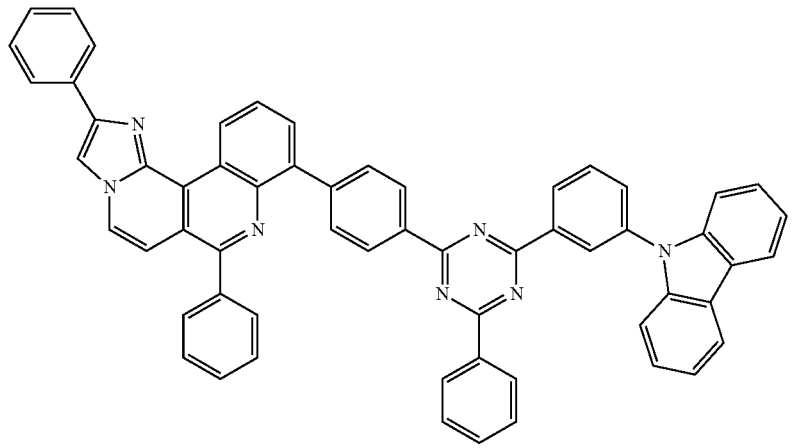
217
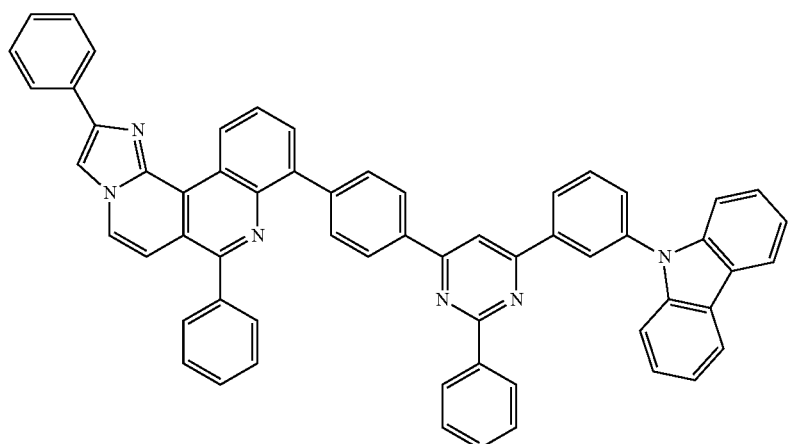
218
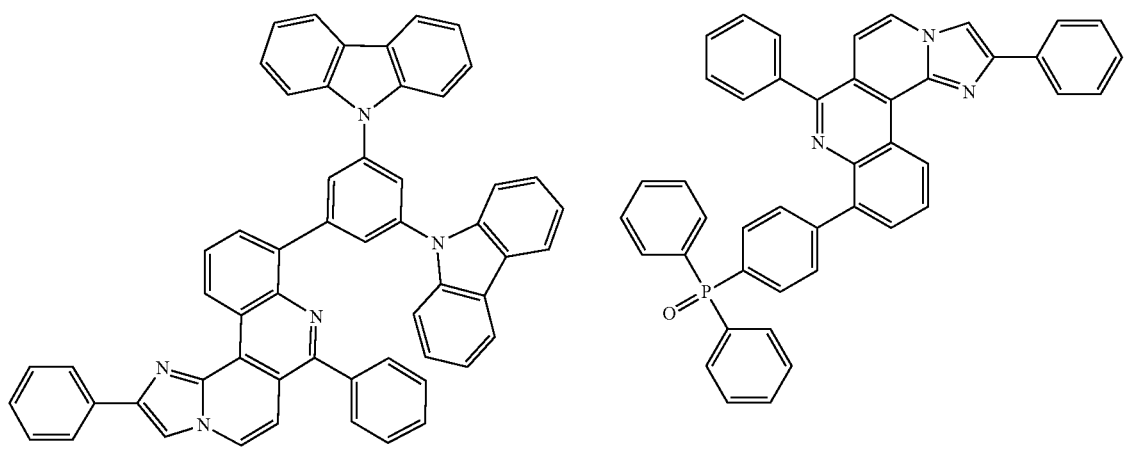
219 220

-continued
221
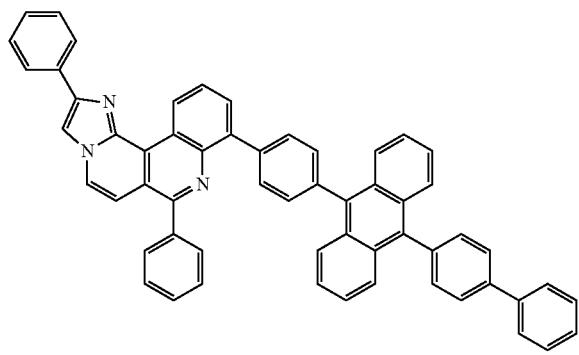
222
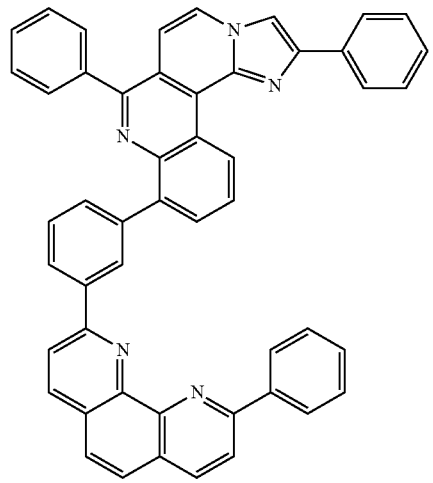
223
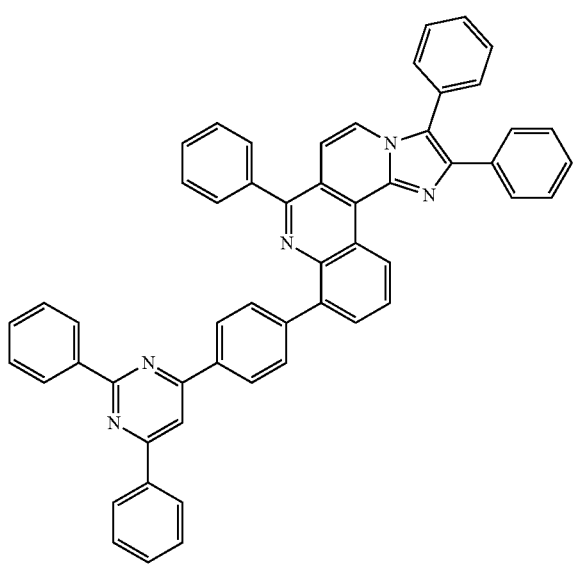
224
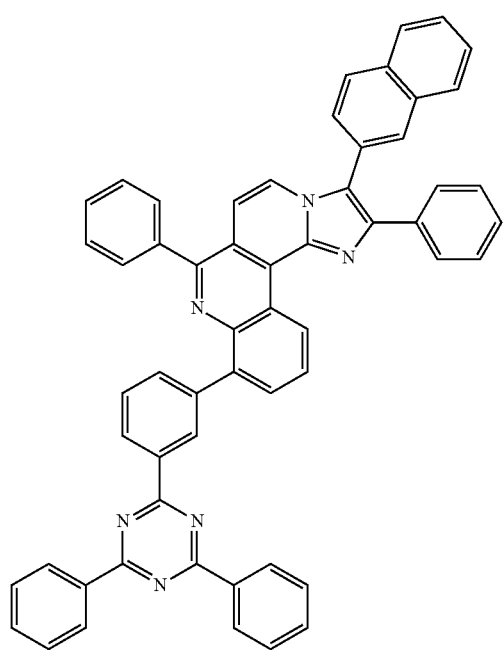

-continued

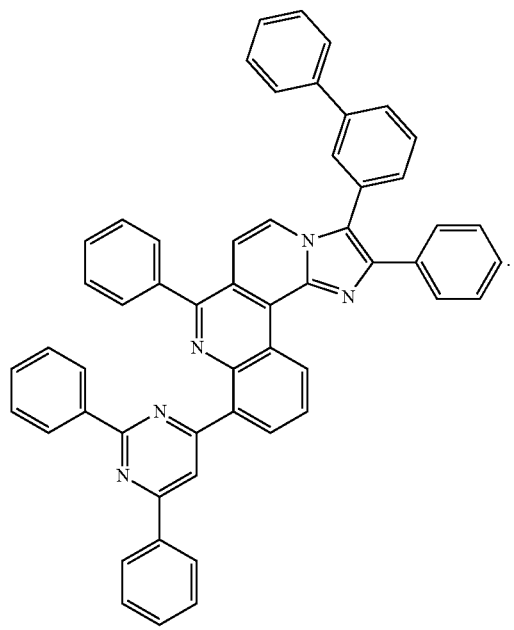

6. An organic light emitting device comprising:
a first electrode;
a second electrode provided opposite to the first electrode; and
one or more organic material layers provided between the first electrode and the second electrode,
wherein one or more layers of the organic material layers comprise the heterocyclic compound of claim 1.

7. The organic light emitting device of claim 6, wherein the organic material layer comprises a light emitting layer, and the light emitting layer comprises the heterocyclic compound.

8. The organic light emitting device of claim 6, wherein the organic material layer comprises an electron injection layer or an electron transfer layer, and the electron injection layer or the electron transfer layer comprises the heterocyclic compound.

9. The organic light emitting device of claim 6, wherein the organic material layer comprises an electron blocking layer or a hole blocking layer, and the electron blocking layer or the hole blocking layer comprises the heterocyclic compound.

10. The organic light emitting device of claim 6, further comprising one, two or more layers selected from the group consisting of a light emitting layer, a hole injection layer, a hole transfer layer, an electron injection layer, an electron transfer layer, an electron blocking layer and a hole blocking layer.

11. The organic light emitting device of claim 6, comprising:
a first electrode;
a first stack provided on the first electrode and comprising a first light emitting layer;
a charge generation layer provided on the first stack;
a second stack provided on the charge generation layer and comprising a second light emitting layer; and
a second electrode provided on the second stack.

12. The organic light emitting device of claim 11, wherein the charge generation layer comprises the heterocyclic compound.

13. The organic light emitting device of claim 12, wherein the charge generation layer is an N-type charge generation layer, and the charge generation layer comprises the heterocyclic compound.

* * * * *